(12) United States Patent
Rivera et al.

(10) Patent No.: US 12,251,370 B2
(45) Date of Patent: *Mar. 18, 2025

(54) SMALL MOLECULE INHIBITORS OF THE BFRB:BFD INTERACTION

(71) Applicants: BOARD OF SUPERVISORS OF LOUISIANA STATE UNIVERSITY AND AGRICULTURAL AND MECHANICAL COLLEGE, Baton Rouge, LA (US); UNIVERSITY OF KANSAS, Lawrence, KS (US); THE BOARD OF REGENTS FOR OKLAHOMA STATE UNIVERSITY, Stillwater, OK (US)

(72) Inventors: Mario Rivera, Baton Rouge, LA (US); Huili Yao, Baton Rouge, LA (US); Richard A. Bunce, Stillwater, OK (US); Baskar Nammalwar, San Diego, CA (US); Krishna Kumar Gnanasekaran, Mississauga (CA); Kate Eshelman, Alexandria, VA (US); Achala N. D. Punchi Hewage, Lawrence, KS (US); Scott Lovell, Shawnee, KS (US)

(73) Assignees: Board of Supervisors of Louisiana State University and Agricultural and Mechanical College, Baton Rouge, LA (US); University of Kansas, Lawrence, KS (US); The Board of Regents for Oklahoma State University, Stillwater, OK (US)

( * ) Notice: Subject to any disclaimer, the term of this patent is extended or adjusted under 35 U.S.C. 154(b) by 783 days.

This patent is subject to a terminal disclaimer.

(21) Appl. No.: 17/299,267

(22) PCT Filed: Dec. 3, 2019

(86) PCT No.: PCT/US2019/064272
§ 371 (c)(1),
(2) Date: Jun. 2, 2021

(87) PCT Pub. No.: WO2020/117832
PCT Pub. Date: Jun. 11, 2020

(65) Prior Publication Data
US 2022/0031661 A1    Feb. 3, 2022

Related U.S. Application Data

(60) Provisional application No. 62/831,616, filed on Apr. 9, 2019, provisional application No. 62/775,304, filed on Dec. 4, 2018.

(51) Int. Cl.
| | | |
|---|---|---|
| A61K 31/4035 | (2006.01) | |
| A61K 31/454 | (2006.01) | |
| A61K 31/496 | (2006.01) | |
| A61K 31/502 | (2006.01) | |
| A61P 31/04 | (2006.01) | |
| C07D 209/48 | (2006.01) | |
| C07D 237/32 | (2006.01) | |
| C07D 401/12 | (2006.01) | |
| C07D 405/12 | (2006.01) | |

(52) U.S. Cl.
CPC ........ *A61K 31/4035* (2013.01); *A61K 31/454* (2013.01); *A61K 31/496* (2013.01); *A61K 31/502* (2013.01); *A61P 31/04* (2018.01); *C07D 209/48* (2013.01); *C07D 237/32* (2013.01); *C07D 401/12* (2013.01); *C07D 405/12* (2013.01)

(58) Field of Classification Search
CPC .............. A61K 31/4035; A61K 31/454; A61K 31/496; A61P 31/04; C07D 209/48; C07D 401/12; C07D 4054/12
See application file for complete search history.

(56) References Cited

U.S. PATENT DOCUMENTS

| | | |
|---|---|---|
| 2014/0296310 A1 | 10/2014 | Alex et al. |
| 2022/0031661 A1 | 2/2022 | Rivera et al. |

FOREIGN PATENT DOCUMENTS

| | | |
|---|---|---|
| WO | WO-2017/049409 | 3/2017 |

OTHER PUBLICATIONS

National Center for Biotechnology Information. PubChem Compound Summary for CID 66659363, 4-[2-(4-Hydroxyphenyl) ethylamino]isoindole-1,3-dione. Created Nov. 30, 2012. (Year: 2012).*

Eshelman, K et al., Inhibiting the BfrB:Bfd Interaction in Pseudomonas aeruginosa Causes 23/1-7, 24/23/1-7, Irreversible Iron Accumulation in Bacterioferritin and Iron Deficiency in the Bacterial Cytosol, 25/23/ 1-7, 26/23/ 1-7 Metallomics. 9(6), pp. 1-28 (pp. 646-659), 2017; abstract.

Hewage, Andp et al., Small Molecule Inhibitors of the BfrB-Bfd Interaction Decrease 1-7 Pseudomonas aeruginosa Fitness and Potentiate Fluoroquinolone Activity, Journal of the American Chemical Society 141, pp. 8171-8184, Apr. 30, 2019; p. 8175, figure 3(8), structures 12-13, 16.

International Search Report and Written Opinion issued in PCT/US2019/064272 dated Jan. 29, 2020.

(Continued)

*Primary Examiner* — Matthew P Coughlin
*Assistant Examiner* — Quincy McKoy
(74) *Attorney, Agent, or Firm* — Venable LLP; Keith G. Haddaway; Hemant Khanna

(57) ABSTRACT

The present technology provides compounds of Formula I and related methods for treating a bacterial infection as well as methods for inhibiting interaction of a bacterioferritin and a bacterioferritin-associated ferredoxin.

20 Claims, 30 Drawing Sheets

(56) References Cited

OTHER PUBLICATIONS

Pubchem CID 66659363, pp. 1-9, Create Date: Nov. 30, 2012; p. 2.
International Preliminary Report on Patentability on PCT/US2019/064272 Dtd Jun. 17, 2021 (9 pages).
O'Connor et al., "Chemical genetics", Chem Soc Rev., (2011), vol. 40, No. 8, pp. 4332-4345.
O'Toole et al., "Initiation of biofilm formation in Pseudomonas fluorescens WCS365 proceeds via multiple, convergent signaling pathways: a genetic analysis", Mol Microbiol., (1998), vol. 28, No. 3, pp. 449-461.
Rivera, "Bacterioferritin: Structure Function and Protein-Protein Interactions", In Handbook of Porphyrin Science, (2014), vol. 30, pp. 136-179.
Rivera, "Bacterioferritin: Structure, Dynamics and Protein-Protein Interactions at Play in Iron Storage and Mobilization", Acc Chem Res., (2017), vol. 50, pp. 331-340.
Rui et al., "Protein dynamics and ion traffic in bacterioferritin", Biochemistry (2012), vol. 51, No. 49, pp. 9900-9910.
Ruvinsky et al., "Local packing modulates diversity of iron pathways and cooperative behavior in eukaryotic and prokaryotic ferritins", J Chem Phys., (2014), vol. 140, No. 11, p. 115104.
Schwyn, "Universal chemical assay for the detection and determination of siderophores", Analytical biochemistry, (1987), vol. 160, No. 1, pp. 47-56.
Sebaugh, "Guidelines for accurate EC50/IC50 estimation", Pharm Stat., (2011), vol. 10, No. 2, pp. 128-134.
Spring, "Chemical genetics to chemical genomics: small molecules offer big insights", Chem Soc Rev., (2005), vol. 34, No. 6, pp. 472-482.
Tacconelli et al., "Discovery, research, and development of new antibiotics: the WHO priority list of antibiotic-resistant bacteria and tuberculosis", Lancet Infect Dis., (2018), vol. 18, No. 3, pp. 318-327.
Vonrhein et al., "Data Processing and Analysis with the AutoPROC Toolbox", Acta Crystallogr D Biol Crystallogr., (2011), vol. D67, pp. 293-302.
Wang et al., "Characterization of the Bacterioferritin/Bacterioferritin Associated Ferredoxin Protein-Protein Interactions in Solution and Determination of Binding Energy Hot Spots", Biochemistry, (2015), vol. 54, No. 40, pp. 6162-6175.
Weeratunga et al., "Binding of Pseudomonas aeruginosa Apobacterioferritin-Associated Ferredoxin to Bacterioferritin B Promotes Heme Mediation of Electron Delivery and Mobilization of Core Mineral Iron", Biochemistry, (2009), vol. 48, No. 31, pp. 7420-7431.
Weeratunga et al., "Structural Studies of Bacterioferritin B (BfrB) from Pseudomonas aeruginosa Suggest a Gating Mechanism for Iron Uptake via the Ferroxidase Center", Biochemistry, (2010), vol. 49, No. 6, pp. 1160-1175.
Weinberg, "Iron Availability and Infection", Biochimica et Biophysica Acta, (2009), vol. 1790, pp. 600-605.
Weiss, "Global indicators of X-ray data quality", Journal of Applied Crystallography, (2001), vol. 34, No. 2, pp. 130-135.
Wijerathne et al., "Bfd, a New Class of [2Fe—2S] Protein That Functions in Bacterial Iron Homeostasis, Requires a Structural Anion Binding Site", Biochemistry, (2018), vol. 57, No. 38, pp. 5533-5543.
Yao et al., "Concerted motions networking pores and distant ferroxidase centers enable bacterioferritin function and iron traffic", Biochemistry (2015), vol. 54, No. 8, pp. 1611-1627.
Yao et al., "The Structure of the BfrB-Bfd Complex Reveals Protein-Protein Interactions Enabling Iron Release from Bacterioferritin", J. Am. Chem. Soc., (2012), vol. 134, No. 32, pp. 13470-13481.
Yeom et al., "Iron homeostasis affects antibiotic-mediated cell death in Pseudomonas species", J Biol Chem., (2010), vol. 285, No. 29, pp. 22689-22695.
Andrews et al., "Control of iron metabolism in bacteria", Met Ions Life Sci., (2013), vol. 12, pp. 203-239.
Abràmoff et al., "Image processing with Image", J. Biophotonics International, (2004), vol. 11, pp. 36-42.
Adams et al., "PHENIX: A Comprehensive Python-Based System for Macromolecular Structure Solution", Acta Cryst., (2010), vol. D66, No. 2, pp. 213-221.
Andrews, "Determination of Minimum Inhibitory Concentrations", J. Antimicrob. Chemother., (2001), vol. 48, Suppl. 1, pp. 5-16.
Arora et al. "Modified microplate method for rapid and efficient estimation of siderophore produced by bacteria", 3 Biotech, (2017), vol. 7, No. 6, p. 381.
Ballouche et al., "Iron Metabolism: A Promising Target for Antibacterial strategies", Recent Patents on Anti-Infective Drug Discovery, (2009), vol. 4, pp. 190-205.
Belenky et al., "Bactericidal Antibiotics Induce Toxic Metabolic Perturbations", Cell Reports, (2015), vol. 13, No. 5, pp. 968-980.
Benson et al., "Heme Uptake and Metabolism in Bacteria", Met. Ions Life Sci., (2013), vol. 12, pp. 279-332.
Blaskovich et al., "Polishing the tarnished silver bullet: the quest for new antibiotics", Essays Biochem., (2017), vol. 61, No. 1, pp. 103-114.
Boucher et al., "Bad Bugs, No Drugs: No. ESKAPE! An Update from the Infectious Diseases Society of America", Clin. Infect. Dis. (2009), vol. 48, pp. 1-11.
Bullen et al., "Iron and Infection: The Heart of the Matter", FEMS Immunol. Med. Microbiol., (2005), vol. 43, pp. 325-330.
Burrows et al., "The Therapeutic Pipeline for Pseudomonas aeruginosa Infections", ACS Infect Dis., (2018), vol. 4, No. 7, pp. 1041-1047.
CDC, "Antibiotic Resistance Threats in the United States", (2019), 150 pages. rwww.cdc.gov/drugresistance/threat-report-2019/ (Reference broken into two parts).
Chen et al., "Initial Drug Dissolution from Amorphous Solid Dispersions Controlled by Polymer Dissolution and Drug-Polymer Interaction", Pharm Res., (2016), vol. 33, No. 10, pp. 2445-2458.
Chen et al., "MolProbity: All-Atom Structure Validation for Macromolecular Crystallography", Acta Cryst., (2010), vol. 66, No. 1, pp. 12-21.
Chung, "A specific iron stain for iron-binding proteins in polyacrylamide gels: application to transferrin and lactoferrin", Anal Biochem., (1985), vol. 148, No. 2, pp. 498-502.
Clinical and Laboratory Standards Institute, (2018), M07 11th Methods for Dilution Antimicrobial Susceptibility Tests for Bacteria That Grow Aerobically. (Refernce broken into three parts).
Cornelis et al., "Iron homeostasis and management of oxidative stress response in bacteria", Metallomics, (2011), vol. 3, No. 6, pp. 540-549.
Crull et al., "Change in Pseudomonas aeruginosa prevalence in cystic fibrosis adults over time", BMC Pulm Med., (2016), vol. 16, No. 1, p. 176.
Diederichs et al., "Improved R-factors for Diffraction Data Analysis in Macromolecular Crystallography", Nature Structural Biology, (1997), vol. 4, pp. 269-275.
Dwyer et al., "Antibiotics induce redox-related physiological alterations as part of their lethality", Proc Natl Acad Sci U S A., (2014), vol. 111, No. 20, pp. E2100-E2109.
Dwyer et al., "Gyrase inhibitors induce an oxidative damage cellular death pathway in *Escherichia coli*", Mol Syst Biol., (2007), vol. 3, pp. 91.
Emsley et al., "Features and Development of Coot", Acta Cryst., (2010), vol. D66, No. 4, pp. 486-501.
Evans, "An Introduction to Data Reduction: Space-Group Determination, scaling and intensity statistics", Acta Cryst., (2011), vol. D67, pp. 282-292.
Evans, "Biochemistry. Resolving some old problems in protein crystallography", Science, (2012), vol. 336, No. 6084, pp. 986-987.
Evans, "Scaling and assessment of data quality", Acta Crystallogr D Biol Crystallogr., (2006), vol. 62, (Pt 1), pp. 72-82.
Fish, "Rapid colorimetric micromethod for the quantitation of complexed iron in biological samples", Methods Enzymol., (1988), vol. 158, pp. 357-364.
Foley et al., "Targeting iron assimilation to develop new antibacterials", Expert Opin Drug Discov., (2012), vol. 7, No. 9, pp. 831-847.

(56) References Cited

OTHER PUBLICATIONS

Goss et al., "Gallium disrupts bacterial iron metabolism and has therapeutic effects in mice and humans with lung infections", Science translational medicine, (2018), vol. 10, No. 460, eaat7520.

Hedayati et al., "An optimised spectrophotometric assay for convenient and accurate quantitation of intracellular iron from iron oxide nanoparticles", Int J Hyperthermia, (2018), vol. 34, No. 4, pp. 373-381.

Heinzl et al., "Iminoguanidines as Allosteric Inhibitors of the Iron-Regulated Heme Oxygenase (HemO) of Pseudomonas aeruginosa", J Med Chem., (2016), vol. 59, No. 14, pp. 6929-6942.

Hennessy et al., "Ferene—a new spectrophotometric reagent for iron", Can. J. Chem., (1984), vol. 62, No. 4, pp. 721-724.

Hood et al., "Nutritional immunity: transition metals at the pathogen-host interface", Nat Rev Microbiol., (2012), vol. 10, No. 8, pp. 525-537.

"Hunting the Nightmare Bacteria." Frontline. PBS. Season 2, episode 13. Television.

Jacobs et al., "A Highly Virulent Isolate of Acinetobacter baumannii, as a Model Strain for the Evaluation of Pathogenesis and Antimicrobial Treatments", MBio., (2014), vol. 5, No. 3, pp. e01076-14. 10.1128/mBio.01076-14.

Jing et al., "Methods for measuring aptamer-protein equilibria: a review", Anal Chem Acta, (2011), vol. 686, Nos. 1-2, pp. 9-18.

Kabsch, "Automatic Indexing of Rotation Diffraction Patterns", J. Appl. Cryst., (1988), vol. 21, pp. 67-72.

Kaneko et al., "The Transition Metal Gallium Disrupts Pseudomonas aeruginosa Iron Metabolism and has Antimicrobial and Antibiofilm Activity", J. Clin. Invest., (2007), vol. 117, pp. 877-887.

Karplus et al., "Linking crystallographic model and data quality", Science, (2012), vol. 336, No. 6084, pp. 1030-1033.

Keyer et al., "Superoxide Accelerates DNA-Damage by Elevating Free-Iron Levels", Proc. Natl. Acad. Sci. USA, (1996), vol. 93, pp. 13635-13649.

Koenig et al., "Ventilator-Associated Pneumonia: Diagnosis, Treatment, and Prevention", Clin. Microbio. Rev., (2006), vol. 19, No. 4, pp. 637-657.

Konstan et al., "MBCHB for the Scientific Advisory Group and the Investigators and Coordinators of the Epidemiologic Study of Cystic Fibrosis, Risk factors for rate of decline in forced expiratory volume in one second in children and adolescents with cystic fibrosis", J Pediatr., (2007), vol. 151, No. 2, pp. 134-139, 139 e1.

Koulenti et al., "Spectrum of practice in the diagnosis of nosocomial pneumonia in patients requiring mechanical ventilation in European intensive care units", Crit. Care Med., (2009), vol. 37, pp. 2360-2368.

Laxminarayan et al., "Antibiotic resistance—the need for global solutions", Lancet Infect Dis., (2013), vol. 13, No. 12, pp. 1057-1098.

Lepre et al., "Theory and Applications of NMR-Based Screening in Pharmaceutical Research", Chem. Rev., (2004), vol. 104, No. 8, pp. 3641-3675.

Liebschner et al., "Polder maps: improving OMIT maps by excluding bulk solvent", Acta Cryst. (2017), vol. 73, No. 2, pp. 148-157.

Ma et al., "Bacterioferritin A Modulates Catalase A (KatA) Activity and Resistance to Hydrogen Peroxide in Pseudomonas aeruginosa", J. Bacteriol., (1999), vol. 181, pp. 3730-3742.

McCoy, et al., "Phaser crystallographic software", J. Appl. Cryst., (2007), vol. 40, pp. 658-674.

McNicholas et al., "Presenting your Structures: The CCPmg Molecular-Graphics Software", Acta Crystallogr D Biol Crystallogr., (2011), vol. 67, No. 4, pp. 386-394.

Mehi et al., "Perturbation of iron homeostasis promotes the evolution of antibiotic resistance", Mol Biol Evol., (2014), vol. 31, No. 10, pp. 2793-2804.

Minandri et al., "Promises and failures of gallium as an antibacterial agent", Future Microbiol., (2014), vol. 9, No. 3, pp. 379-397.

Punchi Hewage et al., "Small Molecule Inhibitors of the BfrB-Bfd Interaction Decrease Pseudomonas aeruginosa Fitness and Potentiate Fluoroquinolone Activity", J Am. Chem. Soc., (2019), vol. 141, No. 20, pp. 8171-8184. 10.1021/jacs.9b00394.

Romling et al., "Biofilm infections, their resilience to therapy and innovative treatment strategies", Journal of Internal Medicine, (2012), vol. 272, No. 6, pp. 541-561. 10.1111/joim.12004.

Singh et al., "A Component of Innate Immunity Prevents Bacterial Biofilm Development", Nature, (2002), vol. 417, No. 6888, pp. 552-555. 10.1038/417552a.

Soldano et al., "Inhibiting Iron Mobilization from Bacterioferritin in Pseudomonas aeruginosa Impairs Biofilm Formation Irrespective of Environmental Iron Availability", ACS Infect. Dis., (2020), vol. 6, No. 3, pp. 447-458. 10.1021/acsinfecdis.9b00398.

Stewart et al., "Antibiotic resistance of bacteria in biofilms", Lancet, (2001), vol. 358, No. 9276, pp. 135-138. 10.1016/s0140-6736(01)05321-1.

Stover et al., "Complete Genome Sequence of Pseudomonas aeruginosa PA01, an Opportunistic Pathogen", Nature, (2000), vol. 406, pp. 959-964. 10.1038/35023079.

Sutherland, "Biofilm exopolysaccharides: a strong and sticky framework", Microbiology, (2001), vol. 147, pp. 3-9. 10.1099/00221287-147-I-3.

Tawakoli et al., "Comparison of different live/dead stainings for detection and quantification of adherent microorganisms in the initial oral biofilm", Clinical Oral Investigations, (2013), vol. 17, No. 3, pp. 841-850. 10.1007/s00784-012-0792-3.

The Pharma Letter, "Healthcare-Associated Gram-Negative market to be worth $3.6 billion by 2026; report", Press Release, (Sep. 20, 2017); <https://www.globaldata.com/healthcare-associated-gra•• negative-market-to-be-worth-3-6-billion-by-2026/>. screen shot of website.

Verderosa et al., "Bacterial Biofilm Eradication Agents: A Current Review", Frontiers in Chemistry, (2019), vol. 7, 17 pages. 10.3389/fchem.2019.00824.

Visca et al., "The dual personality of iron chelators: growth inhibitors or promoters?", Antimicrobial Agents and Chemotherapy, (2013), vol. 57, No. 5, pp. 2432-2433. 10.1128/AAC.02529-12.

Vrany et al., "Comparison of recalcitrance to ciprofloxacin and levofloxacin exhibited by Pseudomonas aeruginosa biofilms displaying rapid-transport characteristics", Antimicrobial Agents and Chemotherapy, (1997), vol. 41, No. 6, pp. 1352-1358. 10.1128/AAC.41.6.1352.

Walters et al., "Contributions of antibiotic penetration, oxygen limitation, and low metabolic activity to tolerance of Pseudomonas aeruginosa biofilms to ciprofloxacin and tobramycin", Antimicrobial Agents and Chemotherapy, (2003), vol. 47, No. 1, pp. 317-323. 10.1128/aac.47.1.317-323.2003.

Werner et al., "Stratified growth in Pseudomonas aeruginosa biofilms", Applied and Environmental Microbiology, (2004), vol. 70, No. 10, pp. 6188-6196. 10.1128/AEM.70.10.6188-6196.2004.

Windus et al., "Fatal Rhizopus Infections in Hemodialysis Patients Receiving Deferoxamine", Annals of Internal Medicine, (1987), vol. 107, No. 5, pp. 678-680. 10.7326/0003-4819-107-5-678.

Winsor et al., "Enhanced annotations and features for comparing thousands of Pseudomonas genomes in the Pseudomonas genome database", Nucleic Acids Research, (2016), vol. 44, pp. D646-653. 10.1093/nar/gkv1227.

Xu et al. "Spatial physiological heterogeneity in Pseudomonas aeruginosa biofilm is determined by oxygen availability", Applied and Environmental Microbiology, (1998), vol. 64, No. 10, pp. 4035-4039. 10.1128/AEM.64.10.4035-4039.1998.

Yamamoto et al., "Trade-off between oxygen and iron acquisition in bacterial cells at the air-liquid interface", FEMS Microbiology Ecology, (2011), vol. 77, No. 1, pp. 83-94. 10.1111/j.1574-6941.2011.01087.x.

Yao et al., "Two Distinct Ferritin-Like Molecules in P. aeruginosa: The Product of the bfrA Gene is a Bacterial Ferritin (FtnA) not a bacterioferritin (Bfr)", Biochemistry, (2011), vol. 50, No. 23, pp. 5236-5248. 10.1021/bi2004119.

Anderl et al., "Role of nutrient limitation and stationary-phase existence in Klebsiella pneumoniae biofilm resistance to ampicillin and ciprofloxacin", Antimicrobial Agents and Chemotherapy, (2003), vol. 47, No. 4, pp. 1251-1256. 10.1128/aac.47.4.1251-1256.2003.

(56) References Cited

OTHER PUBLICATIONS

Anwar et al., "Dynamic interactions of biofilms of mucoid Pseudomonas aeruginosa with tobramycin and piperacillin", Antimicrobial Agents and Chemotherapy, (1992), vol. 36, No. 6, pp. 1208-1214. 10.1128/aac.36.6.1208.

Anwar et al., "Enhanced activity of combination of tobramycin and piperacillin for eradication of sessile biofilm cells of Pseudomonas aeruginosa", Antimicrobial Agents and Chemotherapy, (1990), vol. 34, No. 9, pp. 1666-1671. 10.1128/aac.34.9.1666.

Ayrapetyan et al., "Bridging the gap between viable but non-culturable and antibiotic persistent bacteria", Trends in Microbiology, (2015), vol. 23, No. 1, pp. 7-13. 10.1016/j.tim.2014.09.004.

Banin et al., "Chelator-induced dispersal and killing of Pseudomonas aeruginosa cells in a biofilm", Applied Environmental Microbiology, (2006), vol. 72, No. 3, pp. 2064-2069. 10.1128/AEM.72.3.2064-2069.2006.

Banin et al., "Iron and Pseudomonas aeruginosa biofilm formation", Proc. Natl. Acad Sci., (2005), vol. 102, pp. 11076-11081. 10.1073/pnas.0504266102.

Brauner et al., "Distinguishing between resistance, tolerance and persistence to antibiotic treatment", Nature Reviews Microbiology, (2016), vol. 14, pp. 320-330. 10.1038/nrmicro.2016.34.

Centola et al., "Gallium(III)-Salophen as a Dual Inhibitor of Pseudomonas aeruginosa Heme Sensing and Iron Acquisition", ACS Infectious Diseases, (2020), vol. 6, No. 8, pp. 2073-2085. 10.1021/acsinfecdis.0c00138.

Ceri et al., "The Calgary Biofilm Device: new technology for rapid determination of antibiotic susceptibilities of bacterial biofilms", Journal of Clinical Microbiology, (1999), vol. 37, No. 6, pp. 1771-1776. 10.1128/JCM.37.6.1771-1776.1999.

Chellat et al. "Targeting Antibiotic Resistance", Angewandte Chemie Int. Ed Engl., (2016), vol. 55, pp. 6600-6026. 10.1002/anie.201506818.

Ciccone et al., "Multicomponent mixtures for cryoprotection and ligand solubilization", Biotechnology Reports, (2015), vol. 7, No. a1, pp. 120-127. 10.1016/j.btre.2015.05.008.

Clark et al., "DNA Replication and the Division Cycle in *Escherichia coli*", J Mol. Biol., (1967), vol. 23, pp. 99-112. 10.1016/S0022-2836(67)80070-6.

Costerton et al., "Bacterial Biofilms: A Common Cause of Persistent Infection", Science, (1999), vol. 284, pp. 1318-1322. 10.1126/science.284.5418.1318.

Crabbe et al., "Antimicrobial Tolerance and Metabolic Adaptations in Microbial Biofilms", Trends in Microbiology, (2019), vol. 27, pp. 850-863. 10.1016/j.tim.2019.05.003.

Davies, "Understanding biofilm resistance to antibacterial agents", Nature Reviews Drug Discovery, (2003), vol. 2, No. 2, pp. 114-122. 10.1038/nrd1008.

Ezadi et al., "Antimicrobial Susceptibility Testing for Polymyxins: Challenges, Issues, and Recommendations", Journal of Clinical Microbiology, (2019), vol. 57, No. 4, 21 pages. e01390-18 10.1128/JCM.01390-18.

Friedman et al., "Genes involved in matrix formation in Pseudomonas aeruginosa PAI4 biofilms", Molecular Microbiology, (2004), vol. 51, No. 3, pp. 675-690. 10.1046/j. 1365-2958.2003.03877.x.

Frontline, "Hunting the Nightmare Bacteria", (2011), Frontline, PBS, Season 2, Television Episode 13.

Gnanasekaran et al., "4,7-Diaminoisoindoline-1,3-dione", Organic Preparations and Procedures International, (2018), vol. 50, No. 3, pp. 372-374. 10.1080/00304948.2018.1462072.

Haagensen et al., "Differentiation and distribution of colistin- and sodium dodecyl sulfate-tolerant cells in Pseudomonas aeruginosa biofilms", J Bacteriol., (2007), vol. 189, No. 1, pp. 28-37. 10.1128/JB.00720-06.

Harmsen et al., "An update on Pseudomonas aeruginosa biofilm formation, tolerance, and dispersal", FEMS Immunology and Medical Microbiology, (2010), vol. 59, No. 3, pp. 253-268. 10.1111/j.1574-695X.2010.00690.x.

Hentzer et al., "Attenuation of Pseudomonas aeruginosa virulence by quorum sensing inhibitors", EMBO Journal, (2003), vol. 22, No. 15, pp. 3803-3815. 10.1093/emboj/cdg366.

Heydorn et al., "Quantification of biofilm structures by the novel computer program COMSTAT", Microbiology, (2000), vol. 146, Pt. 10, pp. 2395-2407. 10.1099/00221287-146-10-2395.

Hoiby et al., "Antibiotic resistance of bacterial biofilms", International Journal of Antimicrobial Agents, (2010), vol. 35, No. 4, pp. 322-332. 10.1016/j.ijantimicag.2009.12.011 Dec. 16, 2021.

James et al., "Biofilms in chronic wounds", Wound Repair and Regeneration, (2008), vol. 16, pp. 37-44. 10.1111/j.1524-475X.2007.00321.x.

Ji et al., "Iron transport-mediated drug delivery: practical syntheses and in vitro antibacterial studies of tris-catecholate siderophore-aminopenicillin conjugates reveals selectively potent antipseudomonal activity", Journal of the American Chemical Society, (2012), vol. 134, No. 24, pp. 9898-9901. 10.1021/ja303446w.

Johnson et al., "NCBI BLAST: a better web interface", Nucleic Acids Research, (2008), vol. 36, pp. W5-W9. 10.1093/nar/gkn201.

Kadam et al., "Recent Advances in Non• Conventional Antimicrobial Approaches for Chronic Wound Biofilms: Have We Found the 'Chink in the Armor'?", Biomedicines, (2019), vol. 7, 26 pages. 10.3390/biomedicines7020035.

Kang et al., "Interdependence between iron acquisition and biofilm formation in Pseudomonas aeruginosa", Journal of Microbiology, (2018), vol. 56, pp. 449-457. 10.1007/sl2275-018-8114-3.

Kolpen et al., "Increased bactericidal activity of colistin on Pseudomonas aeruginosa biofilms in anaerobic conditions", Pathogens and Disease, (2016), vol. 74, No. 1, 7 pages, ftv086. 10.1093/femspd/ftv086.

Konstan et al., "Risk factors for rate of decline in forced expiratory volume in one second in children and adolescents with cystic fibrosis", J Pediatr., (2007), vol. 151, pp. 134-139, 139 e1. 10.1016/j.jpeds.2007.03.006.

Lakemeyer et al., "Thinking Outside the Box-Novel Antibacterials To Tackle the Resistance Crisis", Angewandte Chemie Int. Ed Engl., (2018), vol. 57, No. 44, pp. 14440-14475. 10.1002/anie.201804971.

Lam et al., "Production of Mucoid Microcolonies by Pseudomonas aeruginosa Within Infected Lungs in Cystic Fibrosis", Infect. Immun., (1980), vol. 28, pp. 546-556. PMCID PMC550970.

Lawrence et al., "Optical sectioning of microbial biofilms", J Bacteriol., (1991), vol. 173, pp. 6558-6567. 10.1128/jb.173.20.6558-6567.1991.

Li et al., "Colistin: the re-emerging antibiotic for multidrug-resistant Gram-negative bacterial infections", Lancet Infectious Diseases, (2006), vol. 6, No. 9, pp. 589-601. 10.1016/SI473-3099(06)70580-I.

Li, "Reviving Polymyxins: Achievements, Lessons and the Road Ahead. In Polymyxin Antibiotics: From Laboratory Bench to Bedside", Advances in Experimental Medicine and Biology, (2019), vol. 1145, pp. 1-8.

Liu et al., "A Synthetic Dual Drug Sideromycin Induces Gram-Negative Bacteria To Commit Suicide with a Gram-Positive Antibiotic", Journal of Medicinal Chemistry, (2018), vol. 61, No. 9, pp. 3845-3854. 10.1021/acs.jmedchem.8b00218.

Lora-Tamayo et al., "Clinical Use of Colisting in Biofilm-Associated Infections", Advances in Experimental Medicine and Biology, (2019), vol. 1145, pp. 181-195.

Madeira et al., "The EMBL-EBI search and sequence analysis tools APIs in 2019", Nucleic Acids Research, (2019), vol. 47, No. W1, pp. W636-W641. 10.1093/nar/gkz268.

Marques et al., "Discrepancy between viable counts and light output as viability measurements, following ciprofloxacin challenge of self-bioluminescent Pseudomonas aeruginosa biofilms", Journal of Antimicrobial Chemotherapy, (2005), vol. 56, No. 4, pp. 665-671. 10.1093/jac/dki285.

Marques et al., "Pharmacodynamics of ciprofloxacin against Pseudomonas aeruginosa planktonic and biofilm-derived cells", Letters in Applied Microbiology, (2019), vol. 68, No. 4, pp. 350-359. 10.1111/lam.13126.

Mettrick et al., "The Iron-chelator, N,N'-bis (2-hydroxybenzyl) Ethylenediamine-N,N'-Diacetic acid is an Effective Colistin Adjunct against Clinical Strains of Biofilm-Dwelling Pseudomonas aeruginosa", Antibiotics, (2020), vol. 9, 14 pages. 10.3390/antibiotics9040144.

(56) References Cited

OTHER PUBLICATIONS

Moreau-Marquis et al., "Tobramycin and FDA-approved iron chelators eliminate Pseudomonas aeruginosa biofilms on cystic fibrosis cells", American Journal of Respiratory Cell and Molecular Biology, (2009), vol. 41, No. 3, pp. 305-313. 10.1165/rcmb.2008-0299OC.

Nation et al., "Colistin in the 21st century", Current Opinion in Infectious Disease, (2009), vol. 22, No. 6, pp. 535-543. 10.1097/QCO.0b013e328332e672.

Oliver, "Recent findings on the viable but nonculturable state in pathogenic bacteria", FEMS Microbiology Reviews, (2010), vol. 34, No. 4, pp. 415-425. 10.1111/j.1574-6976.2009.00200.x.

O'May et al., "Iron-binding compounds impair Pseudomonas aeruginosa biofilm formation, especially under anaerobic conditions", Journal of Medical Microbiology, (2009), vol. 58, pp. 765-773. 10.1099/jmm.0.004416-0.

Otsu, "A Threshold Selection Method for Gray-Level Histograms", IEEE Transactions on Systems, Man, and Cybernetics, (1979), vol. 9, No. 1, pp. 62-66.

Pamp et al., "Tolerance to the antimicrobial peptide colistin in Pseudomonas aeruginosa biofilms is linked to metabolically active cells, and depends on the pmr and mexAB-oprM genes", Molecular Microbiology, (2008), vol. 68, No. 1, pp. 223-240. 10.1111/j.1365-2958.2008.06152.x.

Parsek et al., "Bacterial biofilms: an emerging link to disease pathogenesis", Annual Review of Microbiology, (2003), vol. 57, pp. 677-701. 10.1146/annurev.micro.57.030502.090720.

Post et al., "Connecting iron acquisition and biofilm formation in the ESKAPE pathogens as a strategy for combatting antibiotic resistance", Medchemcomm, (2019), vol. 10, No. 4, pp. 505-512. 10.1039/c9md00032a.

\* cited by examiner

SMALL MOLECULE INHIBITORS OF THE BFRB:BFD INTERACTION

CROSS-REFERENCE TO RELATED APPLICATIONS

The present application is a U.S. National Phase Application of International Application No. PCT/US2019/064272, filed Dec. 3, 2019, which claims the benefit of and priority to U.S. Provisional Patent Application No. 62/775,304, filed on Dec. 4, 2018, and U.S. Provisional Patent Application No. 62/831,616, filed on Apr. 9, 2019, which are each incorporated herein by reference in their entirety.

U.S. GOVERNMENT RIGHTS

This invention was made with government support under grant numbers AI125529 and GM110761 awarded by the National Institutes of Health, and grant number MCB1158469 awarded by the National Science Foundation. The government has certain rights in the invention.

SUMMARY

In an aspect, a compound according to Formula I is provided,

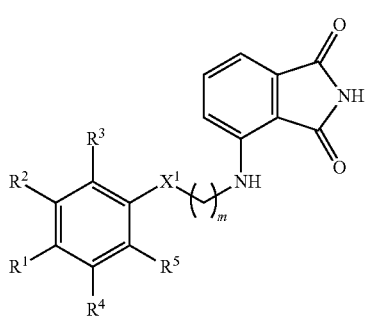

(I)

or a pharmaceutically acceptable salt and/or a solvate thereof, wherein
at least one of $R^1$, $R^2$, and $R^3$ is OH or $C_1$-$C_6$ alkoxy, and the remaining $R^2$ and $R^3$ are each independently $C_1$-$C_6$ alkoxy, H, or OH and the remaining $R^1$ is $C_1$-$C_6$ alkoxy, H, OH, or halo;
$R^4$ and $R^5$ are each independently H or halo;
$X^1$ is $CH_2$ or O; and
m is 0, 1, 2, 3, 4, or 5;
provided that when $X^1$ is O, m is not 0; and
provided that when $R^2$ is OH, $R^1$, $R^3$, $R^4$, and $R^5$ are each independently H, and $X^1$ is $CH_2$, then m is not 0.

In a related aspect, a composition is provided that includes the compound and a pharmaceutically acceptable carrier.

In another related aspect, a pharmaceutical composition is provided, the pharmaceutical composition including an effective amount of the compound for treating a bacterial infection in a subject, and a pharmaceutically acceptable carrier.

In another related aspect, a method of treating a bacterial infection in a subject is provided, the method including administering the compound to the subject. In a further related aspect, a method of inhibiting interaction of a bacterioferritin and a bacterioferritin-associated ferredoxin is provided, the method including contacting the compound to the bacterioferritin, the bacterioferritin-associated ferredoxin, or both the bacterioferritin and the bacterioferritin-associated ferredoxin

BRIEF DESCRIPTION OF THE DRAWINGS

(FIG. 1A) BfrB is a nearly spherical molecule assembled from 24 identical subunits and 12 hemes. The 24-mer assembly harbors a hollow cavity approximately 80 Å in diameter where iron is stored in the form of a $Fe^{3+}$ mineral. (FIG. 1B) Each heme molecule (dark, black) is buried at the interface of a subunit dimer (gray), with the heme propionates protruding into the interior cavity. Each molecule of Bfd binds BfrB at the subunit dimer interface to facilitate electron flow from the [2Fe-2S] cluster (four spheres clustered at top of FIG. 1B) in Bfd to the $Fe^{3+}$ mineral in the interior cavity of BfrB through a heme, thus promoting the mobilization of $Fe^{2+}$. (FIG. 1C) Zoomed-in view of the BfrB-Bfd protein-protein interface, depicting the proximity of the [2Fe-2S] cluster in Bfd to the BfrB surface, as well as the burial of key Bfd residues (Y2 and L5) on pockets formed at the BfrB surface by residues L68 and E81.

(FIG. 2A) Residues Y2 and L5 of Bfd are positioned within pockets at the BfrB subunit dimer interface. (FIG. 2B) Fo-Fc omit map (mesh surrounding fragment 1) contoured at 3σ showing 5-hydroxyaminoisoindoline-1,3-dione (fragment 1) bound within the cleft occupied by L5 in the BfrB-Bfd complex. (FIG. 2C) Hydrogen bond interactions (dashed lines) between fragment 1 and BfrB. Water mediated contacts are indicated by the solid lines.

FIG. 3 illustrates binding modes of analogs 11 and 16 at the Bfd-binding site on BfrB. Subunits A and B of a BfrB subunit dimer are colored gray.

FIGS. 4A and 4B show the time dependent growth retardation of P. aeruginosa cultures treated with analogs 16 and 11, respectively. The black circles correspond to untreated cells (DMSO control), and the open circles to cells treated with ciprofloxacin (0.75 µg/mL). The concentrations of analog 16 in (FIG. 4A) are: 25 µM, 50 µM, 75 µM, 100 µM, and 125 µM; the concentrations of analog 11 in FIG. 4B are: 25 µM, 75 µM, 125 µM, 175 µM, and 250 µM. The corresponding $IC_{50}$ values (FIGS. 4C and 4D) were obtained by calculating the % growth using $OD_{600}$ values at 13 h and fitting to equation 2, as indicated in the Experimental Section. Each of the growth curves was constructed from the average and standard deviation of 5 replicate wells. The $IC_{50}$ values (see Table 1) are the average and standard deviation from three independent experiments.

FIG. 5A shows the time dependent growth retardation of *A. baumannii* cultures treated with analog KM-5-25 and panel FIG. 5B shows the effect of analog KM-5-35.

(FIG. 7A) *P. aeruginosa* cultures treated with analog 16 (125 μM) for 13 h exhibit approximately 30% of the viable cells in the untreated DMSO control. (FIG. 7B) Fluorescence spectra obtained from cell free supernatants (13 h post-inoculation) after a 500-fold dilution in PBS buffer, pH 7.4. The black trace is the spectrum from pyoverdin present in cell-free supernatant from untreated cells (DMSO control), and the red trace is the spectrum from pyoverdin in cell-free supernatant from samples treated with analog 16 (125 μM). The green trace was obtained after a 125 μM solution of analog 16 in M63 media was diluted 500-fold in PBS, to show that the relatively weak intrinsic fluorescence of the analog does not interfere with the strong fluorescence response from pyoverdin. (FIG. 7C) Fluorescence intensity normalized to the number of viable cells (CFU/mL) show that cells treated with analog 16 secrete ~4.5-fold more pyoverdin than cells in the DMSO control. Error bars represent standard deviations from three independent experiments.

(FIG. 9A) Enumerating viable cells shows that cultures treated with analog 16 (open circles) have approximately 2.5-fold fewer cells than untreated control (black circles) at all time points. (FIG. 9B) The iron stored in BfrB was visualized with the aid of native PAGE gels stained with Ferene S, which stains the iron stored in the interior cavity of BfrB blue. Recombinant BfrB (Rec. BfrB) was used to show the electrophoretic mobility of BfrB in the native PAGE gels. Lanes loaded with lysates of untreated control (DMSO) show iron stored in BfrB, with maximum accumulation in late exponential growth (ca. 15 h) and subsequent mobilization in the stationary phase. Lanes loaded with lysates of untreated control diluted 2-fold (0.5×DMSO) to account for the 2-fold larger number of viable cells in the untreated cultures show a similar trend. Lanes loaded with lysates of cells treated with 16 show significant inhibition of iron mobilization from BfrB. (FIG. 9C) Plot of peak areas obtained from densitometry analysis of the native PAGE gels in FIG. 9B. The open circles track the peak area in lanes loaded with lysates of cells treated with 16, while the black circles track the peak area from the untreated control (0.5× DMSO). (FIG. 9D) Analysis of total iron levels normalized to viable cell count (CFU/mL) shows approximately 2-fold higher iron levels in cells treated with 16 (white bars), in agreement with nearly irreversible iron accumulation in BfrB. Error bars represent the standard deviation of three independent experiments. FIGS. 9B and 9C show results from a representative experiment.

(FIGS. 10A-10C) *P. aeruginosa* PAO1 cultures in M63 media supplemented with 4 μM iron were treated with analog 16 only, fluoroquinolone at the reported MIC only, and a combination of analog 16 and fluoroquinolone at the MIC. The fluoroquinolones studied are: (FIG. 10A) ciprofloxacin, 0.25 μg/mL, (FIG. 10B) levofloxacin, 0.5 μg/mL, and (FIG. 10C) norfloxacin 0.9 μg/mL. (FIG. 10D) *P. aeruginosa* clinical isolate MR3B cultures in M63 media supplemented with 4 μM iron were treated with analog 16 only, or ciprofloxacin only (0.2 μg/mL), or a combination of 16 and ciprofloxacin. (FIG. 10E) *P. aeruginosa* clinical isolate MR60 cultures in the same media as above were treated with analog 16, or ciprofloxacin (1.0 μg/mL), or a combination of 16 and ciprofloxacin. Error bars represent the standard deviation from three independent experiments.

DETAILED DESCRIPTION

Figure 1A:
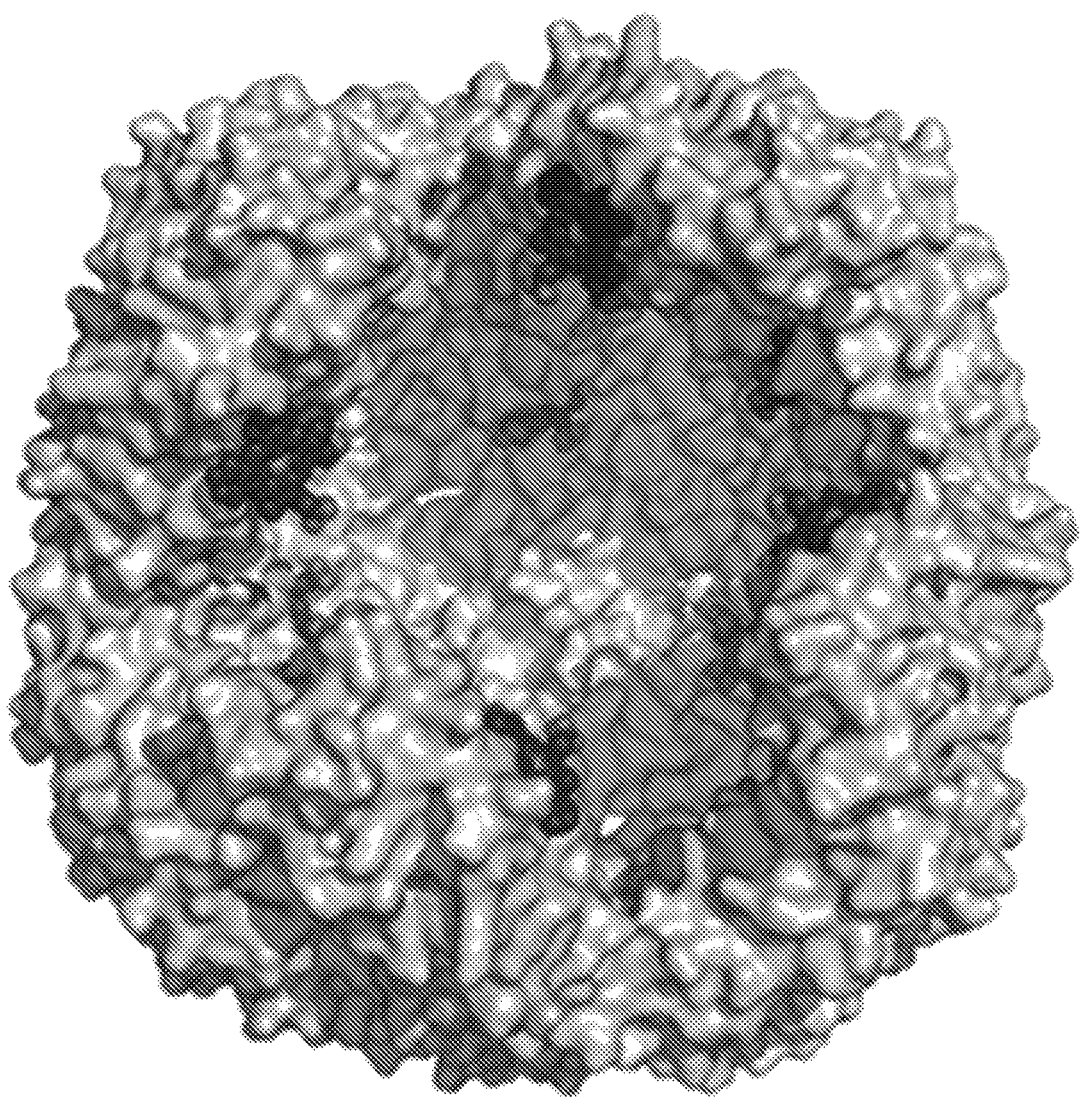
FIGS. 1A-1C illustrate structure and function of BfrB, Bfd and the BfrB-Bfd complex.

In various aspects, the present technology provides compounds, methods for treating a bacterial infection, and methods for inhibiting interaction of a bacterioferritin and a bacterioferritin-associated ferredoxin. The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about"

will mean up to plus or minus 10% of the particular term—for example, "about 10 wt. %" would mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Aryl groups may be substituted or unsubstituted. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted (e.g., tolyl) or substituted more than once. For example, mono-substituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanyl-ethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or unsubstituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. The phrase includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O—. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "pentafluorosulfanyl" refers to —SF$_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

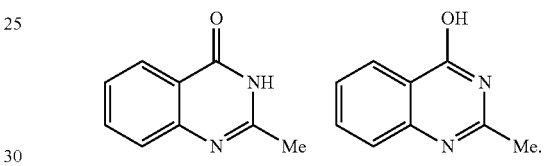

As another example, guanidines may exhibit the following isomeric forms in protic organic solution, also referred to as tautomers of each other:

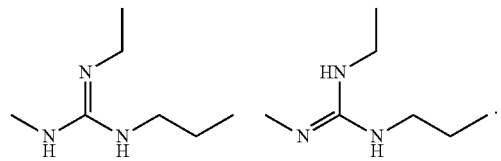

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others.

The identification and preparation of any particular solvate is within the skill of the ordinary artisan of synthetic organic or medicinal chemistry.

The Present Technology

Antibiotic resistant infections are a worldwide threat to public health. The challenge posed by the emergence of antibiotic resistant strains is compounded by slow to nearly stalled development of new antibiotics and validation of new targets.[1-3] Hence, antibiotic resistant infections have the potential to undermine many achievements in modern medicine, such as organ transplantation, major surgery and cancer chemotherapy. The World Health Organization (WHO) published a priority list for research and development of new antibiotics to combat multi-drug resistant bacteria, and assigned critical priority to the Gram-negative carbapenem-resistant *Acinetobacter baumanii* and *Pseudomonas aeruginosa*, and third-generation cephalosporin resistant Enterobacteriaceae.[4] *P. aeruginosa* is one of the leading Gram-negative pathogens associated with hospital infections due to their propensity to colonize urinary catheters and endotracheal tubes,[5-6] and accelerate lung function decay that lowers the survival of cystic fibrosis patients.[7-8] Multidrug resistant forms of *A. baumannii*, defined as resistant to three or more antibiotic drugs, account for approximately 63% of *A baumannii* infections, and are a primary cause of pneumonia or blood stream infections among critically ill patients. The risk of mortality from both bacteria is high, especially among ventilator-associated pneumonia (VAP) patients and sepsis.[60-61] In addition, *A. baumannii* and *P. aeruginosa* biofilms have been implicated in diseases such as cystic fibrosis, periodontitis and urinary tract infections, partly because of an ability to colonize indwelling medical devices. The hospital cost per patent-infection ranges between $16,000-65,000, with most expenses occurring in the upper part of this range. Worldwide, the infection rates in developing countries occur at a higher frequency than in European countries and the US, especially infections causing VAP and central venous catheter-related bloodstream infections. Infections due to MDR *A. baumannii* are also common in combat zones, after natural disasters and in instances of high hospital trauma. The CDC has stated that "This bacteria is a serious concern and requires prompt and sustained action to ensure the problem does not grow."[1] *A. baumannii* has also been profiled in the mass media, most notably in a recent Frontline documentary entitled "Hunting the Nightmare Bacteria."[62] According to a recent GlobalData report, a recognized leader in providing business information and analytics, "The global marketplace for healthcare-associated infections (HAIs) caused by Gram-negative bacteria across the seven major pharmaceutical markets (7MM) is projected to exceed $3.6 billion in sales by 2026, at a Compound Annual Growth Rate (CAGR) of 10.8% from 2016-2026." (https://www.globaldata.com/healthcare-associated-gram-negative-market-to-be-worth-3-6-billion-by-2026/, accessed Aug. 15, 2019). Responding to this call requires vibrant research and continued investment in the early stages of drug development, in order to ensure a pipeline of novel ideas and approaches.[5] In this context, strategies that interfere with bacterial iron acquisition and homeostasis are regarded as having potential as new therapeutic interventions.[9-12] Iron is essential for bacteria because of its involvement in multiple metabolic processes, including respiration and fundamental enzymatic reactions.[13] Pathogenic bacteria must obtain iron from the host, but host nutritional immunity maintains extremely low concentrations of free iron, thus denying the essential nutrient to invading pathogens.[14-17] In addition, the very low solubility of the ferric ion ($Fe^{3+}$) severely limits its bioavailability, and the reactivity of the soluble ferrous iron ($Fe^{2+}$) toward hydrogen peroxide and oxygen induces oxidative stress. Consequently, the processes of bacterial iron homeostasis (acquisition, storage and utilization) are highly regulated to ensure sufficiency for metabolic needs while preventing iron-induced toxicity.[18-19] Herein, the present technology provides an unprecedented approach to dysregulate iron homeostasis in *P. aeruginosa* and *A. baumannii* which utilizes small molecule probes designed to block the interaction between the iron storage protein bacterioferritin B (BfrB) and its cognate partner, the bacterioferritin-associated ferredoxin (Bfd).

Figure 1B:
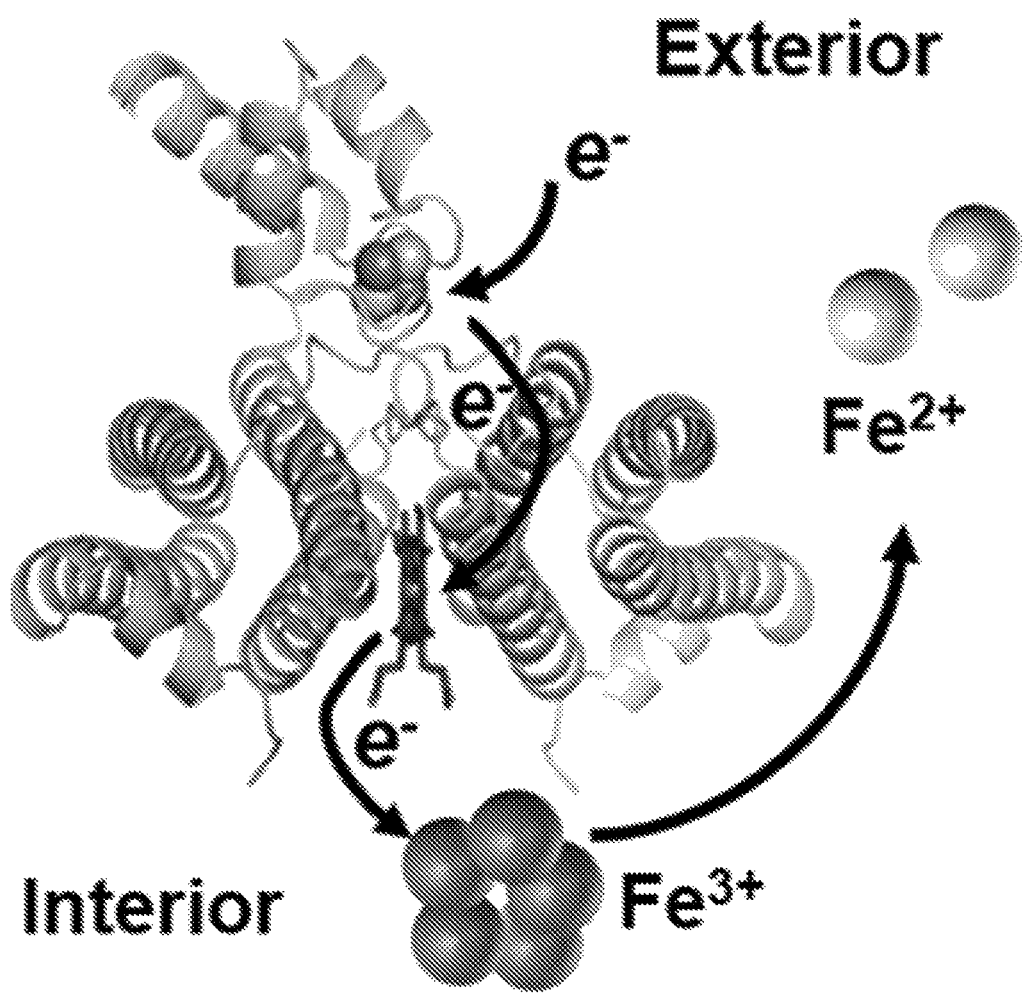
Figure 1C:
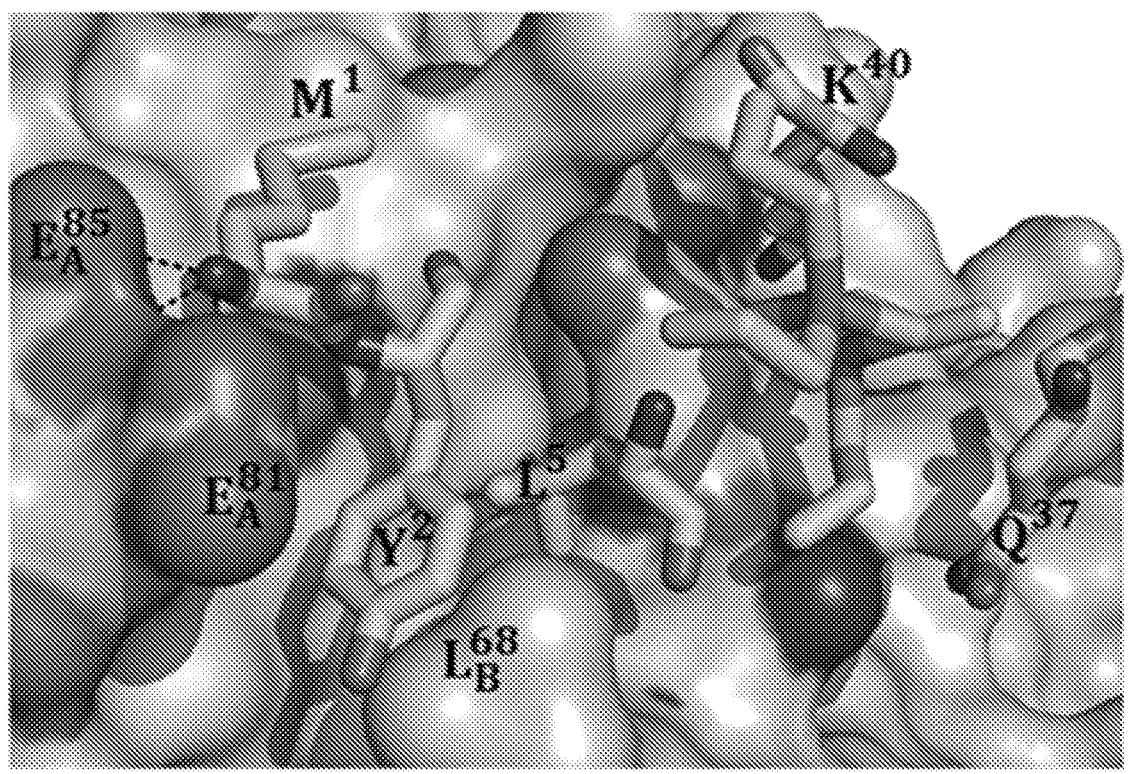

Bacteria store iron reserves in bacterial ferritin (Ftn) and in bacterioferritin (Bfr).[20-22] The roughly spherical and hollow structures of Bfr and bacterial Ftn, which are formed from 24 identical subunits, have an outer diameter of ~120 Å, an inner diameter of ~80 Å, and an interior cavity that can store up to ~3,000 iron ions in the form of a $Fe^{3+}$ mineral (FIG. 1A). Bfrs, which exist only in bacteria, bind 12 heme groups buried under the external protein surface, with the heme propionates protruding into the interior cavity.[20-21] Despite sharing a nearly identical subunit fold and quaternary structures, the eukaryotic Ftns and the Bfrs share less than 20% sequence similarity, which results in divergent subunit packing, 24-mer dynamics and function.[22-25] Although in *P. aeruginosa* the ftnA and bfrB genes encode a bacterial ferritin (FtnA) and a bacterioferritin (BfrB), respectively,[26-27] BfrB functions as the main iron storage protein.[18] Importantly, the mobilization of iron stored in BfrB requires specific interactions with Bfd.[18, 22, 28] A crystal structure of the BfrB-Bfd complex revealed that up to 12 Bfd molecules can bind at identical sites on the BfrB surface, at the interface of subunit dimers, above a heme molecule (FIG. 1B).[29] Characterization of the complex in solution showed that the 12 Bfd binding sites are equivalent and independent, and that Bfd binds to BfrB with a $K_d$ of approximately 3 µM.[30] These investigations also revealed that M1, Y2 and L5 in Bfd form a continuous set of interactions with L68 and E81 in BfrB, which contribute significantly to the stabilization of the BfrB-Bfd complex (FIG. 1C). In agreement, the $K_d$ values for the association between Bfd and the L68A or E81A mutants of BfrB are approximately 100-fold larger, and the association between Bfd and the BfrB L68A/E81A double mutant is undetectable.[30]

Importantly, alignment of the *P. aeruginosa* BfrB and Bfd sequences against Bfr and Bfd sequences from *E. coli* 0157, *Klebsiella pneumoniae, Yersinia pestis, Shigella dysenteriae, Enterobacter* sp., *Acinetobacter* sp., *Salmonella typhimurium* and *Serratia* sp. shows that the key residues at the interface of the BfrB:Bfd complex in *P. aeruginosa* are conserved in the sequences of Bfr and Bfd proteins in the above-listed Gram-negative pathogens.[29, 30] Hence, inhibitors of the BfrB-Bfd complex in *P. aeruginosa* are also expected to inhibit the equivalent complex in these other Gram-negative organisms and be a target for small-molecule inhibition and intervention.

The repercussions of blocking the BfrB-Bfd interaction on *P. aeruginosa* iron metabolism have been investigated by deleting the bfd gene. These investigations, which showed an irreversible accumulation of $Fe^{3+}$ in BfrB with concomitant iron deprivation in the cytosol, established the BfrB-Bfd interaction as a novel target to rationally induce iron homeostasis dysregulation in bacteria.[18] Consequently, it is important to discover small molecule inhibitors of the BfrB-Bfd interaction, which can (in addition to their use for treating bacterial infections) be used as chemical probes to study bacterial iron homeostasis and uncover additional vulnerabilities in the bacterial cell exposed by iron metabolism dysregulation.[31-32]

The present technology provides compounds capable of penetrating the bacterial cells, where they inhibit the mobilization of iron from BfrB and elicit perturbations in iron homeostasis that decrease bacterial fitness, and also may potentiate the bactericidal activity of fluoroquinolone antibiotics.

In an aspect, a compound according to Formula I is provided,

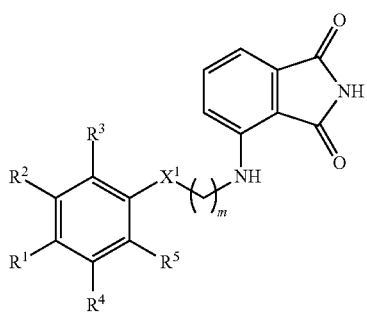

(I)

or a pharmaceutically acceptable salt and/or a solvate thereof, wherein
at least one of $R^1$, $R^2$, and $R^3$ is OH or $C_1$-$C_6$ alkoxy, and the remaining $R^2$ and $R^3$ are each independently $C_1$-$C_6$ alkoxy, H, or OH and the remaining $R^1$ is $C_1$-$C_6$ alkoxy, H, OH, or halo;
$R^4$ and $R^5$ are each independently H or halo;
$X^1$ is $CH_2$ or O; and
m is 0, 1, 2, 3, 4, or 5;
provided that when $X^1$ is O, m is not 0; and
provided that when $R^2$ is OH, $R^1$, $R^3$, $R^4$, and $R^5$ are each independently H, and $X^1$ is $CH_2$, then m is not 0.

In any embodiment disclosed herein, at least one of $R^1$, $R^2$, and $R^3$ is OH, and the remaining $R^1$, $R^2$, and $R^3$ are each independently H or OH; $R^4$ and $R^5$ are each independently H or halo; $X^1$ is $CH_2$ or O; and m is 0, 1, 2, 3, 4, or 5; provided that when $X^1$ is O, m is not 0; and provided that when $R^2$ is OH, $R^1$, $R^3$, $R^4$, and $R^5$ are each independently H, and $X^1$ is $CH_2$, m is not 0.

In any embodiment disclosed herein, it may be that the compound of Formula I is of Formula IA

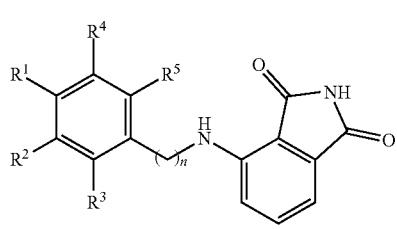

(IA)

or a pharmaceutically acceptable salt and/or a solvate thereof, wherein n is 1, 2, or 3; provided that $R^2$ is not OH when n is 1 and $R^1$, $R^3$, $R^4$, and $R^5$ are each independently H. In any embodiment disclosed herein, it may be that one of $R^1$ and $R^3$ is OH, one of $R^1$ and $R^3$ is H, and $R^2$ is H. In any embodiment disclosed herein, it may be that $R^4$ and $R^5$ are each independently H, chlorine, or fluorine. In any embodiment disclosed herein, it may be that $R^4$ and $R^5$ are each independently H or chlorine.

In an aspect of the present technology, a composition is provided that includes any one of the herein-described embodiments of compounds of Formula I and a pharmaceutically acceptable carrier. In a related aspect, a pharmaceutical composition is provided, the pharmaceutical composition including an effective amount of the compound of any one of the aspects and embodiments of compounds of Formula I for treating a bacterial infection in a subject; and a pharmaceutically acceptable carrier. In a further related aspect, a method is provided that includes administering an effective amount of a compound of any one of the embodiments of compounds of Formula I or administering a pharmaceutical composition including an effective amount of a compound of any one of the embodiments of compounds of Formula I to a subject suffering from a bacterial infection. In any aspect or embodiment disclosed herein, the bacterial infection may include a Gram-negative bacterial infection. In any aspect or embodiment disclosed herein, the bacterial infection may include a *Pseudomonas aeruginosa* infection, a *Acinetobacter baumannii* infection, a *Klebsiella pneumonia* infection, a *Yersinia pestis* infection, a *Shigella dysenteriae* infection, a *Enterobacter* sp. infection, a *Acinetobacter* sp. infection, a *Salmonella typhimurium* infection, a *Serratia* sp. infection, or a combination of any two or more thereof.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of a bacterial infection. As used herein, a "subject" or "patient" is a mammal, such as a cat, dog, rodent or primate. Typically the subject is a human, and, preferably, a human suffering from or suspected of suffering from pain. The term "subject" and "patient" can be used interchangeably.

Thus, the instant present technology provides pharmaceutical compositions and medicaments comprising any of the compounds disclosed herein (e.g., compounds of Formula I) and a pharmaceutically acceptable carrier or one or more excipients or fillers. The compositions may be used in the methods and treatments described herein. Such compositions and medicaments include a therapeutically effective amount of any compound as described herein, including but not limited to a compound of Formula I. The pharmaceutical composition may be packaged in unit dosage form. The unit dosage form is effective in treating a bacterial infection when administered to a subject in need thereof.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like. The compounds and compositions described herein may be used to prepare formulations and medicaments that prevent or treat a bacterial infection. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until, for example, culture of the bacterial infection indicates a reduction in the number of bacteria and/or the symptoms of the bacterial infection decrease (e.g., as indicated by the patient). The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day may be sufficient (e.g., a dosage in the range of about 0.01 to about 10 mg per kg of body weight per day may be sufficient). The specific dosage used, however, can vary or may be adjusted as considered appropriate by those of ordinary skill in the art. For example, the dosage can depend on a number of factors including the requirements of the patient, the severity of the bacterial infection and the pharmacological activity of the compound being used. The determination of optimum dosages for a particular patient is well known to those skilled in the art.

Various assays and model systems can be readily employed to determine the therapeutic effectiveness of the treatment according to the present technology. Effectiveness of the compositions and methods of the present technology may also be demonstrated by a culture of the bacterial infection indicating a reduction in the number of bacteria subsequent to administering a compound and/or composition of the present technology and/or the symptoms of the bacterial infection decrease (e.g., as indicated by the patient).

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The compounds of the present technology can also be administered to a patient along with other conventional therapeutic agents that may be useful in the treatment of a bacterial infection, such as a fluoroquinolone antibiotic. In any embodiment herein, a compound and/or composition of the present technology may be administered along with an effective amount of a fluoroquinolone antibiotic. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistically be effective for the treatment of a bacterial infection.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^3$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, a bacterioferritin, a bacterioferritin-associated ferredoxin, or both a bacterioferritin and a bacterioferritin-associated ferredoxin. Suitable labels are known by those skilled in the art and can include, for example, radioisotopes, radionuclides, isotopes, fluorescent groups, biotin (in conjunction with streptavidin complexation), and chemoluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology.

EXAMPLES

Example 1: Synthesis of Analogs

General Comments

Commercial anhydrous N,N-dimethylformamide (DMF) was stored under dry $N_2$ and transferred by syringe into reactions when needed. Tetrahydrofuran (THF) was dried over KOH pellets and distilled from $LiAlH_4$ prior to use. Pyridine was dried over KOH pellets and distilled under nitrogen prior to use. Most chemicals used for the syntheses were purchased from Combi Blocks (San Diego, CA, USA); 4-aminophthalimide (5-aminoisoindoline-1,3-dione) was purchased from TCI (Portland, OR, USA); 3-aminophthalimide (4-aminoisoindoline-1,3-dione) was purchased from Oxchem Corporation (Wood Dale, IL, USA). Note: Phthalimide is also known as isoindoline-1,3-dione, which uses a different numbering scheme than phthalimide; isoindoline-1,3-dione is used in the present compound nomenclature. All commercial chemicals were used as received. Unless otherwise specified, all reactions were run under dry $N_2$ in oven-dried glassware. The $NaHCO_3$, NaCl, $NH_4Cl$ and HCl used in workup procedures were saturated aqueous solutions. Reactions were monitored by thin layer chromatography (TLC) on silica gel GF plates (Analtech, 21521). Preparative separations were performed by chromatography on silica gel (Davisil®, grade 62, 60-200 mesh, pre-treated with a methanol solution of 3-hydroxy-2-methyl-4-pyrone and then dried at room temperature and at 90° C.) mixed with UV-active phosphor (Sorbent Technologies, No UV-05). Band elution for all chromatographic separations was monitored using a hand-held UV lamp. Melting points were uncorrected. FT-IR spectra were run as thin films on NaCl disks. $^1$H- and $^{13}$C-NMR spectra were measured at 400 MHz ($^1$H) and 101 MHz ($^{13}$C). Chemical shifts (δ) are referenced to internal $(CH_3)_4Si$ and coupling constants (J) are given in Hz. Low-resolution mass spectra (ES/DI) were obtained at 30 eV.

Procedure A: Reductive Amination.

To a solution of the aldehyde (1.0 mmol) in DMF (1 mL) was added AcOH (0.8 mL) and the solution was stirred for 10 min. To this reaction mixture, 4-aminoisoindoline-1,3-dione (0.5 mmol) was added and stirring was continued at 23° C. for 1 h. An additional 1 mL of DMF was added bringing the volume to 2 mL. The reaction was cooled to 0° C. and $NaBH(OAc)_3$ (3.0 mmol) was added portion-wise to the reaction. Stirring continued at this temperature for 30 min and the reaction was gradually warmed to 23° C. for 18 h. The crude reaction mixture was poured into de-ionized water, extracted with EtOAc (3×75 mL) and the combined organic layers were washed with $NaHCO_3$ (2×50 mL) and NaCl (50 mL). The organic layer was dried ($Na_2SO_4$) and concentrated under vacuum. The residue was dissolved in 1 mL of EtOH and the solution was heated at 50° C. for 10 minutes under $N_2$. The resulting solid was filtered and washed with EtOH (2×10 mL). The filtrate was concentrated under vacuum and subjected to silica-gel chromatography (pre-treated with 3-hydroxy-2-methyl-4-pyrone) eluted with 20% EtOAc in hexane to afford the pure product.

Procedure B: Phenol Protection by Silyl Chlorides.

A stirred solution of the phenol (3.00 mmol, 1.0 equiv) in DMF (10 mL) was cooled to 0° C. under nitrogen atmosphere and imidazole (6.00 mmol, 2.0 equiv) was added. The resulting solution was stirred for 20 min and the silyl chloride (3.60 mmol, 1.2 equiv) as a solution in DMF (10 ML) was added drop-wise over a period of 15 min. The reaction mixture was warmed to 23° C. and stirred until TLC analysis indicated the absence of the starting phenol. The crude reaction was poured into water (50 mL), extracted with ether (3×40 mL), and the combined organic layers were washed with NaCl (50 mL). The combined organic layers were dried ($Na_2SO_4$) and concentrated under vacuum. The crude product was purified by column chromatography to afford the silyl ether.

Procedure C: Silyl Deprotection.

A solution of the silyl ether (1.00 mmol) in 10 mL of THF was stirred under nitrogen at 23° C. and 1.0 M TBAF (2.00 mmol) solution in THF was added. When TLC analysis indicated complete consumption of the silyl ether, water (5.00 mL) was added and the THF was evaporated under vacuum. The product was extracted with ethyl acetate (3×40 mL) and the combined organic layers were washed with NaCl (50 mL), dried ($Na_2SO_4$), concentrated under vacuum and purified by column chromatography using pre-treated silica gel.

4-(Benzylamino)isoindoline-1,3-dione Series 4-((2,4,6-Trihydroxybenzyl)amino)isoindoline-1,3-dione: BN-XIV-069

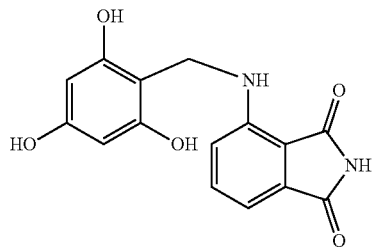 [SMILES: O=C1NC(=O)c2c(NCc3c(O)cc(O)cc3O)cccc21]

Procedure A. Orange solid (212 mg, 59%), mp>300° C. (darkened, but did not melt); $^1$H NMR (DMSO-$d_6$): δ 10.9 (s, 1H), 9.56 (2, 1H), 7.49 (t, J=7.8 Hz, 1H), 7.05 (d, J=8.1 Hz, 1H), 7.00 (d, J=8.2 Hz, 1H), 6.91 (d, J=7.1 Hz, 1H), 6.78 (br t, J=6.1 Hz, 1H), 6.32 (s, 1H), 6.16 (d, J=8.0 Hz, 1H), 4.29 (d, J=6.0 Hz, 1H); $^{13}$C NMR (DMSO-$d_6$): δ 170.8. 168.7, 157.0, 155.5, 145.6, 135.1, 132.9, 129.1, 116.2, 114.4, 110.2, 109.2, 105.4, 101.9, 40.4; MS: m/z 300 ($C_{15}H_{12}N_2O_5$, $M^{+\cdot}$).

4-((3,4-Dihydroxybenzyl)amino)isoindoline-1,3-dione: BN-XIV-055

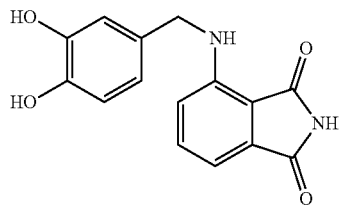 [SMILES: O=C1NC(=O)c2c(NCc3ccc(O)c(O)c3)cccc21]

Procedure A. Yellow solid (228 mg, 67%), mp 213-214° C.; $^1$H NMR (DMSO-$d_6$): δ 11.0 (s, 1H), 8.86 (s, 1H), 8.81 (s, 1H), 7.47 (t, J=7.8 Hz, 1H), 6.92 (m, 3H), 6.73 (d, J=1.8 Hz, 1H), 6.68 (d, J=8.0 Hz, 1H), 6.61 (dd, J=8.0, 1.8 Hz, 1H), 4.43 (d, J=6.0 Hz, 2H); $^{13}$C NMR (DMSO-$d_6$): 171.8, 169.8, 146.5, 145.8, 144.8, 136.2, 134.0, 130.1, 118.5, 117.5, 116.0, 114.9, 111.4, 110.4, 45.7; MS: m/z 284 ($C_{15}H_{12}N_2O_4$, M$^{+•}$).

4-((4-Hydroxybenzyl)amino)isoindoline-1,3-dione: BN-XIV-052

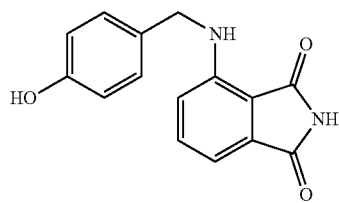 [SMILES: O=C1NC(=O)c2c(NCc3ccc(O)cc3)cccc21]

Procedure A. Off-white solid (232 mg, 72%), mp 194-195° C.; $^1$H NMR (DMSO-$d_6$): δ 11.0 (s, 1H), 9.31 (s, 1H), 7.47 (t, J 7.8 Hz, 1H), 7.17 (d, J 8.2 Hz, 2H), 6.94 (m, 3H), 6.72 (d, J=8.2 Hz, 2H), 4.38 (d, J=6.1 Hz, 2H); $^{13}$C NMR (DMSO-$d_6$): δ 171.8, 169.8, 156.9, 146.5, 136.2, 134.0, 129.4, 128.9, 117.4, 115.7, 111.5 110.5, 45.6; MS: m/z 268 ($C_{15}H_{12}N_2O_3$, M$^{+•}$).

4-((3,5-Dihydroxybenzyl)amino)isoindoline-1,3-dione: BN-XVI-071

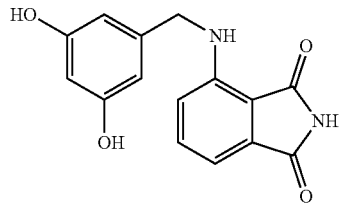 [SMILES: O=C1NC(=O)c2c(NCc3cc(O)cc(O)c3)cccc21]

Procedure A. Yellow solid (245 mg, 70%), mp 253-254° C.; $^1$H NMR NH (DMSO-$d_6$): δ 10.9 (br s, 1H), 9.31 (s, 2H), 7.47 (t, J=7.8 Hz, 1H), 7.01 (br t, J=6.1 Hz, 1H), 6.93 (d, J=7.1 Hz, 1H), 6.86 (d, J=8.8 Hz, 1H), 6.18 (s, 2H), 6.05 (s, 1H), 4.35 (d, J=6.1 Hz, 2H); $^{13}$C NMR (DMSO-$d_6$): δ 171.9, 169.9, 159.0 (2C), 146.6, 141.6, 136.2, 134.0, 117.5, 111.5, 105.1, 101.6, 46.0; MS: m/z 284 ($C_{15}H_{12}N_2O_4$, M$^{+•}$).

4-((2-Chloro-4-hydroxybenzyl)amino)isoindoline-1,3-dione: GKK-007-100

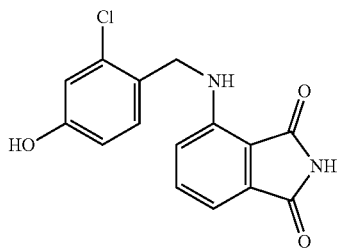

Procedure A. Yellow solid (163 mg, 54%), mp 238-240° C.; $^1$H NMR (DMSO-$d_6$): δ 11.0 (s, 1H), 9.84 (s, 1H), 7.49 (t, J=7.8 Hz, 1H), 7.22 (d, J=8.4 Hz, 1H), 6.95 (coincident t, J=6.4 Hz, 1H and d, J=7.1 Hz, 1H), 6.90 (d, J=8.5 Hz, 1H), 6.86 (d, J=2.5 Hz, 1H), 6.70 (dd, J=8.4, 2.5 Hz, 1H), 4.47 (d, J=6.2 Hz, 2H); $^{13}$C NMR (DMSO-$d_6$): δ 171.8, 169.7, 157.9, 146.2, 136.3, 134.0, 133.0, 130.4, 126.1, 117.2, 116.5, 114.9, 111.8, 110.8, 43.5; MS: m/z 302 ($C_{15}H_{11}{}^{35}ClN_2O_3$, M$^{+•}$).

2-((tert-Butyldiphenylsilyl)oxy)benzaldehyde

Scheme 1: Synthesis of 4-((2-Hydroxybenzyl)amino)isoindoline-1,3-dione: GKK-011-017 (Analog 11).

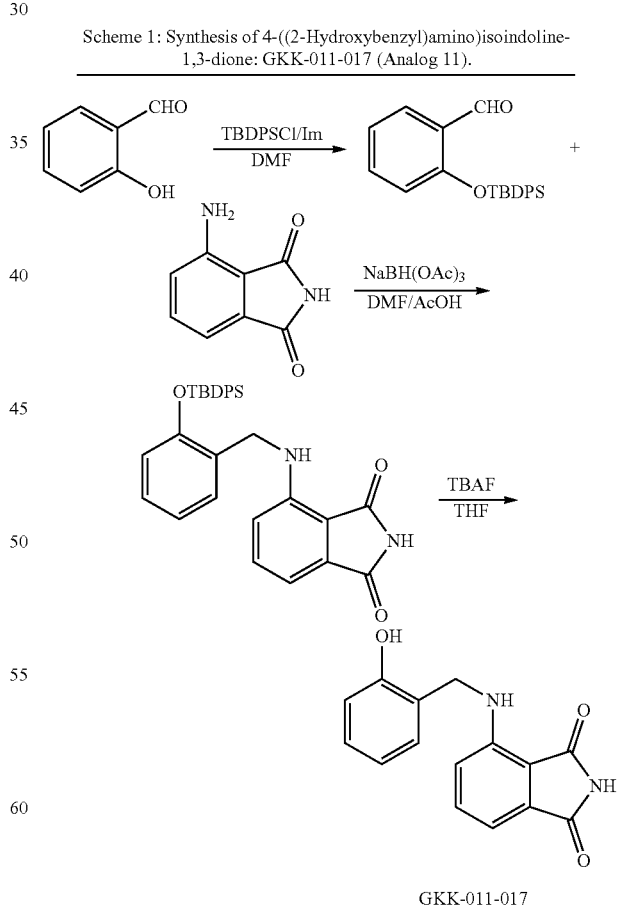

GKK-011-017

This compound was prepared from salicylaldehyde (2.0 g, 16.4 mmol) and TBDPSCl (5.40 g, 19.7 mmol) according to Procedure B to provide the TBDPS-protected salicylaldehyde (3.81 g, 10.6 mmol, 65%) as a white solid. This compound was used without further purification.

4-((2-((tert-Butyldiphenylsilyl)oxy)benzyl)amino)isoindoline-1,3-dione

The reductive amination was performed using Procedure A starting from the silyl ether of salicylaldehyde (720 mg, 2.0 mmol) and 4-aminoisoindoline-1,3-dione (162 mg, 1.0 mmol) to give the silyl-protected 4-((2-hydroxybenzyl)amino)isoindoline-1,3-dione (306 mg, 0.60 mmol, 60%), mp 175-178° C. This compound was used directly in the next step without further purification.

4-((2-Hydroxybenzyl)amino)isoindoline-1,3-dione: GKK-011-017

Using Procedure C, the silyl ether (252 mg, 0.50 mmol) was cleaved to generate the hydroxyl compound (107 mg, 0.40 mmol, 80%) as a yellow solid, mp 192-194° C.; $^1$H NMR (DMSO-d$_6$): δ 11.0 (s, 1H), 9.73 (s, 1H), 7.48 (t, J=7.8 Hz, 1H), 7.20 (d, J=7.4 Hz, 1H), 7.08 (td, J=7.2, 1.4 Hz, 1H), 6.96 (overlapping d, J=8.5 Hz, 1H and br t, J=6.1 Hz, 1H), 6.92 (d, J=7.1 Hz, 1H), 6.84 (d, J=8.0 Hz, 1H), 6.74 (t, J=7.4 Hz, 1H), 4.43 (d, J=6.1 Hz, 2H); $^{13}$C NMR (DMSO-d$_6$): δ 171.8, 169.8, 155.6, 146.6, 136.2, 134.0, 129.0, 128.7, 124.9, 119.4, 117.2, 115.5, 111.4, 110.4, 41.6; MS: m/z 268 (C$_{15}$H$_{12}$N$_2$O$_2$, M$^{+•}$).

acidified using citric acid. The product was extracted with CH$_2$Cl$_2$ (3×50 mL) and the combined organic layers were dried (Na$_2$SO$_4$). The organic layer was concentrated under vacuum to give a brown oil that was used without further purification. A solution of the crude tert-butyl (E)-3-(2,4-dihydroxyphenyl)cinnamate in MeOH (250 mL) was flushed twice with nitrogen and commercial 10% Pd/C (200 mg, 50% wet, 10% w/w) was added. The reaction mixture was stirred at room temperature under hydrogen (1 atm) for 18 h. The reaction was filtered through Celite© and washed with methanol (2×25 mL). The filtrate was concentrated under vacuum to provide tert-butyl 3-(2,4-dihydroxyphenyl)propionate (2.80 g 11.9 mmol, 64% after two steps) as a yellow oil. This compound was used without further purification.

tert-Butyl 3-(2,4-bis((tert-butyldimethylsilyl)oxy)phenyl)propionate

Procedure B was followed to protect both phenols. To a solution of tert-butyl 3-(2,4-dihydroxyphenyl)propionate (2.80 g, 11.9 mmol) in DMF (14 mL) was added imidazole (4.00 g, 59.0 mmol) and the mixture was stirred for 20 min. A solution of TBSCl (4.42 g, 29.0 mmol) in DMF (14 mL) was then added drop-wise over a period of 30 min. The reaction was stirred at 0° C. for 2 h and monitored by TLC. The reaction mixture was added to water, extracted with ether (3×50 mL), dried (Na$_2$SO$_4$) and concentrated under

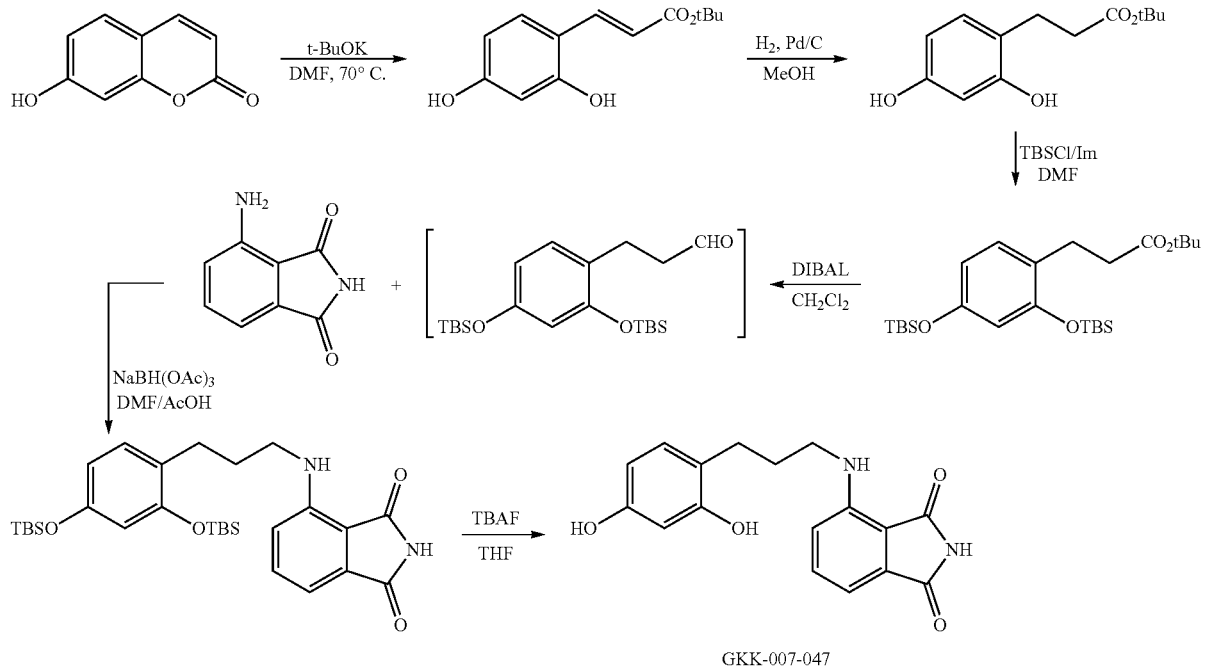

Scheme 2: Synthesis of 4-((3-(2-Hydroxyphenyl)propyl)amino)isoindoline-1,3-dione: GKK-007-047 (Analog 14).

GKK-007-047 tert-Butyl 3-(2,4-dihydroxyphenyl)propionate

To a stirred solution of 7-hydroxycoumarin (3.00 g, 18.5 mmol) in DMF (15 mL) was added t-BuOK (6.30 g, 56.0 mmol) under nitrogen atmosphere. The reaction flask was immersed in a pre-heated oil bath (80° C.) and stirred for 4 h. The reaction mixture was poured into ice-cold water and vacuum to afford the bis-TBS-protected ester (4.98 g, 10.7 mmol, 90%) as a colorless oil.

4-((3-(2-Hydroxyphenyl)propyl)amino)isoindoline-1,3-dione: GKK-007-047

A stirred solution of the bis-TBS-protected ester (2.50 g, 5.36 mmol) in CH$_2$Cl$_2$ (100 mL) was cooled to −78° C., 1.5

M DIBAL-H in toluene (4.50 mL, 6.43 mmol) was added, and stirring was continued at this temperature for 3 h or until TLC analysis indicated the complete consumption of the ester. The reaction was quenched by drop-wise addition of MeOH (10 mL), followed by addition of 1 M HCl (20 mL). The organic layer was separated and the aqueous layer was extracted with $CH_2Cl_2$ (2×50 mL). The combined organic layers were dried ($Na_2SO_4$) and concentrated to provide the aldehyde as a colorless oil, which was used for the next step without further purification. This aldehyde was subjected to reductive amination with 4-aminoisoindoline-1,3-dione according to Procedure A and was used without further purification. Finally, the TBS group was cleaved according to Procedure C to afford 4-((3-(2-hydroxyphenyl)propyl)-amino)isoindoline-1,3-dione (125 mg, 0.40 mmol, 7.5% for 3 steps) as a yellow solid, mp 207-208° C. $^1$H NMR (DMSO-$d_6$): δ 10.9 (br s, 1H), 9.12 (s, 1H), 8.94 (s, 1H), 7.50 (t, J=7.8 Hz, 1H), 6.95 (d, J=8.4 Hz, 1H), 6.92 (d, J=7.2 Hz, 1H), 6.80 (d, J=8.2 Hz, 1H), 6.54 (br t, J=6.3 Hz, 1H), 6.27 (s, 1H), 6.13 (d, J=8.2 Hz, 1H), 3.24 (q, J=6.8 Hz, 2H), 2.48 (t, J=7.0 Hz, 2H), 1.76 (quintet, J=7.2 Hz, 2H); $^{13}$C NMR (DMSO-$d_6$): δ 171.9, 169.8, 156.8, 156.3, 146.8, 136.3, 134.1, 130.4, 118.3, 116.8, 111.2, 110.1, 106.4, 102.8, 41.8, 29.6, 26.6; MS: m/z 312 ($C_{17}H_{16}N_2O_4$, M$^{+\bullet}$).

5-(Benzyloxy)isoindoline-1,3-dione Series

Procedure D: General Procedure for the Synthesis of Substituted Ether Derivatives.

To a stirred solution of dimethyl 4-hydroxyphthalate (500 mg, 2.38 mmol) in acetone (15 mL) was added $K_2CO_3$ (490 mg, 3.6 mmol), followed by the corresponding benzyl bromide (2.50 mmol). The reaction was refluxed for a period of 3-4 h, concentrated under vacuum and the product was extracted into EtOAc (3×35 mL). The organic layer was washed with 1 M HCl (25 mL), water (25 mL), and NaCl (25 mL). The organic solution was dried ($Na_2SO_4$) and concentrated to dryness. The product was obtained in 92-95% yield and was taken to the next step without purification.

To a stirred solution of the diester (1.50 mmol) in THF (10 mL), NaOH (2.40 mmol, 4.0 equiv) dissolved in MeOH/$H_2O$ (10 mL) was added and stirred for a period of 3 h. After completion, the reaction mixture was concentrated to dryness. The residue was dissolved in water, the pH was adjusted to pH 3-4 with 6 M HCl, and the mixture was extracted with EtOAc (3×35 mL). The organic layer was washed with NaCl (30 mL), dried ($Na_2SO_4$) and concentrated to give the diacid. The compounds, obtained in yields of 90-95%, were spectroscopically pure and used directly in the next reaction.

A stirred solution of the diacid (1.47 mmol) in AcOH (3.0 mL), was placed in a pre-heated oil bath at 140° C. and stirred for 2 min. To the reaction mixture ($NH_4)_2CO_3$ (7.50 mmol, 5.0 equiv) was added and stirring was continued for 1 h. [Note: If the reaction was not complete at this time, an additional portion of ($NH_4)_2CO_3$ (1.0 equiv) was added and heating was continued until the reaction was complete]. The reaction mixture was cooled and extracted with EtOAc (3×30 mL). The organic layer was washed with 0.5 M HCl (20 mL), followed by NaHCO$_3$ (30 mL) and NaCl (25 mL), dried ($Na_2SO_4$), and concentrated under vacuum to give the pure 5-benzyloxyisoindoline-1,3-dione. These compounds were further purified by recrystallization from hot EtOH.

5-(Benzyloxy)isoindoline-1,3-dione: BN-XIII-007

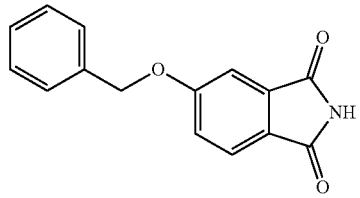 [SMILES: O=C1NC(=O)c2cc(OCc3ccccc3)ccc21]

Procedure D. White solid (325 mg, 87%), mp 154-155° C.; $^1$H NMR (DMSO-$d_6$): δ 11.2 (s, 1H), 7.75 (d, J=8.2 Hz, 1H), 7.48 (d, J 7.2 Hz, 2H), 7.45-7.33 (complex, 5H), 5.30 (s, 2H); $^{13}$C NMR (DMSO-$d_6$): δ 169.30, 169.27, 163.8, 136.6, 135.7, 129.0, 128.6, 128.3, 125.3, 125.1, 121.2, 109.1, 70.6; MS: m/z 253 ($C_{15}H_{10}FNO_3$, M$^{+\bullet}$).

5-((4-Fluorobenzyl)oxy)isoindoline-1,3-dione: BN-XIII-013

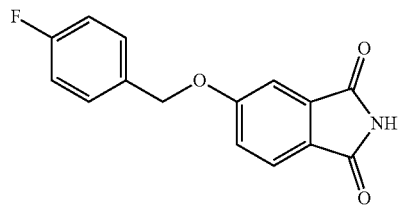 [SMILES: O=C1NC(=O)c2cc(OCc3ccc(F)cc3)ccc21]

Procedure D. White solid (275 mg, 74%), mp 204-205° C.; $^1$H NMR (DMSO-$d_6$): δ 11.2 (s, 1H), 7.75 (d, J=8.2, 1H), 7.54 (dd, J=9.0, 5.5 Hz, 2H), 7.41 (d, J=2.4 Hz, 1H), 7.38 (dd, J=8.2, 2.3 Hz, 1H), 7.25 (t, J=8.9 Hz, 2H), 5.28 (s, 2H); $^{13}$C NMR (DMSO-$d_6$): δ 169.29, 169.26, 163.7, 162.4 (d, J=244.1 Hz), 135.7, 132.9, 130.6 (d, J=8.4 Hz), 125.24, 125.18, 121.2, 115.8 (d, J=21.4 Hz), 109.1, 69.9; MS: m/z 271 ($C_{15}H_{10}F_3NO_3$, M$^{+\bullet}$).

5-((4-(Trifluoromethyl)benzyl)oxy)isoindoline-1,3-dione: BN-XIII-016

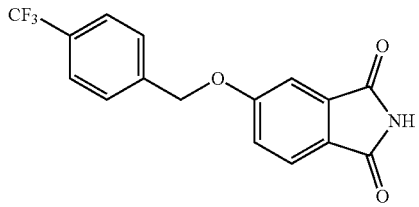 [SMILES: O=C1NC(=O)c2cc(OCc3ccc(C(F)(F)F)cc3)ccc21]

Procedure D. Off-white solid (272 mg, 72%), mp 243-244° C.; $^1$H NMR (DMSO-$d_6$): δ 11.2 (s, 1H), 7.85-7.67 (complex, 5H), 7.44 (s, 1H), 7.41 (d, J=8.2 Hz, 1H), 5.43 (s, 2H); $^{13}$C NMR (DMSO-$d_6$): δ 169.23, 169.20, 163.4, 141.5, 135.7, 129.0 (q, J=31.8 Hz), 128.5, 126.0, 125.9, 125.8, 124.6 (q, J=272.7 Hz), 121.1, 109.1, 69.6; MS: m/z 321 ($C_{16}H_{10}F_3NO_3$, M$^{+\bullet}$).

5-((3-Methoxybenzyl)oxy)isoindoline-1,3-dione: BN-XII-046

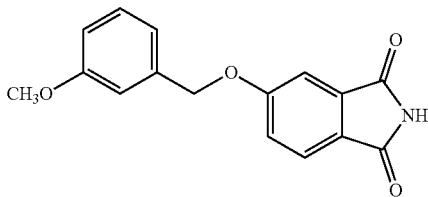

Procedure D. Off-white solid (330 mg, 90%), mp 154-155° C.; $^1$H NMR (DMSO-d$_6$): δ 11.2 (s, 1H), 7.75 (d, J=8.1 Hz, 1H), 7.40 (d, J=2.3 Hz, 1H), 7.30 (dd, J=8.1, 2.3 Hz, 1H), 7.32 (t, J=8.1 Hz, 1H), 7.05 (s, 1H), 7.04 (obscured, 1H), 6.92 (dd, J=8.1, 2.3 Hz, 1H), 5.07 (s, 2H), 3.76 (s, 3H); $^{13}$C NMR (DMSO-d$_6$): δ 169.29, 169.28, 163.7, 159.8, 138.2, 135.7, 130.2, 125.3, 125.1, 121.2, 120.3, 114.0, 113.8, 109.1, 70.4, 55.5; MS: m/z 283 (C$_{16}$H$_{13}$NO$_4$, M$^{+\bullet}$).

5-((3-Nitrobenzyl)oxy)isoindoline-1,3-dione: BN-XII-044

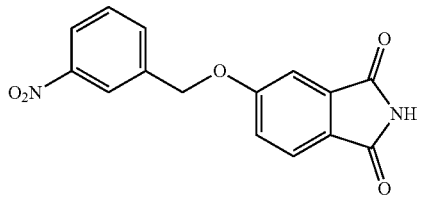 [SMILES: O=C1NC(=O)c2cc(OCc3cccc([N+](=O)[O-])c3)ccc21]

Procedure D. Yellow solid (250 mg, 67%), mp 275-276° C.; $^1$H NMR (DMSO-d$_6$): δ 11.2 (s, 1H), 8.36 (t, J=1.9 Hz, 1H), 8.23 (ddd, J=8.2, 2.3, 0.9 Hz, 1H), 7.95 (d, J=8.1 Hz, 1H), 7.77 (d, J=8.2 Hz, 7.74 (t, J=8.0 Hz, 1H), 7.46 (d, J=2.3 Hz, 1H), 7.42 (dd, J=8.2, 2.3 Hz, 1H), 5.46 (s, 2H); $^{13}$C NMR (DMSO-d$_6$): δ 169.3, 169.2, 163.4, 148.3, 139.0, 135.7, 134.7, 130.7, 125.5, 125.3, 123.5, 122.7, 121.2, 109.1, 69.2; MS: m/z 298 (C$_{15}$H$_{10}$N$_2$O$_5$, M$^{+\bullet}$).

5-Amidoisoindoline-1,3-dione Series

Procedure E1: N-Amidation of Amino Substituted 5-aminoisoindoline-1,3-diones Using the Acid Chloride/Sulfonyl Chloride.

To a stirred solution of 5-aminoisoindoline-1,3-dione (200 mg, 1.25 mmol) in pyridine (5 mL) at 0° C., the acid chloride/sulfonyl chloride (1.15 mmol) was added drop-wise and stirring was continued for 2 h. The reaction mixture was quenched with cold 6 M HCl to pH 2-3 and the crude product was extracted with EtOAc (3×25 mL). The combined organic layers were washed with 2% NaHCO$_3$ (15 mL) and NaCl (15 mL). The resulting organic layer was dried (Na$_2$SO$_4$) and concentrated under vacuum to afford a yellow solid. As the product obtained contained traces of 5-aminoisoindoline-1,3-dione and pyridine, it was purified by recrystallization from EtOH (5 mL). The solid was collected and dried to afford the product as a pale yellow solid.

Procedure E2: N-Amidation of Amino Substituted 4-aminoisoindoline-1,3-dione from the Acid.

To a stirred solution of the carboxylic acid (1.20 mmol) in benzene was added DMF (2 drops) and SOCl$_2$ (3.00 mmol). The mixture was heated at reflux for 1 h and cooled to room temperature (23° C.). The solvent and excess SOCl$_2$ were removed under vacuum and the resulting crude acid chloride was dissolved in 10 mL of pyridine. To this solution was added 4-aminoisoindoline-1,3-dione (1.00 mmol) and the mixture was heated at reflux for 2 h. The reaction mixture was allowed to slowly cool to 23° C., and then further cool in an ice-bath for 15 min. The resulting solid was collected and recrystallized from ethanol/ether (2:1) to give the corresponding amide.

N-(1,3-Dioxoisoindolin-5-yl)acetamide: BN-XII-078

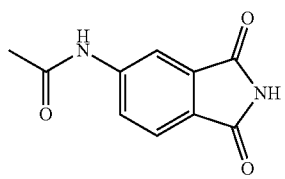

Procedure E1. White solid (216 mg, 86%), mp 333-334° C.; $^1$H NMR (DMSO-d$_6$): δ 11.2 (s, 1H), 10.5 (s, 1H), 8.15 (d, J=1.8 Hz, 1H), 7.84 (dd, J=8.2, 1.9 Hz, 1H), 7.76 (d, J=8.2 Hz, 1H), 2.12 (s, 3H); $^{13}$C NMR (DMSO-d$_6$): δ 168.6, 168.4, 168.3, 144.1, 133.5, 125.7, 123.5, 122.5, 111.8, 23.6; MS: m/z 204 (C$_{10}$H$_8$N$_2$O$_3$, M$^{+\bullet}$).

N-(1,3-Dioxoisoindolin-5-yl)hexanamide: BN-XII-079

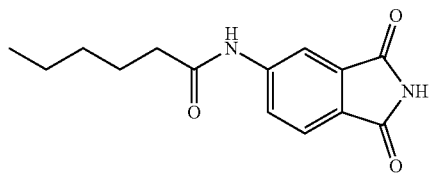 [SMILES: CCCCCC(=O)Nc1ccc2c(c1)C(=O)NC2=O]

Procedure E1. White solid (295 mg, 92%), mp 209-210° C.; $^1$H NMR (DMSO-d$_6$): δ 11.2 (s, 1H), 10.5 (s, 1H), 8.17 (d, J=1.8 Hz, 1H), 7.86 (dd, J=8.2, 1.9 Hz, 1H), 7.76 (d, J=8.2 Hz, 1H), 2.37 (t, J=7.4 Hz, 2H), 1.61 (quintet, J=7.4 Hz, 2H), 1.30 (m, 4H), 0.87 (t, J=6.8 Hz, 3H); $^{13}$C NMR (DMSO-d$_6$): δ 171.6, 168.4, 168.3, 144.1, 133.5, 125.6, 123.5, 122.5, 111.8, 35.9, 30.2, 24.0, 21.3, 13.3; MS: m/z 260 (C$_{14}$H$_{16}$N$_2$O$_3$, M$^{+\bullet}$).

N-(1,3-Dioxoisoindolin-5-yl)benzamide: BN-XII-061

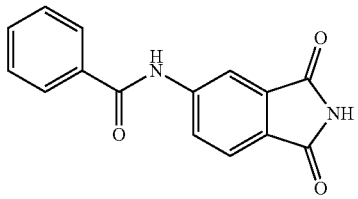 [SMILES: O=C(Nc1ccc2c(c1)C(=O)NC2=O)c1ccccc1]

Procedure E1. White solid (282 mg, 86%), mp 312-313° C.; ¹H NMR (DMSO-d₆): δ 11.3 (s, 1H), 10.8 (s, 1H), 8.34 (d, J=1.6 Hz, 1H), 8.15 (dd, J=8.2, 1.9 Hz, 1H), 8.00-7.98 (complex, 2H), 7.83 (d, J=1.9 Hz, 1H), 7.67-7.62 (complex, 1H), 7.60-7.55 (complex, 2H); ¹³C NMR (DMSO-d₆): δ 169.5, 169.3, 166.7, 145.1, 134.7, 134.4, 132.6, 129.0, 128.3, 127.3, 124.9, 124.4, 114.2; MS: m/z 266 ($C_{13}H_{10}N_2O_3$, M⁺•).

N-(1,3-Dioxoisoindolin-5-yl)-2-fluorobenzamide: BN-XII-060

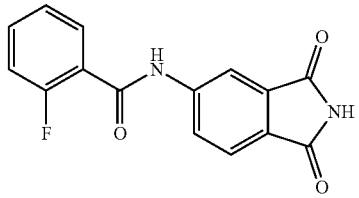 [SMILES: O=C(Nc1ccc2c(c1)C(=O)NC2=O)c1ccccc1F]

Procedure E1. Off-white solid (276 mg, 79%), mp 272-273° C.; ¹H NMR (DMSO-d₆): δ 11.1 (s, 2H), 8.15 (s, 1H), 7.96 (d, J=8.1 Hz, 1H), 7.72 (t, J=8.4 Hz, 2H), 7.61 (q, J=7.5 Hz, 1H), 7.42-7.32 (complex, 2H); ¹³C NMR (DMSO-d₆): δ 172.5, 163.2 (2C), 158.8 (d, J=246.8 Hz), 143.3, 135.7, 133.0 (d, J=8.3 Hz), 130.0 (d, J=2.6 Hz), 128.9, 124.7 (d, J=3.4 Hz), 124.6, 124.4, 123.6 (d, J=13.7 Hz), 116.3 (d, J=21.4 Hz), 112.7; MS: m/z 284 ($C_{15}H_9FN_2O_3$, M⁺•).

N-(1,3-Dioxoisoindolin-5-yl)-4-methoxybenzamide: BN-XII-064

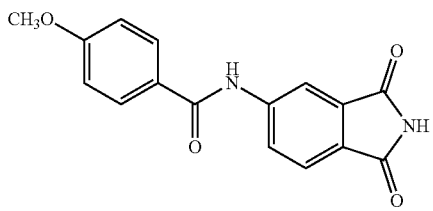

Procedure E1. Pale yellow solid (320 mg, 88%), mp 342-343° C.; ¹H NMR (DMSO-d₆): δ 11.2 (s, 1H), 10.6 (s, 1H), 8.33 (d, J=1.8 Hz, 1H), 8.14 (dd, J=8.2, 1.9 Hz, 1H), 8.00 (d, J=8.8 Hz, 2H), 7.81 (d, J=8.2 Hz, 1H), 7.10 (d, J=8.8 Hz, 2H), 3.86 (s, 3H); ¹³C NMR (DMSO-d₆): δ 169.5, 169.4, 165.9, 162.8, 145.4, 134.4, 130.4, 127.0, 126.7, 124.8, 124.3, 114.2, 114.1, 56.0; MS: m/z 296 ($C_{16}H_{12}N_2O_4$, M⁺•).

N-(1,3-Dioxoisoindolin-5-yl)-4-(trifluoromethoxy)benzamide: BN-XII-059

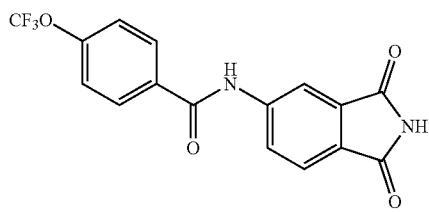

Procedure E1. Off-white solid (390 mg, 90%), mp 345-346° C.; ¹H NMR (DMSO-d₆): δ 11.1 (br s, 2H), 8.30 (d, J=1.5 Hz, 1H), 8.15-8.09 (complex, 3H), 7.81 (d, J=8.2 Hz, 1H), 7.56 (d, J=8.3 Hz, 2H); ¹³C NMR (DMSO-d₆): δ 170.0, 169.8, 165.4, 151.2, 144.8, 134.6, 133.9, 130.8, 127.7, 124.8, 124.3, 121.2, 120.4 (q, J=257.3 Hz), 114.1; MS: m/z 350 ($C_{16}H_9F_3N_2O_4$, M⁺•).

N-(1,3-Dioxoisoindolin-5-yl)-4-nitrobenzamide: BN-XII-063

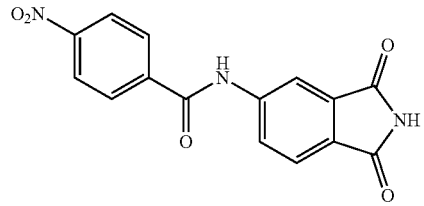 [SMILES: O=C(Nc1ccc2c(c1)C(=O)NC2=O)c1ccc([N+](=O)[O-])cc1]

Procedure E1. Yellow solid (290 mg, 76%), mp 355-356° C.; ¹H NMR (DMSO-d₆): δ 11.3 (s, 1H), 11.1 (s, 1H), 8.40 (d, J=8.4 Hz, 2H), 8.32 (d, J=1.5 Hz, 1H), 8.24 (d, J=8.4 Hz, 2H), 8.13 (dd, J=8.2, 1.7 Hz, 1H), 7.85 (d, J=8.2 Hz, 1H); ¹³C NMR: δ 168.3, 168.2, 164.0, 148.8, 143.5, 139.3, 133.4, 128.8, 126.7, 124.1, 123.4, 123.0, 113.3; MS: m/z 311 ($C_{15}H_9N_3O_5$, M⁺•).

N-(1,3-Dioxoisoindolin-5-yl)isonicotinamide: BN-XII-070

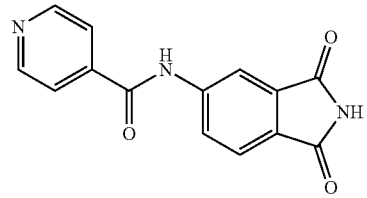 [SMILES: O=C(Nc1ccc2c(c1)C(=O)NC2=O)c1ccncc1]

Procedure E1. Off-white solid (215 mg, 65%), mp 322-323° C.; ¹H NMR (DMSO-d₆): δ 11.3 (s, 1H), 11.0 (s, 1H), 8.84 (d, J=6.0 Hz, 2H), 8.31 (d, J=1.6 Hz, 1H), 8.13 (dd, J=8.2, 1.8 Hz, 1H), 7.91 (d, J=6.0 Hz, 2H), 7.84 (d, J=8.2 Hz, 1H); ¹³C NMR (DMSO-d₆): δ 168.3, 168.2, 164.1, 149.8, 143.4, 140.7, 133.4, 126.8, 124.0, 123.4, 121.1, 113.3; MS: m/z 267 ($C_{14}H_9N_3O_3$, M⁺•).

N-(1,3-Dioxoisoindolin-5-yl)methanesulfonamide: BN-XII-065

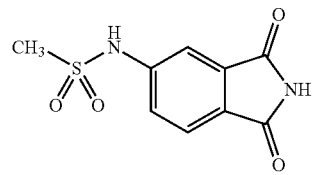 [SMILES: CS(=O)(=O)Nc1ccc2c(c1)C(=O)NC2=O]

Procedure E1. White solid (280 mg, 95%), mp 275-276° C.; ¹H NMR (DMSO-d₆): δ 11.3 (s, 1H), 10.6 (s, 1H), 7.80

(d, J=8.1 Hz, 1H), 7.56 (d, J=2.1 Hz, 1H), 7.53 (dd, J=8.1, 2.1 Hz, 1H), 2.17 (s, 3H); $^{13}$C NMR (DMSO-d$_6$): δ 168.2, 168.1, 143.6, 134.0, 125.9, 124.0, 122.1, 111.1, 39.4; MS: m/z 240 (C$_9$H$_8$N$_2$O$_4$S, M$^{+\cdot}$).

N-(1,3-Dioxoisoindolin-5-yl)-4-methylbenzenesulfonamide: BN-XII-062

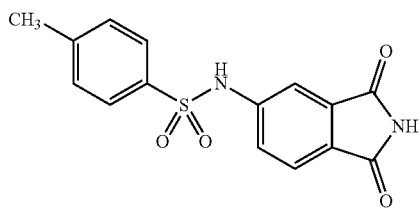 [SMILES: Cc1ccc(S(=O)(=O)Nc2ccc3c(c2)C(=O)NC3=O)cc1]

Procedure E1. White solid (280 mg, 95%), mp 278-279° C.; $^1$H NMR (DMSO-d$_6$): δ 11.2 (s, 1H), 11.1 (s, 1H), 7.73 (d, J=8.2 Hz, 2H), 7.72 (obscured, 1H), 7.46 (dd, J=6.9, 1.9 Hz, 1H), 7.45 (s, 1H), 7.39 (d, J=8.0 Hz, 2H), 2.34 (s, 3H); C NMR (DMSO-d$_6$): δ 169.1, 169.0, 144.5, 144.0, 136.6, 134.9, 130.5, 127.3, 127.2, 125.0, 123.4, 112.3, 21.4; MS: m/z 316 (C$_{15}$H$_{12}$N$_2$O$_4$S, M$^{+\cdot}$).

1-(1,3-Dioxoisoindolin-5-yl)-3-(4-nitrophenyl)urea: BN-XII-071

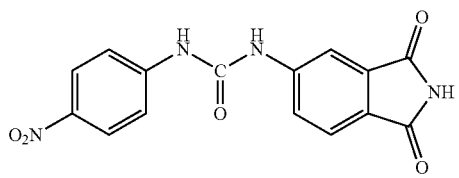 [SMILES: O=C(Nc1ccc([N+](=O)[O-])cc1)Nc1ccc2c(c1)C(=O)NC2=O]

Procedure E1. To a stirred solution of 5-aminoisoindoline-1,3-dione (200 mg, 1.25 mmol) in DMF (5 mL) was added 4-nitrophenylisocyanate (215 mg, 1.29 mmol) and the mixture was stirred for a period of 18 h. The reaction mixture was poured into ice-cold water and stirred for 3 h to obtain a yellow solid. The solid was filtered, dried and recrystallized using hot EtOH (7 mL) to obtain the desired compound as a yellow solid (300 mg, 72%), mp 335-336° C.; $^1$H NMR (DMSO-d$_6$): δ 11.2 (s, 1H), 9.65 (s, 1H), 9.59 (s, 1H), 8.21 (d, J=9.3 Hz, 2H), 8.05 (d, J=1.8 Hz, 1H), 7.76 (d, J=8.2 Hz, 1H), 7.72 (d, J=9.3 Hz, 2H), 7.72 (obscured dd, J=8.2, 1.8 Hz, 1H); $^{13}$C NMR (DMSO-d$_6$): δ 169.5, 169.3, 152.3, 146.2, 145.3, 141.9, 134.8, 126.1, 125.6, 124.6, 123.2, 118.4, 112.3; MS: m/z 326 (C$_{15}$H$_{10}$N$_4$O$_5$, M$^{+\cdot}$).

4-(3-(1,3-Dioxoisoindolin-5-yl)thioureido)benzoic acid: BN-XII-072

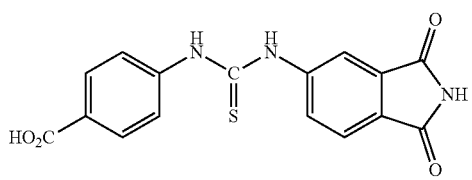 [SMILES: O=C(O)c1ccc(NC(=S)Nc2ccc3c(c2)C(=O)NC3=O)cc1]

Procedure E1. A similar method was used for the preparation of the thiourea compound. In this case, 4-carboxyphenyl-isothiocyanate (225 mg, 1.05 mmol) gave the desired product as an off-white solid (220 mg, 62, mp 337-339° C.; $^1$H NMR (DMSO-d$_6$): δ 12.8 (br s, 1H), 10.6 (s, 1H), 10.5 (s, 1H), 8.14 (d, J=1.6 Hz, 1H), 7.93 (d, J=8.3 Hz, 2H), 7.86 (dd, J=8.2, 1.7 Hz, 1H), 7.79 (d, J=8.2 Hz, 1H), 7.64 (d, J=8.3 Hz, 2H), acid proton not observed; $^{13}$C NMR (DMSO-d$_6$): δ 179.8, 169.3, 169.2, 167.3, 145.6, 143.7, 133.8, 130.5, 127.7, 127.6, 126.8, 124.1, 122.6, 116.8; MS: m/z 341 (C$_{16}$H$_{11}$N$_3$O$_4$S, M$^{+\cdot}$).

4-Amidoisoindoline-1,3-dione Series

Scheme 3: Synthesis of 3-(3,4-Dihydroxyphenyl)-N-(1,3-dioxoisoindolin-4-yl)propanamide: GKK-006-090.

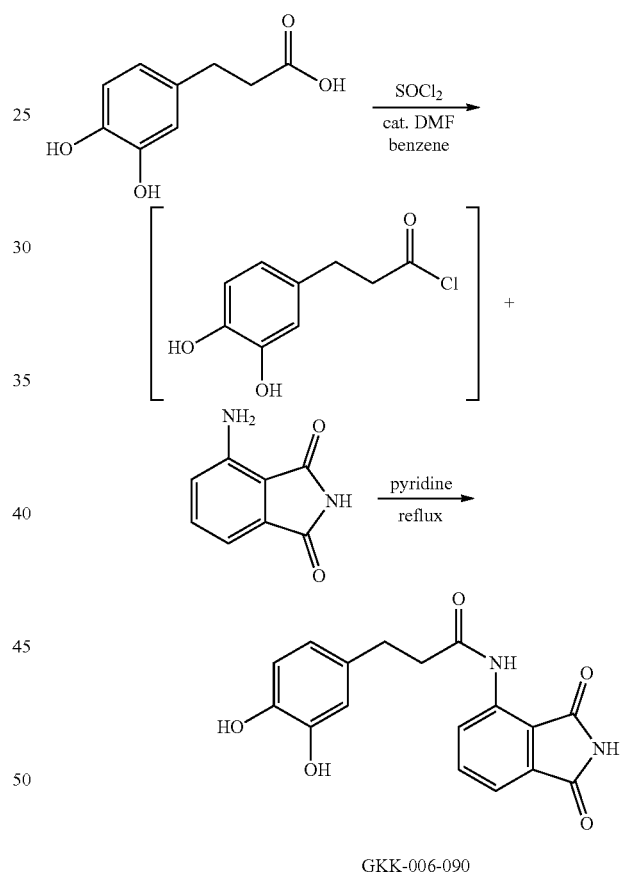

GKK-006-090

Procedure E2. Yellow solid (49 mg, yield 15%), mp 235-236° C.; $^1$H NMR (DMSO-d$_6$): δ 11.4 (s, 1H), 9.67 (s, 1H), 8.76 (s, 1H), 8.68 (s, 1H), 8.48 (d, J=8.4 Hz, 1H), 7.76 (t, J=7.8 Hz, 1H), 7.49 (d, J=7.3 Hz, 1H), 6.64 (s, 1H), 6.63 (d, J=8.4 Hz, 1H), 6.50 (d, J=8.0 Hz, 1H), 2.77 (t, J=7.1 Hz, 2H), 2.69 (t, J=7.1 Hz, 2H)$^{13}$C NMR (DMSO-d$_6$): δ 171.8, 170.8, 169.2, 145.5, 143.9, 136.9, 136.2, 133.3, 131.8, 125.5, 119.3, 118.3, 118.1, 116.2, 115.9, 39.1, 30.4; MS: m/z 326 (C$_{17}$H$_{14}$N$_2$O$_5$, M$^{+\cdot}$).

Scheme 4: Synthesis of 2-(3,4-Dihydroxyphenyl)-N-(1,3-dioxoisoindolin-4-yl)acetamide: GKK-006-082.

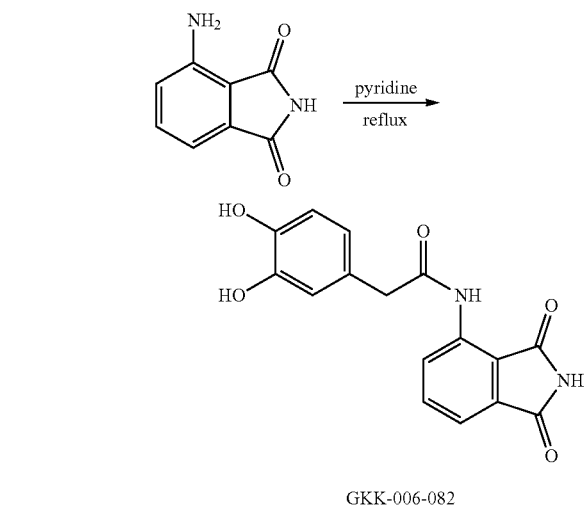

GKK-006-082

Procedure E2. Yellow solid (65 mg, 21%), mp 230-231° C.; $^1$H NMR (DMSO-d$_6$): δ 11.4 (s, 1H), 9.64 (s, 1H), 8.90 (s, 1H), 8.84 (s, 1H), 8.54 (d, J=8.5 Hz, 1H), 7.75 (t, J=7.9 Hz, 1H), 7.47 (d, J=7.3 Hz, 1H), 6.74 (s, 1H), 6.72 (d, J=8.5 Hz, 1H), 6.62 (d, J=7.3 Hz, 1H), 3.62 (s, 2H); $^{13}$C NMR (DMSO-d$_6$): δ 170.1, 169.7, 168.1, 144.8, 143.9, 135.9, 135.2, 132.1, 129.4, 123.5, 119.7, 116.9, 116.8, 116.1, 115.2, 42.8; MS: m/z 312 (C$_{16}$H$_{12}$N$_2$O$_5$, M$^{+•}$).

Scheme 5: Synthesis of N-(1,3-Dioxoisoindolin-4-yl)-2-hydroxybenzamide: GKK-010-075.

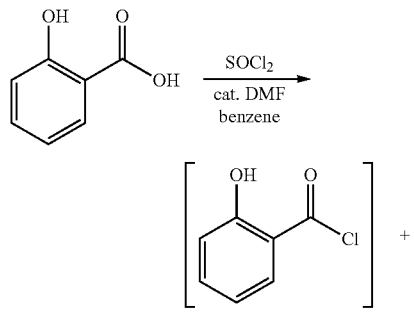

-continued

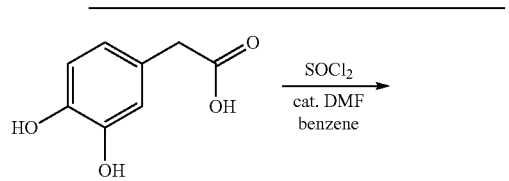

GKK-010-075

Procedure E2. Yellow solid (163 mg, 58%), mp 282-284° C.; $^1$H NMR (DMSO-d$_6$): δ 11.9 (s, 1H), 11.8 (s, 1H), 11.4 (s, 1H), 8.96 (d, J=8.5 Hz, 1H), 8.01 (d, J=7.7 Hz, 1H), 7.81 (t, J=7.8 Hz, 1H), 7.52 (d, J=7.7 Hz, 1H), 7.46 (t, J=7.8 Hz, 1H), 7.06 (d, J=8.2 Hz, 1H), 6.98 (t, J=7.5 Hz, 1H); $^{13}$C NMR (DMSO-d$_6$): δ 169.4, 168.2, 163.9, 155.9, 136.1, 135.1, 133.5, 132.4, 130.6, 124.5, 119.0, 117.7, 117.0, 116.8, 116.2; MS: m/z 282 (C$_{15}$H$_{10}$N$_2$O$_4$, M$^{+•}$).

Scheme 6: Synthesis of 2-((1,3-Dioxoisoindolin-4-yl)carbamoyl)phenyl acetate: GKK-010-070.

GKK-010-070

Procedure E2. Yellow solid (55 mg, 20%), mp 212-214° C.; $^1$H NMR (DMSO-d$_6$): δ 11.5 (s, 1H), 10.4 (s, 1H), 8.7 (d, J=8.4 Hz, 1H), 7.92 (d, J=7.7 Hz, 1H), 7.84 (t, J=7.9 Hz, 1H), 7.69 (t, J=7.7 Hz, 1H), 7.57 (d, J=7.3 Hz, 1H), 7.49 (t, J=7.6 Hz, 1H), 7.35 (d, J=8.1 Hz, 1H), 2.28 (s, 3H); $^{13}$C NMR (DMSO-d$_6$): δ 170.0, 168.5, 168.1, 163.0, 147.4, 135.5, 135.3, 132.6, 132.2, 129.2, 126.6, 125.9, 124.3, 123.3, 117.8, 117.6, 20.3; MS: m/z 324 (C$_{17}$H$_{12}$N$_2$O$_5$, M$^{+\bullet}$).

Scheme 7: Synthesis of N-(1,3-Dioxoisoindolin-4-yl)-2-fluorobenzamide: GKK-010-069.

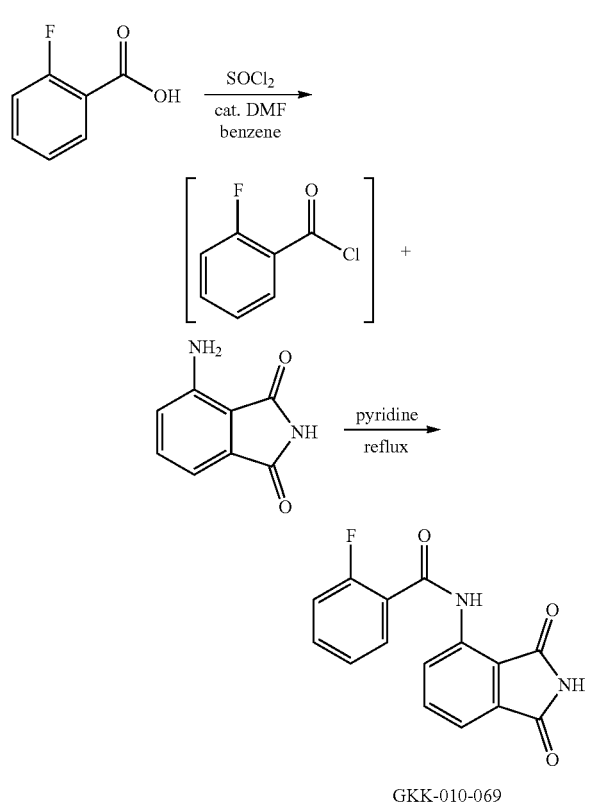

GKK-010-069

Procedure E2. Yellow solid (181 mg, 64%), mp 272-273° C.; $^1$H NMR (DMSO-d$_6$): δ 11.5 (s, 1H), 10.6 (d, J=9.7 Hz, 1H), 8.76 (d, J=8.4 Hz, 1H), 8.02 (td, J=7.8, 1.7 Hz, 1H), 7.85 (t, J=7.8 Hz, 1H), 7.76-7.68 (m, 1H), 7.57 (d, J=7.3 Hz, 1H), 7.50 (d, J=8.3 Hz, 1H), 7.43 (q, J=7.8 Hz, 1H); $^{13}$C NMR (DMSO-d$_6$): δ 171.0, 169.1, 162.1, 160.2 (d, J=247.0 Hz), 136.5, 136.4, 135.3 (d, J=10.0 Hz), 133.2, 131.8, 125.8, 125.2, 121.3 (d, J=8.0 Hz), 118.6, 118.5, 117.2 (d, J=23.0 Hz); MS: m/z 284 (C$_{15}$H$_9$FN$_2$O$_3$, M$^{+\bullet}$).

Scheme 8: Synthesis of tert-Butyl 4-((1,3-dioxoisoindolin-4-yl)carbamoyl)piperidine-1-carboxylate: GKK-010-072.

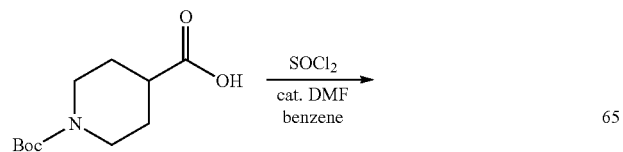

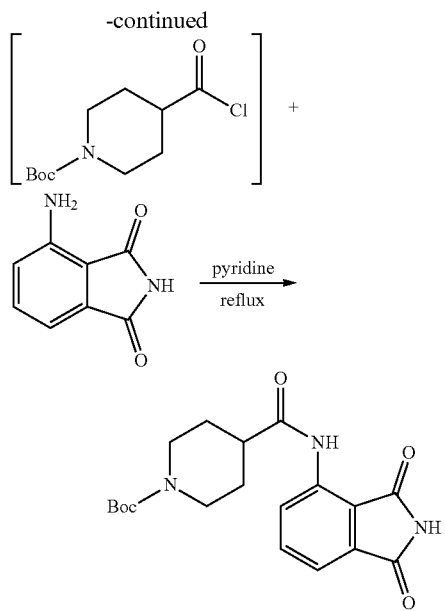

GKK-010-072

Procedure E2. Yellow solid (186 mg, 50%), mp 201-202° C.; $^1$H NMR (DMSO-d$_6$): δ 11.5 (s, 1H), 9.76 (s, 1H), 8.46 (d, J=8.4 Hz, 1H), 7.77 (t, J=7.8 Hz, 1H), 7.51 (d, J=7.3 Hz, 1H), 3.99 (d, J=13.0 Hz, 1H), 2.84 (br s, 2H), 2.68 (tt, J=11.5, 4.1 Hz, 1H), 1.88 (d, J=10.5 Hz, 2H), 1.59-1.35 (complex, 3H), 1.41 (s, 9H); $^{13}$C NMR (DMSO-d$_6$): δ 173.9, 170.9, 169.2, 154.3, 136.8, 136.2, 133.2, 125.7, 118.7, 118.3, 79.2, 43.2, 28.5, two aliphatic carbons coincident with solvent peaks; MS: m/z 373 (C$_{19}$H$_{23}$N$_3$O$_5$, M$^{+\bullet}$).

Scheme 9: Synthesis of N-(1,3-Dioxoisoindolin-4-yl)piperidine-4-carboxamide: GKK-010-073.

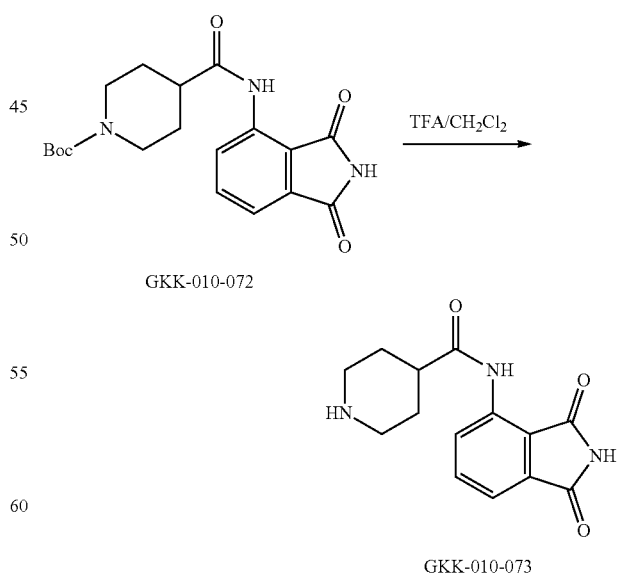

Boc-protected amide GKK-010-072 was treated with trifluoroacetic acid in dichloromethane at room temperature until TLC indicated that the reaction was complete. Extractive workup with NaHCO₃ and NaCl, followed by drying (Na₂SO₄), filtration and concentration yielded amide GKK-010-073 as a white solid (139 mg, 51%), mp 234-236° C.; ¹H NMR (DMSO-d₆): δ 9.75 (s, 1H), 8.49 (d, J=8.4 Hz, 1H), 7.75 (t, J=7.9 Hz, 1H), 7.48 (d, J=7.3 Hz, 1H), 4.01 (br s, 1H), 3.02 (d, J=11.9 Hz, 2H), 2.83 (br s, 1H), 2.55 (obscured, 3H), 1.83 (d, J=12.6 Hz, 2H), 1.53 (apparent q, J=12.3 Hz, 2H); ¹³C NMR (DMSO-d₆): δ 174.2, 171.8, 170.0, 136.9, 136.0, 133.5, 125.2, 118.7, 118.0, 45.5, 43.7, 29.0; MS: m/z 273 (C₁₄H₁₅N₃O₃, M⁺•).

5-Aminoisoindoline-1,3-dione Series 5-(Benzylamino)isoindoline-1,3-dione: BN-XIII-063

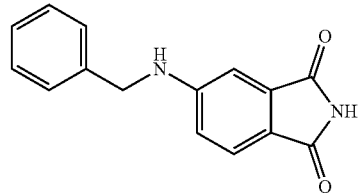

Procedure A. Off-white solid (265 mg, 85%), mp 263-264° C.; ¹H NMR (DMSO-d₆): δ 10.8 (s, 1H), 7.47 (d, J=8.1 Hz, 1H), 7.36 (m, 5H), 7.26 (s, 1H), 6.87 (s, 1H), 6.85 (obscured, 1H), 4.42 (d, J=3.4 Hz, 2H); ¹³C NMR (DMSO-d₆): δ 170.1, 169.7, 154.4, 139.3, 135.8, 129.0, 127.6, 127.5, 124.9, 118.7, 116.2, 105.6, 46.5; MS: m/z 252 (C₁₅H₁₂N₂O₂, M⁺•).

5-((5-Hydroxypentyl)amino)isoindoline-1,3-dione: BN-XIV-035

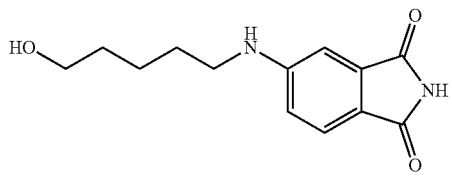 [SMILES: O=C1NC(=O)c2cc(NCCCCCO)ccc21]

Procedure A. Pale yellow solid (260 mg, 86%), mp 197-198° C.; ¹H NMR (DMSO-d₆): δ 10.7 (br s, 1H), 7.54 (d, J=8.3 Hz, 1H), 6.96 (br t, J=4.5 Hz, 1H), 6.86 (s, 1H), 6.80 (d, J=8.3 Hz, 1H), 4.38 (br s, 1H), 3.41 (t, J=6.3 Hz, 2H), 3.14 (q, J=6.3 Hz, 2H), 1.58 (quintet, J=7.2 Hz, 2H), 1.52-1.34 (complex, 4H); ¹³C NMR (DMSO-d₆): δ 170.2, 169.8, 154.6, 135.9, 125.0, 117.9, 115.5, 105.1, 61.1, 43.0, 32.7, 28.7, 23.6; MS: m/z 248 (C₁₃H₁₆N₂O₃, M⁺•).

5-((4-Fluorobenzyl)amino)isoindoline-1,3-dione: BN-XIII-069

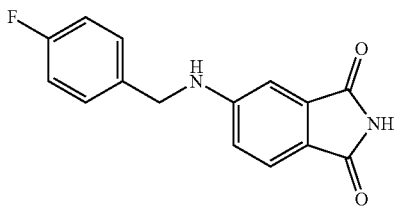 [SMILES: O=C1NC(=O)c2cc(NCc3ccc(F)cc3)ccc21]

Procedure A. Yellow solid (260 mg, 78%), mp 237-238° C.; ¹H NMR (DMSO-d₆): δ 10.8 (s, 1H), 7.55 (br s, 1H), 7.48 (d, J=8.2 Hz, 1H), 7.40 (br s, 2H), 7.28 for t, J=8.8 Hz, 2H), 6.86 (m, 2H), 4.41 (d, J=4.3 Hz, 2H); ¹³C NMR (DMSO-d₆): δ 170.0, 169.7, 161.7 (d, J=242.4 Hz), 154.2, 135.8, 135.4, 129.6, (d, J=8.1 Hz), 125.0, 118.8, 116.3, 115.7 (d, J=21.3 Hz), 105.7, 45.7; MS: m/z 270 (C₁₅H₁₁FN₂O₂, M⁺•).

5-((2-Hydroxybenzyl)amino)isoindoline-1,3-dione: BN-XIII-093

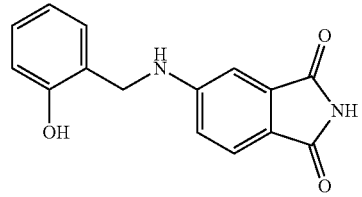 [SMILES: O=C1NC(=O)c2cc(NCc3ccccc3O)ccc21]

Procedure A. Yellow solid (235 mg, 71%), mp 205-206° C.; ¹H NMR (DMSO-d₆): δ 10.7 (s, 1H), 9.66 (s, 1H), 7.48 (d, J=8.3 Hz, 1H), 7.39 (s, 1H), 7.16 (d, J=7.5 Hz, 1H), 7.09 (br t, J=7.8, 1H), 6.92-6.83 (complex, 3H), 6.76 (t, J=7.6 Hz, 1H), 4.32 (d, J=5.1 Hz, 2H); ¹³C NMR (DMSO-d₆): δ 170.1, 169.8, 155.6, 154.5, 135.8, 128.8, 128.5, 124.9, 124.7, 119.4, 118.3, 115.9, 115.5, 105.4, 41.5; MS: m/z 268 (C₁₅H₁₂N₂O₃, M⁺•).

5-((3-Hydroxybenzyl)amino)isoindoline-1,3-dione: BN-XIII-092

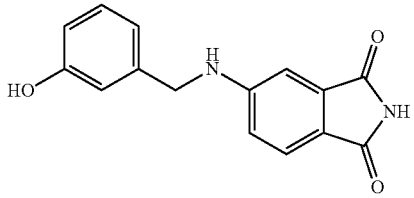 [SMILES: O=C1NC(=O)c2cc(NCc3cccc(O)c3)ccc21]

Procedure A. Off-white solid (225 mg, 68%), mp 218-219° C.; ¹H NMR (DMSO-d₆): δ 10.8 (s, 1H), 9.37 (s, 1H), 7.55 (t, J=6.0 Hz, 1H), 7.48 (d, J=8.3 Hz, 1H), 7.14 (t, J=7.2 Hz, 1H), 6.85 (s, 1H), 6.84 (d, J=7.4 Hz, 1H), 6.77 (d, J=7.4 Hz, 1H), 6.74 (s, 1H), 6.64 (dd, J=8.1, 1.8 Hz, 1H), 4.34 (d, J=5.9 Hz, 2H); ¹³C NMR (DMSO-d₆): δ 170.1, 169.7, 158.0, 154.4, 140.8, 135.8, 130.0, 124.9, 118.6, 118.1, 116.2, 114.4, 114.2, 105.6, 46.4; MS: m/z 268 (C₁₅H₁₂N₂O₃, M⁺•).

5-((4-Hydroxybenzyl)amino)isoindoline-1,3-dione: BN-XIII-068

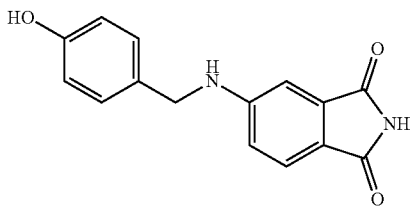 [SMILES: O=C1NC(=O)c2cc(NCc3ccc(O)cc3)ccc21]

Procedure A. Off-white solid (220 mg, 67%), mp 233-234° C.; ¹H NMR (DMSO-d₆): δ 10.7 (br s, 1H), 9.33 (br s, 1H), 7.47 (s, 2H), 7.16 (s, 2H), 6.86 (s, 2H), 6.74 (s, 2H), 4.27 (s, 2H); ¹³C NMR (DMSO-d₆): δ 170.1, 169.8, 156.9, 154.4, 135.8, 129.1, 129.0, 124.9, 118.4, 116.1, 115.7, 105.6, 46.2; MS: m/z 268 ($C_{15}H_{12}N_2O_3$, M⁺˙).

5-((3-Methoxybenzyl)amino)isoindoline-1,3-dione: BN-XIII-070

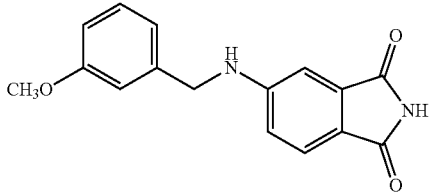

Procedure A. Yellow solid (300 mg, 86%), mp 147-148° C.; ¹H NMR (DMSO-d₆): δ 10.8 (s, 1H), 7.55 (s, 1H), 7.48 (d, J 8.2 Hz, 1H), 7.27 (t, J=8.2 Hz, 1H), 6.93 (s, 2H), 6.90-6.78 (complex, 3H), 4.39 (d, J=4.5 Hz, 2H), 3.74 (s, 3H); ¹³C NMR (DMSO-d₆): δ 170.1, 169.7, 159.9, 154.4, 141.0, 135.8, 130.0, 124.9, 119.7, 118.7, 116.2, 113.4, 112.7, 105.7, 55.4, 46.4; MS: m/z 282 ($C_{16}H_{14}N_2O_3$, M⁺˙).

5-((2,3,4-Trimethoxybenzyl)amino)isoindoline-1,3-dione: BN-XIII-067

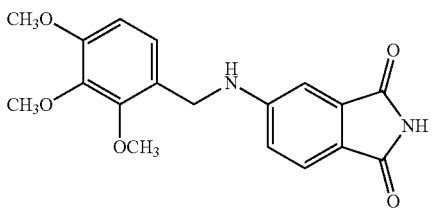

Procedure A. Off-white solid (375 mg, 89%), mp 202-203° C.; ¹H NMR (DMSO-d₆): δ 10.8 (s, 1H), 7.48 (d, J=6.7 Hz, 1H), 7.32 (s, 1H), 7.00-6.73 (complex, 4H), 4.30 (s, 2H), 5.85 (s, 3H), 3.77 (s, 6H); ¹³C NMR (DMSO-d₆): δ 170.1, 169.8, 154.3, 153.3, 151.8, 142.2, 135.8, 125.0, 124.1, 123.4, 118.4, 115.9, 108.2, 105.5, 61.3, 60.8, 56.3, 41.6; MS: m/z 342 ($C_{18}H_{18}N_2O_5$, M⁺˙).

5-((2,3-Dihydroxybenzyl)amino)isoindoline-1,3-dione: BN-XIV-073

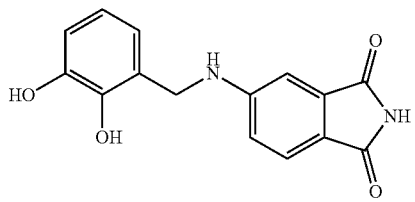 [SMILES: O=C1NC(=O)c2cc(NCc3cccc(O)c3O)ccc21]

Procedure A. White solid (215 mg, 62%), mp 182-184° C.; ¹H NMR (DMSO-d₆): δ 10.7 (br s, 1H), 8.96 (br s, 2H), 7.47 (d, J=8.2 Hz, 1H), 7.37 (br t, J=6.0 Hz, 1H), 6.87 (s, 1H), 6.84 (d, J=8.2 Hz, 1H), 6.71 (d, J=7.7 Hz, 1H), 6.65 (d, J=7.5 Hz, 1H), 6.59 (t, J=7.6 Hz, 1H), 4.32 (d, J=6.0 Hz, 2H); ¹³C NMR: δ 170.1, 169.8, 154.6, 145.5, 143.6, 135.8, 125.6, 124.9, 119.2, 119.1, 118.2, 115.9, 114.7, 105.5, 41.7; MS: m/z 284 ($C_{15}H_{12}N_2O_4$, M⁺˙).

5-((3,4-Dihydroxybenzyl)amino)isoindoline-1,3-dione: BN-XIII-091

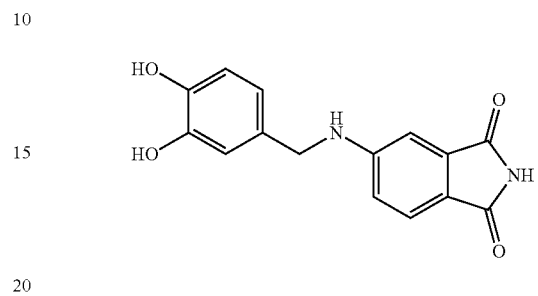

Procedure A. Off-white solid (227 mg, 65%), mp 189-190° C.; ¹H NMR: δ 10.7 (br s, 1H), 8.83 (br s, 2H), 7.45 (overlapping d, J=8.1 Hz, 1H and br t, J=5.6 Hz, 1H), 6.85 (s, 1H), 6.83 (d, J=8.6 Hz, 1H), 6.78 (s, 1H), 6.71 (d, J=8.0 Hz, 1H), 6.61 (d, J=8.0 Hz, 1H), 4.22 (d, J=5.6 Hz, 2H); ¹³C NMR (DMSO-d₆): δ 169.0, 168.7, 153.4, 144.7, 143.7, 134.7, 128.7, 123.8, 117.5, 117.3, 115.0, 114.9, 114.0, 104.5, 45.7; MS: m/z 284 ($C_{15}H_{12}N_2O_4$, M⁺˙).

5-((2,5-Dihydroxybenzyl)amino)isoindoline-1,3-dione: BN-XV-062

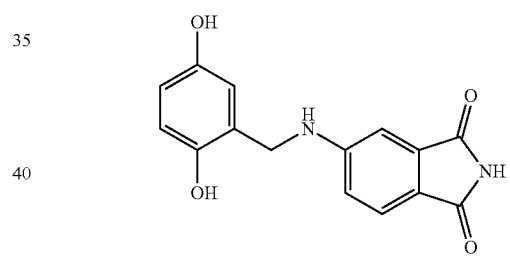

Procedure A. White solid (200 mg, 62%), mp 154-155° C.; ¹H NMR (DMSO-d₆): δ 10.7 (s, 1H), 8.92 (s, 1H), 8.63 (s, 1H), 7.48 (d, J=8.3 Hz, 1H), 7.42 (br t, J=5.8 Hz, 1H), 6.84 (s, 1H), 6.83 (obscured, 1H), 6.66 (d, J=8.5 Hz, 1H), 6.58 (s, 1H), 6.48 (d, J=8.4 Hz, 1H), 4.26 (d, J=5.9 Hz, 2H); ¹³C NMR (DMSO-d₆): δ 169.1, 168.7, 153.5, 149.2, 146.7, 134.8, 124.3, 123.9, 117.2, 115.1, 114.9, 113.9, 113.6, 104.3, 40.4; MS: m/z 284 ($C_{15}H_{12}N_2O_4$, M⁺˙).

5-((2,3,4-Trihydroxybenzyl)amino)isoindoline-1,3-dione: BN-XVI-031

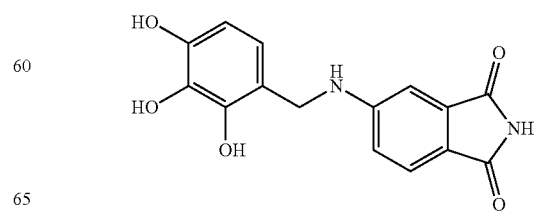

Procedure A. Pale yellow solid (215 mg, 58%), mp 193-194° C.; $^1$H NMR (DMSO-$d_6$): δ 10.7 (s, 1H), 8.98 (s, 1H), 8.47 (s, 1H), 8.30 (s, 1H), 7.45 (d, J=8.3 Hz, 1H), 7.23 (br t, J=5.6 Hz, 1H), 6.86 (s, 1H), 6.82 (d, J=8.6 Hz, 1H), 6.47 (d, J=8.3 Hz, 1H), 6.25 (d, J=8.2 Hz, 1H), 4.20 (d, J=5.5 Hz, 2H); $^{13}$C NMR (DMSO-$d_6$): δ 170.2, 169.8, 154.6, 145.7, 144.8, 135.8, 133.5, 124.9, 118.7, 118.0, 116.3, 115.8, 106.9, 105.5, 41.7; MS: m/z 300 ($C_{15}H_{12}N_2O_5$, M$^{+•}$).

5-((3,4,5-Trihydroxybenzyl)amino)isoindoline-1,3-dione: BN-XVI-037

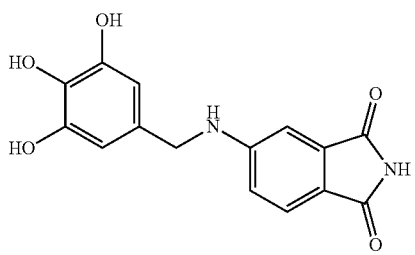 [SMILES: O=C1NC(=O)c2cc(NCc3cc(O)c(O)c(O)c3)ccc21]

Procedure A. Yellow solid (230 mg, 62%), mp 215-216° C.; $^1$H NMR (DMSO-$d_6$): δ 10.7 (s, 1H), 8.78 (s, 2H), 7.97 (s, 1H), 7.44 (d, J=8.1 Hz, 1H), 7.44 (obscured, 1H), 6.86-6.78 (complex, 2H), 6.25 (s, 2H), 4.15 (d, J=5.8 Hz, 2H); $^{13}$C NMR (DMSO-$d_6$): δ 169.0, 168.7, 153.5, 145.5, 134.7, 131.3, 128.0, 123.8, 117.2, 115.1, 105.2, 104.9, 45.3; MS: m/z 300 ($C_{15}H_{12}N_2O_5$, M$^{+•}$).

2-(((1,3-Dioxoisoindolin-5-yl)amino)methyl)benzoic acid: BN-XIV-037

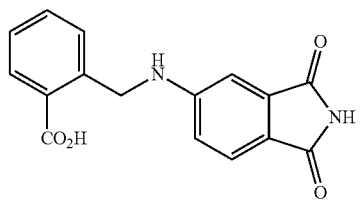 [SMILES: O=C(O)c1ccccc1CNc1ccc2c(c1)C(=O)NC2=O]

Procedure A. Off-white solid (175 mg, 48%), mp 332-333° C.; $^1$H NMR (DMSO-$d_6$): δ 11.3 (s, 1H), 8.44 (d, J=1.8 Hz, 1H), 8.30 (dd, J=8.2, 1.8 Hz, 1H), 7.92 (d, J=8.3 Hz, 1H), 7.86 (d, J=7.6 Hz, 1H), 7.77-7.68 (complex, 2H), 7.59 (t, J=7.2, 1H), 5.18 (s, 2H), acid and amine protons not observed; $^{13}$C NMR (DMSO-$d_6$): δ 169.4, 169.3, 167.9, 145.1, 141.6, 134.6, 133.5, 132.2, 128.9, 127.4, 124.6, 124.1, 123.9, 123.6, 113.1, 51.2; MS: m/z 296 ($C_{16}H_{12}N_2O_4$, M$^{+•}$).

3-(((1,3-oxoisoindolin-5-yl)amino)methyl)benzoic acid: BN-XIII-088

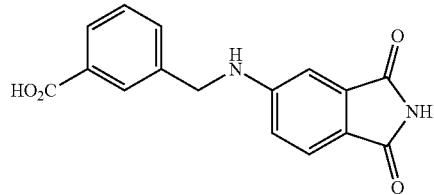 [SMILES: O=C(O)c1cccc(CNc2ccc3c(c2)C(=O)NC3=O)c1]

Procedure A. Off-white solid (183 mg, 50%), mp 303-304° C.; $^1$H NMR (DMSO-$d_6$): δ 10.8 (br s, 1H), 7.95 (s, 1H), 7.82 (d, J=7.6 Hz 1H), 7.66 (br t, J=6.0 Hz, 1H), 7.48 (complex, 2H), 7.40 (t, J=7.6 Hz, 1H), 6.89 (s, 1H), 6.87 (d, J=8.2 Hz, 1H), 4.47 (d, J=6.0 Hz, 2H), carboxylic acid proton not observed; $^{13}$C NMR (DMSO-$d_6$): δ 170.1. 169.7, 168.7, 154.3, 139.3, 135.8, 134.9, 130.6, 128.7, 128.4 (2C), 125.0, 118.7, 116.2, 105.7, 46.3; MS: m/z 296 ($C_{16}H_{12}N_2O_4$, M$^{+•}$).

4-(((1,3-Dioxoisoindolin-5-yl)amino)methyl)benzoic acid: BN-XVI-041

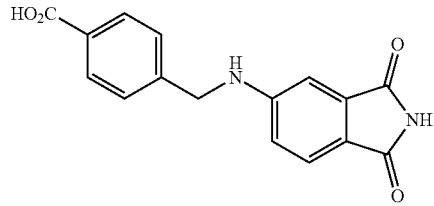 [SMILES: O=C(O)c1ccc(CNc2ccc3c(c2)C(=O)NC3=O)cc1]

Procedure A. Off-white solid (170 mg, 47%), mp 351-353° C.; $^1$H NMR (DMSO-$d_6$): δ 10.8 (s, 1H), 7.82 (d, J 7.7 Hz, 2H), 7.63 (br t, J=5.9 Hz, 1H), 7.46 (s, J=8.2 Hz, 1H), 7.01 (d, J=7.8 Hz, 2H) 6.88 (s, 1H), 6.86 (d, J=8.3 Hz, 1H), 4.41 (d, J=5.9 Hz, 2H); $^{13}$C NMR (DMSO-$d_6$): δ 169.0, 168.7, 167.7, 153.4, 138.6, 138.4, 134.7, 128.6, 125.4, 123.8, 117.5, 115.1, 104.6, 45.4; MS: m/z 296 ($C_{16}H_{12}N_2O_4$, M$^{+•}$).

5-((Cyclopent-1-en-1-ylmethyl)amino)isoindoline-1,3-dione: BN-XIV-031

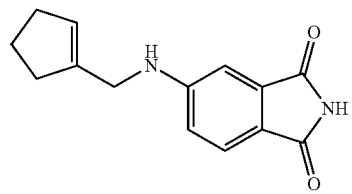 [SMILES: O=C1NC(=O)c2cc(NCC3=CCCC3)ccc21]

Procedure A. White solid (230 mg, 76%), mp 193-194° C.; $^1$H NMR (DMSO-$d_6$): δ 10.8 (s, 1H), 7.48 (d, J=8.3 Hz, 1H), 7.19 (br t, J=6.0 Hz, 1H), 6.88 (s, 1H), 6.83 (d, J=8.7 Hz, 1H), 5.56 (s, 1H), 3.85 (d, J=6.0 Hz, 2H), 2.28 (t, J=7.6 Hz, 4H), 1.86 (quintet, J=7.5 Hz, 2H); $^{13}$C NMR (DMSO-d$_6$): δ 170.1, 169.8, 154.6, 141.6, 135.8, 125.6, 124.9, 118.3, 115.2, 105.5, 43.4, 33.5, 32.3, 23.3; MS: m/z 242 (C$_{14}$H$_{14}$N$_2$O$_2$, M$^{+\cdot}$).

5-(((2-Methylfuran-3-yl)methyl)amino)isoindoline-1,3-dione: BN-XIII-072

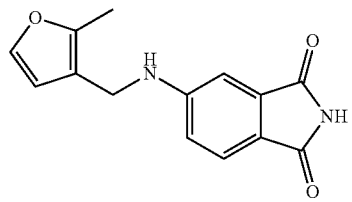 [SMILES: Cc1occc1CNc1ccc2c(c1)C(=O)NC2=O]

Procedure A. Yellow solid (156 mg, 61%), mp 158-159° C.; $^1$H NMR (DMSO-d$_6$): δ 10.8 (s, 1H), 7.49 (d, J=8.4 Hz, 1H), 7.38 (s, 1H), 6.96 (s, 1H), 6.91 (d, J=8.4 Hz, 1H), 6.22 (s, 1H), 6.00 (s, 1H), 4.33 (d, J=4.4 Hz, 2H), 2.23 s, 3); $^{13}$C NMR (DMSO-d$_6$): δ 170.1, 169.8, 154.1, 151.4, 150.4, 135.7, 124.9, 118.9, 116.1, 108.8, 106.8, 105.7, 39.9, 13.8; MS: m/z 256 (C$_{14}$H$_{12}$N$_2$O$_3$, M$^{+\cdot}$).

5-((2-(Phenylthio)benzyl)amino)isoindoline-1,3-dione: BN-XIV-036

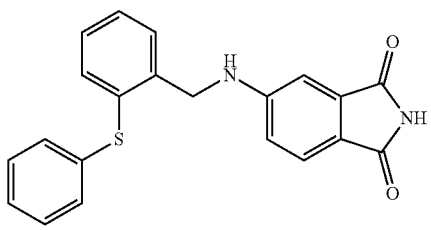 [SMILES: O=C1NC(=O)c2cc(NCc3ccccc3Sc3ccccc3)ccc21]

Procedure A. Yellow solid (375 mg, 84%), mp 192-193° C.; $^1$H NMR (DMSO-d$_6$): δ 10.8 (s, 1H), 7.54 (br t, J=6.0 Hz, 1H), 7.46 (d, J=8.3 Hz, 1H), 7.44-7.26 (complex, 9H), 6.81 (s, 1H), 6.76 (d, J=8.3 Hz, 1H), 4.46 (d, J=6.0 Hz, 2H); $^{13}$C NMR (DMSO-d$_6$): δ 170.0, 169.7, 154.1, 139.8, 135.8, 135.5, 133.8, 133.2, 130.2, 130.1, 128.9, 128.8, 128.6, 127.6, 125.0, 119.0, 116.0, 105.6, 45.2; MS: m/z 360 (C$_{21}$H$_{16}$N$_2$O$_2$S, M$^{+\cdot}$).

4-Aminoisoindoline-1,3-Dione Series 4-((3-Hydroxybenzyl)amino)isoindoline-1,3-dione: BN-XIV-053 (Analog 12)

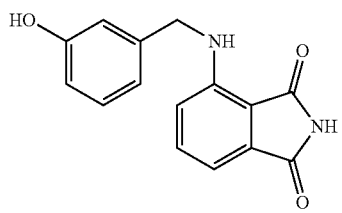 [SMILES: O=C1NC(=O)c2c(NCc3cccc(O)c3)cccc21]

Procedure A. Yellow solid (218 mg, 67%), mp 192-193° C.; $^1$H NMR (DMSO-d$_6$): δ 10.9 (br s, 1H), 9.60 (br s, 1H), 7.47 (t, J=8.0 Hz, 1H), 7.13 (t, J=7.8 Hz, 1H), 7.08 (br t, J=6.3 Hz, 1H), 6.94 (d, J=7.1 Hz, 1H), 6.89 (d, J=8.5 Hz, 1H), 6.78 (d, J=8.4 Hz, 1H), 6.76 (s, 1H), 6.65 (d, J=8.2 Hz, 1H), 4.46 (d, J=6.3 Hz, 2H); $^{13}$C NMR (DMSO-d$_6$): δ 171.8, 169.8, 158.0, 146.5, 141.0, 136.2, 134.0, 130.0, 117.9, 117.4, 114.4, 114.0, 111.5, 110.6, 45.9; MS: m/z 268 (C$_{15}$H$_{12}$N$_2$O$_3$, M$^{+\cdot}$).

4-((2,3-Dihydroxybenzyl)amino)isoindoline-1,3-dione: BN-XIV-074

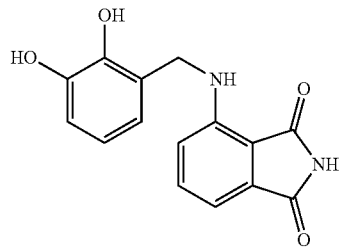 [SMILES: O=C1NC(=O)c2c(NCc3cccc(O)c3O)cccc21]

Procedure A. Yellow solid (220 mg, 67%), mp 182-184° C.; $^1$H NMR (DMSO-d$_6$): δ 10.9 (s, 1H), 9.34 (s, 1H), 8.60 (s, 1H), 7.48 (t, J=7.8 Hz, 1H), 6.99 (d, J=8.5 Hz, 1H), 6.90 (overlapping d, J=7.0 Hz, 1H and br t, J=6.1 Hz, 1H), 6.69 (t, J=7.2 Hz, 2H), 6.57 (t, J=7.7 Hz, 1H), 4.41 (d, J=6.1 Hz, 2H); $^{13}$C NMR (DMSO-d$_6$): δ 170.8, 168.7, 145.6, 144.4, 142.6, 135.1, 132.9, 124.7, 118.3, 118.2, 116.2, 113.8, 110.3, 109.3, 40.6; MS: m/z 284 (C$_{15}$H$_{12}$N$_2$O$_4$, M$^{+\cdot}$).

4-((2,5-Dihydroxybenzyl)amino)isoindoline-1,3-dione: BN-XVI-069

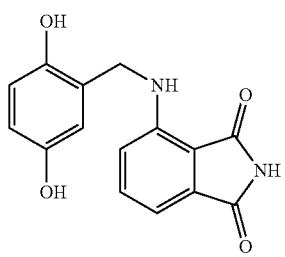 [SMILES: O=C1NC(=O)c2c(NCc3cc(O)ccc3O)cccc21]

Procedure A. White solid (247 mg, 71%), mp 178-179° C.; $^1$H NMR (DMSO-d$_6$): δ 10.9 (s, 1H), 9.35 (s, 1H), 9.18 (s, 1H), 7.49 (t, J=7.7 Hz, 1H), 7.05 (d, J=8.5 Hz, 1H), 7.00 (d, J=8.2 Hz, 1H), 6.91 (d, J=7.1 Hz, 1H), 6.77 (br t, J=6.1 Hz, 1H), 6.32 (s, 1H), 6.16 (d, J=8.0 Hz, 1H), 4.29 (d, J=6.0 Hz, 2H); $^{13}$C NMR (DMSO-d$_6$): δ 170.8, 168.7, 157.0, 155.5, 145.6, 135.1, 132.9, 129.1, 116.2, 114.4, 110.2, 109.2, 105.4, 101.9, 40.4; MS: m/z 284 (C$_{15}$H$_{12}$N$_2$O$_4$, M$^{+\cdot}$).

4-((2,6-Dihydroxybenzyl)amino)isoindoline-1,3-dione: BN-XVI-070

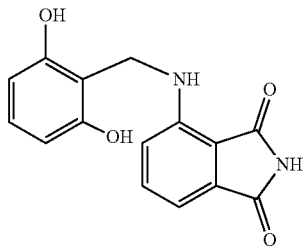 [SMILES: O=C1NC(=O)c2c(NCc3c(O)cccc3O)cccc21]

Procedure A. White solid (260 mg, 73%), mp 166-167° C.; $^1$H NMR (DMSO-$d_6$): δ 10.9 (s, 1H), 9.62 (s, 2H), 7.52 (t, J=7.9 Hz, 1H), 7.31 (d, J=8.5 Hz, 1H), 6.92-6.83 (complex, 2H), 6.77 (br t, J=6.2 Hz, 1H), 6.32 (d, J=8.1 Hz, 2H), 4.37 (d, J=6.2 Hz, 2H); $^{13}$C NMR (DMSO-$d_6$): δ 170.9, 168.7, 155.9, 145.8, 135.2, 132.9, 127.8, 116.1, 110.6, 110.1, 109.1, 105.7, 34.7; MS: m/z 284 ($C_{15}H_{12}N_2O_4$, $M^{+\bullet}$).

3-(((1,3-Dioxoisoindolin-4-yl)amino)methyl)benzoic acid: BN-XIV-059

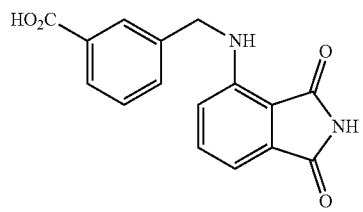 [SMILES: O=C(O)c1cccc(CNc2cccc3c2C(=O)NC3=O)c1]

Procedure A. Yellow solid (310 mg, 85%), mp 253-254° C.; $^1$H NMR (DMSO-$d_6$): δ 13.0 (br s, 1H), 11.0 (s, 1H), 7.97 (s, 1H), 7.82 (d, J=7.7 Hz, 1H), 7.62 (d, J=7.7 Hz, 1H), 7.45 (overlapping t, J≈7.1 Hz, 2H), 7.26 (br t, J=6.5 Hz, 1H), 6.94 (d, J=7.1 Hz, 1H), 6.88 (d, J=8.5 Hz, 1H), 4.61 (d, J=6.4 Hz, 2H); $^{13}$C NMR (DMSO-$d_6$): δ 171.7, 169.8, 167.7, 146.3, 140.3, 136.2, 134.1, 131.9, 131.5, 129.2, 128.4, 128.2, 117.3, 111.7, 110.7, 45.5; MS m/z 296 ($C_{16}H_{12}N_2O_4$, $M^{+\bullet}$).

4-((2,3,4-Trimethoxybenzyl)amino)isoindoline-1,3-dione: BN-XIV-060

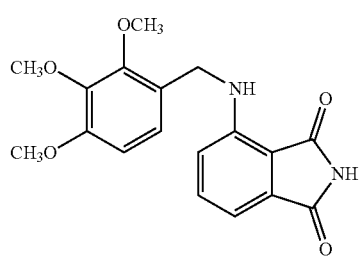

Procedure A. Yellow solid (395 mg, 94%), mp 138-139° C.; $^1$H NMR (DMSO-$d_6$): δ 11.0 (s, 1H), 7.50 (br t, J=8.2 Hz, 1H), 7.00 (d, J=8.5 Hz, 1H), 6.98 (obscured, 2H), 6.85 (s, 1H), 6.76 (d, J=8.7 Hz, 1H), 4.43 (d, J=4.1 Hz, 2H), 3.86 (s, 3H), 3.77 (s, 6H); $^{13}$C NMR (DMSO-$d_6$): δ 171.9, 169.8, 153.3, 151.7, 146.4, 142.2, 136.2, 134.0, 124.8, 123.3, 117.2, 111.5, 110.5, 108.1, 61.3, 60.8, 56.3, 41.3; MS: m/z 342 ($C_{15}H_{15}N_2O_5$, $M^{+\bullet}$).

4-(3-Phenylpropylamino)isoindoline-1,3-dione: BN-XVI-067

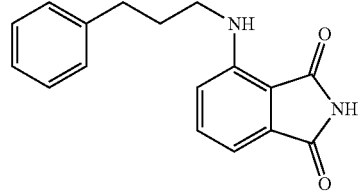 [SMILES: O=C1NC(=O)c2c(NCCCc3ccccc3)cccc21]

Procedure A. Yellow solid (315 mg, 96%), mp 157-158° C.; $^1$H NMR (DMSO-$d_6$): δ 11.0 (s, 1H), 7.51 (t, J=7.8 Hz, 1H), 7.29 (t, J=7.5 Hz, 2H), 7.25-7.15 (complex, 3H), 6.95 (d, J=8.5 Hz, 1H), 6.91 (d, J=7.1 Hz, 1H), 6.53 (br t, J=6.2 Hz, 1H), 3.29 (q, J=6.7 Hz, 2H), 2.67 (t, J=7.7 Hz, 2H), 1.88 (quintet, J=7.4 Hz, 2H); $^{13}$C NMR (DMSO-$d_6$): δ 170.8, 168.7, 145.6, 140.8, 135.3, 133.0, 127.72, 127.65, 125.2, 115.8, 110.2, 109.2, 40.8, 31.8, 29.7; MS: m/z 280 ($C_{17}H_{16}N_2O_2$, $M^{+\bullet}$).

2-(((1,3-Dioxoisoindolin-4-yl)amino)methyl)benzoic acid: GKK-008-060

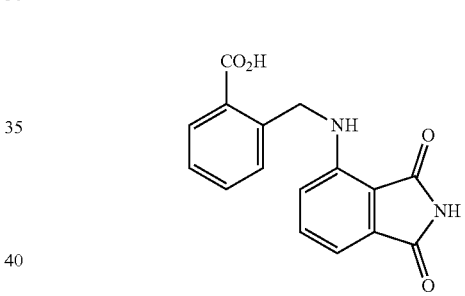

Procedure A. Yellow solid (261 mg, 88%), mp 310-312° C.; $^1$H NMR (DMSO-$d_6$): δ 11.2 (s, 1H), 7.92 (d, J=7.7 Hz, 1H), 7.88 (t, J=7.4 Hz, 1H), 7.78 (d, J=7.9 Hz, 1H), 7.76-7.68 (complex, 2H), 7.49 (d, J=8.4 Hz, 1H), 7.39 (br s, 2H), 7.27 (t, J=7.7 Hz, 1H), acid and amine protons not observed; $^{13}$C NMR (DMSO-$d_6$): δ 171.1, 169.4, 169.1, 145.8, 143.6, 136.5, 135.3, 134.0, 131.3, 127.7, 125.4, 124.1, 119.5, 114.7, 114.3, 85.6; MS: m/z 296 ($C_{16}H_{12}N_2O_4$, $M^{+\bullet}$).

Scheme 10: Synthesis of Potassium 2-(((1,3-dioxoisoindolin-4-yl)amino)methyl)benzoate: GKK-011-011.

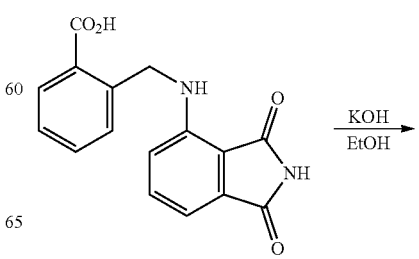

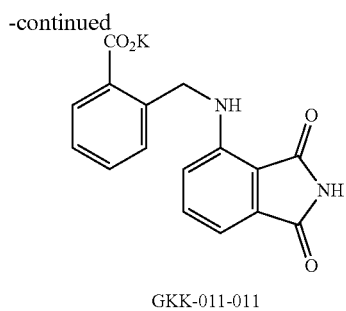

GKK-011-011

To a stirred solution of the acid (200 mg, 0.68 mmol) in ethanol (10 mL) was added KOH (76 mg, 1.36 mmol) and the mixture was stirred at 23° C. for 2 h. The solid was collected by filtration and washed with ethanol (2×2.5 mL) to afford 71 mg (31%) of the potassium carboxylate salt as a yellow solid, mp>300° C.; $^1$H NMR (DMSO-$d_6$): δ 9.24 (s, 1H), 7.95 (d, J=7.6 Hz, 1H), 7.65 (d, J=7.5 Hz, 1H), 7.41-7.33 (complex, 2H), 7.31 (t, J=7.6 Hz, 1H), 7.15 (d, J=7.1 Hz, 1H), 6.94 (d, J=7.8 Hz, 1H), benzylic and amine protons not observed; $^{13}$C NMR (DMSO-$d_6$): δ 183.8, 170.4, 165.7, 149.2, 146.0, 141.3, 134.2, 131.5, 130.2, 129.4, 127.3, 126.7, 124.8, 116.1, 106.8, 100.0.

4-(((1,3-Dioxoisoindolin-4-yl)amino)methyl)benzoic acid: GKK-008-056

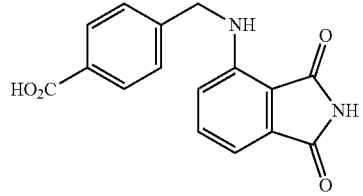 [SMILES: O=C(O)c1ccc(CNc2cccc3c2C(=O)NC3=O)cc1]

Procedure A. Yellow solid (201 mg, 68%), mp 290-291° C.; $^1$H NMR (DMSO-$d_6$): δ 12.9 (s, 1H), 11.0 (s, 1H), 7.90 (d, J=8.0 Hz, 2H), 7.46 (d, J=8.0 Hz, 2H), 7.45 (obscured, 1H), 7.25 (br t, J=6.5 Hz, 1H), 6.93 (d, J=7.1 Hz, 1H), 6.84 (d, J=8.5 Hz, 1H), 4.62 (d, J=6.5 Hz, 2H); $^{13}$C NMR (DMSO-$d_6$): δ 171.7, 169.8, 167.6, 146.2, 145.0, 136.2, 134.1, 130.04, 129.98, 127.4, 117.3, 111.8, 110.7, 45.7; MS: m/z 296 ($C_{16}H_{12}N_2O_4$, M$^{+\cdot}$)

4-((2,4-Dihydroxybenzyl)amino)isoindoline-1,3-dione: GKK-006-092

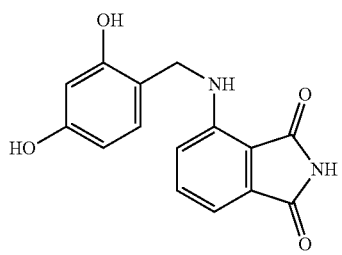

Yellow solid (71 mg, 25%), mp>300° C.; $^1$H NMR (DMSO-$d_6$): δ 10.9 (s, 1H), 9.53 (s, 1H), 9.16 (s, 1H), 7.49 (t, J=7.9 Hz, 1H), 7.04 (d, J=8.5 Hz, 1H), 6.99 (d, J=8.2 Hz, 1H), 6.90 (d, J=7.1 Hz, 1H), 6.77 (br t, J=6.1 Hz, 1H), 6.31 (d, J=2.4 Hz, 1H), 6.16 (dd, J=8.1, 2.4 Hz, 1H), 4.28 (d, J=6.1 Hz, 2H); $^{13}$C NMR (DMSO-$d_6$): δ 170.8, 168.7, 157.0, 155.5, 145.6, 135.1, 132.9, 129.1, 116.2, 114.4, 110.2, 109.2, 105.4, 101.9, 40.4; MS: m/z 284 ($C_{15}H_{12}N_2O_4$, M$^{+\cdot}$).

4-((2-Fluoro-4-hydroxybenzyl)amino)isoindoline-1,3-dione: GKK-010-096A

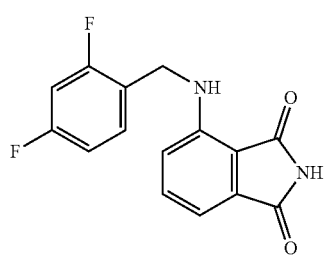 [SMILES: O=C1NC(=O)c2c(NCc3ccc(F)cc3F)cccc21]

Yellow solid (206 mg, 72%), mp 215-217° C.; $^1$H NMR (DMSO-$d_6$): δ 11.0 (s, 1H), 9.84 (s, 1H), 7.50 (t, J=7.8 Hz, 1H), 7.20 (t, J=8.6 Hz, 1H), 6.98 (d, J=8.5 Hz, 1H), 6.95 (d, J=7.0 Hz, 1H), 6.86 (br t, J=6.3 Hz, 1H), 6.58 (br s, 1H), 6.56 (s, 1H), 4.44 (d, J=6.2 Hz, 2H); $^{13}$C NMR (DMSO-$d_6$): δ 170.7, 168.7, 160.2 (d, J=244.4 Hz), 157.6 (d, J=11.1 Hz), 145.2, 135.2, 133.0, 129.5 (d, J=7.1 Hz), 116.0, 114.7 (d, J=15.2 Hz), 110.9, 110.6, 109.7, 102.0 (d, J=23.2 Hz), 38.7; MS: m/z 286 ($C_{15}H_{11}FN_2O_3$, M$^{+\cdot}$).

4-((2,4-Difluorobenzyl)amino)isoindoline-1,3-dione: GKK-010-096B

Yellow solid (216 mg, 75%), mp 178-180° C.; $^1$H NMR (DMSO-$d_6$): δ 11.0 (s, 1H), 7.49 (t, J=7.8 Hz, 1H), 7.43 (q, J=8.4 Hz, 1H), 7.25 (td, J=9.5, 2.3 Hz, 1H), 7.05 (m, 2H), 6.95 (t, J=8.1 Hz, 2H), 4.57 (d, J=6.4 Hz, 2H); $^{13}$C NMR (DMSO-$d_6$): δ 170.6, 168.6, 160.8 (dd, J=245.0, 12.2 Hz), 159.6 (dd, J=247.0, 12.3 Hz), 145.0, 135.3, 133.0, 129.6 (dd, J=9.9, 6.2 Hz), 121.4 (dd, J=15.2, 3.7 Hz), 116.0, 110.9 (dd, J=21.3, 3.4 Hz), 110.8, 109.9, 103.8 (t, J=25.7 Hz), 38.5; MS: m/z 288 ($C_{15}H_{10}F_2N_2O_2$, M$^{+\cdot}$).

Scheme 11: Synthesis of 4-((7-Hydroxychroman-2-yl)amino)isoindoline-1,3-dione: GKK-007-019

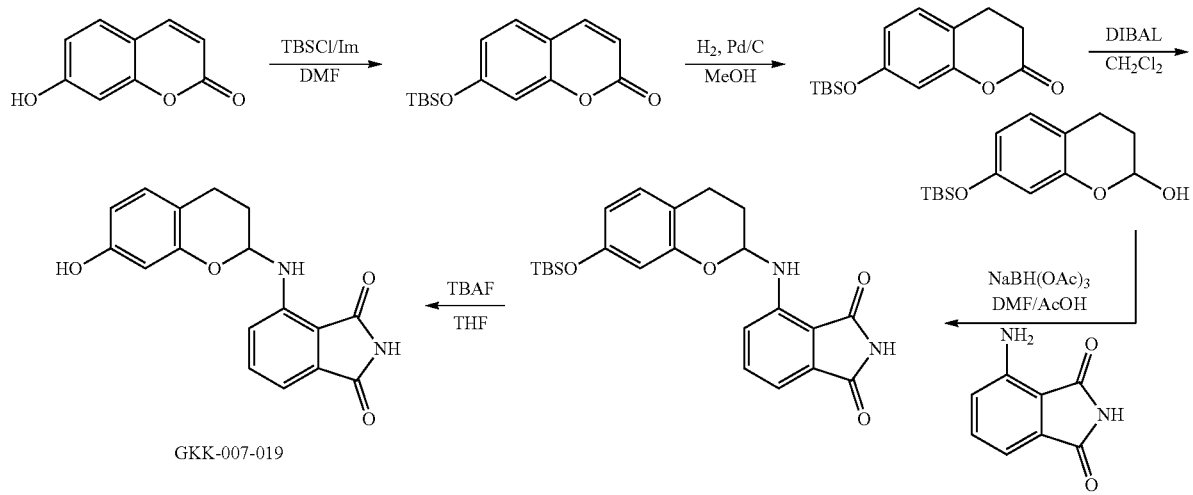

GKK-007-019

7-((tert-Butyldimethylsilyl)oxy)-2H-chromen-2-one

7-Hydroxycoumarin (1.80 g, 12.3 mmol) was silylated with TBSCl (2.08 g, 14.8 mmol) according to Procedure B to give the TBS-protected derivative (3.28 g, 11.9 mmol, 97%) as a white solid. This compound was used without further purification.

7-((tert-Butyldimethylsilyl)oxy)chroman-2-one

A solution of the TBS-protected coumarin (0.60 g, 2.17 mmol) in absolute EtOH (60 mL) was flushed twice with nitrogen and 10% Pd/C (220 mg, 50% wet, 10% w/w) was added. The reaction was stirred under hydrogen (1 atm) for 5 h. The reaction mixture was filtered through Celite® and washed with EtOH (2×25 mL). The filtrate was concentrated under vacuum to provide the 2-chromanone (0.45 g, 1.62 mmol, 74%) as a colorless oil. This compound was used in the next reaction without further purification.

7-((tert-Butyldimethylsilyl)oxy)chroman-2-ol

A solution of the (tert-butyldimethylsilyl)oxy-chromanone (1.10 g, 3.96 mmol) in $CH_2Cl_2$ (10 mL) was cooled to −78° C. and 1.5 M DIBAL-H in toluene (3.2 mL, 4.74 mmol) was added drop-wise with stirring. Stirring was continued at this temperature for 2 h or until TLC analysis indicated the complete consumption of starting material. The reaction was quenched by drop-wise addition of MeOH (10 mL), followed by 1 M HCl (20 mL). The organic layer was separated and the aqueous layer was extracted with $CH_2Cl_2$ (2×50 mL). The combined organic extracts were dried ($Na_2SO_4$) and concentrated under vacuum to provide the crude product, which was purified by column chromatography to give the 2-chromanol (475 mg, 1.70 mmol, 43%) as a colorless oil. This compound existed as a mixture of the open and closed forms and was used without further purification.

4-((7-((tert-Butyldimethylsilyl)oxy)chroman-2-yl)amino)isoindoline-1,3-dione This compound was prepared by reductive amination of 7-((tert-butyldimethylsilyl)oxy)chroman-2-ol (475 mg, 1.70 mmol) with 4-aminoisoindoline-1,3-dione according to Procedure A to afford the TBS protected 4-(7-(hydroxychroman-2-yl)amino)isoindoline-1,3-dione (240 mg, 0.57 mmol, 34%) as a yellow solid, mp 187-189° C. This compound was used in the next step without further purification.

4-((7-Hydroxychroman-2-yl)amino)isoindoline-1,3-dione: GKK-007-019

The TBS group was cleaved from the TBS-protected isoindoline-1,3-dione (230 mg, 0.54 mmol) according to Procedure C to provide 4-((7-hydroxychroman-2-yl)amino)isoindoline-1,3-dione (93 mg, 0.30 mmol, 53%) as a yellow solid, mp 228-229° C.; $^1$H NMR (DMSO-$d_6$): δ 11.1 (s, 1H), 9.18 (s, 1H), 7.64 (t, J=7.9 Hz, 1H), 7.39 (d, J=8.4 Hz, 1H), 7.13 (d, J=7.1 Hz, 1H), 7.03 (d, J=8.7 Hz, 1H), 6.91 (d, J=8.3 Hz, 1H), 6.29 (d, J=8.2 Hz, 1H), 6.09 (s, 1H), 5.74 (t, J=7.9 Hz, 1H), 2.85 (m, 1H), 2.72 (m, 1H), 2.17 (m, 1H), 2.08 (m, 1H); $^{13}$C NMR (DMSO-$d_6$): δ 171.9, 160.6, 157.1, 153.9, 144.3, 136.4, 133.7, 130.2, 119.0, 112.92, 112.85, 111.9, 108.8, 103.5, 78.6, 26.8, 22.0; MS: m/z 310 ($C_{17}H_{14}N_2O_4$, M$^{+\bullet}$).

Scheme 12: Synthesis of 4-((3,4-Dihydroxyphenethyl)amino)isoindoline-1,3-dione: GKK-007-027B.

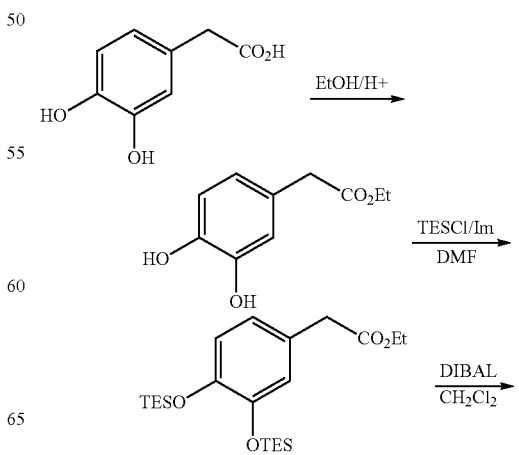

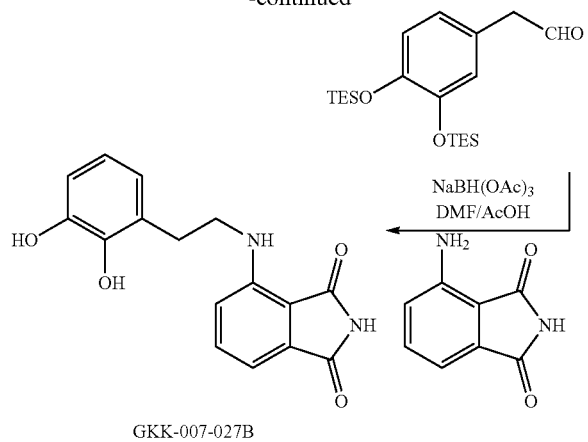

GKK-007-027B

Ethyl 2-(3,4-Dihydroxyphenyl)acetate

To a stirred solution of (3,4-dihydroxyphenyl)acetic acid (2.00 g, 11.9 mmol) in ethanol (10 mL) was added 3 drops of conc. $H_2SO_4$ and the reaction was heated at reflux for 2 h. The ethanol was removed under vacuum and the resulting residue was diluted with water and extracted with ethyl acetate (3×50 mL). The combined organic layers were washed with aqueous $NaHCO_3$ (2×50 mL) and water (50 mL), dried ($Na_2SO_4$) and evaporated under vacuum to afford the ester (2.10 g, 10.7 mmol, 90%) as a colorless oil. This compound was used without further purification.

4-((3,4-Dihydroxyphenethyl)amino)isoindoline-1,3-dione: GKK-007-027B

The hydroxyl groups in ethyl 2-(3,4-dihydroxyphenyl)acetate (2.00 g, 10.2 mmol) were silyl-protected with TESCl (3.93 g, 4.36 mL, 26.0 mmol) according to Procedure B. The crude di-TES-protected product was dissolved in $CH_2Cl_2$ (100 mL), cooled to −78° C. and 1.5 M DIBAL (9.4 mL, 14.0 mmol) in toluene was added drop-wise over a period of 30 min. Stirring was continued for 2 h or until TLC analysis indicated the complete consumption of starting material. The reaction was quenched by drop-wise addition of MeOH (10 mL), followed by 1 M HCl (20 mL). The organic layer was separated and the aqueous layer was extracted using $CH_2Cl_2$ (2×50 mL). The combined organic layers were dried ($Na_2SO_4$) and evaporated to provide the crude aldehyde. This aldehyde was subjected to reductive amination with 4-aminoisoindoline-1,3-dione according to Procedure A to afford 4-((3,4-dihydroxyphenethyl)amino)isoindoline-1,3-dione (160 mg, 0.54 mmol, 5.3% for 4 steps) as a yellow solid, mp 204-205° C. (Note: The TES groups were cleaved during the reductive amination). $^1$H NMR (DMSO-$d_6$): δ 10.9 (s, 1H), 8.74 (s, 1H), 8.69 (s, 1H), 7.53 (t, J=7.8 Hz, 1H), 7.05 (d, J=8.5 Hz, 1H), 6.93 (d, J=7.1 Hz, 1H), 6.65 (d, J=7.1 Hz, 1H), 6.64 (s, 1H), 6.52 (d, J=8.2 Hz, 1H), 6.46 (br t, J=6.5 Hz, 1H), 3.42 (q, J=6.9 Hz, 2H), 2.69 (t, J=7.3 Hz, 2H); $^{13}$C NMR (DMSO-$d_6$): δ 171.8, 169.8, 146.6, 145.6, 144.1, 136.4, 134.0, 130.1, 119.8, 117.0, 116.6, 116.0, 111.2, 110.3, 44.1, 34.6; MS: m/z 298 ($C_{16}H_{14}N_2O_4$, M$^{+\bullet}$).

Scheme 13: Synthesis of 4-((3-(4-Hydroxyphenyl)propyl)amino)isoindoline-1,3-dione: GKK-006-080 (Analog 13).

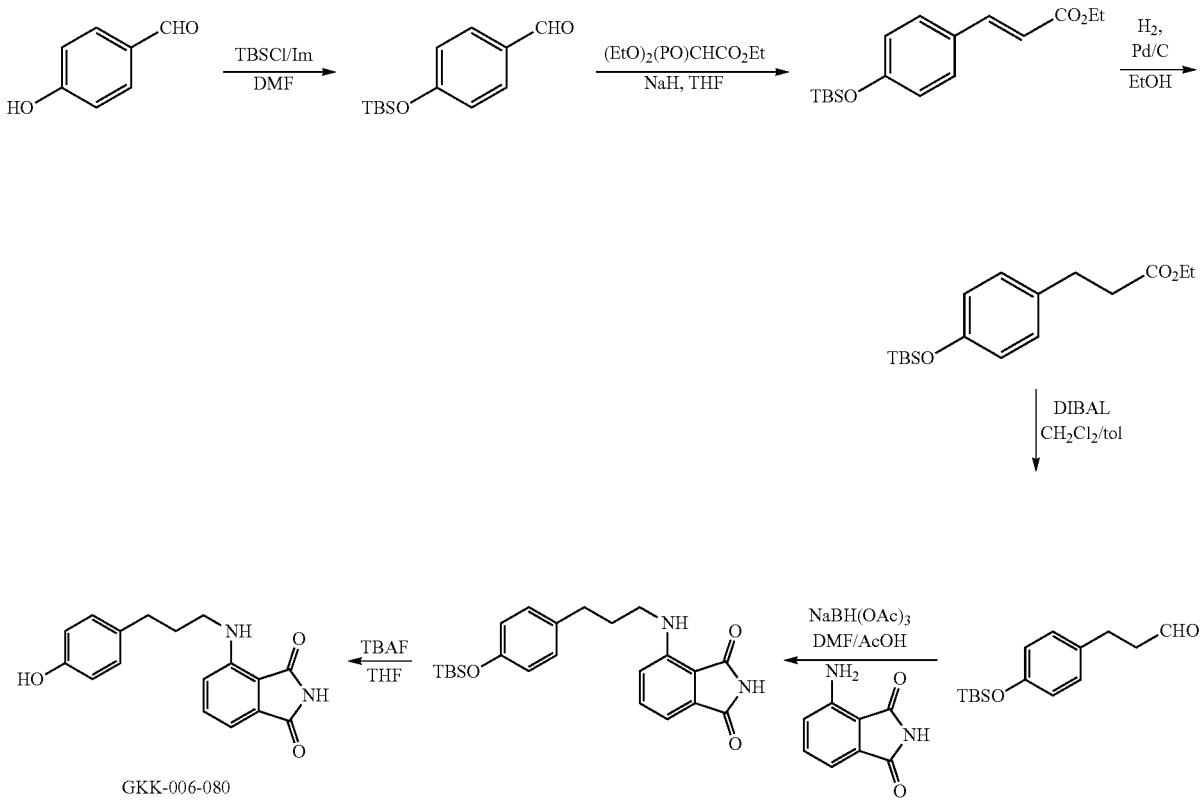

GKK-006-080

4-((tert-Butyldimethylsilyl)oxy)benzaldehyde

4-Hydroxybenzaldehyde (2.00 g, 16.4 mmol) was reacted with TBSCl (2.77 g, 19.7 mmol) according to Procedure B to give the TBS-protected 4-hydroxybenzaldehyde (2.0 g, 10.6 mmol, 65%) as a white solid. This compound was used without further purification.

Ethyl (E)-3-(4-(((tert-butyldimethylsilyl)oxy)phenyl) acrylate

To a stirred suspension of NaH (140 mg of a 60% dispersion in mineral oil, 3.50 mmol) in THF at 0° C. was added a solution of triethylphosphonoacetate (785 mg, 0.70 mL, 3.50 mmol) in THF (5.0 mL) and the reaction was stirred for 15 min. To the resulting mixture was added drop-wise TBS-protected 4-hydroxybenzaldehyde (740 mg, 3.13 mmol) in THF (5.0 mL) and the reaction was allowed to warm to 23° C. At this time, TLC analysis indicated the complete absence of starting material. The reaction was cooled to 0° C. and quenched by drop-wise addition of ice-cold water. The product was extracted into ether (2×25 mL), and the combined organic layers were washed with NaCl (15 mL), dried ($Na_2SO_4$) and evaporated to afford the acrylate (870 mg, 2.84 mmol, 91%) as a colorless oil. This compound was carried forward without further purification.

Ethyl 3-(4-((tert-butyldimethylsilyl)oxy)phenyl) propanoate

A solution of the acrylate ester (766 mg, 2.50 mmol) in ethanol (10 mL) was flushed twice with nitrogen and 5% Pd/C (10% w/w) was added. The reaction was stirred at 23° C. under $H_2$ (1 atm) for 18 h, filtered through Celite® and washed with EtOH (2×25 mL). The filtrate was concentrated to provide the propanoate ester (570 mg, 1.85 mmol, 74%) as a colorless oil. This compound was used directly in the next reaction.

4-((3-(4-Hydroxyphenyl)propyl)amino)isoindoline-1,3-dione: GKK-006-080

The above ester (500 mg, 1.62 mmol) prepared above was dissolved in $CH_2Cl_2$ (10 mL), cooled to −78° C. and a 1.5 M solution of DIBAL (1.3 mL, 1.94 mmol) in toluene was added drop-wise over a period of 30 min. Stirring was continued for 2 h or until TLC analysis indicated the complete absence of starting material. The reaction was quenched by drop-wise addition of MeOH (5 mL), followed by 1 M HCl (10 mL). The layers were separated, the aqueous layer was extracted with $CH_2Cl_2$ (2×50 mL), and the combined organic layers were dried ($Na_2SO_4$) and evaporated to provide the aldehyde as a colorless oil. This crude material was subjected to reductive amination with 4-aminoisoindoline-1,3-dione according to Procedure A, to provide the 4-((3-(4-((tert-butyldimethylsilyl)oxy)phenyl)propyl) amino)isoindoline-1,3-dione. The TBS groups were cleaved according to Procedure C to afford 4-((3-(4-hydroxyphenyl) propyl)amino)isoindoline-1,3-dione (100 mg, 0.34 mmol, 21%, 4.2% overall) as a yellow solid, mp 170-171° C. $^1$H NMR (DMSO-$d_6$): δ 10.9 (s, 1H), 9.13 (s, 1H), 7.51 (t, J=7.9 Hz, 1H), 7.00 (d, J=8.2 Hz, 2H), 6.96 (d, J=8.6 Hz, 1H), 6.92 (d, J=7.1 Hz, 1H), 6.67 (d, J=8.2 Hz, 2H), 6.50 (br t, J=6.0 Hz, 1H), 3.25 (q, J=6.8 Hz, 2H), 2.54 (t, J=7.7 Hz, 2H), 1.82 (quintet, J=7.5 Hz, 2H); $^{13}$C NMR (DMSO-$d_6$): δ 170.8, 168.7, 154.8, 145.6, 135.3, 133.0, 130.7, 128.5, 115.8, 114.5, 110.1, 109.2, 40.7, 30.9, 30.0; MS: m/z 296 ($C_{17}H_{16}N_2O_3$, M$^{+•}$).

Scheme 14: Synthesis of 4-((2-Hydroxyphenethyl)amino)isoindoline-1,3-dione: GKK-010-054.

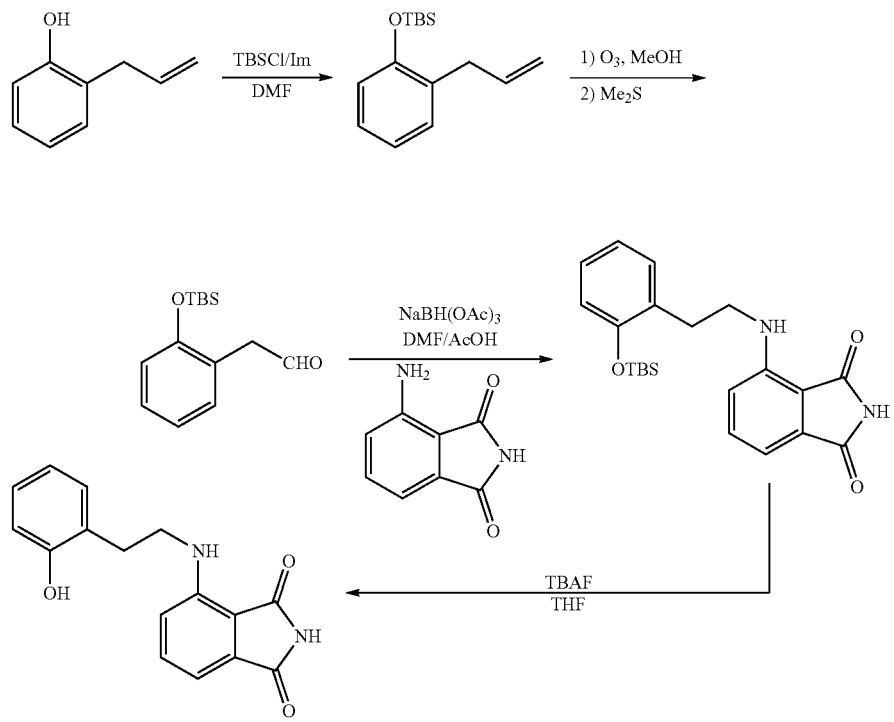

GKK-010-054

(2-Allylphenoxy)(tert-butyl)dimethylsilane

2-Allylphenol (3.00 g, 22.4 mmol) was silylated with TBSCl (3.77 g, 26.9 mmol) according to Procedure B to provide (2-allylphenoxy)(tert-butyl)dimethylsilane (4.59 g, 18.5 mmol, 83%) as a yellow oil. This compound was used without further purification.

4-((2-Hydroxyphenethyl)amino)isoindoline-1,3-dione: GKK-010-054

A stirred solution of TBS-protected 2-allylphenol (4.30 g, 17.3 mmol) in MeOH (50 mL) was treated with ozone gas over a period of 15-20 min at −78° C. When TLC analysis indicated the absence of starting material, the reaction was quenched at low temperature by drop-wise addition of Me$_2$S (1.18 g, 1.40 mL, 19.0 mmol) and then slowly warmed to 23° C. The crude reaction mixture was diluted with water (20 mL), reduced the volume to 20 mL under vacuum (<35° C. bath temperature) and the product was extracted with ether (2×75 mL). The combined organic layers were washed with NaCl (3×50 mL) and concentrated under vacuum. The residual oil was dissolved in DMF and reacted with 4-aminoisoindoline-1,3-dione according to Procedure A to provide the crude 5-((2-((tert-butyldimethylsilyl)oxy)phenethyl)amino)isoindoline-1,3-dione as a yellow solid. This yellow solid was subjected to silyl deprotection using Procedure C to afford 5-((2-hydroxy-phenethyl)amino)isoindoline-1,3-dione (71 mg, 0.25 mmol, 1.4% for 3 steps) as a yellow solid, mp 199-200° C. $^1$H NMR (DMSO-d$_6$): δ 10.9 (s, 1H), 9.50 (s, 1H), 7.53 (t, J=7.8 Hz, 1H), 7.11 (d, J=8.0 Hz, 2H), 7.03 (t, J=7.7 Hz, 1H), 6.93 (d, J=7.1 Hz, 1H), 6.81 (d, J=8.0 Hz, 1H), 6.72 (t, J=7.4 Hz, 1H), 6.60 (br t, J=5.8 Hz, 1H), 3.45 (q, J=6.9 Hz, 2H), 2.83 (t, J=7.3 Hz, 2H); $^{13}$C NMR (DMSO-d$_6$): δ 171.7, 169.8, 155.9, 146.7, 136.3, 134.0, 130.9, 127.9, 125.5, 119.5, 116.9, 115.4, 111.2, 110.3, 42.7, 30.2; MS: m/z 282 (C$_{16}$H$_{14}$N$_2$O$_3$, M$^{+\bullet}$).

Scheme 15: Synthesis of 4-((2-(Hydroxymethyl)benzyl)amino)isoindoline-1,3-dione: GKK-010-091.

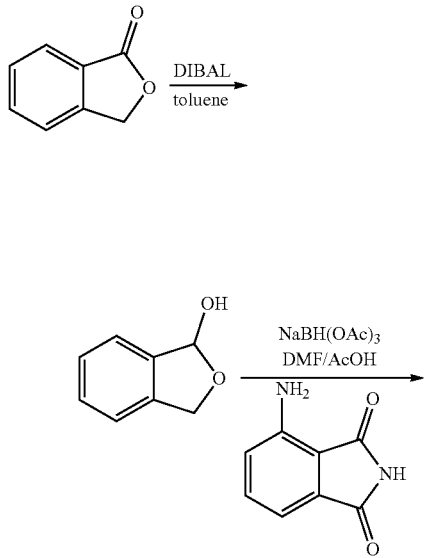

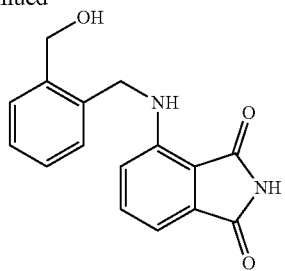

GKK-010-091

A stirred solution of isobenzofuran-1(3H)-one (2.00 g, 14.9 mmol) in toluene (30 mL) was cooled to −78° C. and 1.5 M DIBAL (13.0 mL, 22.4 mmol) in toluene (30 mL) was added drop-wise over a period of 30 min. The resulting mixture was stirred for an additional 30 min and quenched with MeOH (10 mL), followed by 1 M HCl (20 mL). The product was extracted into ether (2×50 mL) and the combined organic layers were washed with aq NaCl (50 mL), dried (Na$_2$SO$_4$) and evaporated to afford the crude lactol as a colorless oil. The lactol was subjected to reductive amination with 4-aminoisoindoline-1,3-dione according to Procedure A to afford 4-((2-(hydroxymethyl)benzyl)amino)isoindoline-1,3-dione (358 mg, 1.27 mmol, 8.5% overall) as a yellow solid, mp 198-200° C. $^1$H NMR (DMSO-d$_6$): δ 11.0 (s, 1H), 7.46 (t, J=7.7 Hz, 1H), 7.91 (d, J=7.2 Hz, 1H), 7.30-7.17 (complex, 3H), 6.98 (br t, J=6.1 Hz, 1H), 6.92 (t, J=7.4 Hz, 2H), 5.23 (t, J=5.3 Hz, 1H), 4.62 (d, J=5.4 Hz, 2H), 4.58 (d, J=6.1 Hz, 2H); $^{13}$C NMR (DMSO-d$_6$): δ 171.8, 169.8, 146.5, 140.2, 136.5, 136.2, 134.0, 128.1, 127.5, 127.3, 127.2, 117.4, 111.6, 110.6, 61.3, 43.3; MS: m/z 282 (C$_{16}$H$_{14}$N$_2$O$_3$, M$^{+\bullet}$).

Scheme 16: Synthesis of 4-(((1-(2,2,2-Trifluoroacetyl)piperidin-4-yl)methyl)amino)isoindoline-1,3-dione: GKK-008-031

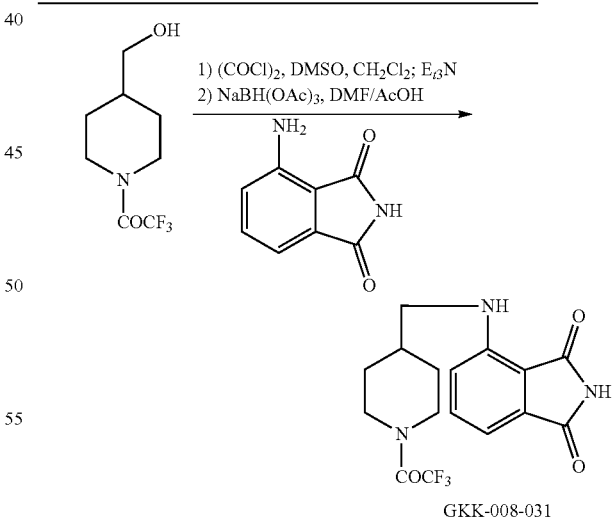

GKK-008-031

A solution of oxalyl chloride (470 mg, 0.31 mL, 3.62 mmol) in CH$_2$Cl$_2$ (20 mL) was cooled to −78° C., DMSO (510 mg, 0.46 mL, 6.54 mmol) was added drop-wise over a period of 20 min and stirring was continued for an additional 20 min. N-Trifluoroacetylpiperidinemethanol (0.38 g, 1.80 mmol) in CH$_2$Cl$_2$ (10 mL) was added over a period of 20 min, and the reaction was stirred for 30 min at −78° C. To this mixture was slowly added triethylamine (1.09 g, 1.5 mL, 10.8 mmol) over a period of 30 min. The reaction mixture was warmed to 0° C., and quenched by drop-wise addition of water (20 mL). The layers were separated, and the product was extracted into CH$_2$Cl$_2$ (2×25 mL). The combined organic extracts were washed with aq NaCl (20 mL), dried (Na$_2$SO$_4$), and evaporated under vacuum to provide the crude N-trifluoroacetylpiperidine-4-carboxaldehyde as a yellow oil. The crude aldehyde was subjected to reductive amination according to Procedure A, which gave 4-(((1-(2,2,2-trifluoroacetyl)piperidin-4-yl)methyl)amino) isoindoline-1,3-dione (135 mg, 0.38 mmol, 21% overall) as a yellow solid, mp 186-187° C. $^1$H NMR (DMSO-d$_6$): δ 11.0 (s, 1H), 7.52 (t, J=7.8 Hz, 1H), 7.09 (d, J=8.7 Hz, 1H), 6.93 (d, J=7.1 Hz, 1H), 6.61 (br t, J=6.5 Hz, 1H), 4.30 (d, J=13.8 Hz, 1H), 3.87 (d, J=13.8 Hz, 1H), 3.22 (m, 3H), 2.87 (t, J=12.1 Hz, 1H), 1.95 (m, 1H), 1.83 (t, J=11.9 Hz, 2H), 1.19 (quintet of doublets, J=12.0, 4.2 Hz, 2H); $^{13}$C NMR (DMSO-d$_6$): δ 171.9, 169.8, 154.2, 146.8, 136.3, 134.1, 117.1, 111.2, 110.3, 47.1, 45.6, 43.5, 35.3, 30.3, 29.3, CF$_3$ not observed; MS: m/z 355 (C$_{16}$H$_{16}$F$_3$N$_3$O$_3$, M$^{+•}$).

Scheme 17: Synthesis of 4-(((1-Benzylpiperidin-4-yl)methyl)amino)isoindoline-1,3-dione: GKK-008-025.

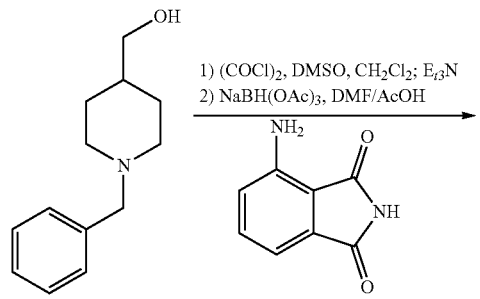

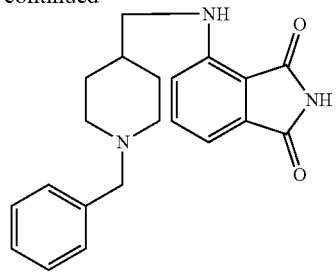

GKK-008-025

A solution of oxalyl chloride (500 mg, 0.33 mL, 3.91 mmol) in CH$_2$Cl$_2$ (20 mL) was cooled to −78° C., DMSO (550 mg, 0.50 mL, 7.08 mmol) was added drop-wise over a period of 20 min and stirring was continued for an additional 20 min. (1-Benzylpiperidin-4-yl)methanol (400 mg, 1.95 mmol) in CH$_2$Cl$_2$ (10 mL) was added over a period of 20 min, and the reaction was stirred for 30 min. To this mixture was slowly added triethylamine (1.18 g, 1.63 mL, 11.7 mmol) over a period of 30 min −78° C. The reaction was warmed to 0° C. and quenched by drop-wise addition of water (20 mL). The layers were separated and the product was extracted into CH$_2$Cl$_2$ (2×25 mL). The combined organic extracts were washed with NaCl (20 mL), dried (Na$_2$SO$_4$), and evaporated under vacuum to provide the crude 1-benzylpiperidine-4-carbaldehyde as a yellow oil. This aldehyde was subjected to reductive amination with 4-aminoisoindoline-1,3-dione according to Procedure A to afford 4-(((1-benzylpiperidin-4-yl)methyl)amino)isoindoline-1,3-dione (70 mg, 0.20 mmol, 10% overall) as a yellow solid, mp 168-169° C. $^1$H NMR (DMSO-d$_6$): δ 10.9 (s, 1H), 7.51 (t, J=7.8 Hz, 1H), 7.34-7.20 (complex, 5H), 7.04 (d, J=8.5 Hz, 1H), 6.92 (d, J=7.0 Hz, 1H), 6.52 (br t, J=6.2 Hz, 1H), 3.43 (s, 2H), 3.18 (t, J=6.5 Hz, 2H), 2.81 (d, J=11.0 Hz, 2H), 1.88 (t, J=8.7 Hz, 2H), 1.66 (d, J=11.8 Hz, 2H), 1.57 (m, 1H), 1.23 (qd, J=12.0, 3.7 Hz, 2H); $^{13}$C NMR (DMSO-d$_6$): δ 172.0, 169.8, 147.0, 139.1, 136.3, 134.0, 129.2, 128.6, 127.2, 117.1, 111.1, 110.2, 62.9, 53.4, 47.8, 35.9, 30.0; MS: m/z 349 (C$_{21}$H$_{23}$N$_3$O$_2$, M$^{+•}$).

Scheme 18: Synthesis of 4-((3-(3-Hydroxyphenyl)propyl)amino)isoindoline-1,3-dione (GKK-011-045) (Analog 16).

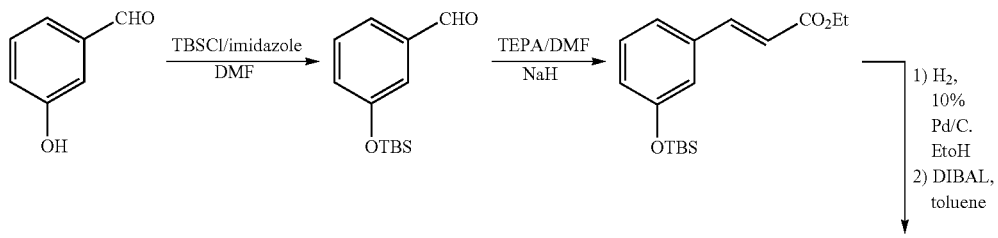

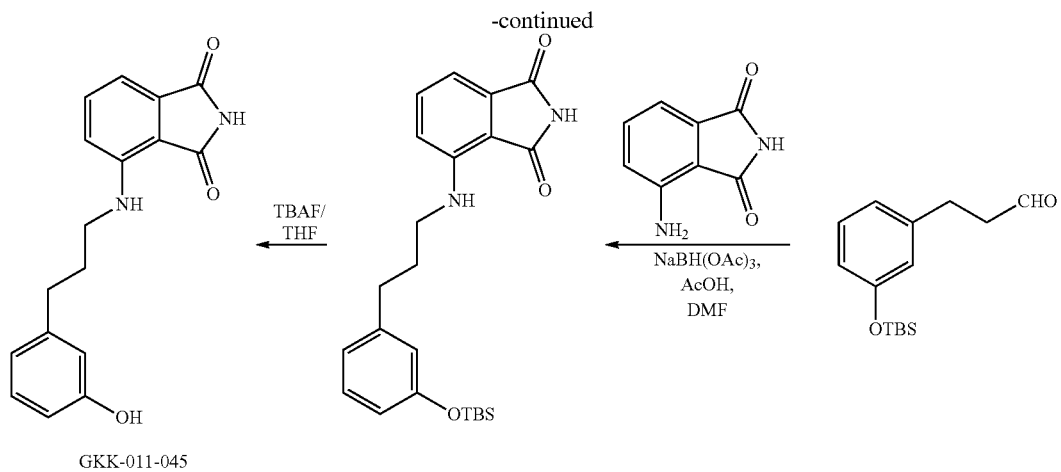

GKK-011-045

3-((tert-Butyldimethylsilyl)oxy)benzaldehyde

The silyl ether of 3-hydroxy-benzaldehyde (1.00 g, 8.20 mmol) was prepared according to Procedure B to provide the TBS-protected benzaldehyde (1.71 g, 7.2 mmol, 88%) as a white solid.

Ethyl 3-(3-((tert-butyldimethylsilyl)oxy)phenyl)propanoate

To a stirred, ice-cold solution of triethylphosphonoacetate (1.84 g, 1.63 mL, 8.1 mmol) in DMF (5.0 mL) was added 60% NaH dispersed in mineral oil (324 mg, 8.1 mmol) and the mixture was stirred for 15 min. To the resulting reaction mixture was added dropwise the TBS-protected benzaldehyde (1.60 g, 6.78 mmol) in DMF (5.0 mL) and the reaction was allowed to warm to room temperature. After TLC analysis indicated the complete consumption of the starting material, the reaction was cooled and quenched by dropwise addition of ice-cold water. The product was extracted with ether (2×25 mL) and the organic extract was washed with saturated aq NaCl (15 mL), dried ($Na_2SO_4$), filtered and evaporated to afford the unsaturated ester as a colorless oil. A solution of the ester in ethanol (20 mL) was flushed twice with nitrogen and 10% Pd/C (160 mg, 50% wet, 10% w/w) was added. The reaction was stirred at room temperature under 1 atm of hydrogen for 18 h. The reaction was filtered through Celite® and washed with ethanol (2×25 mL). The filtrate was concentrated and purified by column chromatography to provide the desired ester (1.70 g, 5.51 mmol, 81%) as a colorless oil.

4-((3-(3-Hydroxyphenyl)propyl)amino)isoindoline-1,3-dione (GKK-011-045)

The ester (1.70 g, 5.51 mmol) prepared above was dissolved in dichloromethane (17 mL), cooled to −78° C. and 1.5 M DIBAL (4.05 mL, 6.08 mmol) in toluene was added dropwise over a 30-min period. Stirring at this temperature was continued for 2 h at which time TLC analysis indicated complete conversion. The reaction was quenched by dropwise addition of methanol (5 mL), followed by 1.0 M HCl (10 mL) and the two phases were separated. The aqueous layer was extracted with dichloromethane (2×50 mL) and the combined organic layers were washed with saturated aq NaCl, dried ($MgSO_4$), filtered and concentrated under vacuum to provide the crude compound as a colorless oil. This crude aldehyde was subjected to reductive amination according to Procedure B, to provide 4-((3-(3-((tert-butyldimethylsilyl)oxy)phenyl)propyl)amino)-isoindoline-1,3-dione and this was carried on to the next step without purification. The TBS group was cleaved according to the general procedure for silyl deprotection (Procedure C) to afford the target compound (180 mg, 0.61 mmol, 11% for 3 steps) as a yellow solid, mp 176-178° C. $^1$H NMR (DMSO-$d_6$) δ 10.9 (s, 1H), 9.23 (s, 1H), 7.51 (t, J=7.8 Hz, 1H), 7.06 (t, J=7.7 Hz, 1H), 6.97 (d, J=8.5 Hz, 2H), 6.93 (d, J=7.1 Hz, 1H), 6.65-6.54 (complex, 3H), 6.52 (br t, J=6.2 Hz, 1H), 3.27 (q, J=6.7 Hz, 2H), 2.57 (t, J=7.7 Hz, 2H), 1.84 (quintet, J=7.4 Hz, 2H); $^{13}$C NMR (DMSO-$d_6$) δ 171.9, 169.8, 157.8, 146.7, 143.3, 136.3, 134.1, 129.7, 119.3, 116.9, 115.6, 113.3, 111.2, 110.3, 41.8, 32.8, 30.7; MS: m/z for $C_{17}H_{16}N_2O_3$: 296 (M$^{+\cdot}$).

Scheme 19: Synthesis of 4-((3-(2-fluoro-4-hydroxyphenyl)propyl)amino)isoindoline-1,3-dione (GKK-011-048).

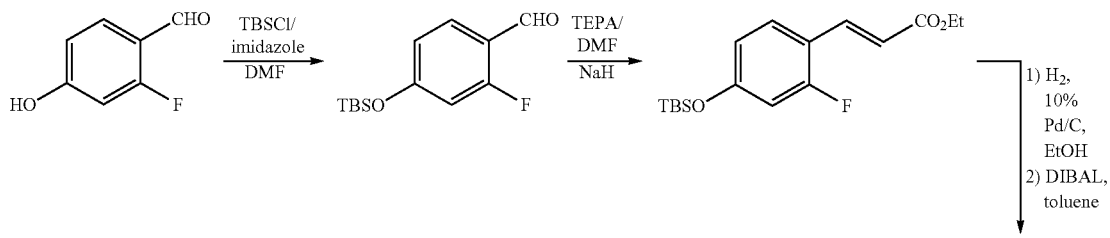

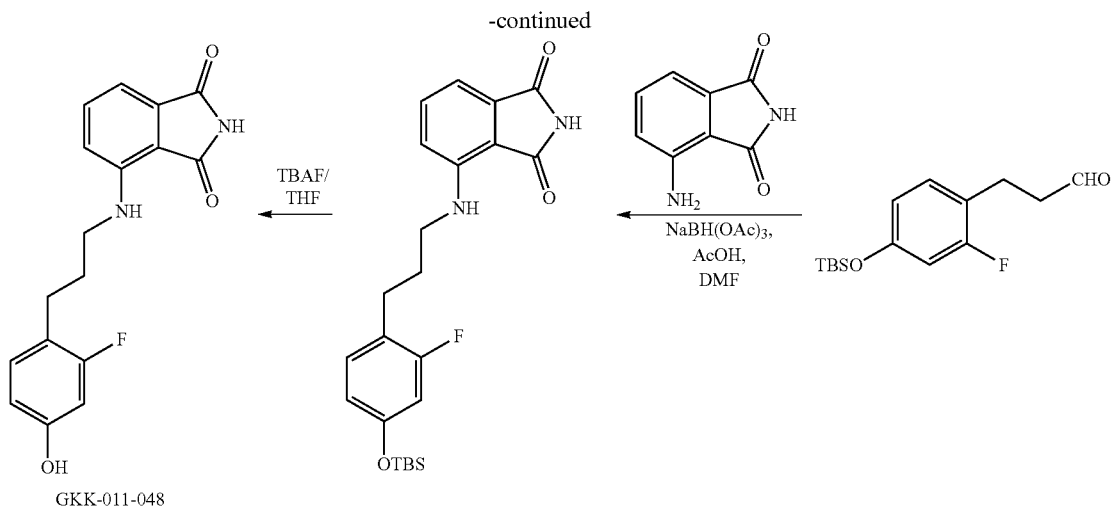

4-((tert-Butyldimethylsilyl)oxy)-2-fluorobenzaldehyde (GKK-011-037)

The silyl ether of 4-hydroxy-2-fluorobenzaldehyde (2.00 g, 14.3 mmol) was prepared according to Procedure B to provide the TBS-protected benzaldehyde (2.95 g, 11.6 mmol, 81%) as a white solid.

Ethyl 3-(4-((tert-butyldimethylsilyl)oxy)-2-fluorophenyl)propanoate (GKK-011-040)

To a stirred, ice-cold solution of triethylphosphonoacetate (2.71 g, 2.40 mL, 12.1 mmol) in DMF (5.0 mL) was added 60% NaH dispersed in mineral oil (484 mg, 12.1 mmol) and the mixture was stirred for 15 min. To the resulting reaction mixture was added dropwise the TBS-protected benzaldehyde (2.80 g, 11.0 mmol) in DMF (5.0 mL), and the reaction was warmed to room temperature. When TLC analysis indicated complete consumption of the starting material, the reaction was cooled and quenched by dropwise addition of ice-cold water. The product was extracted with ether (2×25 mL) and the combined organic extracts were washed with saturated aq NaCl (15 mL), dried (Na$_2$SO$_4$), filtered and evaporated to afford the unsaturated ester as a colorless oil. A solution of the ester in ethanol (20 mL) was flushed twice with nitrogen and 10% Pd/C (280 mg, 50% wet, 10% w/w) was added. The reaction was stirred at room temperature under 1 atm of hydrogen for 18 h. The reaction was filtered through Celite® and washed with ethanol (2×25 mL). The filtrate was concentrated and purified by column chromatography to provide the desired ester (2.33 g, 7.15 mmol, 65%) as a colorless oil.

4-((3-(2-Fluoro-4-hydroxyphenyl)propyl)amino)isoindoline-1,3-dione (GKK-011-048)

The ester (1.72 g, 5.28 mmol) prepared above was dissolved in dichloromethane (17 mL), cooled to −78° C. and 1.5 M DIBAL (3.88 mL, 5.81 mmol) in toluene was added dropwise over a 30-min period. Stirring was continued at this temperature for 2 h at which time TLC analysis indicated complete conversion. The reaction was quenched by dropwise addition of methanol (5 mL), followed by 1.0 M HCl (10 mL) and the organic layer was separated. The aqueous layer was extracted with dichloromethane (2×50 mL), and the combined organic extracts were washed with saturated aq NaCl, dried (MgSO$_4$), filtered and evaporated to provide the crude compound as a colorless oil. This crude aldehyde was subjected to reductive amination according to Procedure A, to provide the 4-((3-(4-((tert-butyldimethylsilyl)oxy)-2-fluorophenyl)propyl)amino)-isoindoline-1,3-dione and this was carried forward to the next step without purification. The TBS group was cleaved according to the general procedure for silyl deprotection (Procedure C) to afford the target compound (158 mg, 0.50 mmol, 9.5% for 3 steps) as a yellow solid, mp 182-183° C. $^1$H NMR (DMSO-d$_6$) δ 10.9 (s, 1H), 9.63 (s, 1H), 7.51 (t, J=7.8 Hz, 1H), 7.07 (t, J=8.7 Hz, 1H), 6.96 (d, J=8.5 Hz, 1H), 6.92 (d, J=7.1 Hz, 1H), 6.56-6.47 (complex, 3H), 3.27 (q, J=6.7 Hz, 2H), 2.57 (t, J=7.6 Hz, 2H), 1.80 (quintet, J=7.4 Hz, 2H); $^{13}$C NMR (DMSO-d$_6$) δ 171.9, 169.8, 161.3 (q, J=244.2 Hz), 157.0 (d, J=12.1 Hz), 146.7, 136.3, 134.1, 131.3 (d, J=7.1 Hz), 118.2 (d, J=17.2 Hz), 116.8, 111.8 (d, J=2.8 Hz), 111.2, 110.3, 102.8 (d, J=24.5 Hz), 47.8, 29.8, 25.4; MS: m/z for C$_{17}$H$_{15}$FN$_2$O$_3$: 314 (M$^{+\bullet}$).

Scheme 20: Synthesis of 4-((3-(3-Fluoro-4-hydroxyphenyl)propyl)amino)isoindoline-1,3-dione (GKK-011-054).

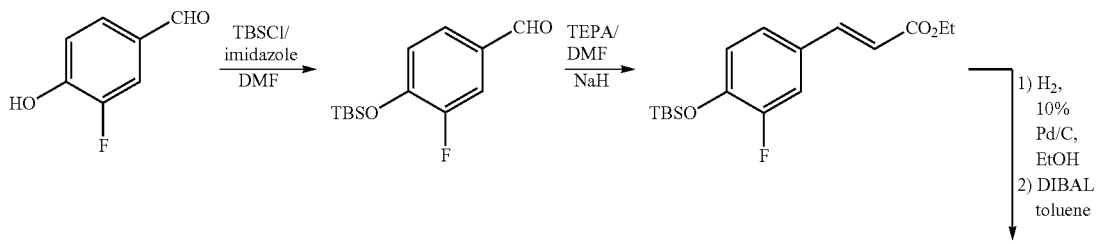

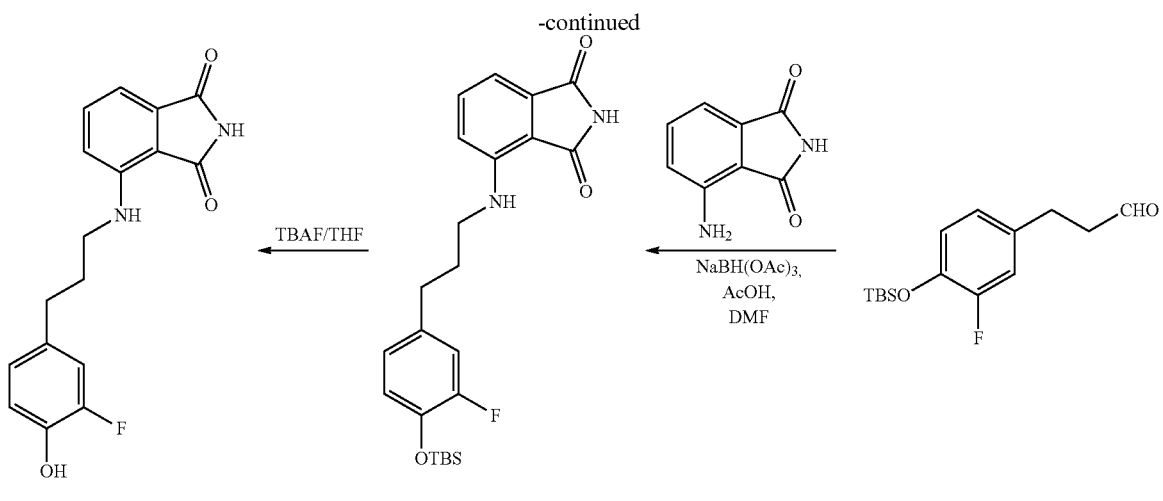

The synthesis of GKK-011-054 was carried out using the same sequence detailed above.

Ethyl 3-(4-((tert-butyldimethylsilyl)oxy)-3-fluorophenyl)propanoate

Yield: 2.60 g (7.98 mmol, 56% for 3 steps).

4-((3-(4-((tert-Butyldimethylsilyl)oxy)-3-fluorophenyl)propyl)amino)isoindoline-1,3-dione Yield: 1.16 g (2.71 mmol, 34% for 2 steps).

4-((3-(3-Fluoro-4-hydroxyphenyl)propyl)amino)isoindoline-1,3-dione (GKK-011-054)

Yield: 140 mg (0.45 mmol, 52%), mp 149-150° C. $^1$H NMR (DMSO-$d_6$) δ 10.9 (s, 1H), 9.54 (s, 1H), 7.51 (t, J=8.4 Hz, 1H), 7.03-6.95 (complex, 2H), 6.92 (d, J=7.1 Hz, 1H), 6.84 (obscured, J=8.2 Hz, 1H), 6.82 (s, 1H), 67.50 (br t, J=6.1 Hz, 1H), 3.26 (q, J=6.7 Hz, 2H), 2.36 (t, J=7.6 Hz, 2H), 1.83 (quintet, J=7.5 Hz, 2H); $^{13}$C NMR (DMSO-$d_6$) δ 171.9, 169.8, 151.3 (d, J=243.8 Hz), 146.7, 143.2 (d, J=12.1 Hz), 136.3, 134.1, 133.2 (d, J=6.1 Hz), 124.6 (d, J=4.0 Hz), 18.0 (d, J=3.0 Hz), 116.9, 116.2 (d, J=17.2 Hz), 111.2, 110.3, 41.8, 31.7, 30.7; MS: m/z for $C_{17}H_{15}FN_2O_3$: 314 (M$^{+•}$).

Scheme 21: Synthesis of 4-((3-(4-Hydroxy-2-methylphenyl)propyl)amino)isoindoline-1,3-dione (GKK-011-059).

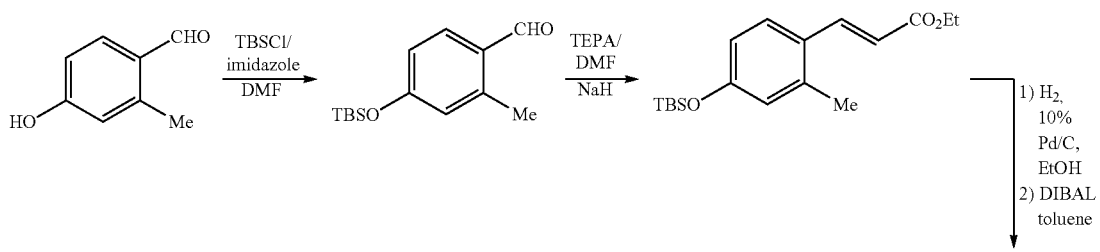

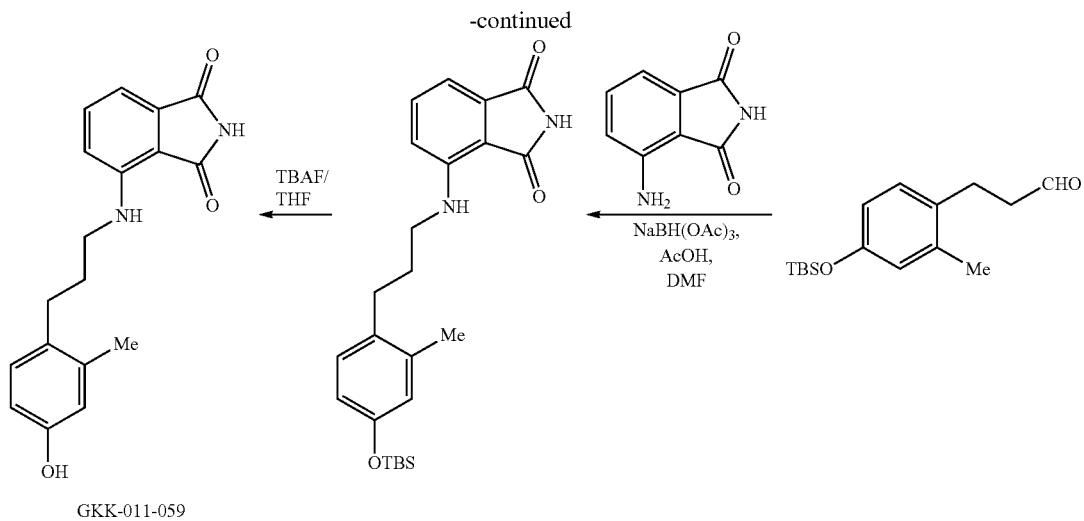

The synthesis of GKK-011-059 was carried out using the same sequence detailed above.

4-((tert-Butyldimethylsilyl)oxy)-2-methylbenzaldehyde

Yield: 2.56 g (10.2 mmol, 78%).

Ethyl 3-(4-((tert-butyldimethylsilyl)oxy)-2-methylphenyl)propanoate

Yield: 2.06 g (6.43 mmol, 67% for 2 steps).

4-((3-(4-Hydroxy-2-methylphenyl)propyl)amino)isoindoline-1,3-dione (GKK-011-059)

Yield: 198 mg (0.64 mmol, 10% for 3 steps), mp 150-152° C. $^1$H NMR (DMSO-$d_6$) δ 10.9 (s, 1H), 9.00 (s, 1H), 7.52 (t, J=7.5 Hz, 1H), 6.98 (d, J=8.5 Hz, 1H), 6.92 (d, J=7.1 Hz, 1H), 6.91 (d, J=8.2 Hz, 1H), 6.54 (s, 1H), 6.57-6.47 (complex, 2H), 3.29 (q, J=6.6 Hz, 2H), 2.53 (t, J=8.1 Hz, 2H), 2.15 (s, 3H), 1.76 (quintet, J=7.3 Hz, 2H); $^{13}$C NMR (DMSO-$d_6$) δ 171.9, 169.8, 155.7, 146.7, 136.9, 136.3, 134.1, 130.2, 129.9, 117.3, 116.9, 113.1, 111.2, 110.3, 42.0, 30.0, 29.4, 19.5; MS: m/z for $C_{18}H_{18}N_2O_3$: 310 (M$^{+\bullet}$).

Scheme 22: Synthesis of (4-((3-(4-Hydroxy-2-methoxyphenyl)pripyl)amino)isoindoline-1,3-dione (GKK-011-067) (Analog 15).

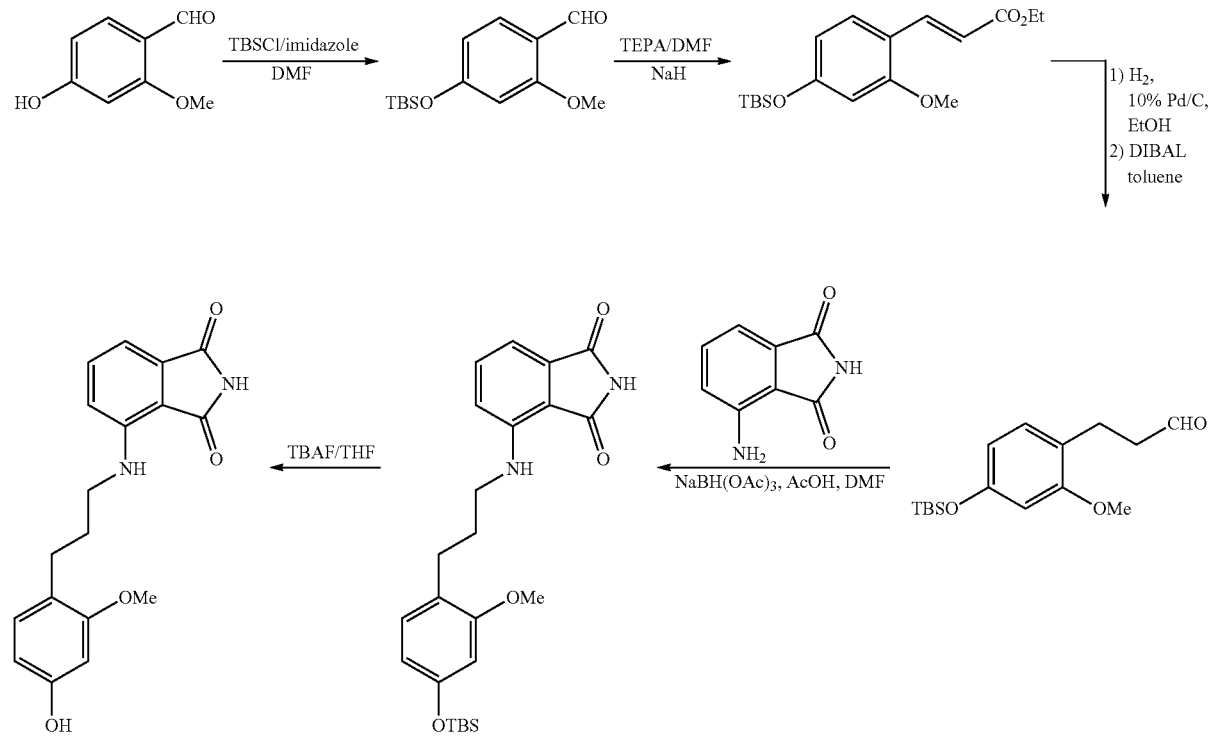

The synthesis of GKK-011-067 was carried out using the same sequence detailed above.

4-((tert-Butyldimethylsilyl)oxy)-2-methoxybenzaldehyde

Yield: 2.59 g (9.74 mmol, 74%).

Ethyl 3-(4-((tert-butyldimethylsilyl)oxy)-2-methoxyphenyl)propanoate

Yield: 1.98 g (5.86 mmol, 61% for 2 steps).

4-((3-(4-Hydroxy-2-methoxyphenyl)propyl)amino) isoindoline-1,3-dione (GKK-011-067)

Yield: 186 mg (0.57 mmol, 28% for 3 steps), mp 166-168° C. $^1$H NMR (DMSO-d$_6$) δ 10.9 (s, 1H), 9.18 (s, 1H), 7.51 (dd, J=8.5, 7.1 Hz, 1H), 6.94 (t, J=8.3 Hz, 1H), 6.92 (d, J=7.1 Hz, 1H), 6.86 (d, J=8.1 Hz, 1H), 6.53 (br t, J=6.1 Hz, 1H), 6.37 (d, J=2.3 Hz, 1H), 6.27 (dd, J=8.0, 2.3 Hz, 1H), 3.72 (s, 3H), 3.22 (q, J=6.6 Hz, 2H), 2.52 (obscured, 2H), 1.76 (quintet, J=7.2 Hz, 2H); $^{13}$C NMR (DMSO-d$_6$) δ 171.9, 169.8, 158.3, 157.3, 146.7, 136.3, 134.1, 130.3, 119.7, 116.9, 111.2, 110.2, 107.9, 99.3, 55.5, 41.7, 29.6, 26.5; MS: m/z for $C_{18}H_{18}N_2O_4$: 326 (M$^{+\bullet}$).

95-100° C. for 18 h. The reaction was cooled to room temperature, filtered through Celite®, washed the Celite® with ethyl acetate and the product was purified by column chromatography to afford 1.00 g (4.42 mmol, 92%) of a white solid.

4-((3-(2-Chloro-4-hydroxyphenyl)propyl)amino) isoindoline-1,3-dione (GKK-011-077)

The above compound (1.00 g, 4.42 mmol) dissolved in ethanol and platinum oxide (100 mg) was added. The resulting solution was stirred under 1 atm of hydrogen for 6 h and then filtered through Celite®. The filtrate was concentrated, dissolved in DMF and cooled to 0° C. Imidazole (0.45 g, 6.62 mmol) was added and the solution was stirred for 20 min. TBSCl (723 mg, 4.80 mmol) was then added and the reaction was slowly warmed to room temperature for 2 h, and poured into cold water. The product was extracted with ether (2×75 mL) and the combined organic extracts were washed with saturated aq NaCl (50 mL), dried (Na$_2$SO$_4$), filtered and concentrated under vacuum. The product was dissolved in dichloromethane (30 mL), cooled to −78° C. and 1.5 M DIBAL (3.2 mL, 4.8 mmol) in toluene was added. The reaction was stirred for 2.0 h at −78° C., and then quenched with NH$_4$Cl solution (10 mL). The layers

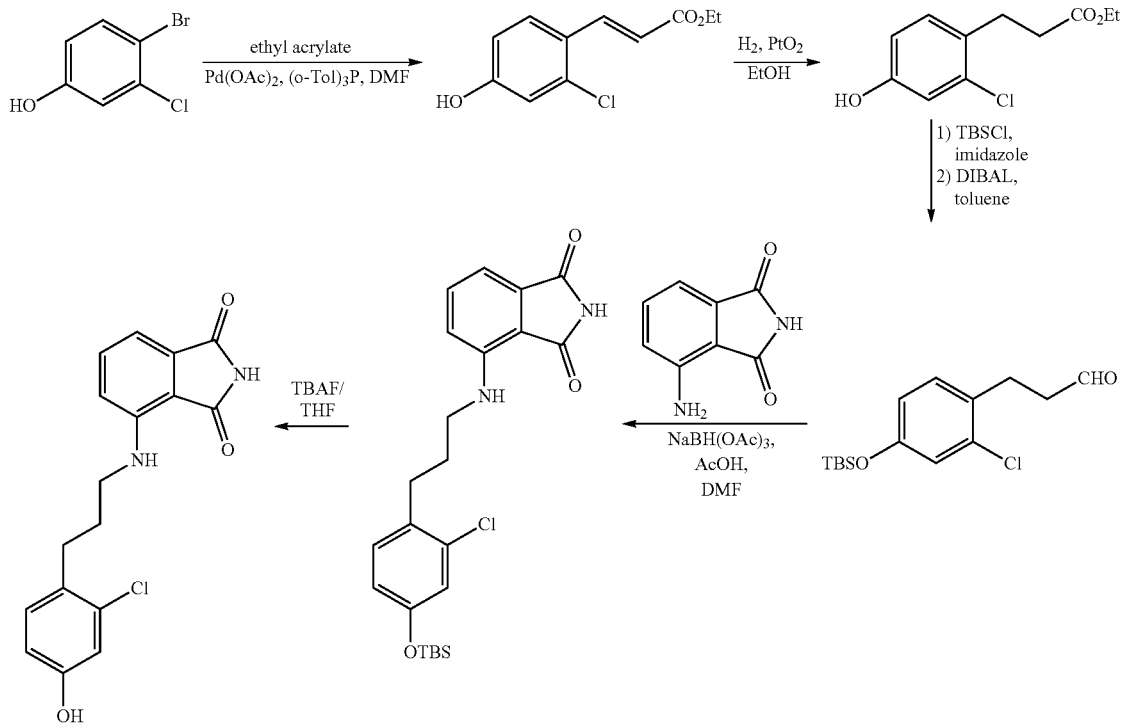

Scheme 23: Synthesis of 4-((3-(2-Chloro-4-hydroxyphenyl)propyl)amino)isoindoline-1,3-dione (GKK-011-077).

GKK-011-077

Ethyl (E)-3-(2-chloro-4-hydroxyphenyl)acrylate

To a stirred solution of 4-bromo-3-chlorophenol (1.00 g, 4.82 mmol) in DMF (1.0 mL) was added ethyl acrylate (1.00 mL, 9.20 mmol), palladium acetate (0.03 g, 0.14 mmol), tri(o-tolyl)phosphine (73 mg, 0.24 mmol), triethylamine (1.00 mL, 7.26 mmol) and the mixture was heated to were separated and the aqueous layer was extracted with dichloromethane. The combined organic layers were washed with distilled water (2×20 mL), dried (Na$_2$SO$_4$) and concentrated under vacuum to give a colorless oil. The crude aldehyde was subjected to reductive amination according to Procedure A, to provide the 4-((3-(4-((tert-butyldimethylsilyl)oxy)-2-fluorophenyl)propyl)amino)isoindoline-1,3-dione. This product was used directly in the next step without purification. The TBS group was cleaved according to the general procedure for silyl deprotection (Procedure C) to afford the target compound (230 mg, 0.70 mmol, 12% for 3 steps) as a yellow solid, mp 182-184° C. $^1$H NMR (DMSO-$d_6$) δ 10.9 (s, 1H), 9.66 (s, 1H), 7.52 (t, J=7.2 Hz, 1H), 7.14 (d, J=8.3 Hz, 1H), 6.98 (d, J=8.5 Hz, 1H), 6.93 (d, J=7.2 Hz, 1H), 6.80 (d, J=2.6 Hz, 1H), 6.68 (dd, J=8.3, 2.6 Hz, 1H), 6.55 (br t, J=6.1 Hz, 1H), 3.30 (q, J=6.6 Hz, 2H), 2.66 (t, J=7.8 Hz, 2H), 1.82 (quintet, J=7.5 Hz, 2H); $^{13}$C NMR (DMSO-$d_6$) δ 171.9, 169.8, 156.9, 146.7, 136.3, 134.1, 133.3, 131.5, 129.2, 116.9, 116.2, 115.0, 111.3, 110.3, 41.8, 29.7, 29.6; MS: m/z for $C_{17}H_{15}ClN_2O_3$: 330 ($M^{+\bullet}$).

Scheme 24: Synthesis of 4,7-Diaminoisoindoline-1,3-dione (GKK-011-016).

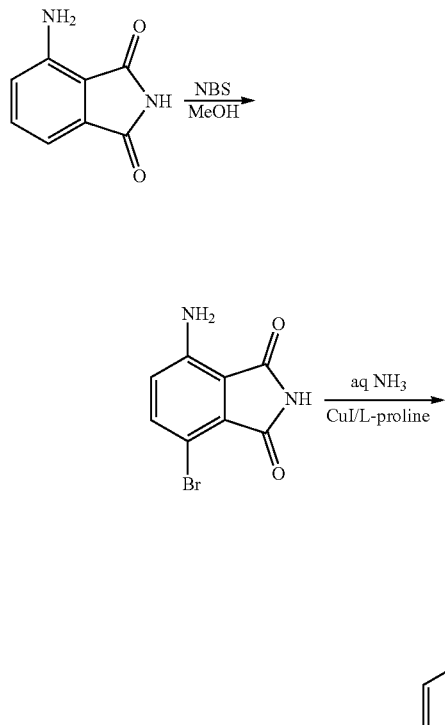

4-Amino-7-bromisoindoline-1,3-dione

4-Aminoisoindoline-1,3-dione (2.00 g, 12.3 mmol) was dissolved in MeOH (200 mL), and the solution was treated with N-bromosuccinimide (2.19 g, 12.3 mmol). The reaction was stirred at room temperature for 50 min. The solid obtained was collected by filtration and washed with MeOH to give 4-amino-7-bromoisoindoline-1,3-dione (2.21 g, 9.21 mmol, 75%) as a yellow powder, mp 287-289° C. $^1$H NMR: δ 11.1 (s, 1H), 7.51 (d, J=8.9 Hz, 1H), 6.90 (d, J=8.9 Hz, 1H), 6.53 (br s, 2H); $^{13}$C NMR: δ 170.0, 167.7, 146.5, 139.6, 130.2, 123.6, 112.4, 101.6; MS: m/z 240 ($C_8H_5{}^{79}BrN_2O_2$, $M^{+\bullet}$).

4,7-Diaminoisoindoline-1,3-dione (GKK-011-016)

A clean, dried 250-mL Chemglass pressure Vessel® (CG-1880-R-03) was charged with 4-amino-7-bromoisoindoline-1,3-dione (1.00 g, 4.17 mmol), copper iodide (80 mg, 10 mol %), L-proline (100 mg, 0.86 mmol) and aq $NH_3$ (5 mL). The reaction vessel was closed and heated to 110° C. for 3 h. The reaction was cooled to 23° C., filtered, and the resulting solid was loaded onto a column packed with silica gel and eluted with 1:1 hexanes:ethyl acetate. The product fractions were concentrated under vacuum to provide the diamine (300 mg, 1.69 mmol, 41%) as a red solid, mp 294-296° C. $^1$H NMR (DMSO-$d_6$): δ 10.5 (s, 1H), 6.82 (s, 2H), 5.75 (s, 4H); $^{13}$C NMR (DMSO-$d_6$): δ 170.8, 138.5, 125.6, 108.8; MS: m/z 177 ($C_8H_7N_3O_2$, $M^{+\bullet}$).

4,7-Diaminoisoindoline-1,3-dione Series

Scheme 25: Synthesis of 2-(((7-Amino-1,3-dioxoisoindolin-4-yl)amino)methyl)benzonic acid (GKK-008-080).

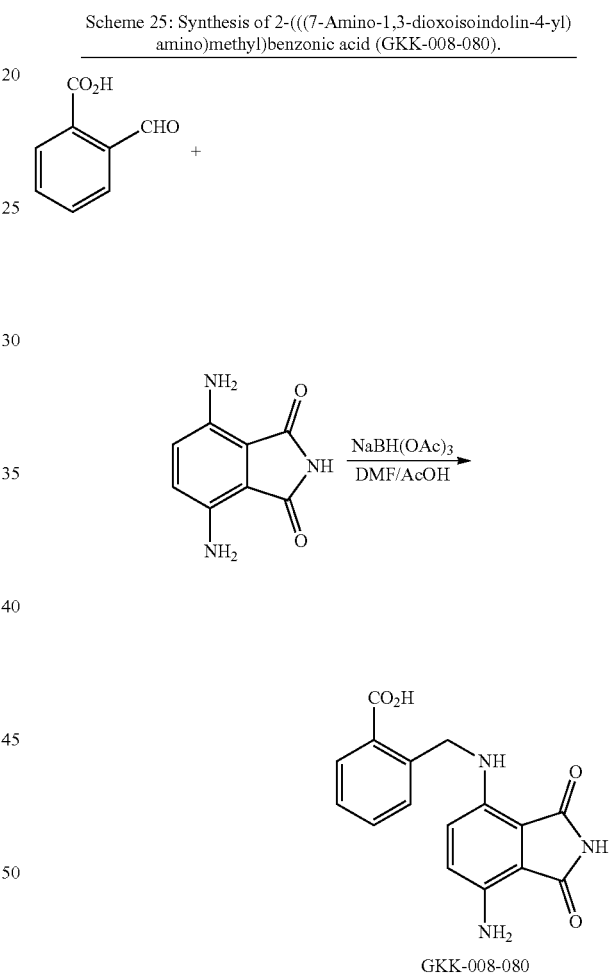

The reductive amination, using 4,7-diaminoisoindoline-1,3-dione (177 mg, 1.00 mmol), was performed according to Procedure A to give the mono-reductive amination product (124 mg, 0.40 mmol, 40%) as a yellow solid, mp 279-281° C. $^1$H NMR (DMSO-$d_6$): δ 11.4 (s, 1H), 7.92 (d, J=7.9 Hz, 1H), 7.88 (t, J=7.5 Hz, 1H), 7.80-7.67 (complex, 3H), 7.53-7.45 (complex, 2H), 7.35 (apparent d, J=10.1 Hz, 1H), acid, amine, and benzylic protons not observed; $^{13}$C NMR (DMSO-$d_6$): δ 168.7, 167.9, 165.9, 144.6, 141.6, 136.5, 134.2, 130.2, 127.7, 126.6, 124.4, 122.3, 120.2, 118.3, 115.1, 84.7; MS: m/z 311 ($C_{16}H_{13}N_3O_4$, $M^{+\bullet}$).

Scheme 26: Synthesis of 4-Amino-7-((2-hydroxybenzyl)amino)isoindoline-1,3-dione (GKK-011-023F2) and 4,7-bis((2-hydroxybenzyl)amino)isoindoline-1,3-dione (GKK-011-023F1).

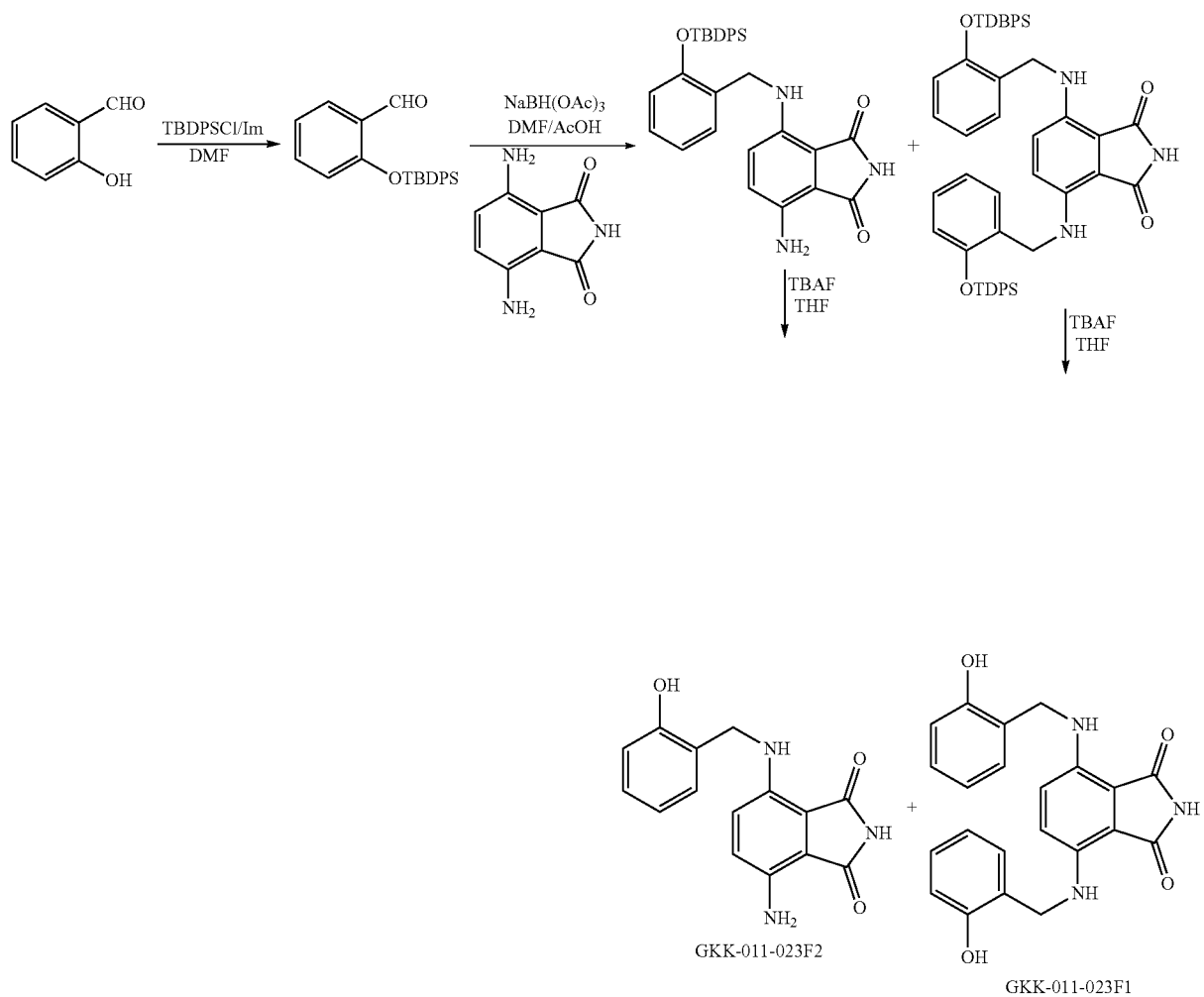

2-((tert-Butyldiphenylsilyl)oxy)benzaldehyde

This compound was prepared from salicylaldehyde (1.22 g, 10.0 mmol) and TBDPSCl (3.29 g, 12.0 mmol) according to Procedure B to provide the TBDPS-protected salicylaldehyde (1.80 g, 6.5 mmol, 65%) as a white solid. This compound was used without further purification.

4,7-Bis((2-hydroxybenzyl)amino)isoindoline-1,3-dione (GKK-011-023F1) and 4-amino-7-((2-hydroxybenzyl)amino)isoindoline-1,3-dione (GKK-011-023F2)

The reductive amination of 4,7-diaminoisoindoline-1,3-dione (0.40 g, 2.26 mmol) with 2-((tert-butyldiphenylsilyl)oxy)-benzaldehyde (1.60 g, 4.44 mmol) was performed using Procedure A to give a mixture of the mono- and dibenzylamino compounds. The TBDPS groups in these compounds were cleaved using Procedure C and isolated by column chromatography using increasing concentrations of ethyl acetate in hexanes. F1: 120 mg (0.31 mmol, 6.9%) as a red solid; mp 237-239° C.; F2: 205 mg (0.72 mmol, 16%) as a red solid, mp 200-203° C. The spectral data for F1 were: $^1$H NMR (DMSO-$d_6$): δ 10.7 (s, 1H), 9.65 (s, 2H), 7.16 (d, J=7.2 Hz, 2H), 7.05 (td, J=7.6, 1.9 Hz, 2H), 6.96 (s, 2H), 6.81 (d, J=8.0 Hz, 2H), 6.71 (t, J=7.4 Hz, 2H), 6.41 (t, J=6.4 Hz, 2H), 4.33 (d, J=6.4 Hz, 4H); $^{13}$C NMR (DMSO-$d_6$): δ 170.9, 155.6, 138.8, 129.1, 128.5, 125.7, 121.5, 119.3, 113.3, 110.3, 42.0; MS: m/z 389 ($C_{22}H_{19}N_3O_4$, M$^{+\bullet}$). The spectral data for F2 were: $^1$H NMR (DMSO-$d_6$): δ 10.6 (s, 1H), 9.64 (s, 1H), 7.17 (d, J=7.3 Hz, 1H), 7.06 (t, J=7.7 Hz, 1H), 6.95 (d, J=9.3 Hz, 1H), 6.87 (d, J=9.0 Hz, 1H), 6.82 (d, J=7.7 Hz, 1H), 6.73 (t, J=7.4 Hz, 1H), 6.42 (br t, J=6.0 Hz, 1H), 5.72 (s, 2H), 4.34 (d, J=6.1 Hz, 2H) $^{13}$C NMR (DMSO-$d_6$): δ 171.0, 170.7, 155.6, 139.3, 138.5, 129.1, 128.5, 125.8, 125.7, 121.52, 121.46, 119.3, 115.5, 109.6, 42.0; MS: m/z 283 ($C_{15}H_{13}N_3O_3$, M$^{+\bullet}$).

Scheme 27: Synthesis of 2,3-Dibutyl-5-((2-hydroxybenzyl)amino)-2,3-dihydrophthalazine-1,4-dione (GKK-011-022).

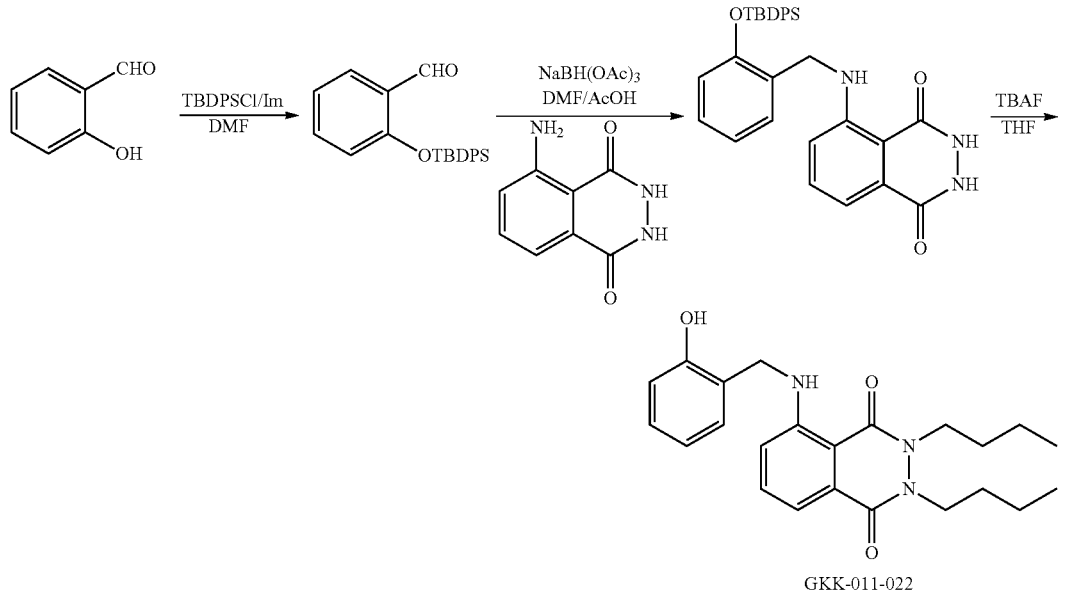

GKK-011-022

The TBDPS-protected salicylaldehyde (2.00 g, 5.55 mmol) was treated with luminol (0.50 g, 2.82 mmol) as per Procedure A to provide the crude 5-((2-((tert-butyldiphenyl-silyl)oxy)benzyl)-amino)-2,3-dihydrophthalazine-1,4-dione. This material was dissolved in 10 mL of THF and treated with 1.0 M solution of TBAF in THF (0.74 mL, 0.74 mmol) under nitrogen atmosphere for 4 h. The precipitate was collected and the filter cake was washed with water and dried under vacuum to afford the title compound (105 mg, 0.27 mmol, 9.4% overall) as a white solid, mp 193-194° C. $^1$H NMR (DMSO-$d_6$): δ 9.97 (br s, 1H), 7.37 (t, J=8.0 Hz, 1H), 7.18 (d, J=7.5 Hz, 1H), 7.04 (apparent t, J=6.5 Hz, 2H), 6.88 (d, J=7.7 Hz, 1H), 6.70 (t, J=7.4 Hz, 1H), 6.65 (d, J=8.2 Hz, 1H), 4.30 (s, 2H), 3.14 (t, J=7.8 Hz, 4H), 1.56 (quintet, J=7.8 Hz, 4H), 1.30 (sextet, J=7.3 Hz, 4H), 0.93 (t, J=7.3 Hz, 6H), amine proton not observed; $^{13}$C NMR (DMSO-$d_6$): δ 161.7, 156.1, 150.3, 133.3, 128.5, 128.2, 125.3, 118.9, 115.6, 112.9, 110.6, 110.4, 58.0, 41.5, 23.5, 19.7, 14.0; MS: m/z 395 ($C_{23}H_{29}N_3O_3$, $M^{+\cdot}$).

Scheme 28: Synthesis of 4-((5-Chloro-2-hydroxybenzyl)amino) isoindoline-1,3-dione (KM-5-25)

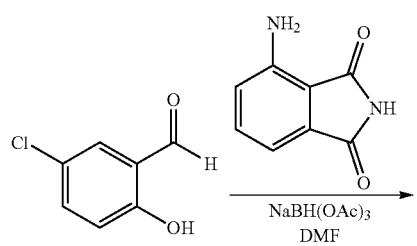

-continued

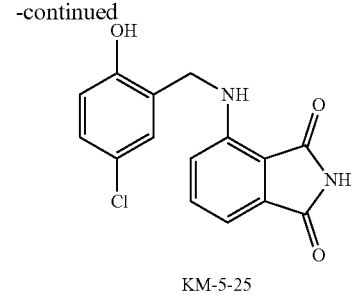

KM-5-25

4-((5-Chloro-2-hydroxybenzyl)amino)isoindoline-1, 3-dione (KM-5-25)

To a solution of 5-chlorosalicylicaldehyde (0.52 g, 3.34 mmol) in DMF (1.5 mL) under $N_2$ was added AcOH (0.8 mL) and the solution was stirred for 10 min. To this reaction mixture was added 3-aminophthalimide (0.27 g, 1.67 mmol) and stirring was continued at 23° C. for 1 h. An additional 1 mL of DMF was added bringing the volume to 3.3 mL. The reaction was heated to 90° C. for 2 h and then cooled to room temperature. NaBH(OAc)$_3$ (1.1 g, 5.01 mmol) was added portion-wise to the reaction at 0° C. and stirring was continued at this temperature for 30 min. The reaction was then gradually warmed to 23° C. and stirred for 18 h. The crude reaction mixture was poured into deionized water, extracted with EtOAc (3×75 mL) and the combined organic layers were washed with NaHCO$_3$ (2×50 mL) and NaCl (50 mL). The organic layer was dried (Na$_2$SO$_4$) and concentrated under vacuum. The residue was dissolved in 1 mL of EtOH and the solution was heated at 50° C. for 10 min under $N_2$. The resulting solid was filtered and washed with EtOH (2×10 mL). The filtrate was concentrated under vacuum and subjected to chromatography (using silica gel pre-treated with 3-hydroxy-2-methyl-4-pyrone) eluted with 20% EtOAc/hexane to afford 298 mg (29%) of the isoindoline- 1,3-dione as a yellow solid, mp 229-230° C. $^1$H NMR (400 MHz, DMSO-d$_6$): δ 11.0 (s, 1H), 10.1 (s, 1H), 7.49 (dd, J=8.2, 7.4 Hz, 1H), 7.22 (d, J=2.6 Hz, 1H), 7.12 (dd, J=8.6, 2.6 Hz, 1H), 7.07 (t, J=6.5 Hz, 1H), 6.96 (d, J=8.6 Hz, 1H), 6.93 (d, J=7.0 Hz, 1H), 6.84 (d, J=8.6 Hz, 1H), 4.42 (d, J=6.4 Hz, 2H); $^{13}$C NMR (101 MHz, DMSO-d$_6$): δ 171.3, 169.3, 154.1, 145.9, 135.9, 133.6, 127.8, 127.7, 127.0, 122.4, 116.6, 111.3, 111.2, 110.2, 40.6.

The following compounds can also be prepared by the above procedure using the appropriately substituted benzaldehyde.

4-((5-Bromo-2-hydroxybenzyl)amino)isoindoline-1,3-dione (KM-5-35)

Yield 335 mg (28%) as a yellow solid, mp 219-220° C.; $^1$H NMR (400 MHz, DMSO-d$_6$): δ 11.0 (s, 1H), 10.1 (s, 1H), 7.49 (t, J=8.0 Hz, 1H), 7.35 (d, J=2.5 Hz, 1H), 7.23 (dd, J=8.6, 2.5 Hz, 1H), 7.06 (t, J=6.4 Hz, 1H), 6.96 (d, J=8.6 Hz, 1H), 6.93 (d, J=7.1 Hz, 1H), 6.79 (d, J=8.6 Hz, 1H), 4.41 (d, J=6.4 Hz, 2H); $^{13}$C NMR (101 MHz, DMSO-d$_6$): δ 171.8, 169.8, 155.0, 146.4, 136.3, 134.1, 131.1, 128.1, 117.7, 117.1, 111.7, 110.6, 110.5, 41.1 (one aromatic carbon not observed).

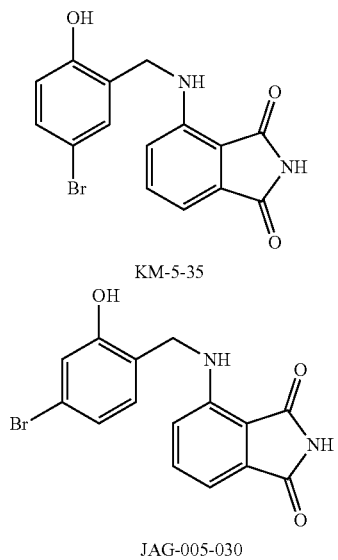

KM-5-35

4-((4-Bromo-2-hydroxybenzyl)amino)isoindoline-1,3-dione (JAG-005-030)

Yield 318 mg (28%) as a yellow solid, mp 226-227° C. $^1$H NMR (400 MHz, DMSO-d$_6$): δ 11.0 (s, 1H), 10.3 (s, 1H), 7.48 (dd, J=8.5, 7.1 Hz, 1H), 7.14 (d, J=8.1 Hz, 1H), 7.01 (t, J=6.4 Hz, 1H), 7.00 (d, J=2.0 Hz, 1H), 6.93 (m, 3H), 6.79 (d, J=8.6 Hz, 1H), 4.40 (d, J=6.4 Hz, 2H); $^{13}$C NMR (101 MHz, DMSO-d$_6$): δ 171.8, 169.8, 156.8, 146.4, 136.3, 134.1, 130.6, 124.9, 122.1, 120.6, 118.1, 117.2, 111.7, 110.6, 41.1

JAG-005-030

Scheme 29: Synthesis of 4-((3-(5-Fluoro-2-hydroxphenyl)propyl)amino)isoindoline-1,3-dione (JAG-005-006)

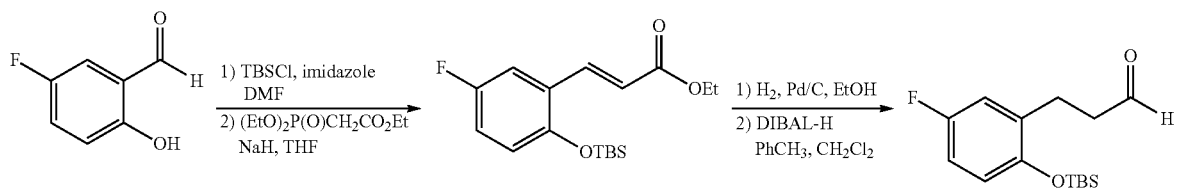

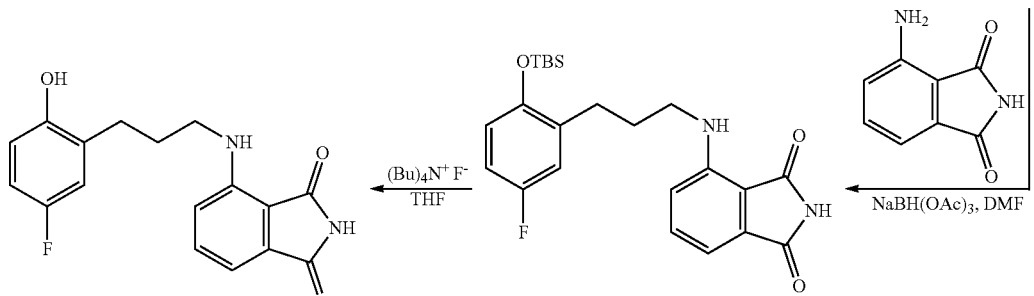

JAG-005-006 tert-Butyldimethylsilyl (TBS) Ether Protection

2-((tert-Butyldimethylsilyl)oxy)-5-fluorobenzaldehyde

A stirred solution of 5-fluoro-2-hydroxybenzaldehyde (1.21 g, 8.65 mmol) in DMF (10 mL) was cooled to 0° C. under $N_2$ and imidazole (1.18 g, 17.3 mmol) was added. The resulting solution was stirred for 20 min and tert-butyldimethylsilyl chloride (1.96 g, 12.98 mmol) was added as a solution in DMF (10 mL) was added dropwise over a period of 15 min. The reaction mixture was warmed to 23° C. and stirred until TLC (5% $Et_2O$/hexane) indicated the complete conversion of the phenolic compound. The crude reaction was poured into water (50 mL), extracted with ether (3×40 mL), and the combined organic layers were washed with satd NaCl (50 mL). The combined organic layers were dried ($Na_2SO_4$), concentrated under vacuum and the crude product was purified by column chromatography to afford the 2-((tert-butyldimethylsilyl)oxy)-5-fluorobenzaldehyde (2.01 g, 91%) as a colorless oil.

Horner Wadsworth-Emmons Reaction

Ethyl (E)-3-(2-((tert-butyldimethylsilyl)oxy)-5-fluorophenyl)acrylate

To a stirred, ice-cold solution of triethyl phosphonoacetate (2.05 g, 1.83 mL, 9.16 mmol) under $N_2$ in THF (5.0 mL) was added 60% NaH dispersed in mineral oil (367 mg, 9.16 mmol) and the mixture was stirred for 15 min. To the resulting tan solution was added drop-wise 2-((tert-butyldimethylsilyl)oxy)-5-fluorobenzaldehyde (1.96 g, 7.70 mmol) in THF (15 mL) and the stirred reaction was allowed warmed to 23° C. After TLC (5% ether/hexane) indicated the complete consumption of starting material, the reaction was cooled and quenched by drop-wise addition of ice-cold water. The product was extracted into ether (2×25 mL), and the organic layer was washed with satd NaCl (15 mL), dried ($Na_2SO_4$) and evaporated to afford the acrylate (2.25 g, 90%) as colorless oil. This compound was carried forward without further purification.

Hydrogenation Reaction

Ethyl 3-(2-((tert-butyldimethylsilyl)oxy)-5-fluorophenyl)propanoate

A solution of ethyl (E)-3-(2-((tert-butyldimethylsilyl)oxy)-5-fluorophenyl)acrylate (2.23 g, 6.87 mmol) in absolute EtOH (15 mL) was flushed twice with nitrogen and 10% $PtO_2$ (223 mg) was added. The reaction was stirred at room temperature under $H_2$ (1 atm) for 12 h until TLC (5% ether/hexane) indicated complete reaction. The crude reaction mixture was filtered through Celite© and washed with EtOH (2×40 mL). The filtrate was concentrated under vacuum and subjected to silica gel column chromatography to afford the ethyl 3-(2-((tert-butyldimethylsilyl)oxy)-5-fluorophenyl)propanoate (2.03 g, 91%) as a colorless oil.

DIBAL-H Ester Reduction

3-(2-((tert-Butyldimethylsilyl)oxy)-5-fluorophenyl)propanal

The ethyl 3-(2-((tert-butyl-dimethylsilyl)oxy)-5-fluorophenyl)propanoate (1.03 g, 3.17 mmol) prepared above was dissolved in dichloromethane (10 mL), cooled to −78° C. under $N_2$ and the solution was treated with the drop-wise addition of 1.5 M DIBAL-H in toluene (2.11 mL, 3.17 mmol) over a period of 30 min. Stirring was continued for 2 h at −78° C. until TLC (5% ether/hexane) indicated the complete absence of starting material. The reaction was quenched by drop-wise addition of methanol (10 mL), followed by addition of 1 M HCl (15 mL). The organic layer was separated, and the aqueous layer was further extracted with dichloromethane (2×50 mL). The combined organic layers were washed with satd NaCl and dried ($Na_2SO_4$). Removal of the solvent under reduced pressure afforded the 3-(2-((tert-butyldimethylsilyl)oxy)-5-fluorophenyl)propanal (0.76 g, 85%) as a colorless oil.

Reductive Amination Procedure

4-((3-(2-((tert-Butyldimethylsilyl)oxy)-5-fluorophenyl)propyl)amino)isoindoline-1,3-dione To a solution of 3-(2-((tert-butyldimethylsilyl)oxy)-5-fluorophenyl)propanal (1.16 g, 4.11 mmol) in DMF (1.2 mL) was added AcOH (0.8 mL) and the solution was stirred under $N_2$ for 10 min at room temperature. To this mixture, 3-aminophthalimide (0.33 g, 2.05 mmol) was added and stirring was continued at 23° C. for 1 h. An additional 1 mL of DMF was added to bring the volume to 3.0 mL. The reaction was cooled to 0° C. and $NaBH(OAc)_3$ (1.31 g, 6.16 mmol) was added portion-wise to the reaction over 25 min. The reaction was further stirred at this temperature for 30 min, and then gradually warmed to 23° C. Stirring was continued for 18 h until TLC (5-20% EtOAc/hexane) indicated complete conversion of the aldehyde. The crude reaction mixture was poured into deionized water, extracted with EtOAc (3×75 mL) and the combined organic layers were washed with $NaHCO_3$ (2×50 mL) followed by NaCl (50 mL). The organic layer was dried ($Na_2SO_4$) and concentrated under vacuum. The residue was dissolved in 1 mL of EtOH and the solution was heated at 50° C. for 10 min under $N_2$. The resulting solid was filtered and washed with EtOH (2×10 mL) and the filtrate was concentrated under vacuum. The crude product was subjected to column chromatography (using silica gel pre-treated with 3-hydroxy-2-methyl-4-pyrone) and eluted with 20% EtOAc/hexane to afford 444 mg (19%) of 4-((3-(2-((tert-butyldimethylsilyl)oxy)-5-fluorophenyl)propyl)amino)isoindoline-1,3-dione as a yellow solid.

Silyl Deprotection

4-((3-(5-Fluoro-2-hydroxyphenyl)propyl)amino)isoindoline-1,3-dione (JAG-005-006)

A solution of the 4-((3-(2-((tert-butyldimethylsilyl)oxy)-5-fluorophenyl)propyl)amino)isoindoline-1,3-dione (0.39 g, 0.92 mmol) in 7 mL of freshly distilled THF was stirred under $N_2$ at 23° C. and 1.0 M tetrabutylammonium fluoride in THF (1.84 mL, 1.84 mmol) was added. Stirring was continued for 1 h and when TLC (20% EtOAc/hexane) indicated the complete consumption of the silyl ether, deionized water (5.0 mL) was added and the THF was evaporated under vacuum. The aqueous layer was extracted with EtOAc (3×40 mL), and the combined organic layers were washed with satd NaCl (50 mL), dried ($Na_2SO_4$) and concentrated under vacuum. Final purification by column chromatography (using silica gel pre-treated with 3-hydroxy-2-methyl-4-pyrone) using 20% EtOAc/hexane afforded 334 mg (80%) of the 4-((3-(5-fluoro-2-hydroxyphenyl)propyl)amino)isoindoline-1,3-dione as an orange solid, mp 163-164° C. $^1$H NMR (400 MHz, DMSO-$d_6$): δ 10.9 (s, 1H), 9.33 (s, 1H), 7.51 (t, J=7.8 Hz, 1H), 6.98 (d, J=8.5 Hz, 1H), 6.92 (d, J=7.0 Hz, 2H), 6.81 (td, J=8.5, 3.2 Hz, 1H), 6.76 (dd, J=8.6, 5.2

Hz, 1H), 6.58 (t, J=6.0 Hz, 1H), 3.28 (q, J=6.6 Hz, 2H), 2.59 (t, J=7.5 Hz, 2H), 1.83 (quintet, J=7.3 Hz, 2H); $^{13}$C NMR (101 MHz, DMSO-$d_6$): δ 171.9, 168.8, 155.9 (d, J=238.9 Hz), 151.8 (d, J=7.3 Hz), 146.7, 136.3, 134.1, 126.9 (d, J=2.4 Hz), 117.2, 116.9, 115.1 (d, J=24.1 Hz), 114.5 (d, 23.3 Hz), 111.2, 110.2, 41.9, 28.9, 27.2.

The following compound can also be prepared by the procedure above using the appropriately substituted benzaldehyde.

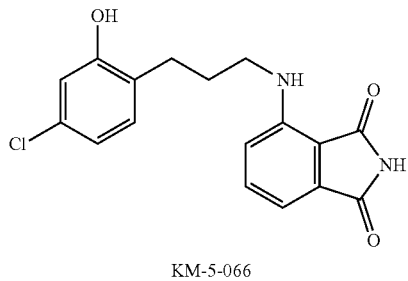 [SMILES: O=C1NC(=O)c2c(NCCCc3ccc(Cl)cc3O)cccc21]

KM-5-066

4-((3-(4-Chloro-2-hydroxyphenyl)propyl)amino) isoindoline-1,3-dione (KM-5-066)

Overall yield 285 mg (9.5%) as a yellow solid, mp 185-186° C.; $^1$H NMR (400 MHz, DMSO-$d_6$): δ 10.9 (s, 1H), 9.77 (s, 1H), 7.52 (dd, J=8.2, 7.4 Hz, 1H), 6.98 (d, J=8.5 Hz, 1H), 6.93 (d, J=7.0 Hz, 1H), 6.70 (m, 1H), 6.61 (t, J=2.0 Hz, 1H), 6.57 (m, 1H), 6.52 (t, J=5.8 Hz, 1H), 3.27 (q, J=6.7 Hz, 2H), 2.57 (t, J=7.4 Hz, 2H), 1.84 (quintet, J=7.4 Hz, 2H); $^{13}$C NMR (101 MHz, DMSO-$d_6$): δ 170.8, 168.7, 157.8, 145.6, 144.2, 135.3, 133.0, 132.6, 118.2, 115.9, 113.5, 112.2, 110.2, 109.2, 40.7, 31.4, 29.3.

Example 2: Analog Binding

Chemicals, Strains, and Growth Media

Chemicals were purchased from Fisher Scientific unless otherwise stated. *Pseudomonas aeruginosa* (PAO1) and *Acinetobacter baumannii* (AB5075) were purchased from the University of Washington Genome Center. The PAO1-derived strain with an unmarked, in-frame deletion of the bfrB gene had been prepared previously.[18] *P. aeruginosa* clinical isolates (MR3B and MR60) were obtained from Seattle Children's Hospital Research Foundation. All *P. aeruginosa* strains were kept on *Pseudomonas* Isolation Agar (PIA) (BD Biosciences, CA). The *A. baumannii* strain was kept on LB agar. M63 media was prepared as previously reported,[33] with a small modification. It contained per liter: 2 g of $(NH_4)_2SO_4$, 13.6 g of $KH_2PO_4$ (Sigma Aldrich), 2 g of glucose, 4 g of citric acid, 0.25 g of tryptophan (Acros organics), 5 g of non-technical grade casamino acids (BD scientific) and 0.24 g of $MgSO_4$ (Alfa Aesar), and the pH was adjusted to 7.0 with KOH. The M63 media also contained 0.1% (w/v) of hypromellose (HPMC, Sigma Aldrich) to prevent aggregation of the analogs in aqueous solution.[34] Colorimetric analysis showed that the M63 media contains 2 μM Fe. When necessary, the M63 media was supplemented with additional iron by addition of a small volume of 1 mM $(NH_4)_2Fe(SO_4)_2$ (pH~2.0) to give the desired final iron concentration. Modified M63 media contained per liter: 2 g of $(NH_4)_2SO_4$, 13.6 g of $KH_2PO_4$(Sigma-Aldrich), 2.5 g of glucose, 10% MEM non-essential amino acid solution (Gibco®), 4% MEM amino acid solution (Gibco®) and 0.12 g of $MgSO_4$ (Alfa Aesar), and the pH was adjusted to 7.0 with KOH. The modified M63 media also contained 0.1% (w/v) of hypromellose and 4 μM iron, supplemented by using a stock of 10 mM $(NH_4)_2Fe(SO_4)_2$ (pH~2.0).

Fragment Library Screening Using Saturation Transfer Difference (STD) NMR Spectroscopy Experimental details are presented in Supplementary Information (disclosed vide infra).

Crystallization, Ligand Soaking and Data Collection

Crystallization screening was conducted in Compact 300 (Rigaku Reagents) sitting drop vapor diffusion plates at 18° C. using equal volumes (0.5 μL) of BfrB and crystallization solution equilibrated against 75 μL of the latter. Three different BfrB constructs were investigated to grow crystals of BfrB suitable for soaking experiments with the different fragments and analogs. BfrB crystals were observed in 1-2 days as follows: C89S/K96C BfrB: Red prismatic crystals were obtained from Wizard 1-2 (Rigaku Reagents) condition E2 (35% (v/v) 2-methyl-2,4-pentanediol, 100 mM MES 6.5, 200 mM $Li_2SO_4$). Apo-BfrB (BfrB devoid of heme): Colorless prismatic, or light yellow crystals, were obtained from the Wizard 3-4 screen (Rigaku Reagents) condition B1 (8% (w/v) PEG 8000, 100 mM Na acetate pH 4.6). BfrB: Red plates grew from the Cryo 1-2 HT screen (Rigaku Reagents) condition H6 (30% (v/v) PEG 200, 100 mM Na acetate pH 4.5, 100 mM NaCl). To prepare for soaking experiments, a stock solution (100 mM in DMSO) of each fragment or analog (compound) was mixed with crystallization solution to obtain a 20 mM compound solution to be used in soaking experiments. Crystals were transferred to these soaking solutions and incubated for 3.0 to 3.5 h before harvesting directly from the drop and storing in liquid nitrogen. Analog 13 was soaked in a 25 mM compound solution for 2 h, and analog 16 was soaked in a 10 mM compound solution for 3 h. The compound soaking solutions, which also served as the cryoprotectant, contained 80% crystallization solution and 20% DMSO. Structures of compounds bound to BfrB were obtained from the following compound/BfrB crystal combinations: Fragment 1/C89S/K96C BfrB, analog 12/apo-BfrB, and analogs 11, 13, 14, 15, 16/BfrB. X-ray diffraction data were collected at the Advanced Photon Source beamline 17-ID using a Dectris Pilatus 6M pixel array detector.

Structure Solution and Refinement

Intensities were integrated using XDS,[35] via Autoproc[36] and the Laue class analysis and data scaling were performed with Aimless.[37] Structure solution was conducted by molecular replacement with Phaser[38] and structure refinement/manual model building were performed with Phenix[39] and Coot,[40] respectively. Electron density omit maps for the ligands were calculated using the Polder omit routine[41] with the Phenix software suite. Structure validation was carried out with Molprobity[42] and figures were prepared with CCP4 mg.[43] The search models used for molecular replacement were as follows: C89S/K96C BfrB (PDB: 4TOF)[25] and BfrB (PDB: 5D80).[30] Apo-BfrB: Structure solution was carried out using a single subunit of a previously determined structure of BfrB as the search model (PDB: 3IS7).[27] The top solution was obtained in the space group $C222_1$ with 12 molecules in the asymmetric unit.

Growth Curves, $IC_{50}$ and MIC Determination

Pre-cultures (5 mL LB media) were grown for 12 h at 37° C. and 220 rpm in 50 mL conical tubes (VWR International, PA) covered with an air permeable membrane. The cells were then centrifuged at 4,000 rpm for 10 min, the resultant cell pellets washed twice in M63 media and then diluted in M63 media to $OD_{600}$=0.01. Stock solutions (100 mM) of analog in DMSO were prepared weekly and stored at 4° C.

Prior to initiating experiments in 96 well plates, the analog stock solution was serially diluted to make 10 mM or 1 mM working solutions in DMSO. A small volume of the appropriate working solution was transferred to a glass vial, diluted with DMSO to 30 µL, and then diluted to a final volume of 1.5 mL with pre-culture cell suspension with an $OD_{600}$=0.01. The resultant cell suspension (200 µL) was transferred to a clear-bottom polystyrene 96 well plate (VWR), and incubated at 35° C. and 205 cpm for 13 h in an Epoch 2 microplate spectrophotometer (Biotek Instruments, Inc., Vermont). The growth curve in the presence of Ciprofloxacin was obtained in the same plate. To this end, 11.2 µL of a Ciprofloxacin working solution (100 µg/mL) was mixed with 30 µL of DMSO prior to diluting to a final volume of 1.5 mL with cell suspension having an $OD_{600}$=0.01 and transferring to the plate. The resultant concentration of ciprofloxacin in the wells was 0.75 µg/mL, which is equivalent to 3 times the reported MIC.[44] Each condition was replicated in 5 wells of the plate, so the growth curves shown in FIG. 5 are constructed from the average and standard deviation of 5 replicates. The growth % was estimated using the $OD_{600}$ values obtained 13 h post-inoculation and equation 1, where $OD_T$ is the optical density of the culture treated with analog, $OD_U$ is the optical density of the untreated control, and $OD_{Cip}$ is the optical density of the culture treated with ciprofloxacin. To calculate the $IC_{50}$ values, the growth % was plotted as a function of log[analog (µM)], and fitted to equation 2, where the terms are defined as above and b is the slope factor.[45] Similar experiments were conducted with *A. baumannii* in 48 well-plates with minor modifications: Cells were cultured in modified M63 media; the final culture volume was 1 mL/well and the cells were incubated at 35° C. and 205 cpm using a Synergy H1 microplate spectrophotometer. MIC determinations were carried out using standard broth microdilution methods in 48 well plates and modified M63 media. Cells were incubated at 35° C. The MIC of analogs was determined as the lowest concentration that completely inhibited bacterial growth as detected by the unaided eye.[63]

$$\text{growth \%} = \frac{(OD_T - OD_{Cip})}{(OD_U - OD_{Cip})} \times 100 \qquad \text{(Eq. 1)}$$

$$\text{growth \%} = OD_{Cip} + \frac{OD_U - OD_{Cip}}{1 + \left(\frac{\log[\text{analog}(\mu M)]}{IC_{50}}\right)^b} \qquad \text{(Eq. 2)}$$

Analysis of Secreted Pyoverdin

These experiments were carried out in 96 well plates, as described above. *P. aeruginosa* cells treated with analog 11 or 16 (125 µM final concentration) were cultured for 13 h before the contents of each well was serially diluted in phosphate buffered saline (PBS, pH 7.4) and then plated on PIA plates to enumerate viable cells. The 500-fold diluted solution was centrifuged and the cell-free supernatant was analyzed for pyoverdin by fluorescence spectrophotometry in a Synergy H1 microplate reader (BioTek) with excitation at 400 nm and emission at $\lambda_{max}$=455 nm. Full emission spectra (430-550 nm) were also recorded using a Perkin Elmer LS50B spectrophotometer.

CAS Assay for Siderophore Detection

These experiments were carried out in 48 well-plates in a Synergy H1 microplate spectrophotometer as described above for obtaining *A. baumannii* growth curves. Cultures treated with analog KM-5-25 at 64 µM final concentration were used in these experiments. The cell-free supernatants (25 µL) collected after the 24-h growth curves had been completed was mixed with 175 µL of the CAS assay reagent (10 mM hexadecyltrimethyl ammonium bromide (HDTMA), 1 mM $FeCl_3 \cdot 6H_2O$, 2 mM azurol S-CAS in 145 mM PIPES buffer, pH 5.9).[64] The absorbance at 630 nm was read in an Epoch2 microplate spectrophotometer after 2 h and used to calculate the percent siderophore (PSU) with the aid of equation 3,[65] where $A_r$ is the absorbance of the reference solution (CAS solution and un-inoculated media) and $A_s$ is the absorbance of the sample (CAS solution and cell-free supernatant). PSU values were normalized to CFU/mL.

$$PSU = \frac{(A_r - A_s)}{A_r} \times 100 \qquad \text{Eq. (3)}$$

Imaging of Iron Stored in BfrB and Analysis of Total Iron Levels

Pre-cultures were grown as described above and cells were diluted in M63 media supplemented with 4 µM Fe (6 µM total Fe) to $OD_{600}$=0.1 in 50 mL conical tubes. The resultant cell suspensions (5 mL) were mixed with a small volume of a 10 mM working solution of analog 16 in DMSO to give a 125 µM solution and 2% DMSO, or simply 2% DMSO (control). The conical tubes were covered with a sterile air permeable membrane and the cultures incubated at 35° C. and 120 rpm for 6, 9, 12, 15, 18, 21 and 24 h. Prior to separating the cells by centrifugation (4,000 rpm, 15 min), a 100 µL aliquot was withdrawn from each conical tube and serially diluted for plating and enumerating viable cells. The separated pellet was washed with 5 mL of PBS and frozen at −20° C. for subsequent analysis. The corresponding cell free supernatants were used for iron analysis in the spent media, as described below. The cell pellets were used to image iron stored in BfrB according to a previously described method[18] with some minor modifications. Briefly, cell pellets were suspended in 300 µL of lysis buffer (50 mM Tris pH 8.0, 20% glycerol, 20 mg/mL lysozyme, 0.2 mg/mL DNAse, 100 mM NaCl, 10 mM $MgCl_2$, and 1% Triton X) and freeze-thawed twice using liquid $N_2$. The resultant suspensions were incubated at 25° C. for 90 min in a rocker and then centrifuged at 12,500 rpm for 15 min at 4° C. Lysate solutions (100 µL) were each mixed with 10 µL of the loading dye and the samples (100 µL) loaded onto a 3 mm-thick native polyacrylamide gel (8% resolving gel and 4% stacking gel) for separation. Electrophoretic separation was carried out at 60 V for 7 h at 4° C. and the gels were stained with Ferene S[46] for 10 min in a solution containing 0.049 g of Ferene S, 250 µL of thioglycolic acid, 2.5 mL of acetic acid and 100 mL of water. The scanned images were processed and compared using Image J.[47]

To determine the total iron levels of cells treated with analog 16 or DMSO only (control), 5 mL cultures were grown in M63 media supplemented with 4 µM iron, as described above, and analyzed at 12, 15, 21, 24, and 28 h. Prior to separating the cells by centrifugation (4,000 rpm, 15 min), a 100 µL aliquot was withdrawn from each conical tube and serially diluted for plating, in order to enumerate viable cells. Cell pellets were washed twice with 10 mL of PBS and the total levels of cellular iron were measured using a published protocol.[18, 48] In brief, cell pellets were mixed with 500 µL of freshly prepared digestion reagent (1:1 v/v 1.2 N HCl and 4.5% w/v $KMnO_4$ in water), thoroughly mixed by vortexing, and incubated at 65° C. for 4 h. The digested solutions were cooled to 25° C., mixed with 500 μL of iron chelating agent (6.5 mM Ferene S, 13.1 mM neocuproine, 2 M ascorbic acid, 5 M ammonium acetate) and then incubated at 25° C. for 30 min. The iron concentration of the resultant solution was measured from the absorbance of the $Fe^{2+}$-Ferene S complex at 593 nm ($\varepsilon$=34,500 $M^{-1}$ $cm^{-1}$)[49] using a Cary 60 UV-vis spectrophotometer, normalized by cell count and reported as Fe atoms per CFU (colony forming unit). The colorimetric determination of total intracellular iron offers a sensitive, accurate and low cost analytical technique, which has been shown to produce results similar to those obtained by atomic inductively coupled plasma-mass spectrometry.[50]

Effect of Analogs on the Potency of Fluoroquinolone Antibiotics

Cultures were treated with (i) analog 16 only, (ii) ciprofloxacin 0.25 μg/mL, levofloxacin 0.5 μg/mL, or norfloxacin 0.9 μg/mL only, and (iii) both fluorquinolone (concentration as above) and analog 16. To treat cells with analog only, pre-cultures were grown as described above; the cells were then diluted in M63 media supplemented with 4 μM Fe to $OD_{600}$=0.1 in 50 mL conical tubes. The resultant cell suspensions (5 mL) were mixed with a small volume of a 10 mM working solution of analog 16 in DMSO to give the desired analog concentration (75, 100, or 125 μM) and 2% DMSO, or simply with DMSO (untreated control). The conical tubes were covered with an air permeable membrane and the cultures were incubated for 18 h at 35° C. and 120 rpm. The resultant cultures were serially diluted in PBS and plated on PIA for enumeration of viable cells. To treat cells with ciprofloxacin only, the procedure was identical except that the cell suspensions (5 mL) were mixed with a small volume of ciprofloxacin working solution (100 μg/mL) to give the desired antibiotic concentration and 2% DMSO. The combined treatment was carried out similarly, ensuring that the final concentration of DMSO was 2%.

Results

Screening and Detection of Fragment Binding to the Bfd Binding Site on BfrB

Structural information obtained from the BfrB-Bfd complex was used to design a fragment library to screen for molecules that bind BfrB at the Bfd-binding site. Bfd residues M1, Y2, and L5 and BfrB residues L68 and E81 dominate the buried surface area at the protein-protein interface (FIG. 1C) and contribute significantly to the binding energy of the BfrB-Bfd complex.[30] Consequently, the fragment library was focused on fragments that may bind at the sites occupied by Y2 and L5 from Bfd and included groups with chemical properties similar to the aromatic and aliphatic side chains of Tyr and Leu, also utilizing standard fragment criteria (MW<300 Da, c log P<3, and total count of hydrogen bond acceptors/donors<3 each). In addition, fragments capable of π-π stacking were included with both electron rich and deficient aromatic rings. To screen the library in search of fragments that bind BfrB at the Bfd-binding site a competition assay was developed that utilizes saturation transfer difference (STD) NMR spectroscopy. This technique is ideally suited to screen fragments that bind to the large BfrB (~440 kDa) because protein resonance assignments are not necessary and very low protein concentrations are required. In addition, the large rotational correlation time ($\tau_c$) of BfrB enhances spin diffusion and therefore saturation transfer within the protein and to the ligand.[51] Two solutions were prepared for each fragment: a solution of the fragment alone, and a solution of the fragment and BfrB. Three spectra were obtained for each fragment. The $^1H$ spectrum of the fragment alone was used to determine fragment integrity and solubility, the $^1H$ spectrum of the fragment in the presence of BfrB was used to corroborate that fragment integrity and solubility is not affected by BfrB, and the STD spectrum of the solution containing the fragment and BfrB was used to assess fragment binding. This strategy uncovered 18 compounds that bind BfrB. The specificity criterion for fragment binders, however, is that these bind BfrB specifically at the Bfd-binding site. To eliminate non-specific binders, a displacement strategy was implemented that utilizes Bfd as a specific competitor. For this purpose, a STD spectrum was acquired from a solution containing fragment, BfrB and Bfd. Nearly complete disappearance of the STD signal indicates that the fragment binds BfrB at the Bfd-binding site. With the aid of this competitive displacement strategy, it was determined that of the 18 fragments that bind BfrB, 5-hydroxyisoindoline-1,3-dione; 6-acetyl-2H-benzo[b][1,4]oxazin-3(4H)-one; N-(4-bromophenyl)acetamide; N-(4-cyanophenyl)methanesulfonamide; 4-amino-N—(S-methylisoxazol-3-yl)benzenesulfonamide; and 5-(3-bromo phenyl)-1H-tetrazole bind at the Bfd-binding site. These fragments were advanced to the next stage, which was focused on uncovering structural information of fragment binding. Results from these experiments are presented below.

Structure-Based Optimization of Fragment Binders

A structure-guided approach was used to synthetically elaborate fragments discovered to bind BfrB at the Bfd binding site into analogs capable of binding with higher affinity. The affinity and selectivity of the fragments and analogs for the Bfd-binding site on BfrB were investigated by X-ray crystallography, surface plasmon resonance (SPR) and fluorescence polarization methods. The structures of fragments and derived analogs which have been demonstrated to bind BfrB at the Bfd-binding site using X-ray crystallography are shown in FIG. 2B. During the course of these experiments, crystals obtained from three different BfrB constructs were tested in ligand soaking experiments, in an effort to identify the "best" crystals for the study. Hence, crystals of BfrB (PDB 5D80), C98S/K96C BfrB (PDB 4TOF), and apo-BfrB were soaked in crystallization solution containing the various analogs. The structure of 5-hydroxyisoindoline-1,3-dione (fragment 1) bound to BfrB was obtained by soaking crystals of C98S/K96C BfrB in a solution of the fragment, as described in the Experimental Section. In subsequent experiments, crystals of apo-BfrB were used because this protein formed robust, highly reproducible crystals. These experiments culminated in the structure of analog 12 bound to BfrB. It is important to underscore that the structure of apo-BfrB is nearly identical to that of BfrB, at the subunit level (RMSD=0.18 Å), as well as the biological assembly level, including the Bfd-binding sites. Additional evidence indicating that the Bfd-binding sites on apo-BfrB are unaffected relative to the holo-protein was obtained in the dissociation constant for the interaction between Bfd and apo-BfrB ($K_d$=3.1 μM), which is nearly identical to that previously reported for the interaction between Bfd and holo-BfrB ($K_d$=3.4 μM).[30,52] Finally, the BfrB protein also produced reproducible crystals that were isomorphs with those formed by apo-BfrB. Consequently, the structures of analogs 11 and 13-16 bound to BfrB were obtained by soaking crystals of BfrB in solutions of each of the analogs.

Figure 2A:
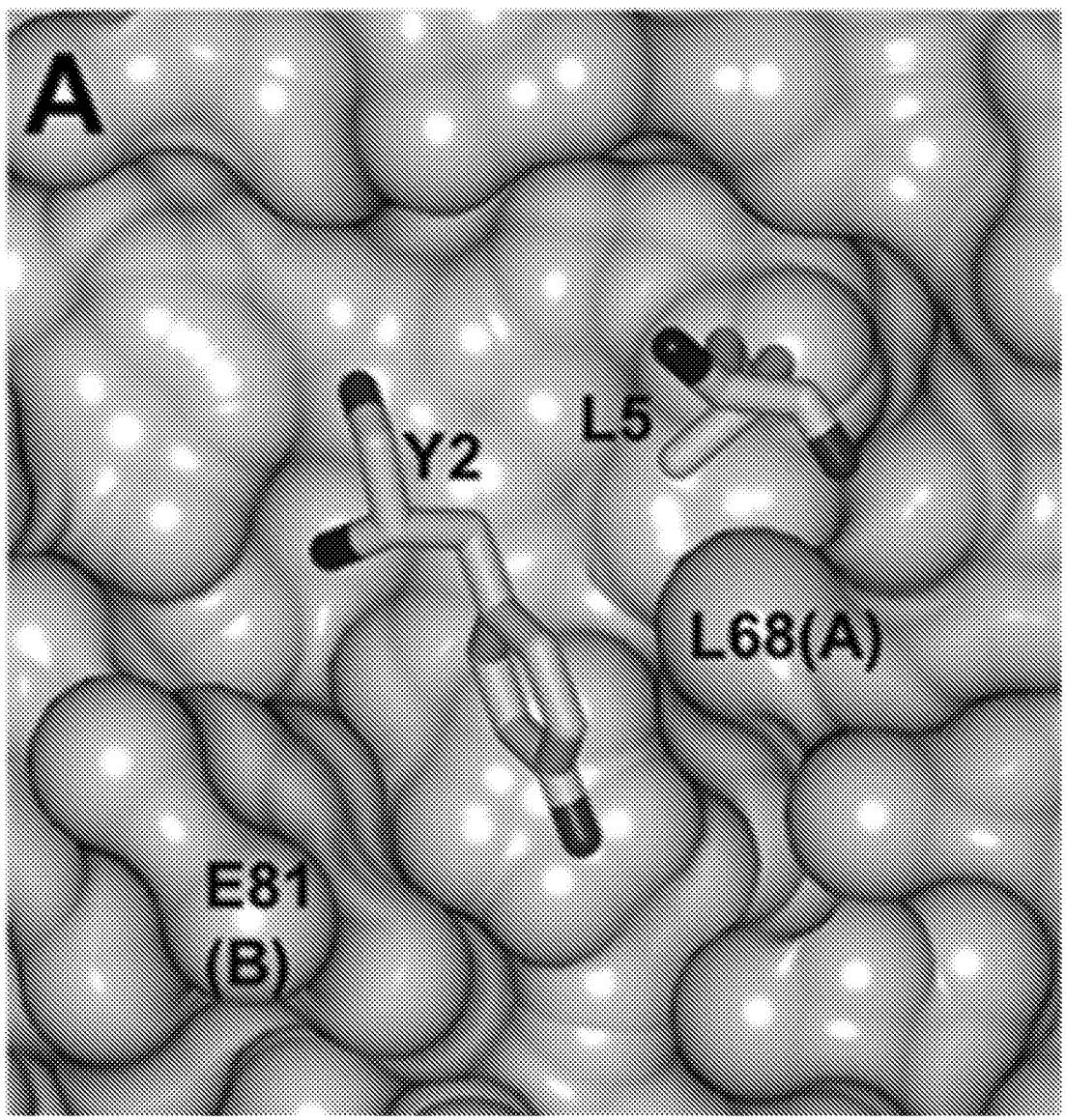
FIGS. 2A-2C illustrate the protein-protein interaction interface of the BfrB-Bfd complex. Subunits A and B of a BfrB subunit dimer are colored gray.
Figure 2B:
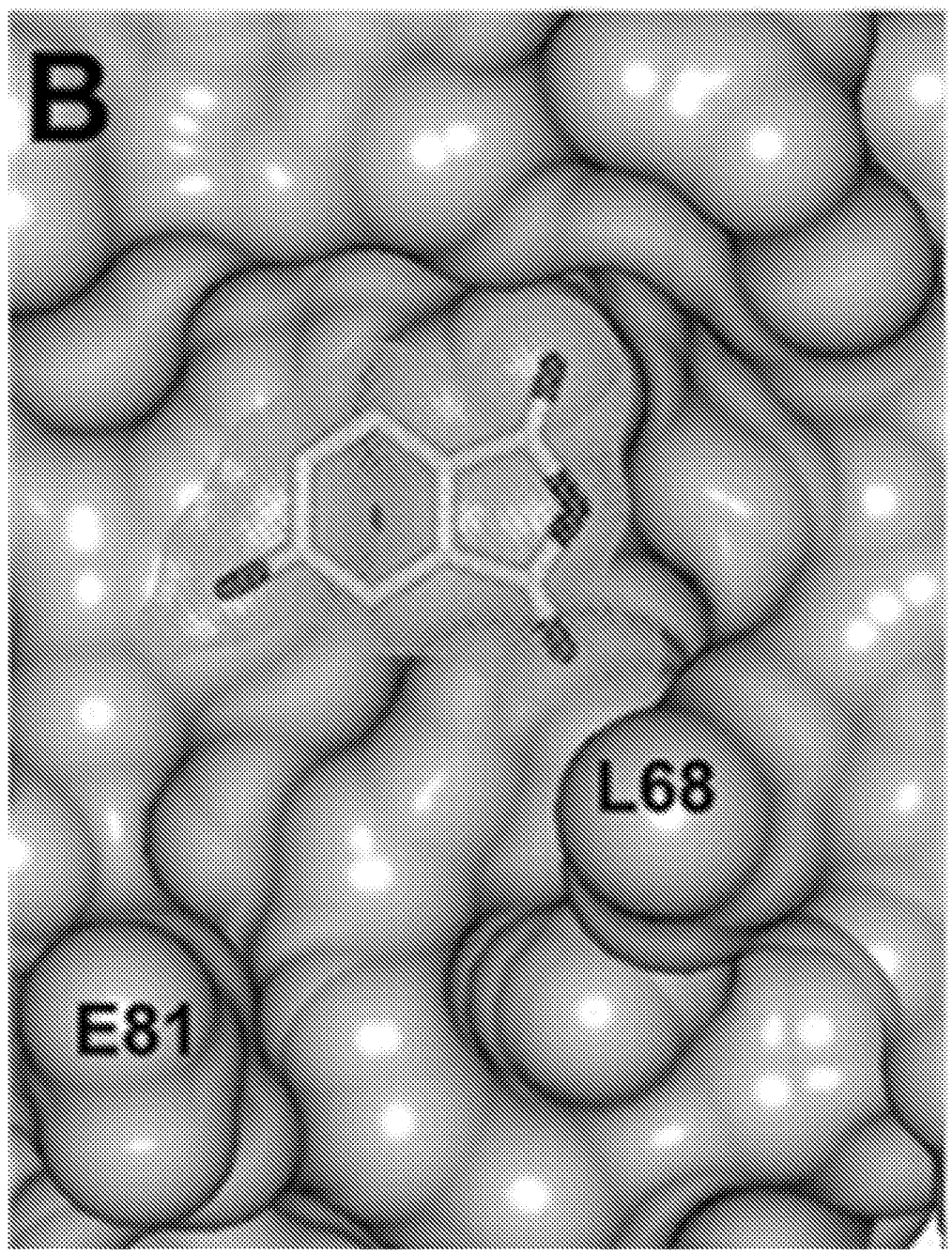
Figure 2C:
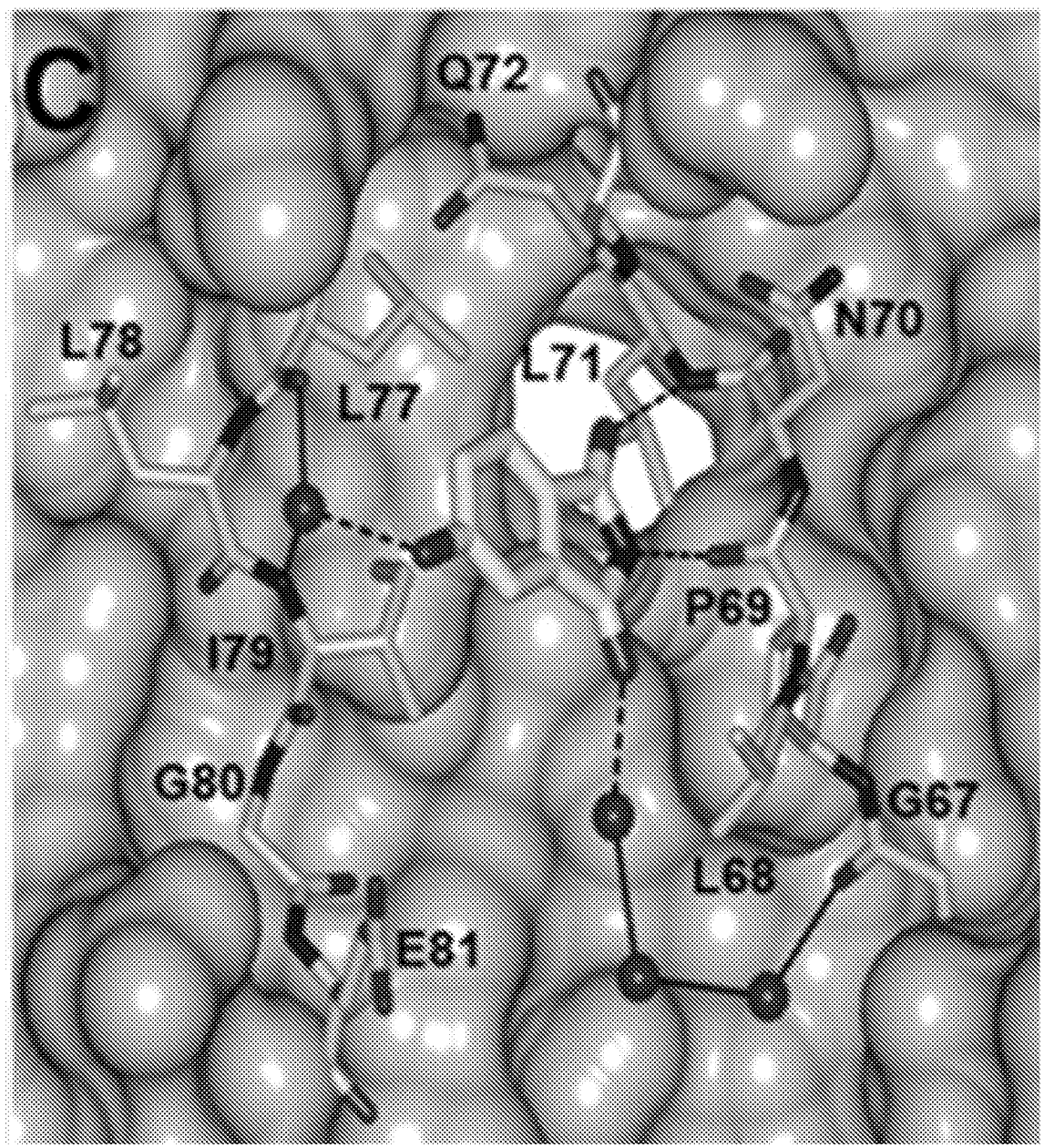

FIG. 2A depicts a portion of the BfrB-Bfd complex interface and illustrates how Y2 and L5 in Bfd (cyan cylinders) contribute to anchor Bfd to the BfrB surface. A prior study indicated that interactions between L68 and E81 in BfrB and Y2 and L5 in Bfd contribute significantly to the binding energy of the BfrB-Bfd complex.[30] It was therefore surmised that fragments capable of binding to this region of the BfrB surface would be good candidates for subsequent structure-guided synthetic elaboration aimed at discovering inhibitors of the BfrB-Bfd interaction. To obtain the structures of fragments bound to BfrB, crystals of the protein were soaked in crystallization solution containing each of the 6 fragments found to bind BfrB at the Bfd-binding site with the aid of the competitive displacement STD NMR strategy described above. These efforts culminated in a 1.5 Å resolution co-crystal structure of 5-hydroxyisoindoline-1,3-dione (1) bound to BfrB (FIGS. 2B and 2C), which showed that 1 binds BfrB at the Bfd-binding site, in the same pocket where L5 from Bfd would bind. The fragment rests on a platform at the base of a shallow depression on the BfrB surface formed by the side chains of $L_B^{77}$ and $I_B^{79}$ (the subscript denotes subunit and the superscript denotes residue number), surrounded by a semicircular wall comprised by the side chain and backbone atoms of $L_A^{68}$, $N_A^{70}$, $Q_A^{72}$, and $L_B^{77}$.

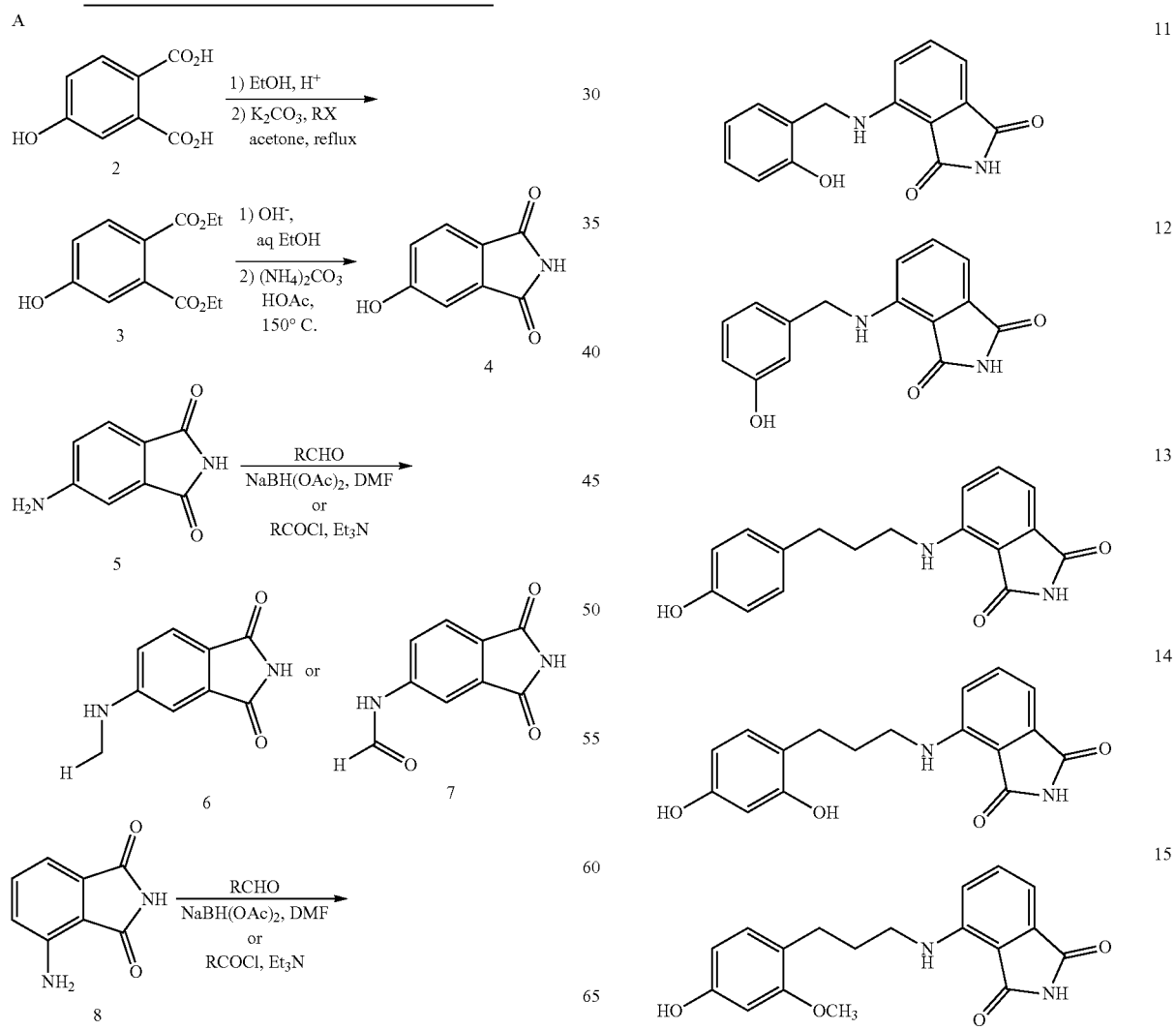

16

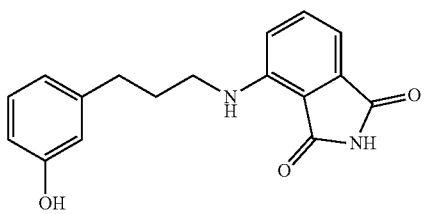

One of the carbonyl-oxygen atoms of 1 accepts a H-bond from the backbone NH of $L_A^{71}$, and its N—H group forms a H-bond to the backbone carbonyl of $P_A^{69}$. Additional stabilization for binding probably stems from the network of H-bonded waters linking a carbonyl oxygen in 1 and $G_A^{67}$ in BfrB. This structural information suggested a strategy to grow 1, or its analogs 4-aminoisoindoline-1,3-dione (8) and 5-aminoisoindoline-1,3-dione (5), by branching from the isoindoline ring carbons C4 or C5 to engage the cleft formed by the side chains of L68 and E81 in BfrB, where Y2 from Bfd anchors.

A general synthetic approach (Scheme 30A) was formulated to generate a series of ether analogs represented by 4, amine analogs represented by 6 or 9, and amide analogs represented by 7 or 10. Preparation of the ether analogs of 4 started with the esterification of the acid groups in 4-hydroxyphthalic acid 2, followed by alkylation of the phenolic oxygen to produce 3 and subsequent base cleavage of the esters and cyclization to produce the isoindoline-1,3-dione ethers 4. Synthesis of the amine analogs represented by 6 and 9 was carried out by reductive amination of 5 or 8, respectively, with a series of aldehydes, whereas amide analogs 7 and 10 were obtained from 5 or 8, respectively, via reactions with a series of acid chlorides. The collection of ether, amine and amide analogs prepared for this study, as well as the details of their synthetic preparation and characterization, are presented in the Supplementary Information section of this disclosure.

Figure 3A:
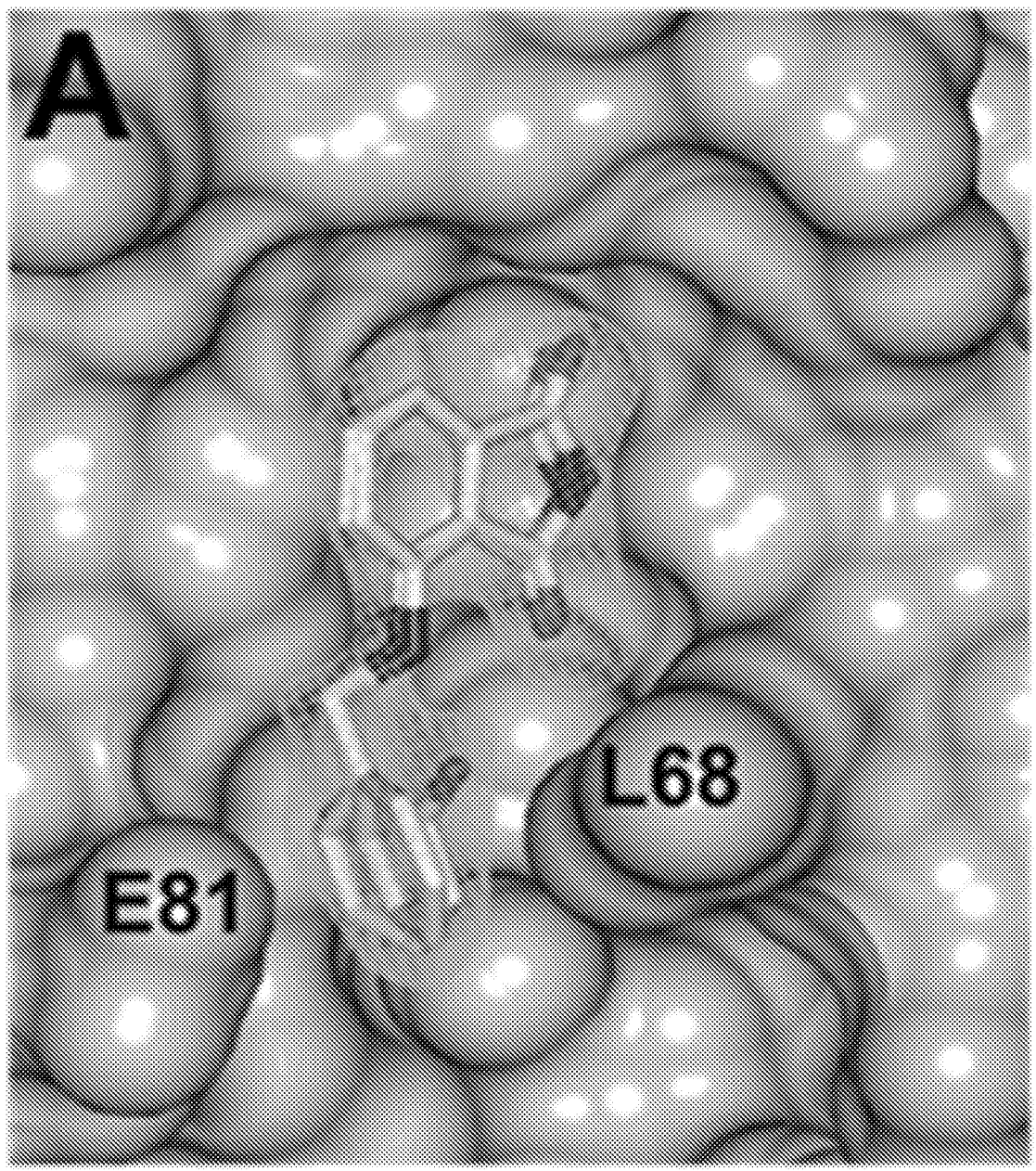
(FIG. 3A) Fo-Fc omit map (mesh) contoured at 3a from analog 11 bound at the Bfd-binding site on BfrB.
Figure 3B:
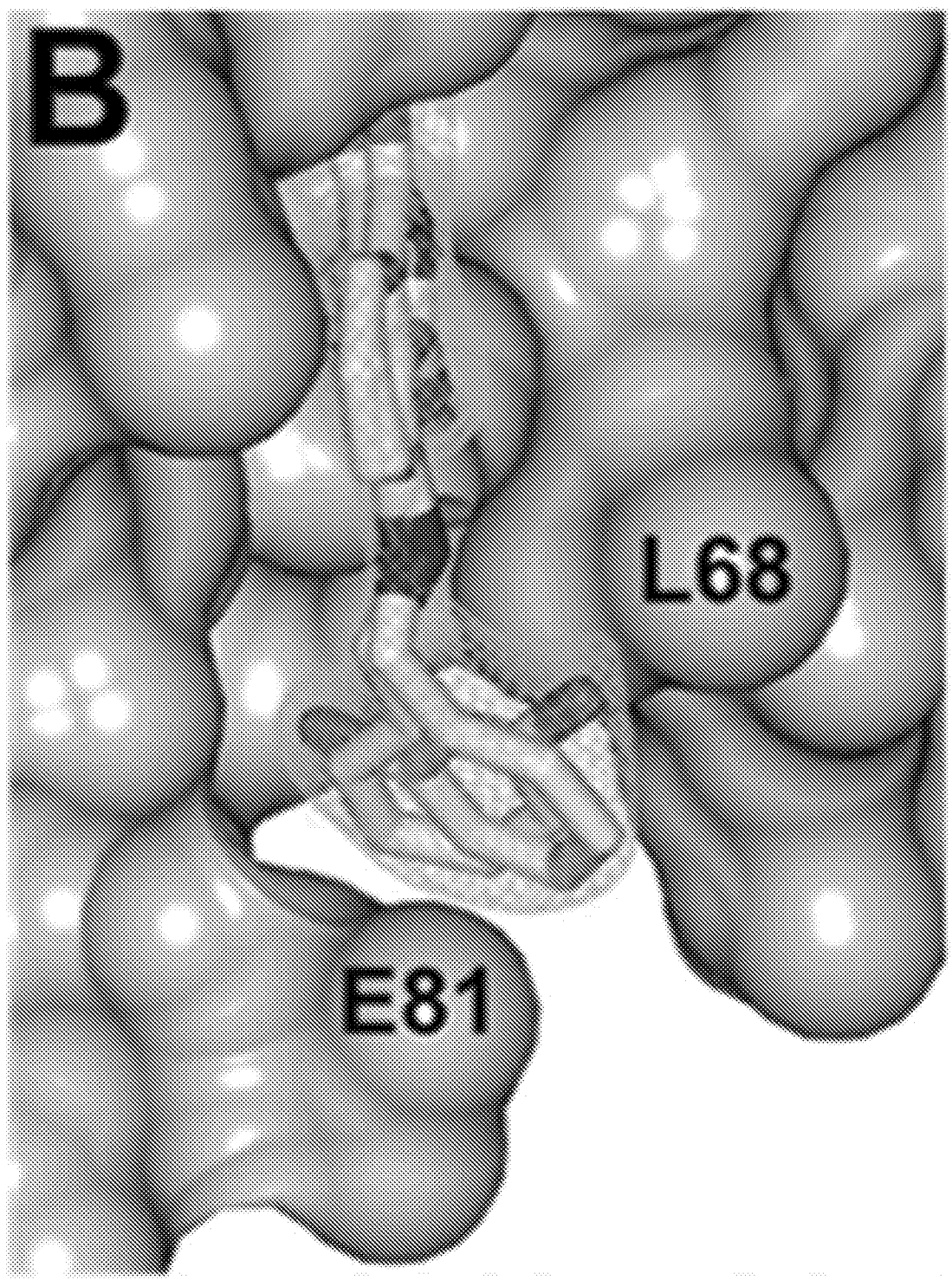
(FIG. 3B) Same as FIG. 3A but showing a different perspective to illustrate the two orientations modeled for the o-hydroxyphenyl ring of analog 11.
Figure 3C:
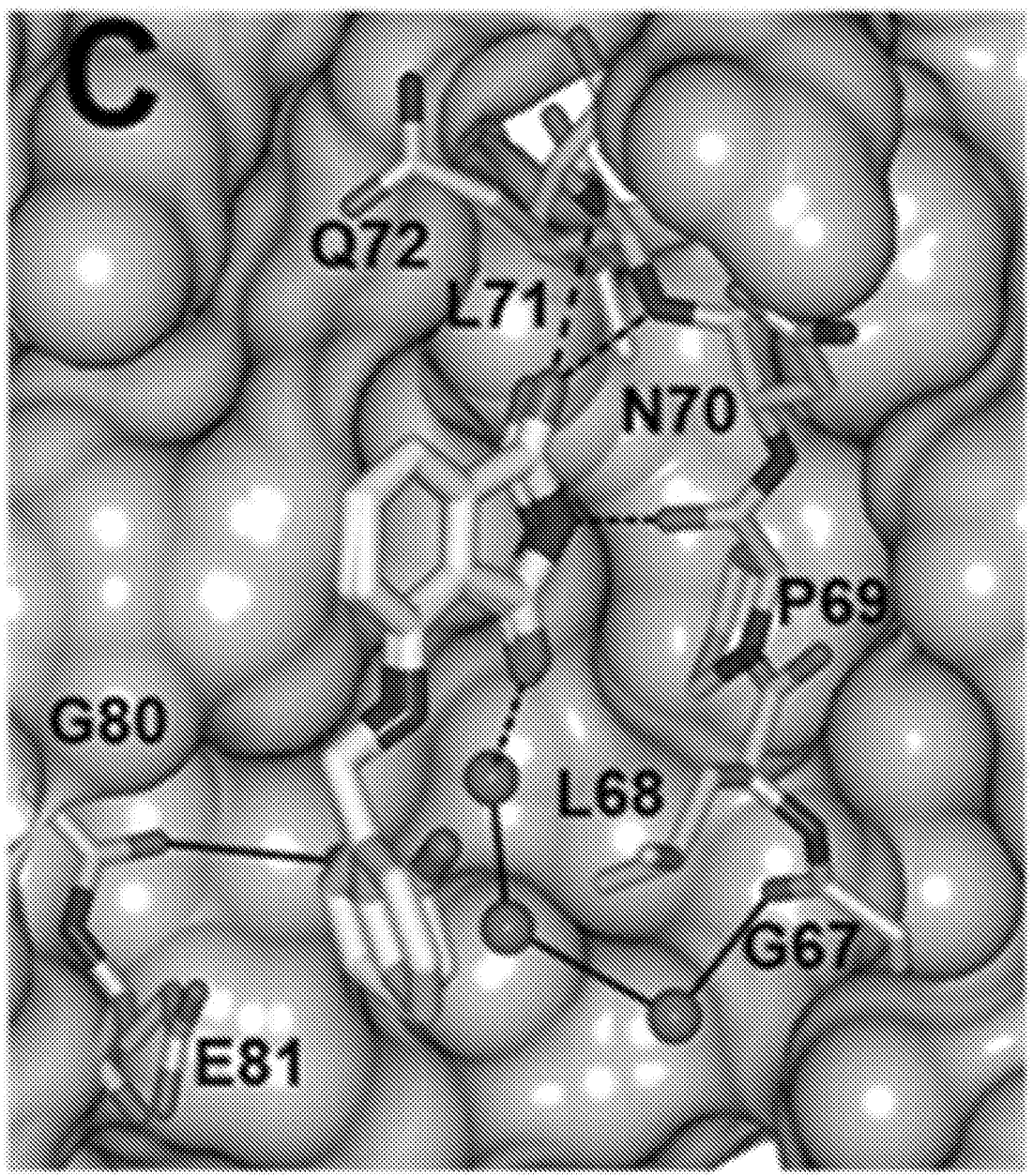
(FIG. 3C) Hydrogen bond interactions (dashed lines) between analog 11 and BfrB. Water mediated contacts are indicated by the solid lines.
Figure 3D:
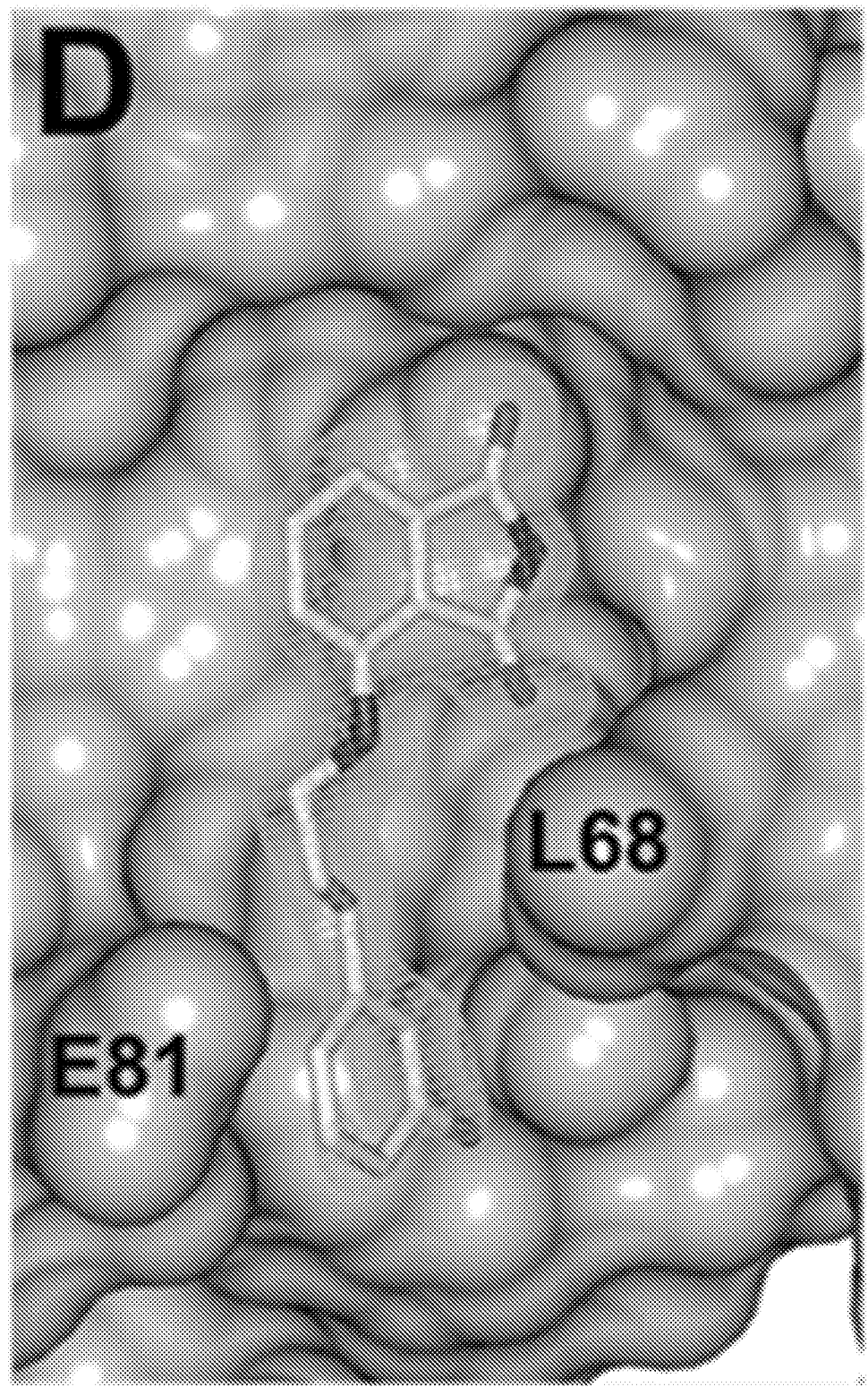
(FIG. 3D) Fo-Fc omit map (mesh) contoured at 3σ from analog 16 bound at the Bfd-binding site on BfrB.

Although all of the compounds synthesized for each of the analog types shown in Scheme 30A were tested in crystal soaking experiments, structures of analog-bound BfrB were obtained only for analogs 11-16 (Scheme 30B), which are derivatives of 4-aminoisoindoline-1,3-dione (8) with —(CH$_2$)— and —(CH$_2$)$_3$— linkers. The pose of each of these analogs in the Bfd-binding site of BfrB is shown in FIGS. 3A-3F. Inspection reveals that the isoindoline-1,3-dione moiety in all the compounds invariably binds BfrB in a manner identical to that described above for fragment 1 binding to BfrB (see FIGS. 2A-2C). In addition, and as was expected, the benzyl portion of the analogs extends to engage the cleft formed by the side chains of $L_A^{68}$ and $E_B^{81}$ in BfrB via hydrophobic packing interactions. The interactions experienced by analog 11 at the Bfd-binding site on BfrB are illustrated in FIGS. 3A-3C. Strong electron density consistent with the compound can be observed in 9 of the 12 subunits in the asymmetric unit; the 3 subunits in which compound 11 was not modeled displayed electron density not associated with the protein at the Bfd-binding site, but this electron density was too weak to model the ligand. The o-hydroxyphenyl ring of 11 is observed in two orientations that differ by a 180° rotation of the ring; one orientation places the hydroxyl group pointing toward the base of the cleft, where it forms a hydrogen bond with $G_B^{80}$, while the second orientation places the hydroxyl group toward the solvent and enables packing of the o-hydroxyphenyl ring and the —(CH$_2$)— moiety bridging the phenyl and isonindoline rings against the side chains of $M_B^{31}$ and $I_B^{79}$, respectively. Additional stabilization for binding probably stems from the network of H-bonded waters linking a carbonyl oxygen in 11 and $G_A^{67}$, similar to the network of H-bonded water molecules observed in the structure of 1 bound to BfrB (see FIG. 2C). The structure of a similar analog (12) bound to BfrB shows identical interactions of the isoindoline-1,3-dione moiety with BfrB and similar interactions of the phenyl ring with the cleft formed by the side chains of $L_A^{68}$ and $E_B^{81}$ on the BfrB surface.

A similar close view of compound 16 bound at the Bfd binding site on BfrB (FIGS. 3D-3F) illustrates how the isoindoline-1,3-dione ring presents the same pose and set of interactions as those described above for fragment 1 and analogs 11 and 12. Clear electron density consistent with the compound can be observed in all 12 subunits in the asymmetric unit, but the m-hydroxyphenyl ring was partially disordered in several of the subunits. The m-hydroxyphenyl ring and the —(CH$_2$)$_3$— linker pack against the $L_A^{68}$ and hydrophobic portion of the $E_B^{81}$ side chains, with additional stabilization probably stemming from a network of H-bonded waters connecting a carbonyl oxygen in the isoindoline-1,3-dione ring, the hydroxyl group on aromatic ring and the carbonyl oxygen in $L_A^{68}$. The structures of four additional compounds similar to 16 bound to BfrB, which show a nearly identical pose of the isoindoline-1,3-dione moieties and very similar interactions of the linkers and phenyl rings, demonstrate the specificity with which the series of 4-amino derivatives listed in Table 1 engage the Bfd-binding site on BfrB.

Prior to testing the effect that the 4-substituted isoindoline-1,3-dione derivatives might exert on *P. aeruginosa* cells, the strength of their interaction with BfrB was evaluated in vitro with a fluorescence polarization assay developed based on the intrinsic fluorescence of the isoindoline-1,3-dione moiety. Because initial fluorescence spectroscopic measurements revealed that the heme groups in BfrB interfere with the signal of the fluorescent ligand, apo-BfrB was utilized for these measurements, capitalizing on earlier findings that the Bfd-binding sites in apo-BfrB are nearly identical to those in BfrB, and that the $K_d$ for the interaction between apo-BfrB and Bfd is very similar to that measured for the interaction between BfrB and Bfd. Hence, the $K_d$ values were measured by titrating apo-BfrB into a fixed concentration of the appropriate fluorescent 4-aminoisondoline-1,3-dione ligand while analyzing fluorescence polarization and intensity near the emission $\lambda_{max}$. The $K_d$ values (Table 1) show that analogs 11-16 exhibit significantly higher affinity than fragment 8, observations that are in agreement with the structural insights, which revealed that growing the fragments from the isoindoline ring carbon C4 makes it possible to engage the cleft formed by the side chains of L68 and E81 in BfrB. The two derivatives with a —(CH$_2$)— linker exhibit binding affinities approximately 2 to 5-fold lower than derivatives with a —(CH$_2$)$_3$— linker, also in agreement with a relatively more efficient hydrophobic packing facilitated by the longer linker.

Figure 3E:
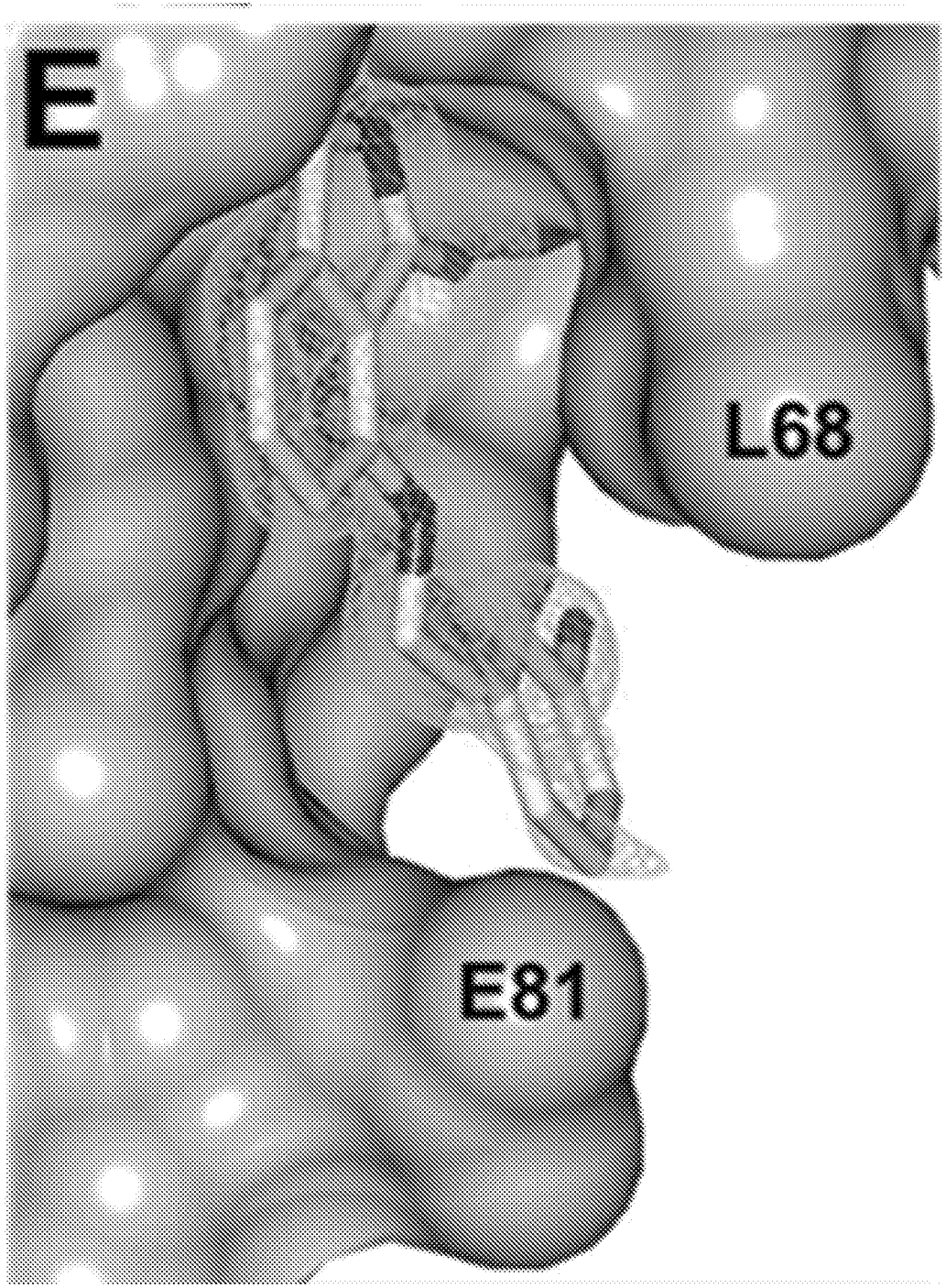
(FIG. 3E) Same as FIG. 3D but rotated to illustrate the m-hydroxyphenyl ring of analog 16 positioned between the cleft formed by the side chains of $L_A^{68}$ and $E_B^{81}$ in BfrB.
Figure 3F:
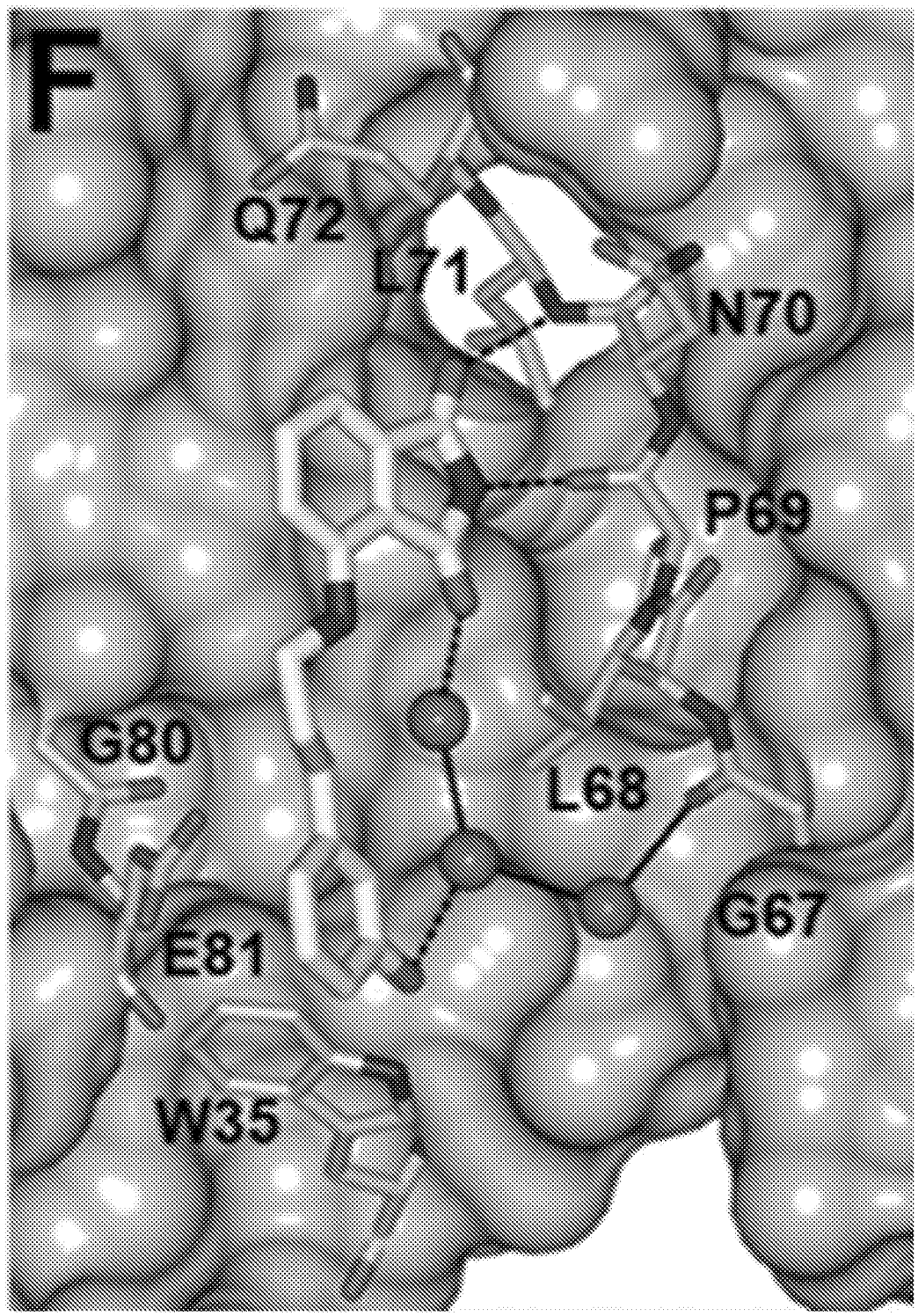
(FIG. 3F) Hydrogen bond interactions (dashed lines) between analog 16 and BfrB. Water mediated contacts are indicated by the solid lines.

As indicated above, the crystal structure of analog 11 bound to BfrB revealed clear electron density defining the 4-aminoisoindoline-1,3-dione moiety. In comparison, the o-hydroxy-phenyl ring is present in two orientations and is less well defined by electron density (FIG. 3B), suggesting that disorder caused by rotation of the phenyl ring in the cleft formed by L68 and E81 may adversely affect the strength of its association for BfrB. Similar disorder appears to affect the m-hydroxyphenyl ring of analog 16 (FIG. 3E). These structural insights prompted a more recent SAR study aimed at introducing a relatively bulky halogen in the phenyl ring of the analogs, to slow or prevent rotational disorder. Testing the effect of the halogenated analogs (KM-5-25, KM-5-35, JAG-005-030, KM-5-66, and JAG-005-006 in Table 1) on *P. aeruginosa* and *A. baumannii* growth shows improved potency, evidenced by significant reduction of the $IC_{50}$ values and by evaluation of MIC values (see Table 1).

Figures 4A, 4B:
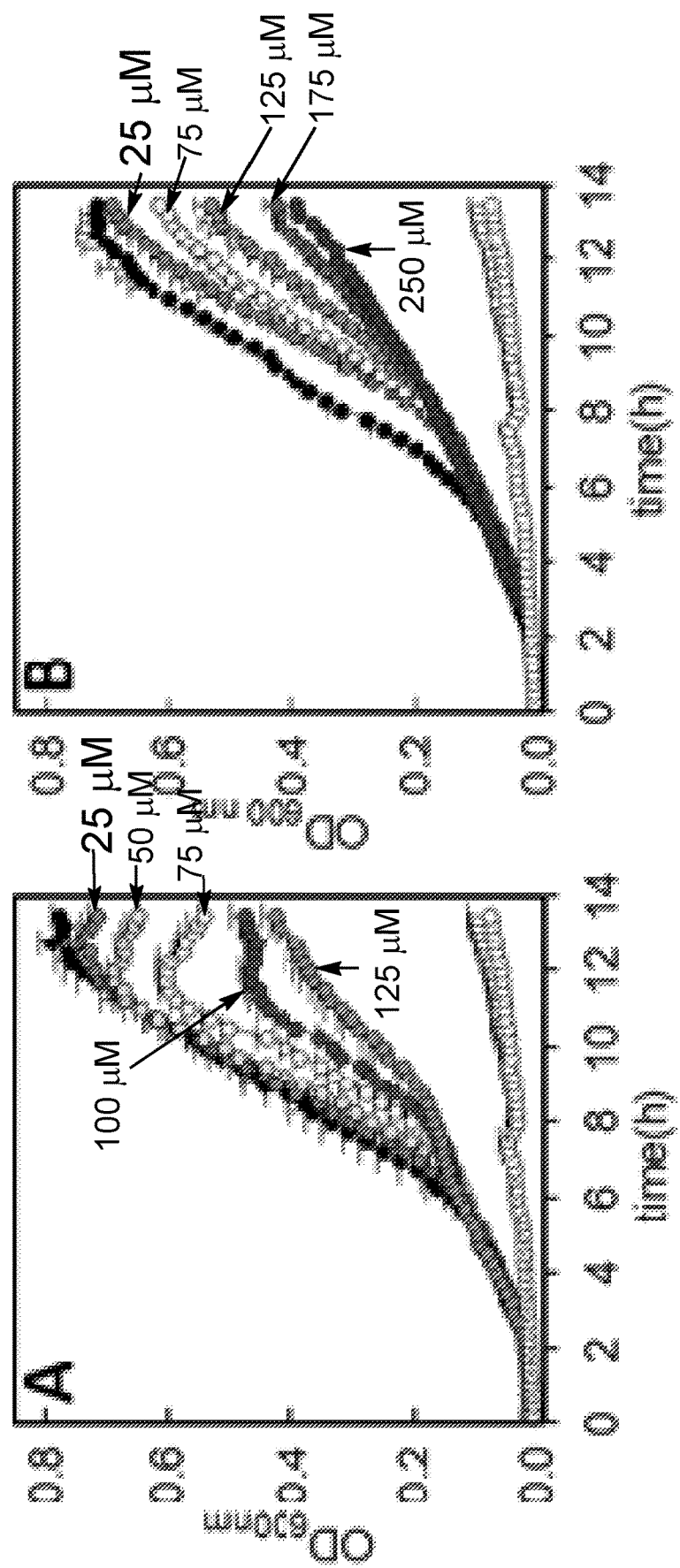
FIG. 4A-4D illustrates analogs of 4-aminoisoindoline-1,3-dione elicit a growth defect in P. aeruginosa.
Figure 4C:
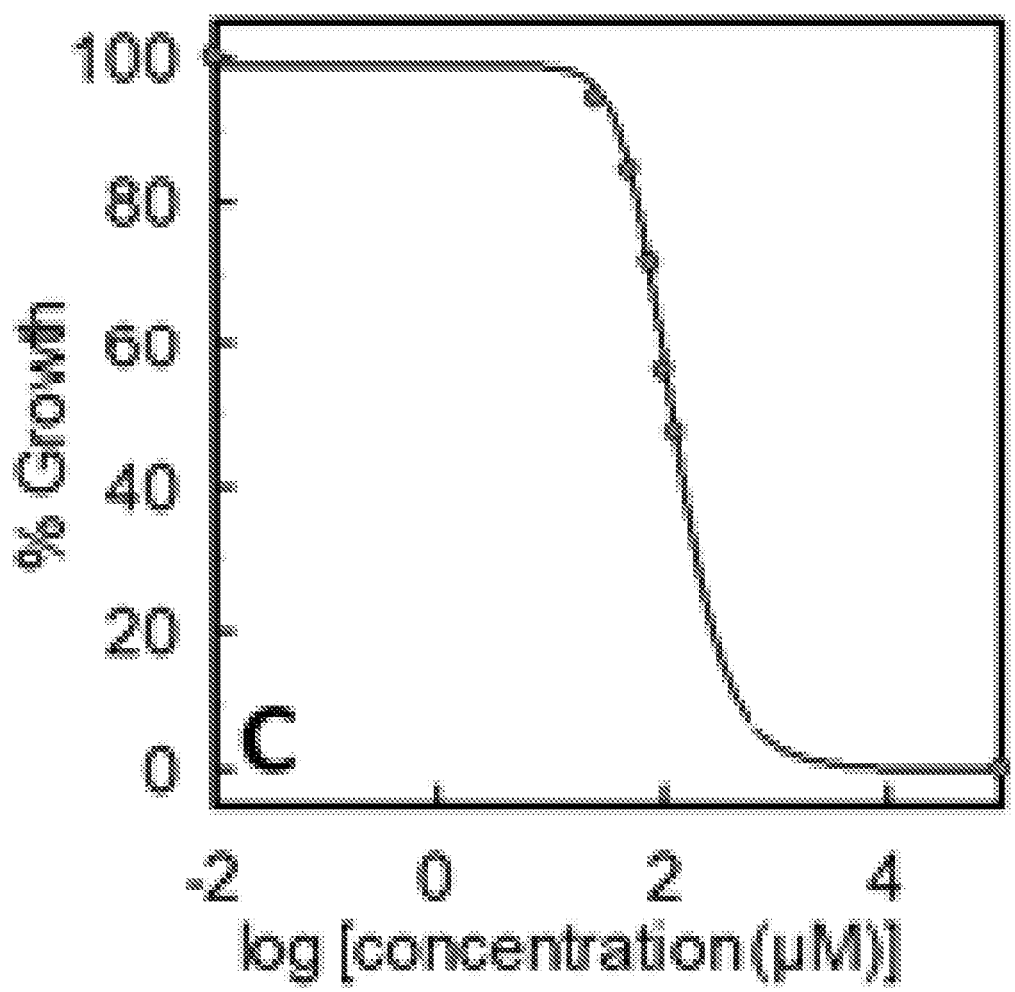
Figure 4D:
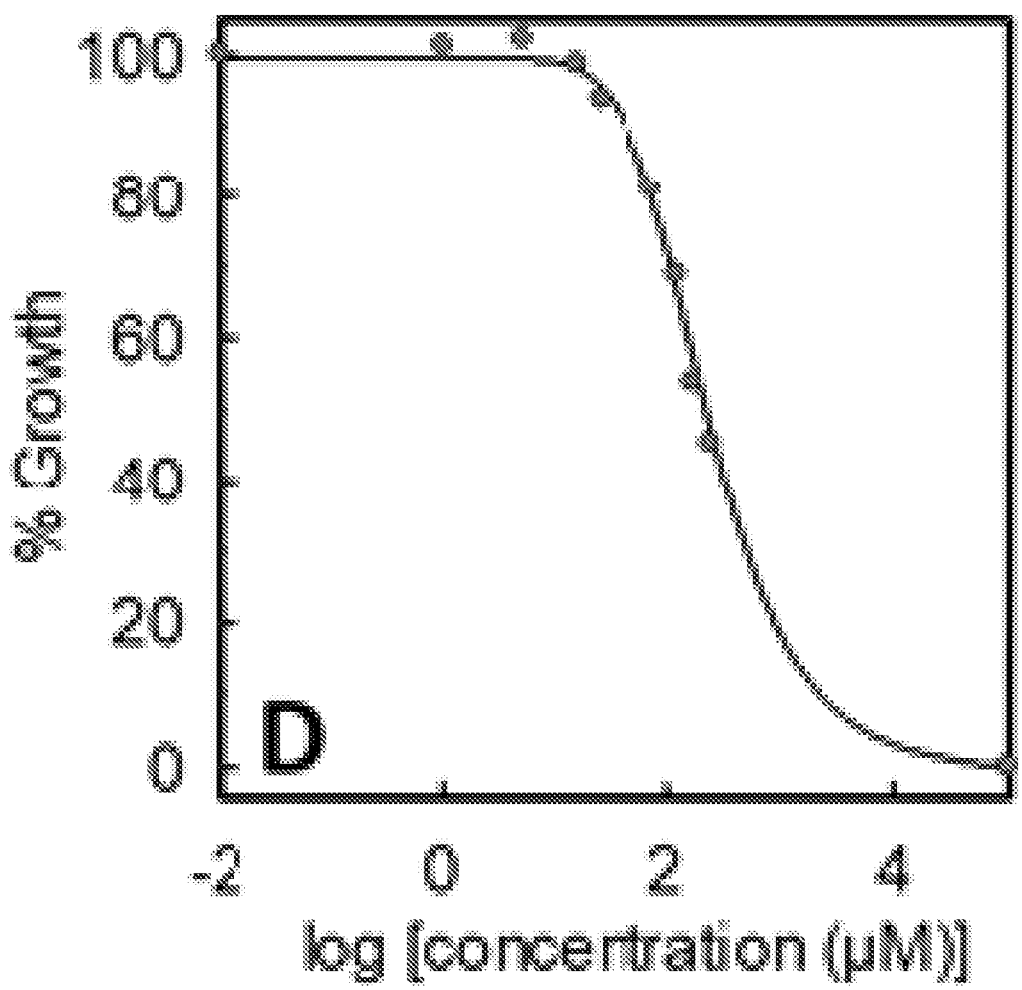

4-Aminoisoindoline-1,3-Dione Derivatives Elicit a Growth Retardation Phenotype in *P. aeruginosa* and *A. baumannii* Cells The binding affinity and structural information indicate that most of the analogs in Table 1 bind BfrB at the Bfd binding site with a strength comparable to that of the BfrB-Bfd association ($K_d$=3 µM), therefore suggesting that these compounds may be capable of interfering with the BfrB-Bfd interaction in the *P. aeruginosa* cytosol. As will be described below, this idea was investigated, first by demonstrating that the analogs elicit a growth phenotype in *P. aeruginosa*, and then by showing that one of the most potent analogs inhibits the mobilization of iron from BfrB in the bacterial cytosol. To investigate the effect of the analogs on cell growth, cultures of *P. aeruginosa* in M63 media were challenged with 4-aminoisoindoline-1,3-dione derivatives, and their growth was monitored in 96 well plates by following the $OD_{600}$. FIGS. 4A and 4B illustrate the dose-dependent growth inhibition observed upon challenging the cultures with analogs 11 and 16, respectively; the highest concentration of analog used was determined by its solubility in PBS buffer, 250 µM for analog 11, and 125 µM for analog 16. Growth curves from similar experiments conducted with the other analogs in Table 1 were similarly obtained. In order to facilitate a quantitative comparison of the effect exerted by the analogs on *P. aeruginosa* growth, $IC_{50}$ values were calculated. To this end, the growth inhibition caused by each of the analogs was compared to that of the untreated culture (100% growth) and to the growth in the presence of ciprofloxacin present at a concentration equivalent to 3 times the reported MIC (0% growth). Hence, the relative growth in the presence of a 4-aminoisoindoline-1,3-dione analog, measured 13 h post-inoculation, is defined by equation 1. The $IC_{50}$ values, obtained from fitting the plots relating growth % and analog concentration to equation 2 (FIGS. 4C and 4D), are listed in Table 1. Comparison of these values shows that analog 16 is very efficacious at inhibiting cell growth, despite a very similar binding affinity for BfrB when compared to similar analogs such as 13, 14, and 15. The reasons for the higher efficacy of analog 16 to inhibit cell growth are not yet evident, but it is possible to speculate that these may be related to their relative ability to penetrate the *P. aeruginosa* cell and/or their reactivity/stability in cell culture.

Figure 5A:
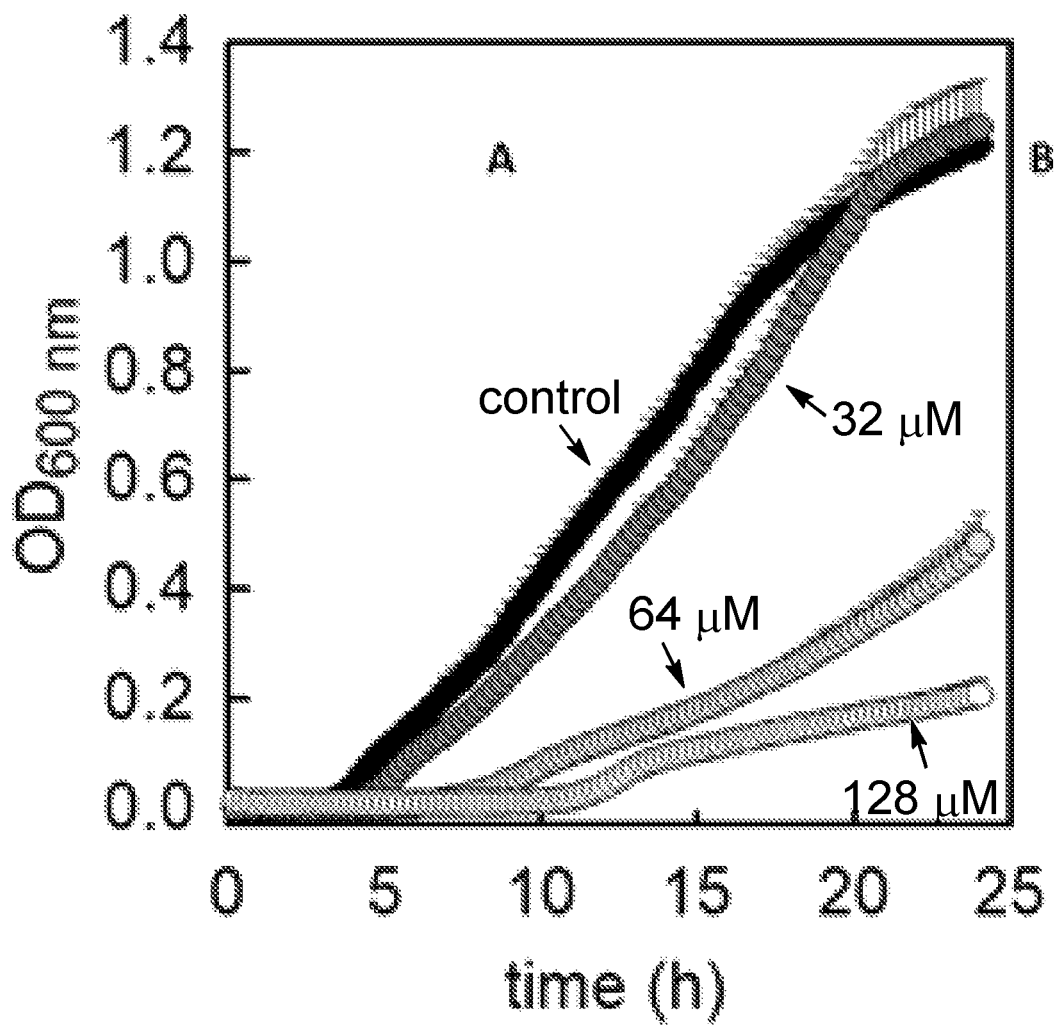
FIGS. 5A and 5B illustrate that analogs of 4-aminoisoindoline-1,3 dione penetrate *A. baumanni* cells and elicit a growth defect.
Figure 5B:
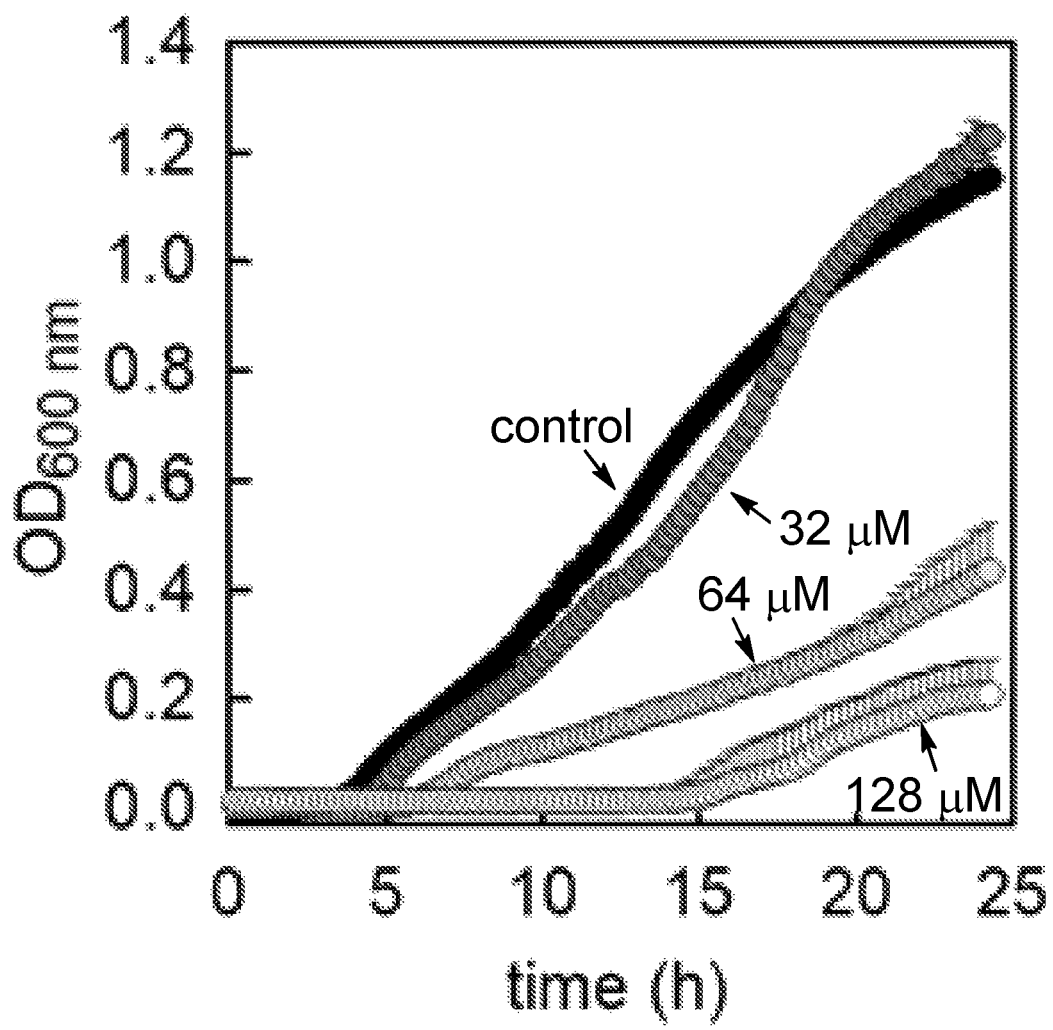

As indicated above, key residues in BfrB and Bfd that participate at the BfrB-Bfd complex interface in *P. aeruginosa* are conserved in multiple Gram-negative pathogens, suggesting that 4-aminoisoindoline-1,3-dione derivatives may also inhibit the Bfr-Bfd complex in these other Gram-negative organisms. This idea was tested with *A. baumanni* AB5075, a highly virulent isolate, which has been proposed as a model strain for the evaluation of pathogenesis and antimicrobial treatments.[66] Sequence alignment against *P. aeruginosa* showed near perfect conservation of key residues participating at the BfrB-Bfd interface, with only one conservative replacement, Q at the position occupied by E81 in *P. aeruginosa* BfrB. Challenging the *A. baumannii* AB5075 strain with the recently synthesized 4-aminoisoindoline-1,3-dione derivatives, such as KM-5-25 and KM-5-35, resulted in a dose-dependent growth phenotype (FIGS. 5A-5B). The corresponding $IC_{50}$ and MIC values are reported in Table 1. These findings support the hypothesis that 4-aminoisoindoline-1,3-dione derivatives can inhibit the BfrB-Bfd interaction in Gram-negative pathogens where Bfr and Bfd residues participating at the protein-protein interface are conserved.

TABLE 1

Structure, binding affinity, $IC_{50}$, and MIC of 4-aminoisoindoline-1,3-dione derivatives

| | | | P. aeruginosa | | A. baumannii | |
|---|---|---|---|---|---|---|
| Analog | Structure | $K_d$ ; µM | $IC_{50}$ (µM) | MIC (µM) | $IC_{50}$ (µM) | MIC (µM) |
| 8 | | 300 ± 50 | Not active | | | |
| 11 | | 11 ± 1 | 258 | | | |

TABLE 1-continued

Structure, binding affinity, IC$_{50}$, and MIC of 4-aminoisoindoline-1,3-dione derivatives

| Analog | Structure | K$_d$ ; μM | P. aeruginosa IC$_{50}$ (μM) | P. aeruginosa MIC (μM) | A. baumannii IC$_{50}$ (μM) | A. baumannii MIC (μM) |
|---|---|---|---|---|---|---|
| 12 | 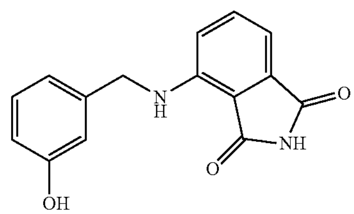 [SMILES: O=C1NC(=O)c2c(NCc3cccc(O)c3)cccc21] | 15 ± 2 | Not active | | | |
| 13 | 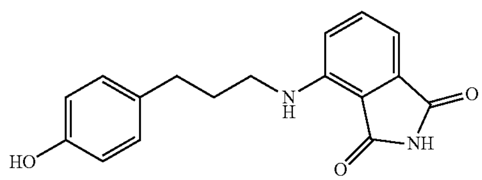 [SMILES: O=C1NC(=O)c2c(NCCCc3ccc(O)cc3)cccc21] | 3 ± 1 | 201 | | | |
| 14 | 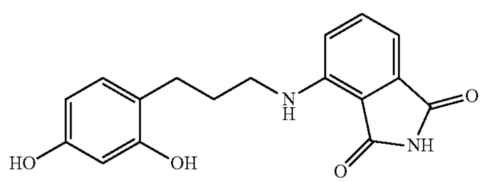 [SMILES: O=C1NC(=O)c2c(NCCCc3ccc(O)cc3O)cccc21] | 4 ± 2 | 143 | | | |
| 15 | 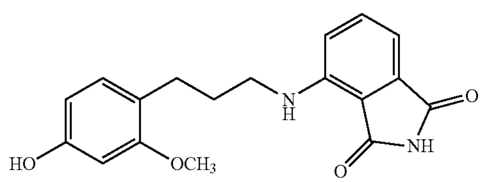 [SMILES: COc1cc(O)ccc1CCCNc1cccc2c1C(=O)NC2=O] | 5 ± 2 | 227 | | | |
| 16 | 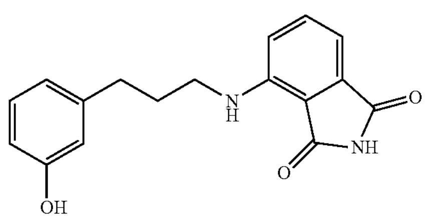 [SMILES: O=C1NC(=O)c2c(NCCCc3cccc(O)c3)cccc21] | 6 ± 1 | 121 | | 128 | |
| KM-5-25 | 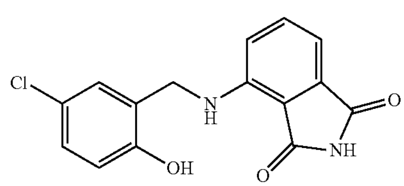 | 2.9 ± 1.9 | 64 | * | 64 | 128 |
| KM-5-35 | 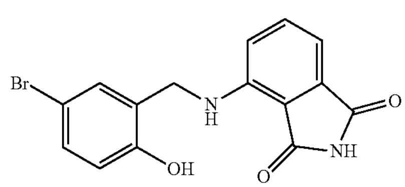 [SMILES: O=C1NC(=O)c2c(NCc3cc(Cl)ccc3O)cccc21] | 2.0 ± 1.4 | 48 | * | 64 | 80-128 |

TABLE 1-continued

Structure, binding affinity, IC$_{50}$, and MIC of 4-aminoisoindoline-1,3-dione derivatives

| | | | P. aeruginosa | | A. baumannii | |
|---|---|---|---|---|---|---|
| Analog | Structure | $K_d$; µM | IC$_{50}$ (µM) | MIC (µM) | IC$_{50}$ (µM) | MIC (µM) |
| JAG-005-030 | | * | * | * | 48 | 80-128 |
| KM-5-66 | 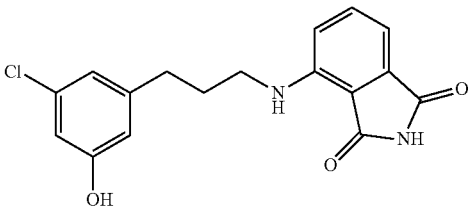 [SMILES: O=C1NC(=O)c2c(NCCCc3cc(O)cc(Cl)c3)cccc21] | * | 48 | * | <32 | 80-128 |
| JAG-005-006 | 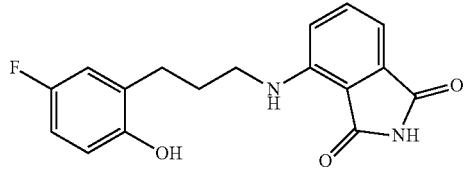 [SMILES: O=C1NC(=O)c2c(NCCCc3cc(F)ccc3O)cccc21] | * | 48 | * | * | 128 |

*Not Yet Determined

Figure 6A:
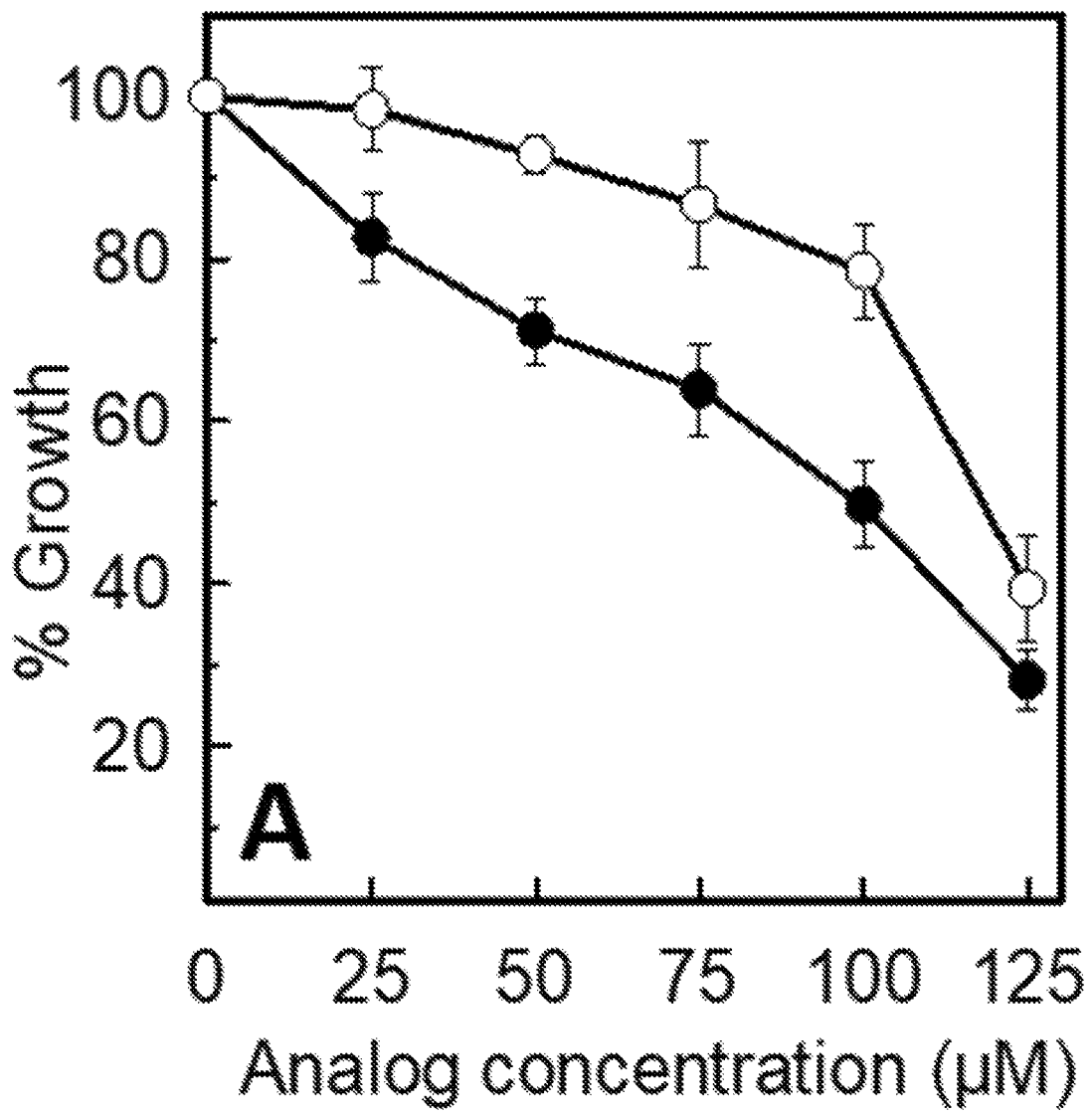
FIG. 6 illustrates deleting the bfrB gene (ΔbfrB) changes the monophasic dose-dependent growth response exhibited by the wild type *P. aeruginosa* cells to analogs 16 and 11 into a biphasic response, which is nearly independent of analog until ~100 μM and rapidly toxic thereafter. The plots illustrate the growth % of the ΔbfrB (○) and wild type (●) cells relative to untreated control as a function of analog 16 (FIG. 6A) and analog 11 (FIG. 6B) concentration. The values at each point are the average and standard deviation from three independent experiments.
Figure 6B:
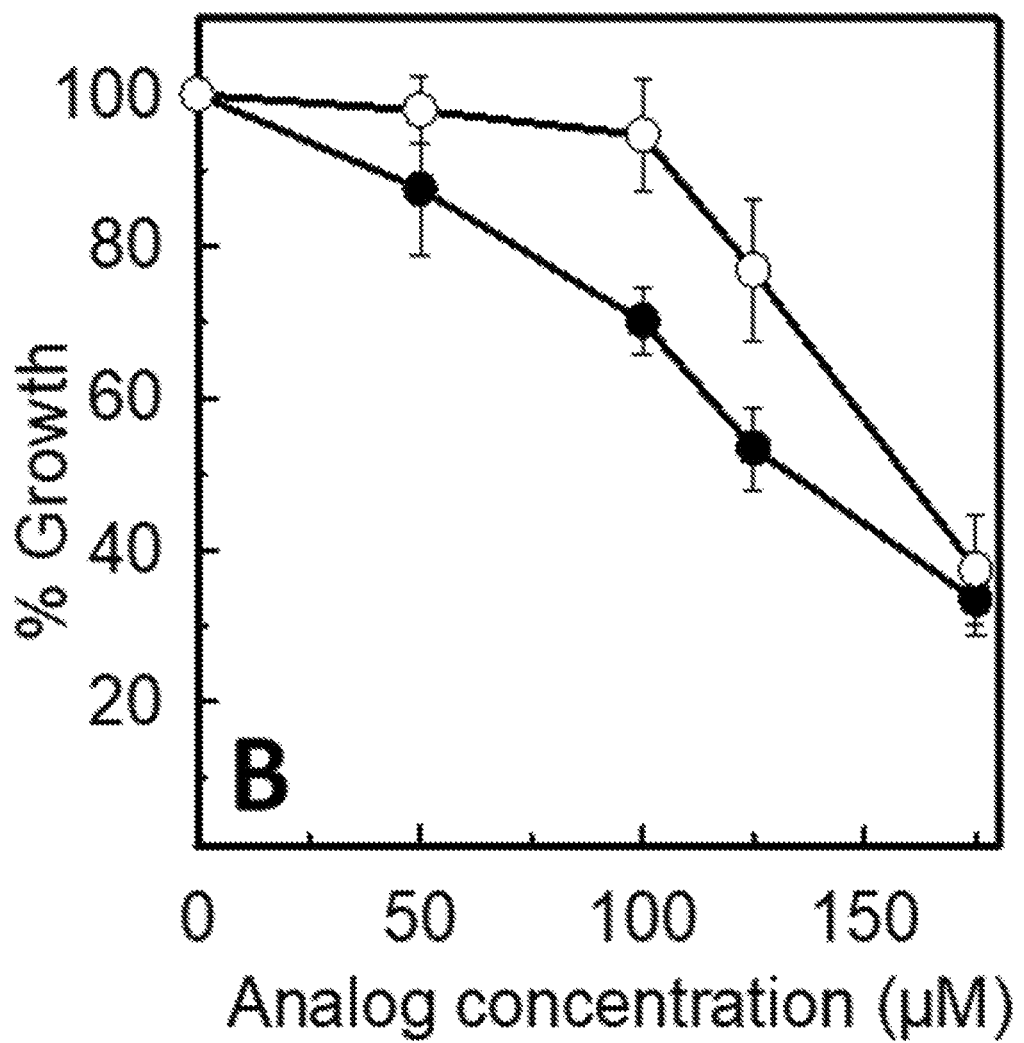

To obtain initial insights on the selectivity of the analogs for their intended target in *P. aeruginosa*, mutant cells with a deletion of the bfrB gene (ΔbfrB) were challenged with analog 11 or 16. To this end, wild type and ΔbfrB cells were cultured in M63 media supplemented with 4 µM Fe, in the presence of different concentrations of analog. The effect of the analogs on cell growth was evaluated 15 h post-inoculation by plating and enumerating viable cells and comparing the cell growth of each strain to the corresponding untreated control (FIGS. 6A and 6B). As expected, the analogs elicit a monophasic dose-dependent growth defect on the wild type cells. In comparison, the analogs induce a biphasic growth response on the ΔbfrB mutant cells, which consists of a shallow first phase (0-~100 µM) that is nearly independent of analog concentration, followed by a steep second phase where the analogs become rapidly toxic. Since BfrB is not essential, it is likely that the cell can compensate for the absence of the iron storage protein. Nevertheless, the nearly independent growth defect observed in the first phase, which is in good agreement with the absence of BfrB, supports the idea that analogs 11 and 16 exhibit significant selectivity for BfrB in the *P. aeruginosa* cell. The sudden onset of toxicity observed in the second phase, which is not observed with the wild type cells, is probably related to off-target effects that expose a fitness vulnerability caused by the absence of BfrB. Consequently, it is possible to conclude that the dose-dependent growth defect elicited by 11 or 16 on wild type *P. aeruginosa* cells is largely a consequence of the interaction between the small molecule inhibitors and BfrB in the bacterial cell. This issue was investigated in additional detail (see below) by probing the phenotypic and biochemical response of wild type cells treated with the small molecule inhibitors.

Figure 7A:
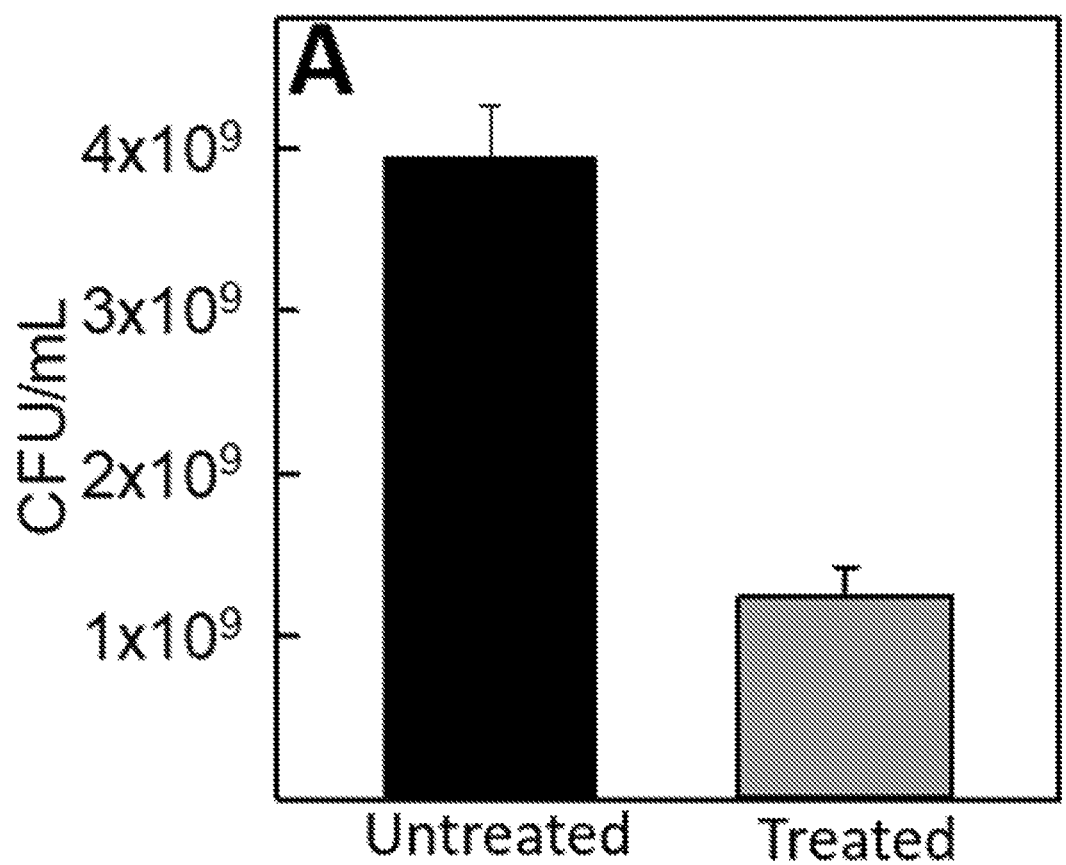
FIGS. 7A-7C illustrate *P. aeruginosa* cells treated with analog 16 overproduce pyoverdin.
Figure 7B:
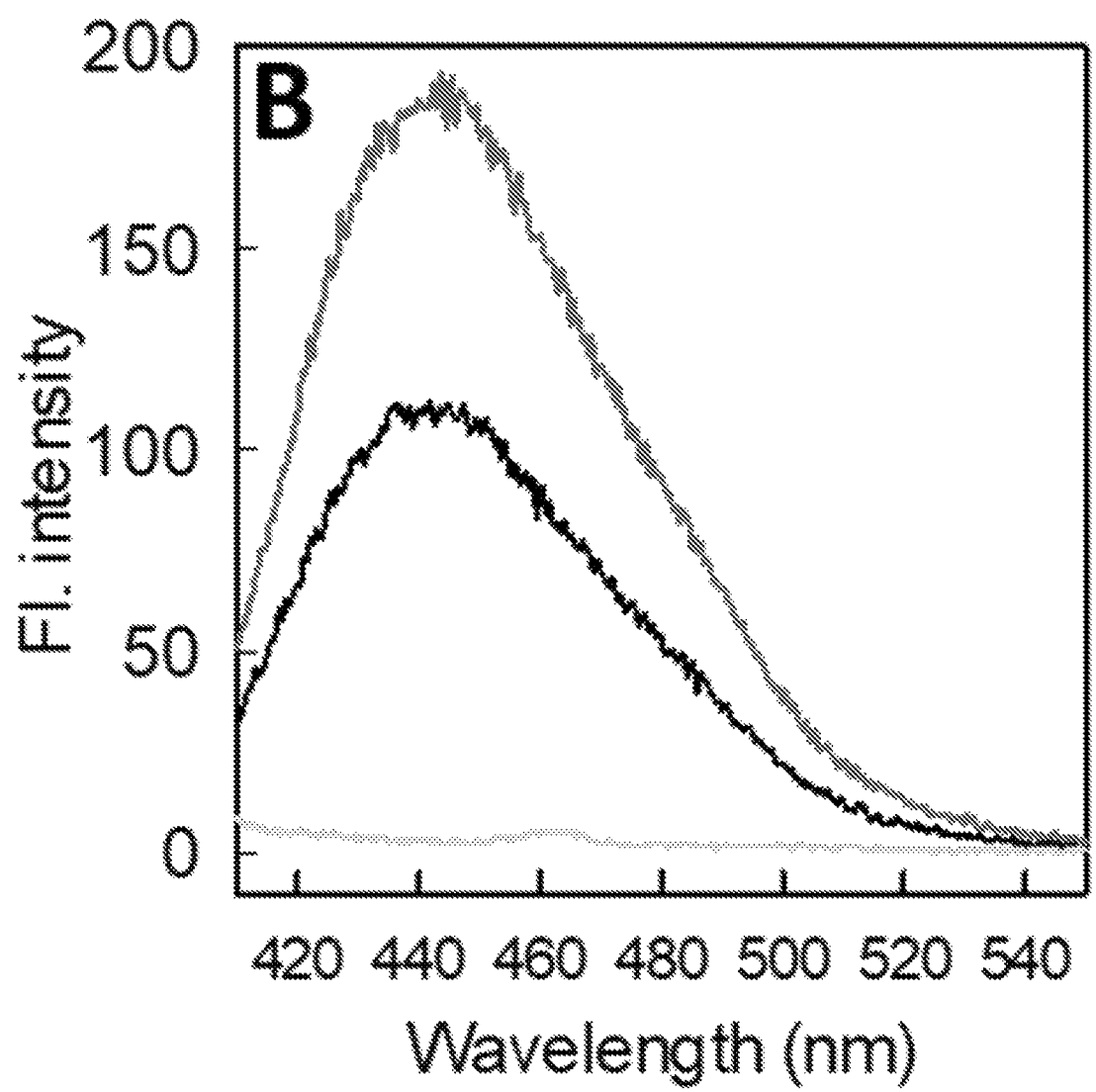
Figure 7C:
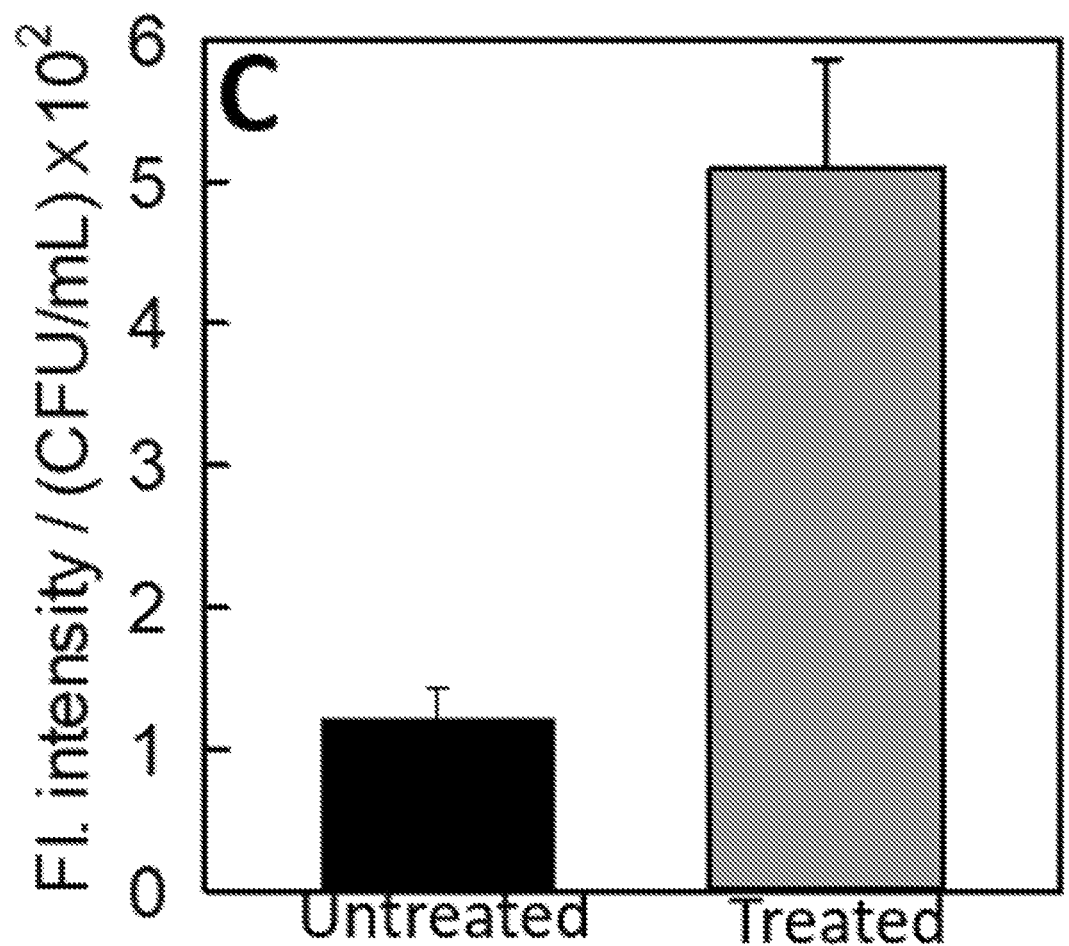

4-Aminoisoindoline-1,3 Dione Derivatives Engage their Target (BfrB) in *P. aeruginosa* Cells Studies conducted to determine whether the analogs are capable of engaging BfrB and inhibiting iron mobilization from the bacterioferritin in the *P. aeruginosa* cytosol were conducted mainly with the most efficacious analog (16), and when practical, also with analog 11, which is the most active of the two compounds harboring a —(CH$_2$)— linker. As indicated above, genetic manipulations were used in prior work to delete the bfd gene (Δbfd) and evaluate the consequences of inhibiting the BfrB-Bfd interaction in *P. aeruginosa*.[18] Preventing the BfrB-Bfd interaction in the Δbfd mutant cells dysregulates iron homeostasis by causing the irreversible accumulation of iron in BfrB and the concomitant depletion of free iron levels in the cytosol. The resultant phenotype is overproduction of the siderophore pyoverdin, which is ~4-fold larger than that secreted by wild type cells.[18] If the 4-aminoisoindoline-1,3-dione analogs are capable of binding BfrB, blocking the BfrB-Bfd interaction and consequently inhibiting iron mobilization from BfrB in the *P. aeruginosa* cytosol, then they would be expected to elicit a similar pyoverdin hyper-production phenotype. To investigate whether 4-aminoisoindoline-1,3-dione derivatives indeed elicit such a phenotype, *P. aeruginosa* cells cultured in M63 media were treated with analog 16 at a concentration of 125 µM. As expected, cell cultures treated with the analog exhibited ca. 30% of viable cells relative to cells in the untreated control (FIG. 7A). To analyze the levels of secreted pyoverdin, cells were pelleted and the supernatant was diluted 500-fold prior to measuring the fluorescence intensity at 455 nm (FIG. 7B). Normalizing the intensity of pyoverdin fluorescence to cell density (CFU/ mL) shows that cells treated with 16 secrete ~4-fold more pyoverdin than the untreated control (FIG. 7C). To demonstrate that the intrinsic fluorescence of 16, which is significantly weaker than that of pyoverdin, does not interfere with the measurement, the fluorescence spectrum from a solution of analog 16 (125 µM) after a 500-fold dilution in PBS is shown in the green trace of FIG. 7B. Similar observations are made when cell cultures are treated with analog 11, albeit with a less pronounced phenotype, which is in agreement with the lower affinity of the analog for BfrB and correspondingly higher IC$_{50}$. These findings, which indicate that the analogs elicit the anticipated pyoverdin hyper-production phenotype in *P. aeruginosa*, suggest that they bind BfrB in the *P. aeruginosa* cytosol, block the BfrB-Bfd interaction and inhibit iron mobilization from BfrB.

Figure 8A:
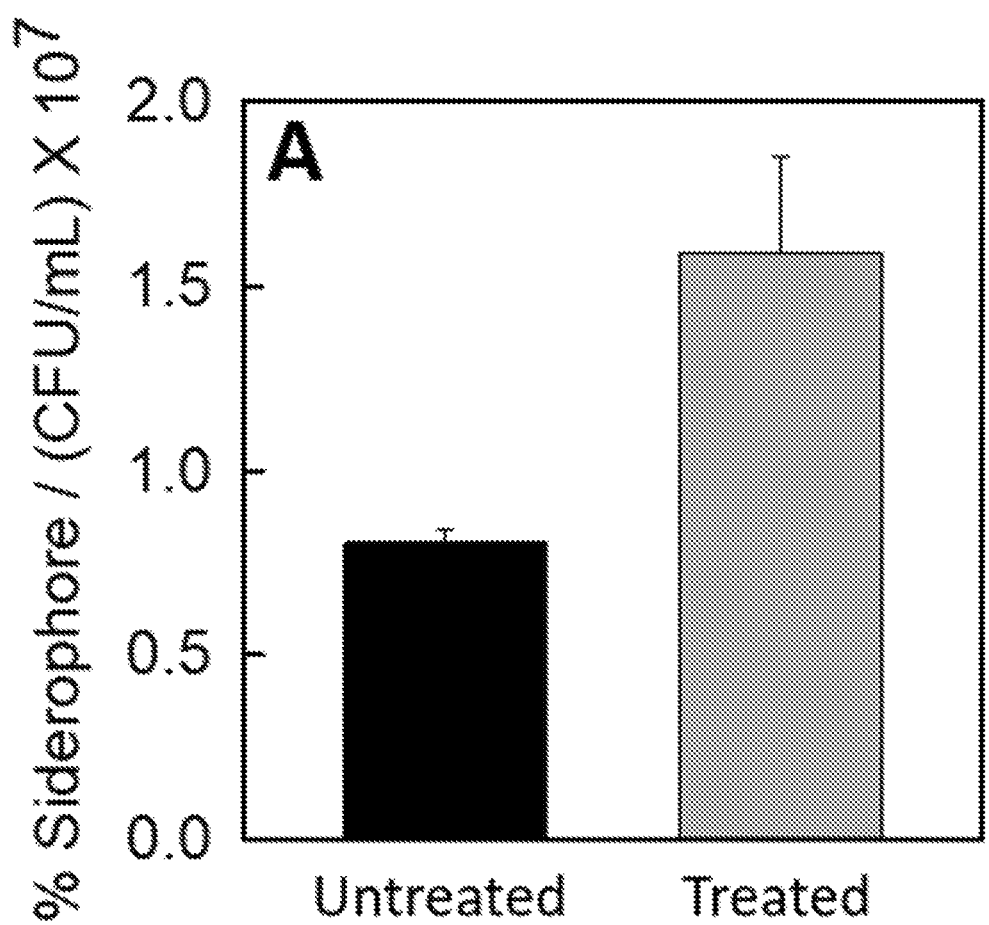
FIGS. 8A and 8B illustrate *A. baumannii* cells treated with 4-aminoisoindoline-1,3-dione analogs overproduce siderophores. The content of siderophore secreted to the culture media was calculated using equation 3 and normalized to the number of viable cells (CFU/mL). The plots show that *A. baumannii* cells treated with 64 μM (FIG. 3A) KM-5-25 or (FIG. 3B) KM-5-35 produce approximately 2-fold more siderophores than the untreated control.
Figure 8B:
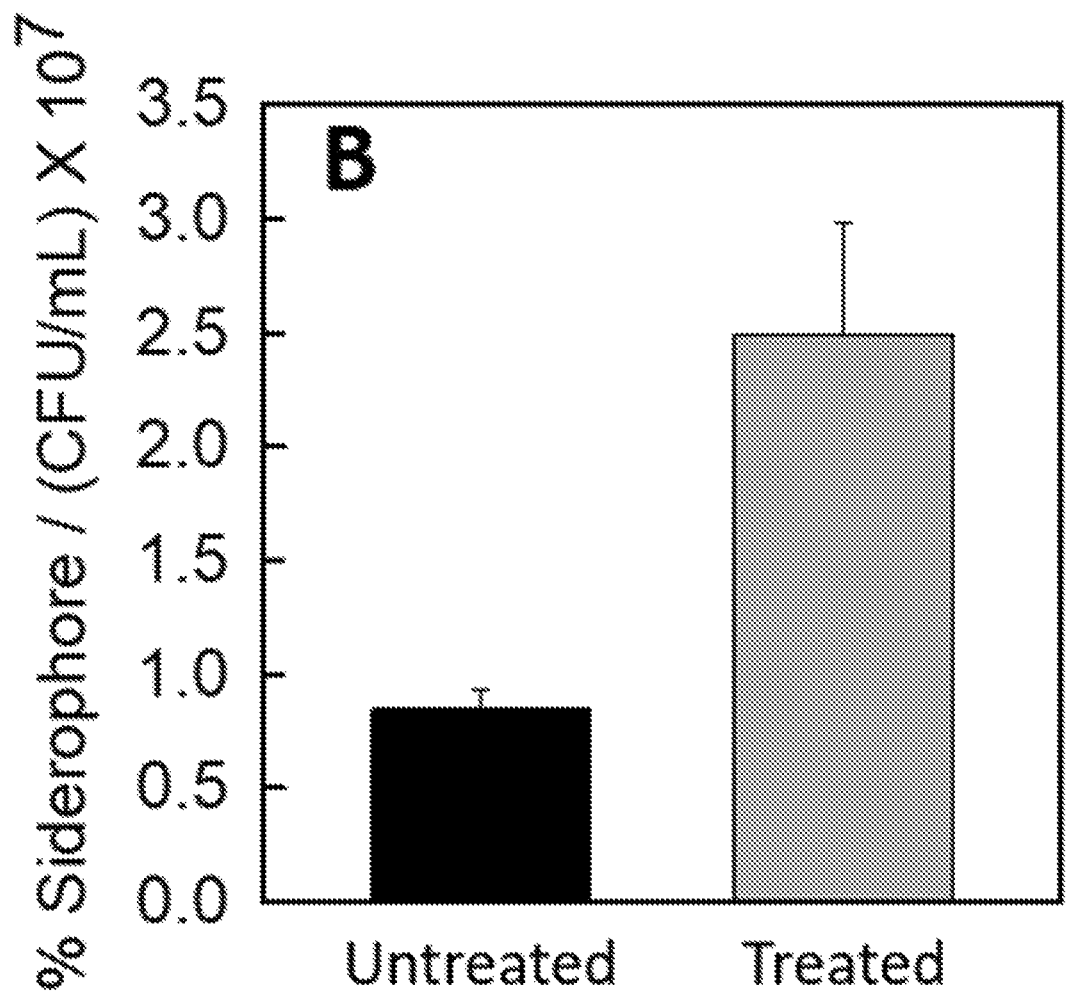

To demonstrate that the 4-aminoisoindoline-1,3-dione analogs are also capable of dysregulating iron homeostasis and eliciting a siderophore overproduction phenotype in *A. baumanni* cells, Applicant resorted to the universal siderophore assay that uses chrome azurol (CAS) and hexadecyltrimethylammonium bromide (HDTMA) as indicators. The results are illustrated in FIGS. 8A and 8B with observations made when *A. baumannii* cells are cultured at 35° C. in modified M63 media treated with analogs KM-5-25 and KM-5-35. It is evident that cells treated with the analogs secrete on average twice as much siderophores as the untreated control. These observations are in agreement with the idea that 4-aminoisoindoline-1,3-dione analogs block the Bfr-Bfd interaction in the *A. baumanni* cytosol and inhibit iron mobilization from BfrB, which causes a depletion of cytosolic $Fe^{2+}$ and stimulation of siderophore production.

Figure 9A:
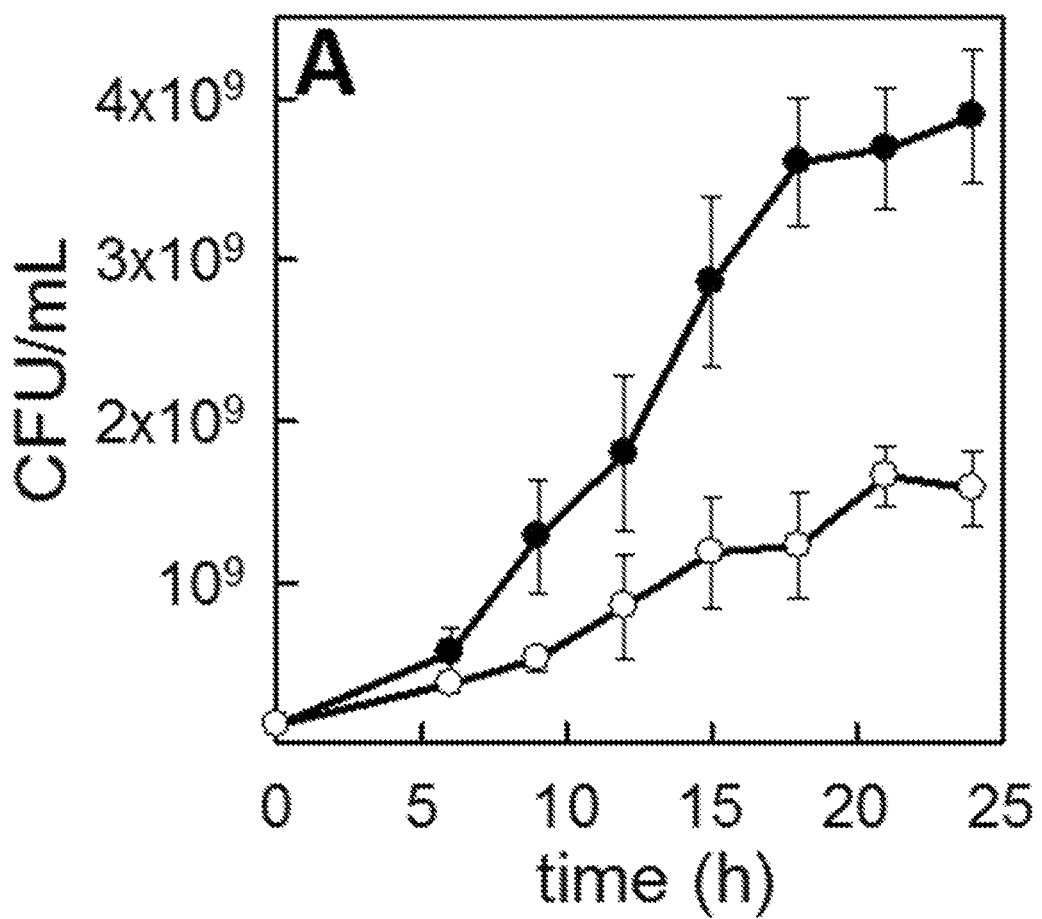
FIGS. 9A-9D illustrate that analog 16 inhibits iron mobilization from BfrB in *P. aeruginosa*. Cells cultured in M63 media supplemented with 4 μM Fe were treated with analog 16 (125 μM) or with an equivalent volume of DMSO (control).
Figure 9B:
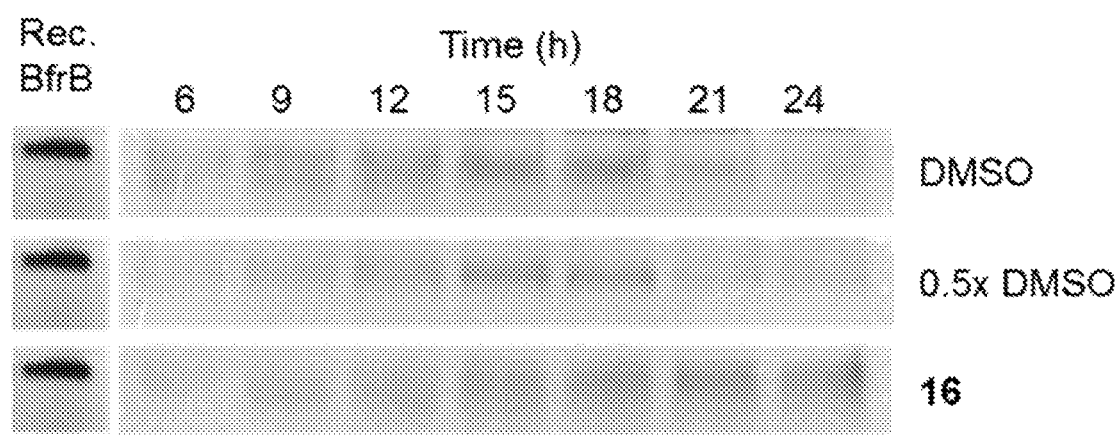
Figure 9C:
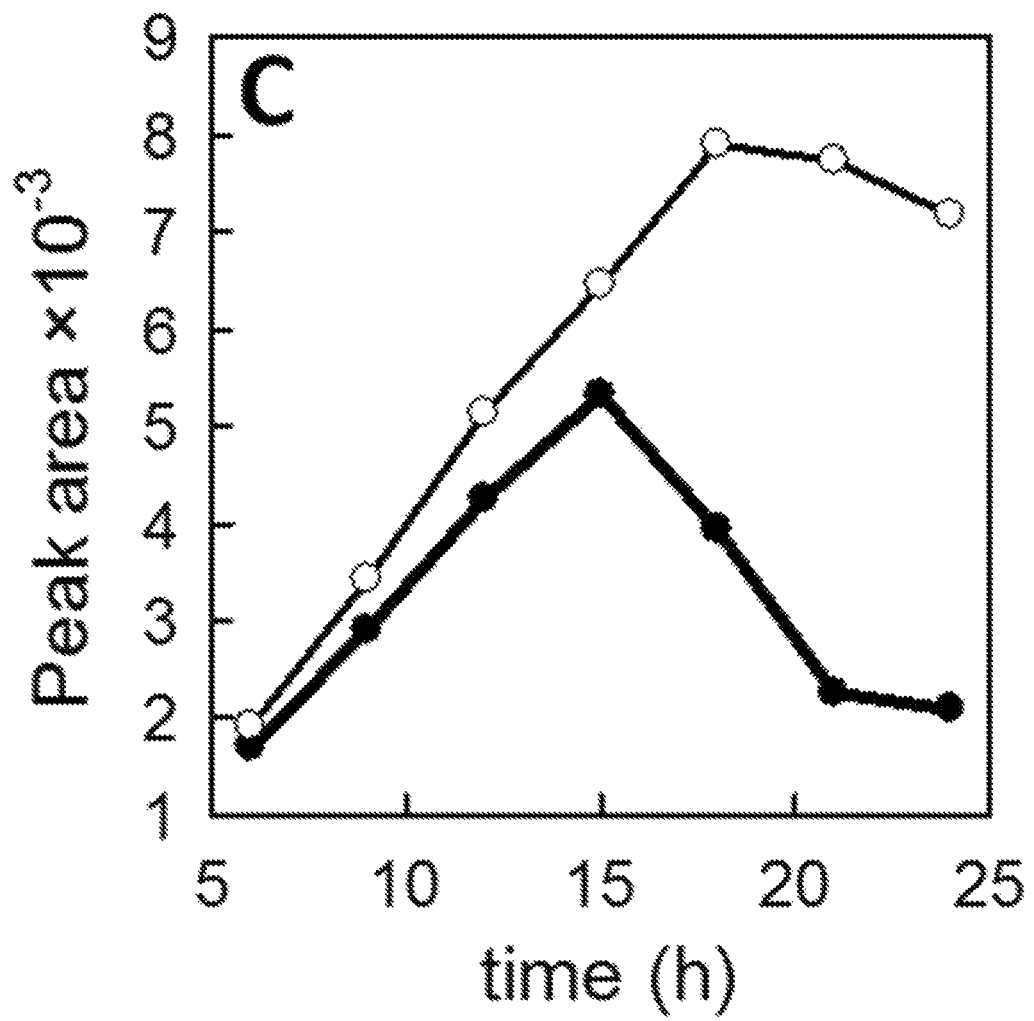
Figure 9D:
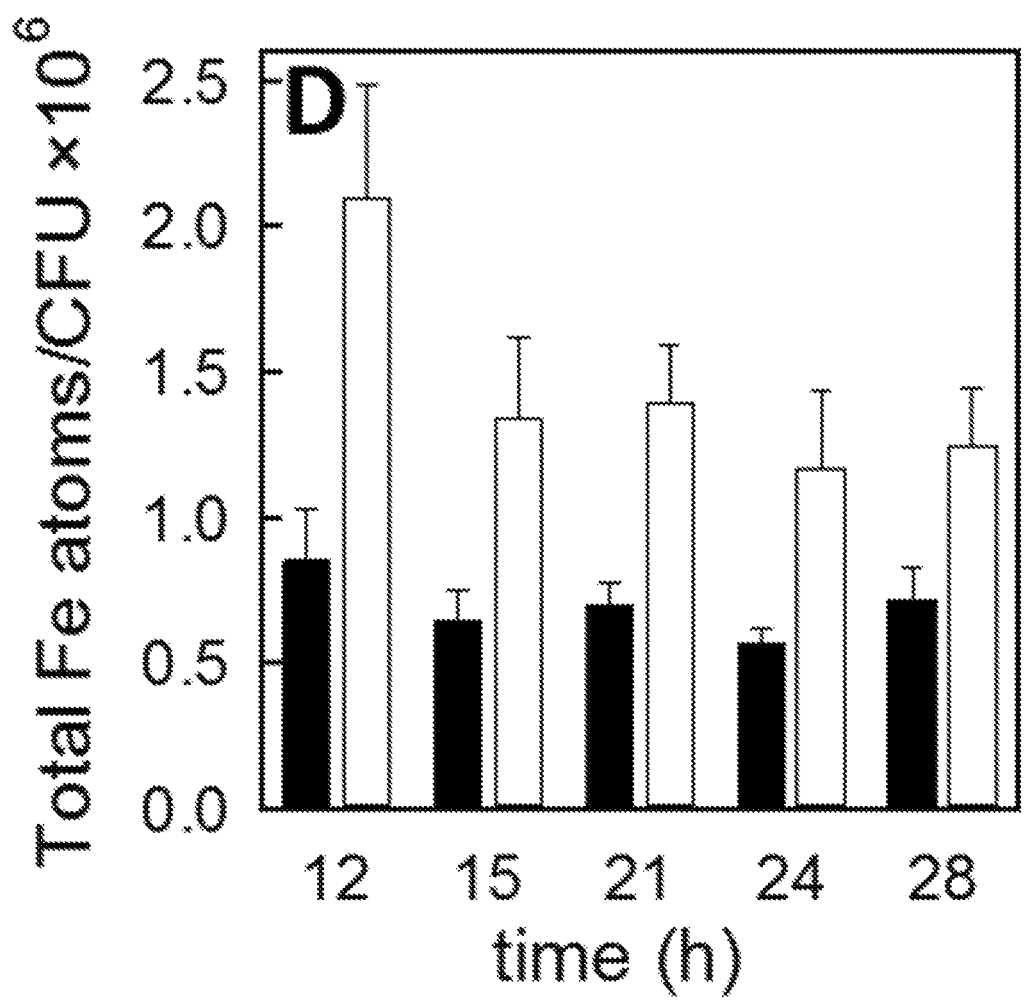

To obtain additional evidence that 16 blocks the BfrB-Bfd interaction and inhibits iron mobilization from BfrB in the *P. aeruginosa* cytosol, Applicant resorted to visualizing BfrB-iron in native PAGE gels stained with Ferene S. A similar approach has been used to demonstrate that the Δbfd mutant irreversibly accumulates iron in BfrB.[18] To this end, cells cultured in M63 media supplemented with 4 μM iron were treated with 16 (125 μM) or with an equivalent volume of DMSO (control). At different time points cells were harvested by centrifugation after a small aliquot had been sampled to enumerate cell density (CFU/mL). The growth curves (FIG. 9A) show that at every time point the number of viable cells in the untreated cultures is approximately 2.5-fold larger than in cultures treated with 16. To visualize iron stored in BfrB, the cells harvested at different time points were lysed and the clarified supernatants loaded onto native PAGE gels for separation and subsequent staining with Ferene S (FIG. 9B); recombinant BfrB mineralized with an iron core of approximately 400 iron ions was used as a standard for the electrophoretic mobility of BfrB. Lanes loaded with lysate from untreated cells (DMSO) show that iron accumulating in BfrB reaches a maximum at ca. 15 h, and then is mobilized. A similar trend is observed if the lysate solutions of untreated cells are diluted 2-fold prior to loading the gels (0.5×DMSO in FIG. 10B), in order to account for the nearly 2-fold larger CFU/mL observed at each time point relative to the treated culture. In contrast, the lanes loaded with lysates obtained from cultures treated with 16 show only iron accumulation in BfrB. The distinct trends of iron accumulation in BfrB observed with the treated vs untreated (0.5×DMSO) cultures can be readily visualized in the plot of FIG. 9C, which was constructed with the aid of densitometry analysis of the gel bands. It is evident that the untreated cells store iron in BfrB during the logarithmic growth phase and then mobilize the stored reserves during the stationary phase. In contrast, when cells are treated with 16, the flow of iron into BfrB appears to be mostly unidirectional, with much slower (inhibited) mobilization of iron from BfrB. Consistent with the nearly irreversible accumulation of iron in BfrB when cultures are treated with 16, measurements of total cellular iron levels normalized to viable cell counts show that *P. aeruginosa* cells harbor approximately twice as much iron in the treated cultures relative to the untreated control (FIG. 9D). Taken together, these observations strongly support the idea that blockade of the BfrB-Bfd interaction by 16 inhibits iron mobilization from BfrB and leads to nearly an irreversible accumulation of unusable iron in the bacterial cell.

Figures 10A, 10B, 10C:
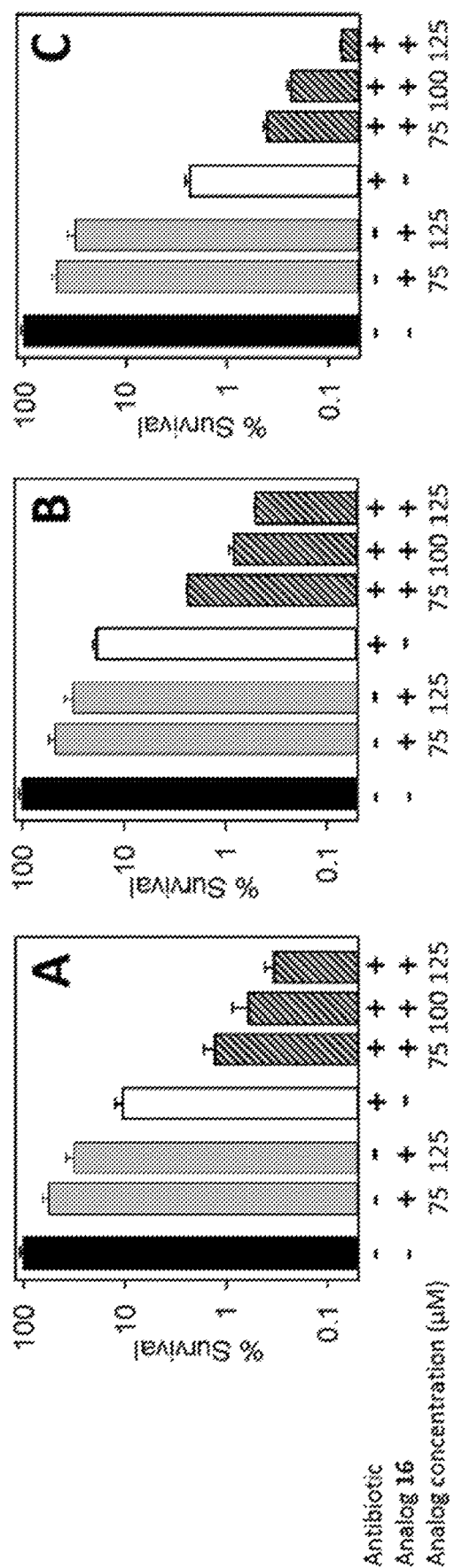
FIGS. 10A-10E illustrate that analog 16 potentiates the activity of fluoroquinolones.
Figures 10D, 10E:
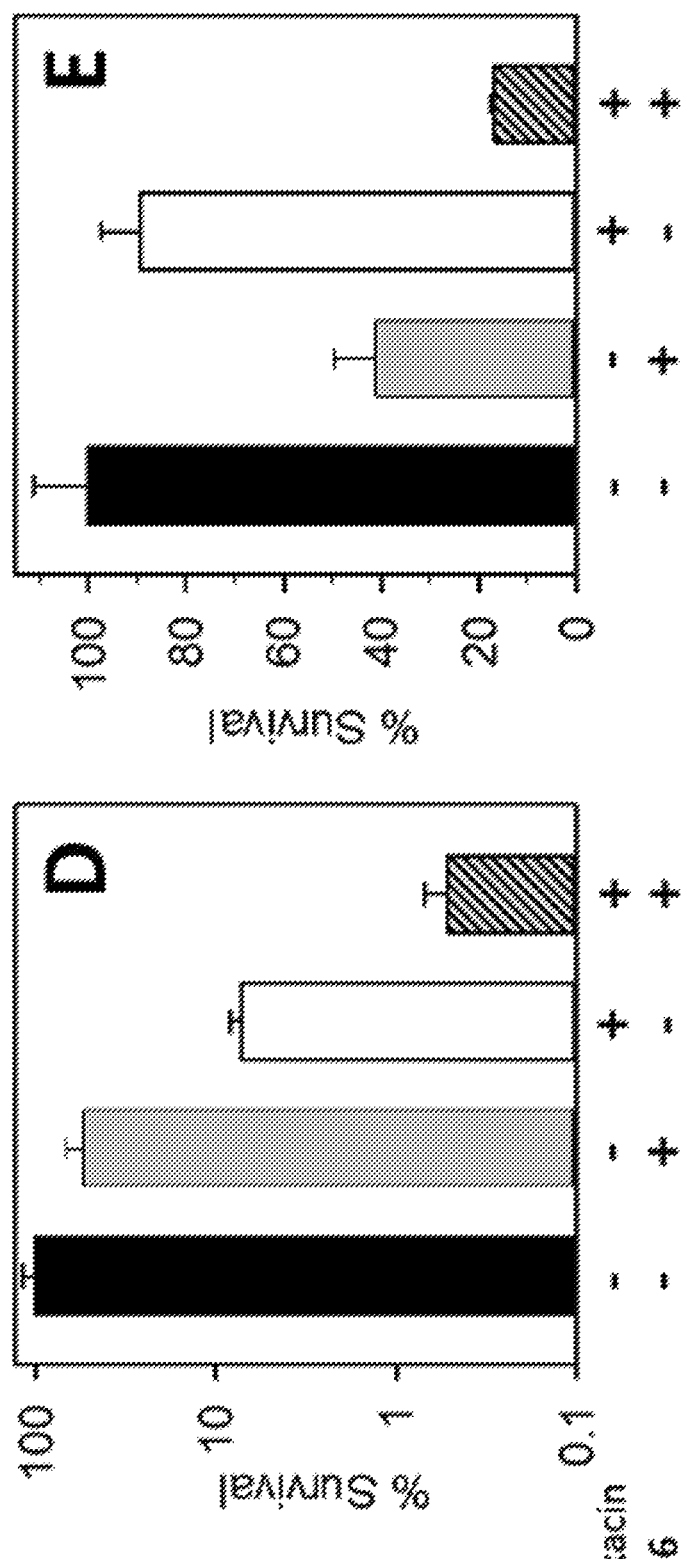

4-Aminoisoindoline-1,3-Dione Derivatives Enhance the Killing Activity of Fluoroquinolones Previous studies demonstrated that intact iron homeostasis is essential for bacterial cell survival under antibiotic stress, which suggests that bacterial iron homeostasis may be a potential target for boosting the action of antibiotics.[53-54] Consequently, it was asked whether the 4-aminoisoindoline-1,3-dione probes developed to disrupt bacterial iron homeostasis by blocking the BfrB-Bfd interaction would also potentiate the killing activity of antibiotics. The idea was initially tested by treating *P. aeruginosa* PAO1 cultures with (i) analog 16, (ii) ciprofloxacin at the reported MIC[44] (0.25 μg/mL), and (iii) a combination of ciprofloxacin and analog 16. The effect was evaluated 18 h post treatment by plating, enumerating viable cells (CFU/mL) and comparing the results to untreated cells (FIG. 10A). Cultures treated with only analog 16 (125 μM) experienced the anticipated ~30% survival, and cultures treated with only ciprofloxacin experienced approximately 10% survival relative to untreated control. In comparison, cultures treated with a combination of ciprofloxacin and analog 16 experienced significantly lower survival, in an analog-concentration dependent manner, such that when analog 16 was present at 125 μM the % survival was ~50-fold lower relative to treatment with ciprofloxacin alone. Similar experiments carried out with the fluoroquinolones levofloxacin and norfloxacin revealed a similar enhancement of bactericidal activity, with approximately 50-fold lower cell survival of cultures treated with a combination of 16 (125 μM) and fluoroquinolone, relative to treatment with only the fluoroquinolone. Related experiments conducted with tobramycin and gentamycin (protein synthesis inhibitors) and with ceftazidime and imipenem (cell wall biosynthesis inhibitors) showed no enhancement of the antibacterial activity of these antibiotics when used in combination with the small molecule inhibitors of the BfrB-Bfd interaction (data not shown).

To extend these observations to include additional strains of *P. aeruginosa*, Applicant conducted similar investigations with two cystic fibrosis clinical isolates (MR3B and MR60), obtained from Seattle Children's Hospital Research Foundation. Observations made with strain MR3B (FIG. 11D) are similar to those made with strain PAO1 in that cultures of M3B treated with analog 16 (125 μM) experienced ca. 50% survival and cultures treated with ciprofloxacin (0.2 μg/mL) experienced ca. 10% survival. In comparison, cultures treated with a combination of analog 16 and ciprofloxacin experienced 0.5% survival, or approximately 20-fold lower survival relative to treatment with ciprofloxacin alone. Strain MR60 is significantly more resistant to ciprofloxacin. When treated with ciprofloxacin at a concentration of 1 μg/mL, which is 4-5 fold higher than the dose used in experiments with strains PAO1 or MR3B, the MR60 strain experienced ca. 90% survival (FIG. 11E). In comparison, MR60 cultures treated with analog 16 (125 μM) experienced ca. 40% survival and cultures treated with a combination of analog 16 and ciprofloxacin experienced ca. 10% survival, or approximately 4-fold lower survival relative to treatment with ciprofloxacin alone. These findings indicate that analogs of 4-aminoisoindoline-1,3-dione, such as analog 16, inhibit the BfrB-Bfd interaction and enhance the activity of fluoroquinolones in a variety of *P. aeruginosa* strains.

Discussion

Iron metabolism is emerging as an important unconventional target for the development of antibacterial strategies.

The essentiality of iron for most pathogens, together with innate immune defenses which function to maintain very low concentrations of free iron in vivo (~$10^{-20}$ M), present a formidable challenge to host-colonization by pathogens, and suggest that dysregulation of iron homeostasis constitutes a significant bacterial vulnerability. In agreement, gallium has been shown to disrupt bacterial iron metabolism,[55-56] and a recent report showed that systemic gallium treatment improves lung function in patients with chronic *P. aeruginosa* infection.[11] $Ga^{3+}$, which has an ionic radius similar to that of $Fe^{3+}$ is thought to perturb iron homeostasis by replacing $Fe^{3+}$ in vital iron-utilizing proteins. Since $Ga^{3+}$ cannot be reduced under physiological conditions, iron-utilizing proteins become inhibited, adversely affecting important metabolic paths. These observations, which underscore the significance of targeting iron metabolism as a viable approach to treat infections, also highlight the importance of developing rational means to dysregulate bacterial iron homeostasis to validate new targets and implement new strategies to develop novel antimicrobial therapies.

Previous investigations with *P. aeruginosa* showed that bacterial iron homeostasis can be perturbed by specifically interfering with the process of iron storage/mobilization from bacterioferritin.[18] Encouraged by these results a systematic, iterative strategy was pursued based on fragment screening, structural characterization of fragment binding and synthetic elaboration of fragment hits to discover inhibitors of the BfrB-Bfd protein-protein interaction (Table 1). These small molecule analogs of 4-aminoisoindoline-1,3 dione selectively bind BfrB at the Bfd binding site and engage pockets on the BfrB surface where Y2 and L5 from Bfd anchor. X-ray crystallographic studies showed that analogs in Table 1 bind at the Bfd-binding site on BfrB with nearly identical poses and interactions. These observations, which underscore the selectivity of the analogs for the Bfd-binding site on the BfrB surface, validate the structure-guided approach that led to their identification as inhibitors of the protein-protein interaction. The binding selectivity of the analogs for the Bfd binding site on BfrB endows analogs such as 16 with their ability to bind BfrB in the *P. aeruginosa* cytosol, perturb its interaction with Bfd and inhibit the mobilization of BfrB-iron. Consequently, the observations reported herein illustrate the usefulness of chemical probes designed to perturb iron homeostasis by rationally interfering with a specific protein-protein interaction in the bacterial cell. Blockade of the BfrB-Bfd interaction with these chemical probes inhibits iron mobilization from BfrB and establishes a nearly unidirectional flow of iron into BfrB, which causes a significant fraction of the cellular iron to be "trapped" in BfrB, and therefore accumulate as an unusable resource for the cell. The nearly irreversible accumulation of iron in BfrB is probably accompanied by a depletion of free iron in the cytosol, similar to that observed with the Δbfd mutant,[18] which as expected, is manifested in a pyoverdin hyperproduction phenotype. In this context, the growth defect elicited by the inhibitors is probably related to an intracellular iron limitation induced by blockade of the BfrB-Bfd interaction, which in turn is likely to exert an inhibitory effect on the biosynthesis and repair of iron-dependent enzymes that function in central physiological processes.

An important feature of utilizing chemical probes for dissecting biological systems is that these can be used alone, or in combination with other synergistic or antagonistic probes. Previous studies have shown that some antibiotics disrupt bacterial iron homeostasis and that the iron homeostasis machinery is important for bacterial cell survival in the presence of antibiotics.[53, 57-58] Given that the results show that the inhibitors of the BfrB-Bfd interaction dysregulate iron homeostasis, Applicant asked if the inhibitors would also boost the activity of antibiotics. This idea was tested initially with ciprofloxacin, and then with two other fluoroquinolones, norfloxacin and levofloxacin. The results show that the small molecule inhibitors of the BfrB-Bfd interaction boost the bactericidal activity of the fluoroquinolones approximately 50-fold. Additional work is clearly required to understand the reasons behind these observations. It is tempting, however, to speculate that the enhancement of the killing activity brought by the inhibitors of the BfrB-Bfd interaction may be related to the intracellular iron depletion caused by inhibiting the mobilization of iron from BfrB, which limits the pool of iron required to support the biogenesis or the repair of iron-dependent enzymes. In this context, it has been proposed that bactericidal antibiotics have well-established mechanisms of action, but that in addition to these distinct mechanisms, subsequent metabolic changes such as elevated concentrations of TCA metabolites, active breakdown of the metabolic pool and elevated redox state also contribute to defining bactericidal activity.[59] It is therefore possible that the intracellular limitation of iron caused by inhibition of the BfrB-Bfd interaction impairs the biogenesis or the repair of important enzymes such as aconitase and succinate dehydrogenase of the TCA cycle, thus decreasing cell fitness and increasing the bacterial cell susceptibility to fluoroquinolone antibiotics. This provides for therapeutic strategies where inhibitors of the BfrB-Bfd interaction are used in combination with existing fluoroquinolone antibiotics.

Example 3: Animal Safety, Pharmacokinetic and Efficacy

Compounds of the present technology will be formulated to obtain formulations of 5-10 mg/mL to enable doses up to 25-50 mg/kg with dosing volumes of 5-10 mL/kg in a 25 g mouse. If these concentrations cannot be obtained in PBS or saline, a variety of commonly used vehicles will be screened, such as carboxymethyl cellulose, PEG300, β-cyclodextrin.

Prior to carrying out pharmacokinetic (PK) and efficacy testing, in vivo tolerability will be assessed in CD-1 mice. Compounds according to the present technology will be administered by IP in a single dose (n=6; 3 male, 3 female) and the animals observed for 3 days, recording behavioral, weight gain and survival. Maximum tolerated doses (MTD) will be defined as those that produce no adverse or weight changes (>10%) compared to vehicle control animals.

PK studies will be carried out to determine bioavailability following oral administration in CD-1 mice. Compounds with 25% F and suitable PK (ability to achieve blood levels over the MIC>8 h) will be chosen.

Animal efficacy studies will include murine bacteremia and thigh infection models. These studies will evaluate analog activity in *P. aeruginosa* and *A. baumannii* systemic and local tissue infections, respectively. These studies will provide proof-of-concept for in vivo efficacy and the starting doses for compounds.

The expected outcomes via compounds of the present technology are:
  i) Have similar or better potency than standard of care (SOC) colistin against MDR *P. aeruginosa* and *A. baumannii*.

ii) Have suitable ADME (absorption, distribution, metabolism, and excretion) and PK properties for once a day PO and/or IV administration.
iii) Have little or no cytochrome P450 (Cyp) inhibitory activity against the seven Cyp isoforms most likely to cause exposure variability and drug-drug interactions.
iv) Have little or no activity in a manual patch clam assay to assess hERG (human Ether Ether-á-go-go-Related Gene product) activity, greatly lowering the risk of the compound to cause cardiac arrhythmias.

REFERENCES

1. CDC. Antibiotic Resistance Threats in the United States 2013. www.cdc.gov/drugresistance/threat-report-2013/.
2. Blaskovich, M. A.; Butler, M. S.; Cooper, M. A., Polishing the tarnished silver bullet: the quest for new antibiotics. *Essays Biochem* 2017, 61 (1), 103-114.
3. Laxminarayan, R.; Duse, A.; Wattal, C.; Zaidi, A. K.; Wertheim, H. F.; Sumpradit, N.; Vlieghe, E.; Hara, G. L.; Gould, I. M.; Goossens, H.; Greko, C.; So, A. D.; Bigdeli, M.; Tomson, G.; Woodhouse, W.; Ombaka, E.; Peralta, A. Q.; Qamar, F. N.; Mir, F.; Kariuki, S.; Bhutta, Z. A.; Coates, A.; Bergstrom, R.; Wright, G. D.; Brown, E. D.; Cars, O., Antibiotic resistance—the need for global solutions. *Lancet Infect Dis* 2013, 13 (12), 1057-98.
4. Tacconelli, E.; Carrara, E.; Savoldi, A.; Harbarth, S.; Mendelson, M.; Monnet, D. L.; Pulcini, C.; Kahlmeter, G.; Kluytmans, J.; Carmeli, Y.; Ouellette, M.; Outterson, K.; Patel, J.; Cavaleri, M.; Cox, E. M.; Houchens, C. R.; Grayson, M. L.; Hansen, P.; Singh, N.; Theuretzbacher, U.; Magrini, N.; Group, W. H. O. P. P. L. W., Discovery, research, and development of new antibiotics: the WHO priority list of antibiotic-resistant bacteria and tuberculosis. *Lancet Infect Dis* 2018, 18 (3), 318-327.
5. Burrows, L. L., The Therapeutic Pipeline for *Pseudomonas aeruginosa* Infections. *ACS Infect Dis* 2018, 4 (7), 1041-1047.
6. Boucher, H. W.; Talbot, G. H.; Bradley, J. S.; Edwards, J. E.; Gilbert, D.; Rice, L. B.; Scheld, M.; Spellberg, B.; Bartlett, J., Bad Bugs, No Drugs: No ESKAPE! An Update from the Infectious Diseases Society of America. *Clin. Infect. Dis.* 2009, 48, 1-11.
7. Konstan, M. W.; Morgan, W. J.; Butler, S. M.; Pasta, D. J.; Craib, M. L.; Silva, S. J.; Stokes, D. C.; Wohl, M. E.; Wagener, J. S.; Regelmann, W. E.; Johnson, C. A.; MBCHB for the Scientific Advisory Group and the Investigators and Coordinators of the Epidemiologic Study of Cystic Fibrosis, Risk factors for rate of decline in forced expiratory volume in one second in children and adolescents with cystic fibrosis. *J Pediatr* 2007, 151 (2), 134-9, 139 el.
8. Crull, M. R.; Ramos, K. J.; Caldwell, E.; Mayer-Hamblett, N.; Aitken, M. L.; Goss, C. H., Change in *Pseudomonas aeruginosa* prevalence in cystic fibrosis adults over time. *BMC Pulm Med* 2016, 16 (1), 176.
9. Ballouche, M.; Cornelis, P.; Baysse, C., Iron Metabolism: A Promising Target for Antibacterial strategies. *Recent Patents on Anti-Infective Drug Discovery* 2009, 4, 190-205.
10. Foley, T. L.; Simeonov, A., Targeting iron assimilation to develop new antibacterials. *Expert Opin Drug Discov* 2012, 7 (9), 831-47.
11. Goss, C. H.; Kaneko, Y.; Khuu, L.; Anderson, G. D.; Ravishankar, S.; Aitken, M. L.; Lechtzin, N.; Zhou, G.; Czyz, D. M.; McLean, K., Gallium disrupts bacterial iron metabolism and has therapeutic effects in mice and humans with lung infections. *Science translational medicine* 2018, 10 (460), eaat7520.
12. Heinzl, G. A.; Huang, W.; Yu, W.; Giardina, B. J.; Zhou, Y.; MacKerell, A. D., Jr.; Wilks, A.; Xue, F., Iminoguanidines as Allosteric Inhibitors of the Iron-Regulated Heme Oxygenase (HemO) of *Pseudomonas aeruginosa*. *J Med Chem* 2016, 59 (14), 6929-42.
13. Cornelis, P.; Wei, Q.; Andrews, S. C.; Vinckx, T., Iron homeostasis and management of oxidative stress response in bacteria. *Metallomics* 2011, 3 (6), 540-9.
14. Bullen, J. J.; Rogers, H. J.; Spalding, P. B.; Ward, C. G., Iron and Infection: The Heart of the Matter. *FEMS Immunol. Med. Microbiol.* 2005, 43, 325-330.
15. Weinberg, E. D., Iron Availability and Infection. *Biochim. et Biophys. Acta* 2009, 1790, 600-605.
16. Hood, M. I.; Skaar, E. P., Nutritional immunity: transition metals at the pathogen-host interface. *Nat Rev Microbiol* 2012, 10 (8), 525-37.
17. Benson, D. R.; Rivera, M., Heme Uptake and Metabolism in Bacteria. *Met. Ions Life Sci.* 2013, 12, 279-332.
18. Eshelman, K.; Yao, H.; Punchi Hewage, A. N. D.; Deay, J. J.; Chandler, J. R.; Rivera, M., Inhibiting the BfrB:Bfd Interaction in *Pseudomonas aeruginosa* Causes Irreversible Iron Accumulation in Bacterioferritin and Iron Deficiency in the Bacterial Cell. *Metallocmics* 2017, 9, 646-659.
19. Keyer, K.; Imlay, J. A., Superoxide Accelerates DNA-Damage by Elevating Free-Iron Levels. *Proc. Natl. Acad. Sci. USA* 1996, 93, 13635-13649.
20. Rivera, M., Bacterioferritin: Structure Function and Protein-Protein Interactions. In *Handbook of Porphyrin Science*, Kadish, K. K.; Smith, K. M.; Guilard, R., Eds. 2014; Vol. 30, pp 136-179.
21. Andrews, S.; Norton, I.; Salunkhe, A. S.; Goodluck, H.; Aly, W. S.; Mourad-Agha, H.; Cornelis, P., Control of iron metabolism in bacteria. *Met Ions Life Sci* 2013, 12, 203-39.
22. Rivera, M., Bacterioferritin: Structure, Dynamics and Protein-Protein Interactions at Play in Iron Storage and Mobilization. *Acc Chem Res* 2017, 50, 331-340.
23. Ruvinsky, A. M.; Vakser, I. A.; Rivera, M., Local packing modulates diversity of iron pathways and cooperative behavior in eukaryotic and prokaryotic ferritins. *J Chem Phys* 2014, 140 (11), 115104.
24. Rui, H.; Rivera, M.; Im, W., Protein dynamics and ion traffic in bacterioferritin. *Biochemistry* 2012, 51 (49), 9900-10.
25. Yao, H.; Rui, H.; Kumar, R.; Eshelman, K.; Lovell, S.; Battaile, K. P.; Im, W.; Rivera, M., Concerted motions networking pores and distant ferroxidase centers enable bacterioferritin function and iron traffic. *Biochemistry* 2015, 54 (8), 1611-27.
26. Ma, J.-F.; Ochsner, U. A.; Klotz, M. G.; Nanayakkara, V. K.; Howell, M. L.; Johnson, Z.; Posey, J. E.; Vasil, M. L.; Monaco, J. J.; Hassett, D. J., Bacterioferritin A Modulates Catalase A (KatA) Activity and Resistance to Hydrogen Peroxide in *Pseudomonas aeruginosa*. *J. Bacteriol.* 1999, 181, 3730-3742.
27. Weeratunga, S.; Lovell, S.; Yao, H.; Battaile, K. P.; Fischer, C. J.; Gee, C. E.; Rivera, M., Structural Studies of Bacterioferritin B (BfrB) from *Pseudomonas aeruginosa* Suggest a Gating Mechanism for Iron Uptake via the Ferroxidase Center. *Biochemistry* 2010, 49, 1160-1175.
28. Weeratunga, S.; Gee, C. E.; Lovell, S.; Zeng, Y.; Woodin, C. L.; Rivera, M., Binding of *Pseudomonas aeruginosa* Apobacterioferritin-Associated Ferredoxin to Bacterioferritin B Promotes Heme Mediation of Electron Delivery and Mobilization of Core Mineral Iron. *Biochemistry* 2009, 48, 7420-7431.
29. Yao, H.; Wang, Y.; Lovell, S.; Kumar, R.; Ruvinsky, A. M.; Battaile, K. P.; Vakser, I. A.; Rivera, M., The Structure of the BfrB-Bfd Complex Reveals Protein-Protein Interactions Enabling Iron Release from Bacterioferritin. *J. Am. Chem. Soc.* 2012, 134 (32), 13470-81.
30. Wang, Y.; Yao, H.; Cheng, Y.; Lovell, S.; Battaile, K. P.; Middaugh, C. R.; Rivera, M., Characterization of the Bacterioferritin/Bacterioferritin Associated Ferredoxin Protein-Protein Interactions in Solution and Determination of Binding Energy Hot Spots. *Biochemistry* 2015, 54, 6162-6175.
31. Spring, D. R., Chemical genetics to chemical genomics: small molecules offer big insights. *Chem Soc Rev* 2005, 34 (6), 472-82.
32. O'Connor, C. J.; Laraia, L.; Spring, D. R., Chemical genetics. *Chem Soc Rev* 2011, 40 (8), 4332-45.
33. O'Toole, G. A.; Kolter, R., Initiation of biofilm formation in *Pseudomonas fluorescens* WCS365 proceeds via multiple, convergent signalling pathways: a genetic analysis. *Mol Microbiol* 1998, 28 (3), 449-461.
34. Chen, Y.; Wang, S.; Wang, S.; Liu, C.; Su, C.; Hageman, M.; Hussain, M.; Haskell, R.; Stefanski, K.; Qian, F., Initial Drug Dissolution from Amorphous Solid Dispersions Controlled by Polymer Dissolution and Drug-Polymer Interaction. *Pharm Res* 2016, 33 (10), 2445-58.
35. Kabsch, W., Automatic Indexing of Rotation Diffraction Patterns. *J. Appl. Cryst.* 1988, 21, 67-72.
36. Vonrhein, C.; Flensburg, C.; Keller, P.; Sharff, A.; Smart, O.; Paciorek, W.; Womack, T.; Bricogne, G., Data Processing and Analysis with the AutoPROC Toolbox. *Acta Crystallogr D Biol Crystallogr* 2011, D67, 293-302.
37. Evans, P. R., An Introduction to Data Reduction: Space-Group Determination, scaling and intensity statistics. *Acta Cryst.* 2011, D67, 282-292.
38. McCoy, A. J.; Grosse-Kunstleve, R. W.; Adams, P. D.; Winn, M. D.; Storoni, L. C.; Read, R. J., Phaser crystallographic software. *J. Appl. Cryst.* 2007, 40, 658-674.
39. Adams, P. D.; Afonine, P. V.; Brunkózci, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H., PHENIX: A Comprehensive Python-Based System for Macromolecular Structure Solution. *Acta Cryst.* 2010, D66, 213-221.
40. Emsley, P.; Lohkamp, B.; Scott, W. G.; Cowan, K., Features and Development of Coot. *Acta Cryst.* 2010, D66, 486-501.
41. Liebschner, D.; Afonine, P. V.; Moriarty, N. W.; Poon, B. K.; Sobolev, O. V.; Terwilliger, T. C.; Adams, P. D., Polder maps: improving OMIT maps by excluding bulk solvent. *Acta Cryst. D* 2017, 73 (2), 148-157.
42. Chen, V. B.; Arendall, W. B. r.; Headd, J. J.; Keedy, D. A.; Immormino, R. M.; Kapral, G. J.; Murray, L. W.; Richardson, J. S.; Richardson, D. C., MolProbity: All-Atom Structure Validation for Macromolecular Crystallography. *Acta Cryst. D* 2010, 66, 12-21.
43. McNicholas, S.; Potterton, E.; Wilson, K. S.; Noble, M. E., Presenting your Structures: The CCPmg Molecular-Graphics Software. *Acta Crystallogr D Biol Crystallogr* 2011, 67, 386-394.
44. Andrews, J. M., Determination of Minimum Inhibitory Concentrations. *J. Antimicrob. Chemother.* 2001, 48 Suppl. 1, 5-16.
45. Sebaugh, J. L., Guidelines for accurate EC50/IC50 estimation. *Pharm Stat* 2011, 10 (2), 128-34.
46. Chung, M. C., A specific iron stain for iron-binding proteins in polyacrylamide gels: application to transferrin and lactoferrin. *Anal Biochem* 1985, 148 (2), 498-502.
47. Abrámoff, M. D.; Magalhães, P. J.; Ram, S. J., Image processing with ImageJ. *Biophotonics International* 2004, 11, 36-42.
48. Fish, W. W., Rapid colorimetric micromethod for the quantitation of complexed iron in biological samples. *Methods Enzymol* 1988, 158, 357-64.
49. Hennessy, D. J.; Reid, G. R.; Smith, F. E.; Thompson, S. L., Ferene—a new spectrophotometric reagent for iron. *Can. J. Chem.* 1984, 62, 721-724.
50. Hedayati, M.; Abubaker-Sharif, B.; Khattab, M.; Razavi, A.; Mohammed, I.; Nejad, A.; Wabler, M.; Zhou, H.; Mihalic, J.; Gruettner, C.; DeWeese, T.; Ivkov, R., An optimised spectrophotometric assay for convenient and accurate quantitation of intracellular iron from iron oxide nanoparticles. *Int J Hyperthermia* 2018, 34 (4), 373-381.
51. Lepre, C. A.; Moore, J. M.; Peng, J. W., Theory and Applications of NMR-Based Screening in Pharmaceutical Research. *Chem. Rev.* 2004, 104, 3641-3675.
52. Wijerathne, H.; Yao, H.; Wang, Y.; Lovell, S.; Battaile, K. P.; Rivera, M., Bfd, a New Class of [2Fe-2S] Protein That Functions in Bacterial Iron Homeostasis, Requires a Structural Anion Binding Site. *Biochemistry* 2018, 57, 5533-5543.
53. Yeom, J.; Imlay, J. A.; Park, W., Iron homeostasis affects antibiotic-mediated cell death in *Pseudomonas* species. *J Biol Chem* 2010, 285 (29), 22689-95.
54. Mehi, O.; Bogos, B.; Csorgo, B.; Pal, F.; Nyerges, A.; Papp, B.; Pal, C., Perturbation of iron homeostasis promotes the evolution of antibiotic resistance. *Mol Biol Evol* 2014, 31 (10), 2793-804.
55. Kaneko, Y.; Thoendel, M.; Olakanmi, O.; Britigan, B. E.; Singh, P. K., The Transition Metal Gallium Disrupts *Pseudomonas aeruginosa* Iron Metabolism and has Antimicrobial and Antibiofilm Activity. *J. Clin. Invest.* 2007, 117, 877-887.
56. Minandri, F.; Bonchi, C.; Frangipani, E.; Imperi, F.; Visca, P., Promises and failures of gallium as an antibacterial agent. *Future Microbiol* 2014, 9 (3), 379-97.
57. Dwyer, D. J.; Belenky, P. A.; Yang, J. H.; MacDonald, I. C.; Martell, J. D.; Takahashi, N.; Chan, C. T.; Lobritz, M. A.; Braff, D.; Schwarz, E. G.; Ye, J. D.; Pati, M.; Vercruysse, M.; Ralifo, P. S.; Allison, K. R.; Khalil, A. S.; Ting, A. Y.; Walker, G. C.; Collins, J. J., Antibiotics induce redox-related physiological alterations as part of their lethality. *Proc Natl Acad Sci USA* 2014, 111 (20), E2100-9.
58. Dwyer, D. J.; Kohanski, M. A.; Hayete, B.; Collins, J. J., Gyrase inhibitors induce an oxidative damage cellular death pathway in *Escherichia coli*. *Mol Syst Biol* 2007, 3, 91.
59. Belenky, P.; Ye, J. D.; Porter, C. B. M.; Cohen, N., R.; Lobritz, M. A.; Ferrante, T.; Jain, S.; Korry, B. J.; Schwarz, E. G.; Walker, G. C.; Collins, J. J., Bactericidal Antibiotics Induce Toxic Metabolic Perturbations. *Cell Reports* 2015, 13, 968-980.
60. Koenig, S. M.; Truwit, J. D. Ventilator-Associated Pneumonia: Diagnosis, Treatment, and Prevention. *Clin. MIcrobio. Rev.,* 2006, 19, 637-657.
61. Koulenti, D.; Lisboa, T.; Brun-Buisson, C.; Krueger, W.; Macor, A.; Sole-Violan, J.; Diaz, E.; Topeli, A.; DeWaele, A.; Carneiro, A.; Martin-Loeches, I.; Armaganidis, A.; Rello, J. Spectrum of practice in the diagnosis of nosocomial pneumonia in patients requiring mechanical ventilation in European intensive care units. *Crit. Care Med.*, 2009, 37, 2360-2368.
62. "Hunting the Nightmare Bacteria." *Frontline.* PBS. Season 2, episode 13. Television.
63. Clinical and Laboratory Standards Institute (2015). Methods for Dilution Antimicrobial Susceptibility Tests for Bacteria That Grow Aerobically. 10th edn. Wayne, PA: CLSI (Approved standard M07-A10).
64. Schwyn, Bernhard, and J. B. Neilands. "Universal chemical assay for the detection and determination of siderophores." *Analytical biochemistry* 160.1, 1987, 47-56.
65. Arora, Naveen Kumar, et al. "Modified microplate method for rapid and efficient estimation of siderophore produced by bacteria." 3 *Biotech* vol. 7, 6 2017, 381.
66. Jacobs, A. C., et al., (2014) AB5075, "A Highly Virulent Isolate of *Acinetobacter baumannii*, as a Model Strain for the Evaluation of Pathogenesis and Antimicrobial Treatments." *MBio* 5, e01076-14. 10.1128/mBio.01076-14

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound according to Formula I

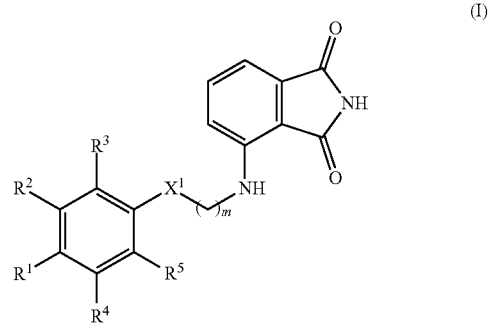

or a pharmaceutically acceptable salt and/or a solvate thereof, wherein
at least one of $R^1$, $R^2$, and $R^3$ is OH or $C_1$-$C_6$ alkoxy, and the remaining $R^2$ and $R^3$ are each independently $C_1$-$C_6$ alkoxy, H, or OH and the remaining $R^1$ is $C_1$-$C_6$ alkoxy, H, OH, or halo;

$R^4$ and $R^5$ are each independently H or halo;

$X^1$ is $CH_2$ or O; and m is 0, 1, 2, 3, 4, or 5;

provided that when $X^1$ is O, m is not 0; and provided that when $R^2$ is OH, $R^1$, $R^3$, $R^4$, and $R^5$ are each independently H, and $X^1$ is $CH_2$, then m is not 0.

B. The compound of Paragraph A, or a pharmaceutically acceptable salt and/or a solvate thereof, wherein at least one of $R^1$, $R^2$, and $R^3$ is OH, and the remaining $R^1$, $R^2$, and $R^3$ are each independently H or OH;

$R^4$ and $R^5$ are each independently H or halo;

$X^1$ is $CH_2$ or O; and m is 0, 1, 2, 3, 4, or 5;

provided that when $X^1$ is O, m is not 0; and provided that when $R^2$ is OH, $R^1$, $R^3$, $R^4$, and $R^5$ are each independently H, and $X^1$ is $CH_2$, then m is not 0.

C. The compound of Paragraph A or paragraph B, wherein $X^1$ is $CH_2$.

D. The compound of any one of Paragraphs A-C, wherein the compound is of Formula IA

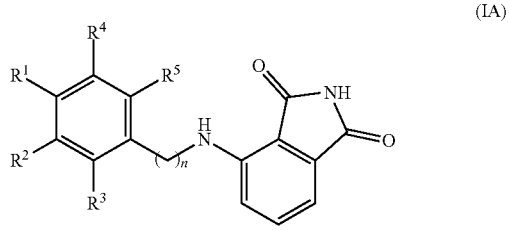

(IA)

or a pharmaceutically acceptable salt and/or a solvate thereof, wherein n is 1, 2, or 3;

provided that $R^2$ is not OH when n is 1 and $R^1$, $R^3$, $R^4$, and $R^5$ are each independently H.

E. The compound of any one of Paragraphs A-D, wherein one of $R^1$ and $R^3$ is OH, one of $R^1$ and $R^3$ is H, and $R^2$ is H.

F. The compound of any one of Paragraphs A-E, wherein $R^4$ and $R^5$ are each independently H, chlorine, or fluorine.

G. The compound of any one of Paragraphs A-F, wherein $R^4$ and $R^5$ are each independently H or chlorine.

H. A composition comprising a compound of any one of Paragraphs A-G and a pharmaceutically acceptable carrier.

I. A pharmaceutical composition comprising an effective amount of a compound of any one of Paragraphs A-G for treating a bacterial infection in a subject, and a pharmaceutically acceptable carrier.

J. The pharmaceutical composition of Paragraph I, wherein the bacterial infection comprises a Gram-negative bacterial infection.

K. The pharmaceutical composition of paragraph I or paragraph J, wherein the bacterial infection comprises a *Pseudomonas aeruginosa* infection, a *Acinetobacter baumannii* infection, a *Klebsiella pneumonia* infection, a *Yersinia pestis* infection, a *Shigella dysenteriae* infection, a *Enterobacter* sp. infection, a *Acinetobacter* sp. infection, a *Salmonella typhimurium* infection, a *Serratia* sp. infection, or a combination of any two or more thereof.

L. A method of treating a bacterial infection in a subject, the method comprising administering a compound of any one of Paragraphs A-G to the subject.

M. The method of Paragraph L, wherein the method comprises administering an effective amount of the compound.

N. The method of Paragraph L or Paragraph M, the method further comprising administering a fluoroquinolone antibiotic to the subject.

O. The method of any one of Paragraphs L-N, the method further comprising administering an effective amount of fluoroquinolone antibiotic to the subject.

P. The method of any one of Paragraphs L-O, wherein the bacterial infection comprises a Gram-negative bacterial infection.

Q. The method of any one of Paragraphs L-P, wherein the bacterial infection comprises a *Pseudomonas aeruginosa* infection, a *Acinetobacter baumannii* infection, a *Klebsiella pneumonia* infection, a *Yersinia pestis* infection, a *Shigella dysenteriae* infection, a *Enterobacter* sp. infection, a *Acinetobacter* sp. infection, a *Salmonella typhimurium* infection, a *Serratia* sp. infection, or a combination of any two or more thereof.

R. A method of treating a bacterial infection in a subject, the method comprising administering a pharmaceutical composition of any one of Paragraphs I-K to the subject.

S. The method of Paragraph R, the method further comprising administering a fluoroquinolone antibiotic to the subject.

T. The method of Paragraph R or Paragraph S, the method further comprising administering an effective amount of fluoroquinolone antibiotic to the subject.

U. The method of any one of Paragraphs R-T, wherein the bacterial infection comprises a Gram-negative bacterial infection.

V. The method of any one of Paragraphs R-U, wherein the bacterial infection comprises a *Pseudomonas aeruginosa* infection, a *Acinetobacter baumannii* infection, a *Klebsiella pneumonia* infection, a *Yersinia pestis* infection, a *Shigella dysenteriae* infection, a *Enterobacter* sp. infection, a *Acinetobacter* sp. infection, a *Salmonella typhimurium* infection, a *Serratia* sp. infection, or a combination of any two or more thereof.

W. A method of inhibiting interaction of a bacterioferritin and a bacterioferritin-associated ferredoxin, the method comprising contacting a compound of any one of Paragraphs A-G to the bacterioferritin, the bacterioferritin-associated ferredoxin, or both the bacterioferritin and the bacterioferritin-associated ferredoxin.

X. The method of Paragraph W, wherein the contacting is in vitro contacting.

Y. The method of Paragraph W or Paragraph X, wherein the bacterioferritin is a *Pseudomonas aeruginosa*, a *Acinetobacter baumannii*, a *Klebsiella pneumonia*, a *Yersinia pestis*, a *Shigella dysenteriae*, a *Enterobacter* sp., a *Acinetobacter* sp., a *Salmonella typhimurium*, a *Serratia* sp., or a combination of any two or more thereof.

Z. The method of any one of Paragraphs W-Y, wherein the bacterioferritin-associated ferredoxin is a *Pseudomonas aeruginosa* bacterioferritin-associated ferredoxin, a *Acinetobacter baumannii* bacterioferritin-associated ferredoxin, a *Klebsiella pneumonia* bacterioferritin-associated ferredoxin, a *Yersinia pestis* bacterioferritin-associated ferredoxin, a *Shigella dysenteriae* bacterioferritin-associated ferredoxin, a *Enterobacter* sp. bacterioferritin-associated ferredoxin, a *Acinetobacter* sp. bacterioferritin-associated ferredoxin, a *Salmonella typhimurium* bacterioferritin-associated ferredoxin, a *Serratia* sp. bacterioferritin-associated ferredoxin, or a combination of any two or more thereof.

Other embodiments are set forth in the following claims, along with the full scope of equivalents to which such claims are entitled.

What is claimed is:

1. A compound according to Formula I

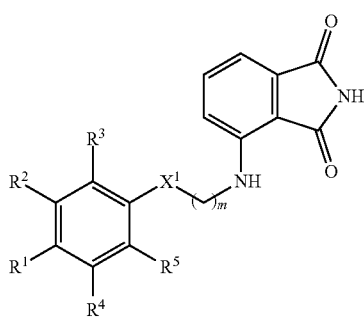

(I)

or a pharmaceutically acceptable salt and/or a solvate thereof, wherein
$R^2$ and $R^3$ are each independently $C_1$-$C_6$ alkoxy, H, or OH, and $R^1$ is $C_1$-$C_6$ alkoxy, H, OH, or halo, and at least one of $R^1$, $R^2$, and $R^3$ is OH or $C_1$-$C_6$ alkoxy;
$R^4$ and $R^5$ are each independently H or halo;
$X^1$ is $CH_2$ or O; and
m is 0, 2, 3, 4, or 5;
provided that when $X^1$ is O, m is not 0; and
provided that when $R^2$ is OH, $R^1$, $R^3$, $R^4$, and $R^5$ are each H, $X^1$ is $CH_2$, and m is not 0.

2. The compound of claim 1, wherein
$R^1$, $R^2$, and $R^3$ are each independently H or OH, and at least one of $R^1$, $R^2$, and $R^3$ is OH;
$R^4$ and $R^5$ are each independently H or halo;
$X^1$ is $CH_2$ or O; and
m is 0, 2, 3, 4, or 5;
provided that when $X^1$ is O, m is not 0; and
provided that when $R^2$ is OH, $R^1$, $R^3$, $R^4$, and $R^5$ are each H, $X^1$ is $CH_2$, and m is not 0.

3. The compound of claim 1, wherein the compound is of Formula IA

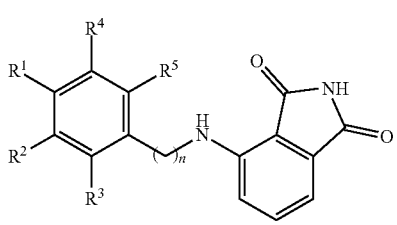

(IA)

or a pharmaceutically acceptable salt and/or a solvate thereof, wherein
n is 1, or 3;
provided that $R^2$ is not OH when n is 1 and $R^1$, $R^3$, $R^4$, and $R^5$ are each H.

4. The compound of claim 1, wherein one of $R^1$ and $R^3$ is OH, one of $R^1$ and $R^3$ is H, and $R^2$ is H.

5. The compound of claim 1, wherein $R^4$ and $R^5$ are each independently H, chlorine, or fluorine.

6. The compound of claim 1, wherein $R^4$ and $R^5$ are each independently H or chlorine.

7. A composition comprising a compound of claim 1 and a pharmaceutically acceptable carrier.

8. A pharmaceutical composition comprising:
an amount of a compound of claim 1; and
a pharmaceutically acceptable carrier,
wherein the amount of the compound is effective for treating a bacterial infection in a subject.

9. The pharmaceutical composition of claim 8, wherein the bacterial infection comprises a Gram-negative bacterial infection.

10. The pharmaceutical composition of claim 8, wherein the bacterial infection comprises a *Pseudomonas aeruginosa* infection, a *Acinetobacter baumannii* infection, a *Klebsiella pneumonia* infection, a *Yersinia pestis* infection, a *Shigella dysenteriae* infection, a *Enterobacter* sp. infection, a *Acinetobacter* sp. infection, a *Salmonella typhimurium* infection, a *Serratia* sp. infection, or a combination of any two or more thereof.

11. A method of treating a bacterial infection in a subject, the method comprising administering an effective amount of a compound of claim 1 to the subject.

12. The method of claim 11, the method further comprising administering an effective amount of fluoroquinolone antibiotic to the subject.

13. The method of claim 11, wherein the bacterial infection comprises a Gram-negative bacterial infection.

14. The method of claim 11, wherein the bacterial infection comprises a *Pseudomonas aeruginosa* infection, a *Acinetobacter baumannii* infection, a *Klebsiella pneumonia* infection, a *Yersinia pestis* infection, a *Shigella dysenteriae* infection, a *Enterobacter* sp. infection, a *Acinetobacter* sp. infection, a *Salmonella typhimurium* infection, a *Serratia* sp. infection, or a combination of any two or more thereof.

15. A method of treating a bacterial infection in a subject, the method comprising administering a pharmaceutical composition of claim 8 the subject.

16. The method of claim 15, wherein the bacterial infection comprises a Gram-negative bacterial infection.

17. The method of claim 15, wherein the bacterial infection comprises a *Pseudomonas aeruginosa* infection, a *Acinetobacter baumannii* infection, a *Klebsiella pneumonia* infection, a *Yersinia pestis* infection, a *Shigella dysenteriae* infection, a *Enterobacter* sp. infection, a *Acinetobacter* sp. infection, a *Salmonella typhimurium* infection, a *Serratia* sp. infection, or a combination of any two or more thereof.

18. A method of inhibiting interaction of a bacterioferritin and a bacterioferritin-associated ferredoxin, the method comprising contacting a compound of claim 1 the bacterioferritin, the bacterioferritin-associated ferredoxin, or both the bacterioferritin and the bacterioferritin-associated ferredoxin.

19. The method of claim 18, wherein the bacterioferritin is a *Pseudomonas aeruginosa*, a *Acinetobacter baumannii*, a *Klebsiella pneumonia*, a *Yersinia pestis*, a *Shigella dysente-* riae, a *Enterobacter* sp., a *Acinetobacter* sp., a *Salmonella typhimurium*, a *Serratia* sp., or a combination of any two or more thereof.

20. The method of claim 18, wherein the bacterioferritin-associated ferredoxin is a *Pseudomonas aeruginosa* bacterioferritin-associated ferredoxin, a *Acinetobacter baumannii* bacterioferritin-associated ferredoxin, a *Klebsiella pneumonia* bacterioferritin-associated ferredoxin, a *Yersinia pestis* bacterioferritin-associated ferredoxin, a *Shigella dysenteriae* bacterioferritin-associated ferredoxin, a *Enterobacter* sp. bacterioferritin-associated ferredoxin, a *Acinetobacter* sp. bacterioferritin-associated ferredoxin, a *Salmonella typhimurium* bacterioferritin-associated ferredoxin, a *Serratia* sp. bacterioferritin-associated ferredoxin, or a combination of any two or more thereof.

\* \* \* \* \*